US011414494B2

(12) United States Patent
Delfino et al.

(10) Patent No.: US 11,414,494 B2
(45) Date of Patent: *Aug. 16, 2022

(54) ANTI-GITR ANTIBODIES AND USES THEREOF

(71) Applicant: REGENERON PHARMACEUTICALS, INC., Tarrytown, NY (US)

(72) Inventors: Frank Delfino, Poughquag, NY (US); Dimitris Skokos, New York, NY (US); Bei Wang, Hastings-on-Hudson, NY (US)

(73) Assignee: REGENERON PHARMACEUTICALS, INC., Tarrytown, NY (US)

( * ) Notice: Subject to any disclaimer, the term of this patent is extended or adjusted under 35 U.S.C. 154(b) by 106 days.

This patent is subject to a terminal disclaimer.

(21) Appl. No.: 16/913,963

(22) Filed: Jun. 26, 2020

(65) Prior Publication Data

US 2021/0147565 A1    May 20, 2021

Related U.S. Application Data

(63) Continuation of application No. 15/619,068, filed on Jun. 9, 2017, now Pat. No. 10,738,126.

(60) Provisional application No. 62/348,353, filed on Jun. 10, 2016, provisional application No. 62/432,023, filed on Dec. 9, 2016, provisional application No. 62/500,312, filed on May 2, 2017.

(51) Int. Cl.
| | |
|---|---|
| *C07K 16/28* | (2006.01) |
| *A61K 39/395* | (2006.01) |
| *A61K 45/06* | (2006.01) |
| *A61K 39/00* | (2006.01) |

(52) U.S. Cl.
CPC .... *C07K 16/2878* (2013.01); *A61K 39/39541* (2013.01); *A61K 45/06* (2013.01); *C07K 16/2803* (2013.01); *C07K 16/2818* (2013.01); *A61K 2039/507* (2013.01); *C07K 2317/21* (2013.01); *C07K 2317/33* (2013.01); *C07K 2317/565* (2013.01); *C07K 2317/75* (2013.01); *C07K 2317/76* (2013.01); *C07K 2317/92* (2013.01); *C07K 2317/94* (2013.01)

(58) Field of Classification Search
CPC .......... C07K 16/2878; C07K 2317/565; A61K 45/06; A61K 39/39541; A61K 2039/507
See application file for complete search history.

(56) References Cited

U.S. PATENT DOCUMENTS

| | | | |
|---|---|---|---|
| 5,500,362 A | 3/1996 | Robinson et al. | |
| 5,821,337 A | 10/1998 | Carter et al. | |
| 6,503,184 B1 | 1/2003 | Ni et al. | |
| 6,689,607 B2 | 2/2004 | Ni et al. | |
| 7,025,962 B1 | 4/2006 | Gorman et al. | |
| 7,618,632 B2 | 11/2009 | Collins et al. | |
| 7,812,135 B2 | 10/2010 | Smith et al. | |
| 8,388,967 B2 | 3/2013 | Smith et al. | |
| 8,709,424 B2 | 4/2014 | Schebye et al. | |
| 9,028,823 B2 | 5/2015 | Smith et al. | |
| 9,175,308 B2 | 11/2015 | Shiku et al. | |
| 9,228,016 B2 | 1/2016 | Wang et al. | |
| 9,309,321 B2 | 4/2016 | Kwon | |
| 9,464,139 B2 | 10/2016 | Beers et al. | |
| 9,493,572 B2 | 11/2016 | Smith et al. | |
| 9,701,751 B2 | 7/2017 | Schebye et al. | |
| 9,745,379 B2 | 8/2017 | Wang et al. | |
| 9,987,500 B2 | 6/2018 | Papadopoulos et al. | |
| 2006/0099171 A1 | 3/2006 | Tone et al. | |
| 2007/0098719 A1 | 5/2007 | Smith et al. | |
| 2007/0280945 A1 | 12/2007 | Stevens et al. | |
| 2009/0136494 A1 | 5/2009 | Ponath et al. | |
| 2010/0061984 A1 | 3/2010 | Greene et al. | |
| 2011/0059109 A1 | 3/2011 | Smith et al. | |
| 2011/0212086 A1 | 9/2011 | Shankara et al. | |
| 2012/0189639 A1 | 7/2012 | Schebye et al. | |
| 2013/0108641 A1 | 5/2013 | Baurin et al. | |
| 2013/0183321 A1 | 7/2013 | Smith et al. | |
| 2014/0072565 A1 | 3/2014 | Kwon | |
| 2014/0072566 A1 | 3/2014 | Kwon | |
| 2014/0348841 A1 | 11/2014 | Schebye et al. | |
| 2015/0064204 A1 | 3/2015 | Beers et al. | |
| 2015/0203579 A1 | 7/2015 | Papadopoulos et al. | |
| 2015/0353637 A1 | 12/2015 | Wang et al. | |
| 2015/0368349 A1 | 12/2015 | Seibert et al. | |
| 2017/0355774 A1 | 12/2017 | Delfino et al. | |

FOREIGN PATENT DOCUMENTS

| | | |
|---|---|---|
| EP | 1462114 | 9/2004 |
| WO | 199806842 A1 | 2/1998 |
| WO | 199925834 | 5/1999 |

(Continued)

OTHER PUBLICATIONS

Barbee, et al. (2016) "Novel Tetravalent Anti-GITR Antibody is a Potent Anti-Tumor Agent in Vivo", Annual Meeting in National Harbor, Maryland, Poster #175, Nov. 11, 2016, 1 page.

(Continued)

*Primary Examiner* — Ruixiang Li

(74) *Attorney, Agent, or Firm* — FisherBroyles, LLP; Cara L. Crowley-Weber; Lisa Dornbach Flanagan

(57) ABSTRACT

Provided herein are antibodies, and antigen-binding fragments thereof that specifically bind glucocorticoid-induced tumor necrosis factor receptor (GITR) and methods of using the same, including, e.g., methods of treatment using the same.

26 Claims, 32 Drawing Sheets

Specification includes a Sequence Listing.

(56) References Cited

FOREIGN PATENT DOCUMENTS

| | | |
|---|---|---|
| WO | 2004107618 | 12/2004 |
| WO | 2006105021 A2 | 10/2006 |
| WO | 2011028683 A1 | 3/2011 |
| WO | 2015026684 A1 | 2/2015 |
| WO | 2015031667 | 3/2015 |
| WO | 2015184099 A1 | 12/2015 |
| WO | 2016054638 | 4/2016 |
| WO | 2016057846 | 4/2016 |
| WO | WO 2016/070051 A2 | 5/2016 |

OTHER PUBLICATIONS

Clouthier et al. (2014) "Cell-Specific and Context-Dependent Effects of GITR in Cancer, Autoimmunity, and Infection", Cytokine & Growth Factor Reviews, 25(2): 91-106.

Clynes et al. (1998) "Fc Receptors are Required in Passive and Active Immunity to Melanoma", The National Academy of Sciences, 95:652-656.

Gershoni et al. (2007) "Epitope Mapping, The First Step in Developing Epitope-Baed Vaccines", Biodrugs, 21(3):145-56.

International Search Report and Written Opinion received in PCT/US2017/036818 dated Nov. 6, 2017 (30 pages).

Kanamaru et al. (2004) "Costimulation via Glucocorticoid-Induced TNF Receptor in Both Conventional and CD25+ Regulatory CD4+ T Cells", J. Immunol. 172:7306-7314 (10 pages) http://www.jimmunol.org/content/172/12/7306.

Kazane et al. (2013) "Self-Assembled Antibody Multimers Through Peptide Nucleic Acid Conjugation", J Am Chem Soc., 135(1):340-346.

Klein, et al. (2012) "Progress in Overcoming the Chain Association Issue in Bispecific Heterodimeric IgG Antibodies", Landes Bioscience, 4(6):653-663.

Knee et al. (2016) "Rationale for Anti-GITR Cancer Immunotherapy", European Journal of Cancer, 67:1-10.

Lu et al. (2014) "Combined PD-1 Blockade and GITR Triggering Induce a Potent Antitumor Immunity in Murine Cancer Models and Synergizes with Chemotherapeutic Drugs", Journal of Translational Medicine, 12:36 (11 pages).

National Library of Medicine (2017) "Tumor Necrosis Factor Receptor Superfamily Member 18 Isoform 1 Precursor [Homo sapiens]", NCBI Reference Sequence.

Nocentini, et al. (2015) "Modulation of Tumour Immunity: a Patent Evaluation of WO 2015/026684A1", Expert Opinion on Therapeutic Patents, 32 pages.

Perez De La Lastra (1999) "Epitope Mapping 10 Monoclonal Antibodies Against the Pig Analogue of Human Membrane Cofactor Protein (MCP)", Immunology, 96:663-670.

Reddy et al. (2000) "Elimination of Fc Receptor-Dependent Effector Functions of a Modified IgG4 Monoclonal Antibody to Human CD4", The Journal of Immunology, 164:1925-1933.

Rudikoff et al. (1982) "Single Amino Acid Substitution Altering Antigen-Bidning Specificity", Proc. Natl. Acad. Sci., 79:1979-1983 (5pages).

Schaer et al. (2012) "Modulation of GITR for Cancer Immunotherapy", Curr. Opin. Immunol., 24:217-224.

Shevach and Stephens (2006) "The GITR-GITRL Interaction: Co-Stimulation or Contrasuppression of Regulatory Activity?", Nat. Rev. Immunol., 6:613-618.

Shields et al. (2002) "Lack of Fucose on Human IgG1 N-Linked Oligosaccharide Improves Binding to Human Fc RIII and Antibody-dependent Cellular Toxicity", The Journal of Biological Chemistry, 277(30):26733-26740.

Taylor et al. (1922) "A Transgenic Mouse That Expresses a Diversity of Human Sequence Heavy and Light Chain Immunoglobulins", Oxford University Press, Nucleic Acids Research, 20(23):6287-6295.

Yang et al. (2015) "TCRklass: A New K-String-Based Algorithm Characterization for Human and Mouse TCR Repertoire", The Journal of Immunology, 194:446-454.

Zhao et al. (2015) "Expression of GITR Enhances Multiple Myeloma Cell Sensitivity to Bortezomib", PLoS ONE, pp. 1-12.

Altschul et al. (1990) "Basic Local Alignment Search Tool", J. Mol. Biol., 215:403-410.

Altschul et al. (1997) "Gapped BLAST and PSI-BLAST: A New Generation of Protein Database Search Programs", Nucleic Acids Res., 25(17):3389-402.

Angal et al. (1993) "A Single Amino Acid Substitution Abolishes the Heterogeneity of Chimeric Mouse/Human (IgG4) Antibody", Molecular Immunology, 30(1):105-108.

Ehring (1999) "Hydrogen Exchange/Electrospray Ionization Mass Spectrometry Studies of Structural Features of Proteins and Protein/Protein Interactions", Analytical Biochemistry, 267(2):252-259.

Engen and Smith (2001) Anal. Chem. 73:256A-265A.

Gonnet et al. (1992) "Exhaustive Matching of the Entire Protein Sequence Database", Science 256: 1443-1445.

Harlow and Lane (2014) "Antibodies", (Cold Spring Harbor Press, Cold Spring Harb., NY).

Junghans et al. (1990) "Anti-Tac-H, a Humanized Antibody to the Interleukin 2 Receptor with New Features for Immunotherapy in Malignant and Immune Disorders", Cancer Res., 50:1495-1502.

Kazane et al. (2012) "Synthesis of Bispecific Antibodies using Genetically Encoded Unnatural Amino Acids", J. Am. Chem. Soc., [Epub: Dec. 4, 2012]).

Krausz et al. (2007) "GITR-GITRL System, A Novel Player in Shock and Inflammation", The Scientific World Journal, 7: 533-566.

Kufer et al. (2004) "A Revival of Bispecific Antibodies", Trends Biotechnol., 22(5):238-244.

Langer (1990) "New Methods of Drug Delivery", Science, 249:1527-1533.

Langer and Wise (eds.), (1974) "Medical Applications of Controlled Release", vol. 2, CRC Pres., Boca Raton, Florida, pp. 115-138.

Mordenti et al. (1991) "Interspecies Scaling of Clearance and Volume of Distribution Data for Five Therapeutic Proteins", Pharmaceut. Res., 8:1351-1359.

NCBI Accession #NP_004186.1.

Padlan et al. (1995) "Identification of Specificity-Determining Residues in Antibodies", FASEB J., 9:133-139.

Pearson (1994) "Using the FASTA Program to Search Protein and DNA Sequence Database", Methods Mol. Biol., 24: 307-331.

Pearson (2000) "Flexible Sequence Similarity Searching with the FASTA3 Program Package", Methods in Molecular Biology, 132:185-219.

Powell et al. (1998) "Compendium of Excipients for Parenteral Formulations" PDA, J Pharm Sci Technol, 52:238-311.

Reineke, (2004) "Antibody Epitope Mapping Using Arrays of Synthetic Peptides", Methods Mol Biol, 248:443-463.

Sefton (1987) "Implantable Pumps", CRC Crit. Ref. Biomed. Eng., 14(3):201-240.

Shimizu et al. (2002) "Stimulation of CD25(+)CD4(+) Regulatory T Cells Through GITR Breaks Immunological Self-Tolerance", Nature Immunology, 3(2): 135-142.

Tomer et al. (2000) "Characterization of a Discontinuous Epitope of the Human Immunodeficiency Virus (HIV) Core Protein p24 by Epitope Excision and Differential Chemical Modification Followed by Mass Spectrometric Peptide Mapping Analysis", Protein Science 9:487-496.

Tutt et al. (1991) "Trispecific F(ab')3 Derivatives That Use Cooperative Signaling Via the TCR/CD3 Complex and CD2 to Activate and Redirect Resting Cytotoxic T Cells", J. Immunol., 147:60-69.

Vajdos et al. (2002) "Comprehensive Functional Maps of the Antigen-binding Site of an Anti-ErbB2 Antibody Obtained with Shotgun Scanning Mutagenesis", J Mol Biol, 320:415-428.

Wu et al. (1987) "Receptor-Mediated in Vitro Gene Transformation by a Soluble DNA Carrier System", J. Biol. Chem., 262:4429-4432.

International Search Report and Written Opinion received in PCT/US2021/021109 dated Jun. 21, 2021 (15 pages).

ANTI-GITR ANTIBODIES AND USES THEREOF

FIELD

The present invention relates to antibodies and antigen-binding fragments thereof that specifically bind glucocorticoid-induced tumor necrosis factor receptor (GITR) and methods of use thereof.

BACKGROUND

Glucocorticoid-induced tumor necrosis factor receptor (GITR) is a member of the tumor necrosis factor receptor superfamily (TNFRSF). GITR expression is constitutively high on regulatory T cells, low/intermediate on naïve T cells, NK cells and granulocytes, and inducible upon activation. GITR interacts with its ligand GITRL, which is mainly expressed on antigen-presenting cells. GITR receptor activation can both augment effector T-cell proliferation and function as well as attenuate the suppression induced by regulatory T cells. Consequently, the modulation of GITR activity can serve as a basis for cancer immunotherapy and immune disorders. Thus, there is a need for agents, e.g., antibodies that modulate the activity of GITR.

BRIEF SUMMARY

The present invention provides antibodies and antigen-binding fragments thereof that bind glucocorticoid-induced tumor necrosis factor receptor (GITR). The antibodies of the invention are useful, inter alia, for targeting immune cells, e.g., effector T-cells, regulatory T-cells, and NK cells that express GITR.

The antibodies of the invention can be full-length (for example, an IgG1 or IgG4 antibody) or may comprise only an antigen-binding portion (for example, a Fab, F(ab')$_2$ or scFv fragment), and may be modified to affect functionality, e.g., to eliminate residual effector functions (Reddy et al., 2000, J. Immunol. 164:1925-1933).

Exemplary anti-GITR antibodies of the present invention are listed in Tables 1 and 2 herein. Table 1 sets forth the amino acid sequence identifiers of the heavy chain variable regions (HCVRs), light chain variable regions (LCVRs), heavy chain complementarity determining regions (HCDR1, HCDR2 and HCDR3), and light chain complementarity determining regions (LCDR1, LCDR2 and LCDR3) of the exemplary anti-GITR antibodies. Table 2 sets forth the nucleic acid sequence identifiers of the HCVRs, LCVRs, HCDR1, HCDR2 HCDR3, LCDR1, LCDR2 and LCDR3 of the exemplary anti-GITR antibodies.

The present invention provides antibodies or antigen-binding fragments thereof that specifically bind GITR, comprising an HCVR comprising an amino acid sequence selected from any of the HCVR amino acid sequences listed in Table 1, or a substantially similar sequence thereof having at least 90%, at least 95%, at least 98% or at least 99% sequence identity thereto.

The present invention also provides antibodies or antigen-binding fragments thereof that specifically bind GITR, comprising an LCVR comprising an amino acid sequence selected from any of the LCVR amino acid sequences listed in Table 1, or a substantially similar sequence thereof having at least 90%, at least 95%, at least 98% or at least 99% sequence identity thereto.

The present invention also provides antibodies or antigen-binding fragments thereof that specifically bind GITR, comprising an HCVR and an LCVR amino acid sequence pair (HCVR/LCVR) comprising any of the HCVR amino acid sequences listed in Table 1 paired with any of the LCVR amino acid sequences listed in Table 1. According to certain embodiments, the present invention provides antibodies, or antigen-binding fragments thereof, comprising an HCVR/LCVR amino acid sequence pair contained within any of the exemplary anti-GITR antibodies listed in Table 1. In certain embodiments, the HCVR/LCVR amino acid sequence pair is selected from the group consisting of: 98/106; 162/170; 194/202; 242/250; 290/298; 338/402; and 346/402.

The present invention also provides antibodies or antigen-binding fragments thereof that specifically bind GITR, comprising a heavy chain CDR1 (HCDR1) comprising an amino acid sequence selected from any of the HCDR1 amino acid sequences listed in Table 1 or a substantially similar sequence thereof having at least 90%, at least 95%, at least 98% or at least 99% sequence identity.

The present invention also provides antibodies or antigen-binding fragments thereof that specifically bind GITR, comprising a heavy chain CDR2 (HCDR2) comprising an amino acid sequence selected from any of the HCDR2 amino acid sequences listed in Table 1 or a substantially similar sequence thereof having at least 90%, at least 95%, at least 98% or at least 99% sequence identity.

The present invention also provides antibodies or antigen-binding fragments thereof that specifically bind GITR, comprising a heavy chain CDR3 (HCDR3) comprising an amino acid sequence selected from any of the HCDR3 amino acid sequences listed in Table 1 or a substantially similar sequence thereof having at least 90%, at least 95%, at least 98% or at least 99% sequence identity.

The present invention also provides antibodies or antigen-binding fragments thereof that specifically bind GITR, comprising a light chain CDR1 (LCDR1) comprising an amino acid sequence selected from any of the LCDR1 amino acid sequences listed in Table 1 or a substantially similar sequence thereof having at least 90%, at least 95%, at least 98% or at least 99% sequence identity.

The present invention also provides antibodies or antigen-binding fragments thereof that specifically bind GITR, comprising a light chain CDR2 (LCDR2) comprising an amino acid sequence selected from any of the LCDR2 amino acid sequences listed in Table 1 or a substantially similar sequence thereof having at least 90%, at least 95%, at least 98% or at least 99% sequence identity.

The present invention also provides antibodies or antigen-binding fragments thereof that specifically bind GITR, comprising a light chain CDR3 (LCDR3) comprising an amino acid sequence selected from any of the LCDR3 amino acid sequences listed in Table 1 or a substantially similar sequence thereof having at least 90%, at least 95%, at least 98% or at least 99% sequence identity.

The present invention also provides antibodies or antigen-binding fragments thereof that specifically bind GITR, comprising an HCDR3 and an LCDR3 amino acid sequence pair (HCDR3/LCDR3) comprising any of the HCDR3 amino acid sequences listed in Table 1 paired with any of the LCDR3 amino acid sequences listed in Table 1. According to certain embodiments, the present invention provides antibodies, or antigen-binding fragments thereof, comprising an HCDR3/LCDR3 amino acid sequence pair contained within any of the exemplary anti-GITR antibodies listed in Table 1. In certain embodiments, the HCDR3/LCDR3 amino acid sequence pair is selected from the group consisting of: 104/112; 168/176; 200/208; 248/256; 296/304; 344/408; and 352/408.

The present invention also provides antibodies or antigen-binding fragments thereof that specifically bind GITR, comprising a set of six CDRs (i.e., HCDR1-HCDR2-HCDR3-LCDR1-LCDR2-LCDR3) contained within any of the exemplary anti-GITR antibodies listed in Table 1. In certain embodiments, the HCDR1-HCDR2-HCDR3-LCDR1-LCDR2-LCDR3 amino acid sequences set is selected from the group consisting of: 100-102-104-108-110-112; 164-166-168-172-174-176; 196-198-200-204-206-208; 244-246-248-252-254-256; 292-294-296-300-302-304; 340-342-344-404-406-408; and 348-350-352-404-406-408.

In a related embodiment, the present invention provides antibodies, or antigen-binding fragments thereof that specifically bind GITR, comprising a set of six CDRs (i.e., HCDR1-HCDR2-HCDR3-LCDR1-LCDR2-LCDR3) contained within an HCVR/LCVR amino acid sequence pair as defined by any of the exemplary anti-GITR antibodies listed in Table 1. For example, the present invention includes antibodies or antigen-binding fragments thereof that specifically bind GITR, comprising the HCDR1-HCDR2-HCDR3-LCDR1-LCDR2-LCDR3 amino acid sequences set contained within an HCVR/LCVR amino acid sequence pair selected from the group consisting of: 98/106; 162/170; 194/202; 242/250; 290/298; 338/402; and 346/102. Methods and techniques for identifying CDRs within HCVR and LCVR amino acid sequences are well known in the art and can be used to identify CDRs within the specified HCVR and/or LCVR amino acid sequences disclosed herein. Exemplary conventions that can be used to identify the boundaries of CDRs include, e.g., the Kabat definition, the Chothia definition, and the AbM definition. In general terms, the Kabat definition is based on sequence variability, the Chothia definition is based on the location of the structural loop regions, and the AbM definition is a compromise between the Kabat and Chothia approaches. See, e.g., Kabat, "Sequences of Proteins of Immunological Interest," National Institutes of Health, Bethesda, Md. (1991); Al-Lazikani et al., *J. Mol. Biol.* 273:927-948 (1997); and Martin et al., *Proc. Natl. Acad. Sci. USA* 86:9268-9272 (1989). Public databases are also available for identifying CDR sequences within an antibody.

The present invention also provides nucleic acid molecules encoding anti-GITR antibodies or portions thereof. For example, the present invention provides nucleic acid molecules encoding any of the HCVR amino acid sequences listed in Table 1; in certain embodiments the nucleic acid molecule comprises a polynucleotide sequence selected from any of the HCVR nucleic acid sequences listed in Table 2, or a substantially similar sequence thereof having at least 90%, at least 95%, at least 98% or at least 99% sequence identity thereto.

The present invention also provides nucleic acid molecules encoding any of the LCVR amino acid sequences listed in Table 1; in certain embodiments the nucleic acid molecule comprises a polynucleotide sequence selected from any of the LCVR nucleic acid sequences listed in Table 2, or a substantially similar sequence thereof having at least 90%, at least 95%, at least 98% or at least 99% sequence identity thereto.

The present invention also provides nucleic acid molecules encoding any of the HCDR1 amino acid sequences listed in Table 1; in certain embodiments the nucleic acid molecule comprises a polynucleotide sequence selected from any of the HCDR1 nucleic acid sequences listed in Table 2, or a substantially similar sequence thereof having at least 90%, at least 95%, at least 98% or at least 99% sequence identity thereto.

The present invention also provides nucleic acid molecules encoding any of the HCDR2 amino acid sequences listed in Table 1; in certain embodiments the nucleic acid molecule comprises a polynucleotide sequence selected from any of the HCDR2 nucleic acid sequences listed in Table 2, or a substantially similar sequence thereof having at least 90%, at least 95%, at least 98% or at least 99% sequence identity thereto.

The present invention also provides nucleic acid molecules encoding any of the HCDR3 amino acid sequences listed in Table 1; in certain embodiments the nucleic acid molecule comprises a polynucleotide sequence selected from any of the HCDR3 nucleic acid sequences listed in Table 2, or a substantially similar sequence thereof having at least 90%, at least 95%, at least 98% or at least 99% sequence identity thereto.

The present invention also provides nucleic acid molecules encoding any of the LCDR1 amino acid sequences listed in Table 1; in certain embodiments the nucleic acid molecule comprises a polynucleotide sequence selected from any of the LCDR1 nucleic acid sequences listed in Table 2, or a substantially similar sequence thereof having at least 90%, at least 95%, at least 98% or at least 99% sequence identity thereto.

The present invention also provides nucleic acid molecules encoding any of the LCDR2 amino acid sequences listed in Table 1; in certain embodiments the nucleic acid molecule comprises a polynucleotide sequence selected from any of the LCDR2 nucleic acid sequences listed in Table 2, or a substantially similar sequence thereof having at least 90%, at least 95%, at least 98% or at least 99% sequence identity thereto.

The present invention also provides nucleic acid molecules encoding any of the LCDR3 amino acid sequences listed in Table 1; in certain embodiments the nucleic acid molecule comprises a polynucleotide sequence selected from any of the LCDR3 nucleic acid sequences listed in Table 2, or a substantially similar sequence thereof having at least 90%, at least 95%, at least 98% or at least 99% sequence identity thereto.

The present invention also provides nucleic acid molecules encoding an HCVR, wherein the HCVR comprises a set of three CDRs (i.e., HCDR1-HCDR2-HCDR3), wherein the HCDR1-HCDR2-HCDR3 amino acid sequence set is as defined by any of the exemplary anti-GITR antibodies listed in Table 1.

The present invention also provides nucleic acid molecules encoding an LCVR, wherein the LCVR comprises a set of three CDRs (i.e., LCDR1-LCDR2-LCDR3), wherein the LCDR1-LCDR2-LCDR3 amino acid sequence set is as defined by any of the exemplary anti-GITR antibodies listed in Table 1.

The present invention also provides nucleic acid molecules encoding both an HCVR and an LCVR, wherein the HCVR comprises an amino acid sequence of any of the HCVR amino acid sequences listed in Table 1, and wherein the LCVR comprises an amino acid sequence of any of the LCVR amino acid sequences listed in Table 1. In certain embodiments, the nucleic acid molecule comprises a polynucleotide sequence selected from any of the HCVR nucleic acid sequences listed in Table 2, or a substantially similar sequence thereof having at least 90%, at least 95%, at least 98% or at least 99% sequence identity thereto, and a polynucleotide sequence selected from any of the LCVR nucleic acid sequences listed in Table 2, or a substantially similar sequence thereof having at least 90%, at least 95%, at least 98% or at least 99% sequence identity thereto. In certain embodiments according to this aspect of the invention, the nucleic acid molecule encodes an HCVR and LCVR, wherein the HCVR and LCVR are both derived from the same anti-GITR antibody listed in Table 1.

The present invention also provides recombinant expression vectors capable of expressing a polypeptide comprising a heavy or light chain variable region of an anti-GITR antibody. For example, the present invention includes recombinant expression vectors comprising any of the nucleic acid molecules mentioned above, i.e., nucleic acid molecules encoding any of the HCVR, LCVR, and/or CDR sequences as set forth in Table 1. Also included within the scope of the present invention are host cells into which such vectors have been introduced, as well as methods of producing the antibodies or portions thereof by culturing the host cells under conditions permitting production of the antibodies or antibody fragments, and recovering the antibodies and antibody fragments so produced.

The present invention includes anti-GITR antibodies having a modified glycosylation pattern. In some embodiments, modification to remove undesirable glycosylation sites may be useful, or an antibody lacking a fucose moiety present on the oligosaccharide chain, for example, to increase antibody dependent cellular cytotoxicity (ADCC) function (see Shield et al. (2002) JBC 277:26733). In other applications, modification of galactosylation can be made in order to modify complement dependent cytotoxicity (CDC).

In another aspect, the invention provides a pharmaceutical composition comprising a recombinant human antibody or fragment thereof which specifically binds GITR and a pharmaceutically acceptable carrier. In a related aspect, the invention features a composition which is a combination of an anti-GITR antibody and a second therapeutic agent. In one embodiment, the second therapeutic agent is any agent that is advantageously combined with an anti-GITR antibody. The present invention also provides antibody-drug conjugates (ADCs) comprising an anti-GITR antibody conjugated to a cytotoxic agent. Exemplary combination therapies, co-formulations, and ADCs involving the anti-GITR antibodies of the present invention are disclosed elsewhere herein.

In yet another aspect, the invention provides therapeutic methods for killing tumor cells or for inhibiting or attenuating tumor cell growth, or otherwise treating a patient afflicted with cancer, using an anti-GITR antibody or antigen-binding portion of an antibody of the invention. The therapeutic methods according to this aspect of the invention comprise administering a therapeutically effective amount of a pharmaceutical composition comprising an antibody or antigen-binding fragment of an antibody of the invention to a subject in need thereof. The disorder treated is any disease or condition which is improved, ameliorated, inhibited or prevented by targeting GITR and/or by increasing T-cell proliferation or function and/or inhibiting suppression activity induced by regulatory T cells.

In yet another aspect, the invention provides therapeutic methods for killing tumor cells or for inhibiting or attenuating tumor cell growth, or otherwise treating a patient afflicted with cancer, using a combination of an anti-GITR antibody or antigen-binding portion of an anti-GITR antibody and an anti-PD1 antibody or antigen-binding portion of an anti-PD1 antibody. The therapeutic methods according to this aspect of the invention comprise administering a therapeutically effective amount of a pharmaceutical composition comprising a combination of an anti-GITR and anti-PD1 antibody or antigen-binding fragment composition to a subject in need thereof. The disorder treated is any disease or condition which is improved, ameliorated, inhibited or prevented by targeting both GITR and PD1.

Other embodiments will become apparent from a review of the ensuing detailed description.

BRIEF DESCRIPTION OF THE DRAWINGS

FIG. 18 F is a bar chart depicting IL-2 secretion in picograms per milliliter upon ex vivo TCR stimulation of splenocytes with anti-CD3+anti-CD28 Ab for 16 hours. Splenocytes from CD226−/− (solid bars) or wild type (WT) (open bars) mice were stimulated with anti-CD3+anti-CD28 Ab for 16 hours.

FIG. 18 G is a bar chart depicting TNF-α secretion in picograms per milliliter upon ex vivo TCR stimulation of splenocytes with anti-CD3+anti-CD28 Ab for 16 hours. Splenocytes from CD226−/− (solid bars) or wild type (WT) (open bars) mice were stimulated with anti-CD3+anti-CD28 Ab for 16 hours.

FIG. 18 H is a bar chart depicting IL-6 secretion in picograms per milliliter upon ex vivo TCR stimulation of splenocytes with anti-CD3+anti-CD28 Ab for 16 hours. Splenocytes from CD226−/− (solid bars) or wild type (WT) (open bars) mice were stimulated with anti-CD3+anti-CD28 Ab for 16 hours.

FIG. 18 I is a bar chart depicting IL-5 secretion in picograms per milliliter upon ex vivo TCR stimulation of splenocytes with anti-CD3+anti-CD28 Ab for 16 hours. Splenocytes from CD226−/− (solid bars) or wild type (WT) (open bars) mice were stimulated with anti-CD3+anti-CD28 Ab for 16 hours.

FIG. 19A depicts CD226 KO mice (rose lines) or WT littermates (black lines) challenged with MC38 tumor cells and treated with either anti-GITR+anti-PD-1 Ab (filled circles and squares) or isotype Abs (open circles and squares). FIGS. 19B-19D depict the effect of antibody treatment on (B) animals treated with antibodies blocking CD28 signaling (10 mg/kg CTLA-4-Ig; FIG. 19B, green lines); (C) animals treated with antibodies blocking OX40 signaling (10 mg/kg OX40L blocking antibody; FIG. 19C); and (D) animals treated with antibodies blocking 4-1 BB signaling (10 mg/kg 4-1BBL blocking antibody; FIG. 19D).

DETAILED DESCRIPTION

Figure 1:
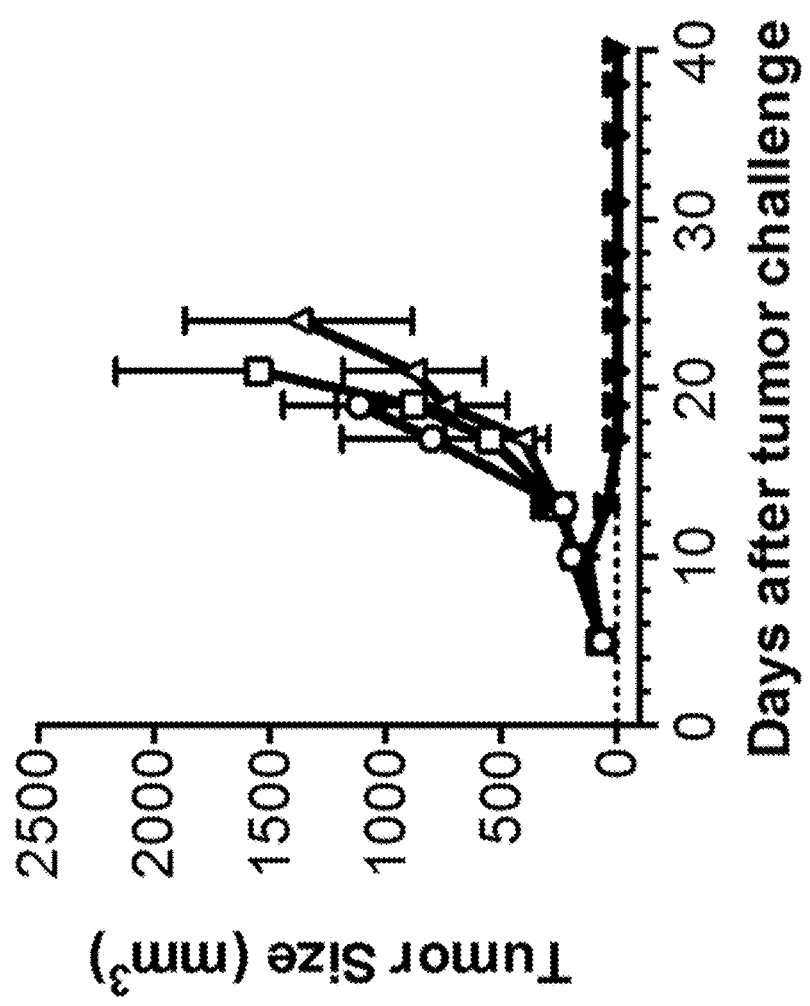
FIG. 1 depicts average tumor volumes for each treatment group ($mm^3 \pm SEM$) plotted against days after tumor challenge as described in Example 7. Mice were treated with either isotype antibody (open circles, ○), anti-PD-1 antibody (open squares, □), anti-GITR antibody (open pyramids, Δ), or a combination of anti-PD-1 and anti-GITR (closed inverted pyramids, ▼).

Before the present invention is described, it is to be understood that this invention is not limited to particular methods and experimental conditions described, as such methods and conditions may vary. It is also to be understood that the terminology used herein is for the purpose of describing particular embodiments only, and is not intended to be limiting, since the scope of the present invention will be limited only by the appended claims.

Unless defined otherwise, all technical and scientific terms used herein have the same meaning as commonly understood by one of ordinary skill in the art to which this invention belongs. As used herein, the term "about," when used in reference to a particular recited numerical value, means that the value may vary from the recited value by no more than 1%. For example, as used herein, the expression "about 100" includes 99 and 101 and all values in between (e.g., 99.1, 99.2, 99.3, 99.4, etc.).

Although any methods and materials similar or equivalent to those described herein can be used in the practice or testing of the present invention, the preferred methods and materials are now described. All patents, applications and non-patent publications mentioned in this specification are incorporated herein by reference in their entireties.

Definitions

The expression glucocorticoid-induced tumor necrosis factor receptor, "GITR," and the like, as used herein, refers to the human glucocorticoid-induced tumor necrosis factor receptor, comprising the amino acid sequence as set forth in SEQ ID NO: 413 (NCBI Accession #NP_004186.1). The expression "GITR" includes both monomeric and multimeric GITR molecules. As used herein, the expression "monomeric human GITR" means a GITR protein or portion thereof that does not contain or possess any multimerizing domains and that exists under normal conditions as a single GITR molecule without a direct physical connection to another GITR molecule. An exemplary monomeric GITR molecule is the molecule referred to herein as "hGITR.mmh" comprising the amino acid sequence of SEQ ID NO: 409 (see, e.g., Example 3, herein). As used herein, the expression "dimeric human GITR" means a construct comprising two GITR molecules connected to one another through a linker, covalent bond, non-covalent bond, or through a multimerizing domain such as an antibody Fc domain. Exemplary dimeric GITR molecules include those molecules referred to herein as "hGITR.mFc" and "hGITR.hFc", comprising the amino acid sequence of SEQ ID NO: 410 and SEQ ID NO: 411 respectively (see, e.g., Example 3, herein).

All references to proteins, polypeptides and protein fragments herein are intended to refer to the human version of the respective protein, polypeptide or protein fragment unless explicitly specified as being from a non-human species. Thus, the expression "GITR" means human GITR unless specified as being from a non-human species, e.g., "mouse GITR," "monkey GITR," etc.

As used herein, the expression "cell surface-expressed GITR" means one or more GITR protein(s), or the extracellular domain thereof, that is/are expressed on the surface of a cell in vitro or in vivo, such that at least a portion of a GITR protein is exposed to the extracellular side of the cell membrane and is accessible to an antigen-binding portion of an antibody. A "cell surface-expressed GITR" can comprise or consist of a GITR protein expressed on the surface of a cell which normally expresses GITR protein. Alternatively, "cell surface-expressed GITR" can comprise or consist of GITR protein expressed on the surface of a cell that normally does not express human GITR on its surface but has been artificially engineered to express GITR on its surface.

As used herein, the expression "anti-GITR antibody" includes both monovalent and monospecific bivalent antibodies with a single specificity, as well as bispecific antibodies comprising a first arm that binds GITR and a second arm that binds a second (target) antigen, wherein the anti-GITR arm comprises any of the HCVR/LCVR or CDR sequences as set forth in Table 1 herein. The expression "anti-GITR antibody" also includes antibody-drug conjugates (ADCs) comprising an anti-GITR antibody or antigen-binding portion thereof conjugated to a drug or toxin (i.e., cytotoxic agent). The expression "anti-GITR antibody" also includes antibody-radionuclide conjugates (ARCs) comprising an anti-GITR antibody or antigen-binding portion thereof conjugated to a radionuclide.

The term "antibody", as used herein, means any antigen-binding molecule or molecular complex comprising at least one complementarity determining region (CDR) that specifically binds to or interacts with a particular antigen (e.g., GITR). The term "antibody" includes immunoglobulin molecules comprising four polypeptide chains, two heavy (H) chains and two light (L) chains inter-connected by disulfide bonds, as well as multimers thereof (e.g., IgM). Each heavy chain comprises a heavy chain variable region (abbreviated herein as HCVR or $V_H$) and a heavy chain constant region. The heavy chain constant region comprises three domains, $C_H1$, $C_H2$ and $C_H3$. Each light chain comprises a light chain variable region (abbreviated herein as LCVR or $V_L$) and a light chain constant region. The light chain constant region comprises one domain ($C_L1$). The $V_H$ and $V_L$ regions can be further subdivided into regions of hypervariability, termed complementarity determining regions (CDRs), interspersed with regions that are more conserved, termed framework regions (FR). Each $V_H$ and $V_L$ is composed of three CDRs and four FRs, arranged from amino-terminus to carboxy-terminus in the following order: FR1, CDR1, FR2, CDR2, FR3, CDR3, FR4. In different embodiments of the invention, the FRs of the anti-GITR antibody (or antigen-binding portion thereof) may be identical to the human germline sequences, or may be naturally or artificially modified. An amino acid consensus sequence may be defined based on a side-by-side analysis of two or more CDRs.

The term "antibody", as used herein, also includes antigen-binding fragments of full antibody molecules. The terms "antigen-binding portion" of an antibody, "antigen-binding fragment" of an antibody, and the like, as used herein, include any naturally occurring, enzymatically obtainable, synthetic, or genetically engineered polypeptide or glycoprotein that specifically binds an antigen to form a complex. Antigen-binding fragments of an antibody may be derived, e.g., from full antibody molecules using any suitable standard techniques such as proteolytic digestion or recombinant genetic engineering techniques involving the manipulation and expression of DNA encoding antibody variable and optionally constant domains. Such DNA is known and/or is readily available from, e.g., commercial sources, DNA libraries (including, e.g., phage-antibody libraries), or can be synthesized. The DNA may be sequenced and manipulated chemically or by using molecular biology techniques, for example, to arrange one or more variable and/or constant domains into a suitable configuration, or to introduce codons, create cysteine residues, modify, add or delete amino acids, etc.

Non-limiting examples of antigen-binding fragments include: (i) Fab fragments; (ii) F(ab')2 fragments; (iii) Fd fragments; (iv) Fv fragments; (v) single-chain Fv (scFv) molecules; (vi) dAb fragments; and (vii) minimal recognition units consisting of the amino acid residues that mimic the hypervariable region of an antibody (e.g., an isolated complementarity determining region (CDR) such as a CDR3 peptide), or a constrained FR3-CDR3-FR4 peptide. Other engineered molecules, such as domain-specific antibodies, single domain antibodies, domain-deleted antibodies, chimeric antibodies, CDR-grafted antibodies, diabodies, triabodies, tetrabodies, minibodies, nanobodies (e.g. monovalent nanobodies, bivalent nanobodies, etc.), small modular immunopharmaceuticals (SMIPs), and shark variable IgNAR domains, are also encompassed within the expression "antigen-binding fragment," as used herein.

An antigen-binding fragment of an antibody will typically comprise at least one variable domain. The variable domain may be of any size or amino acid composition and will generally comprise at least one CDR which is adjacent to or in frame with one or more framework sequences. In antigen-binding fragments having a $V_H$ domain associated with a $V_L$ domain, the $V_H$ and $V_L$ domains may be situated relative to one another in any suitable arrangement. For example, the variable region may be dimeric and contain $V_H$-$V_H$, $V_H$-$V_L$ or $V_L$-$V_L$ dimers. Alternatively, the antigen-binding fragment of an antibody may contain a monomeric $V_H$ or $V_L$ domain.

In certain embodiments, an antigen-binding fragment of an antibody may contain at least one variable domain covalently linked to at least one constant domain. Non-limiting, exemplary configurations of variable and constant domains that may be found within an antigen-binding fragment of an antibody of the present invention include: (i) $V_H$-$C_H$1; (ii) $V_H$-$C_H$2; (iii) $V_H$-$C_H$3; (iv) $V_H$-$C_H$1-$C_H$2; (V) $V_H$-$C_H$1-$C_H$2-$C_H$3; (vi) $V_H$-$C_H$2-$C_H$3; (vii) $V_H$-$C_L$; $V_L$-$C_H$1; (ix) $V_L$-$C_H$2; (x) $V_L$-$C_H$3; (xi) $V_L$-$C_H$1-$C_H$2; (xii) $V_L$-$C_H$1-$C_H$2-$C_H$3; (xiii) $V_L$-$C_H$2-$C_H$3; and (xiv) $V_L$-$C_L$. In any configuration of variable and constant domains, including any of the exemplary configurations listed above, the variable and constant domains may be either directly linked to one another or may be linked by a full or partial hinge or linker region. A hinge region may consist of at least 2 (e.g., 5, 10, 15, 20, 40, 60 or more) amino acids which result in a flexible or semi-flexible linkage between adjacent variable and/or constant domains in a single polypeptide molecule. Moreover, an antigen-binding fragment of an antibody of the present invention may comprise a homo-dimer or hetero-dimer (or other multimer) of any of the variable and constant domain configurations listed above in non-covalent association with one another and/or with one or more monomeric $V_H$ or $V_L$ domain (e.g., by disulfide bond(s)).

As with full antibody molecules, antigen-binding fragments may be monospecific or multispecific (e.g., bispecific). A multispecific antigen-binding fragment of an antibody will typically comprise at least two different variable domains, wherein each variable domain is capable of specifically binding to a separate antigen or to a different epitope on the same antigen. Any multispecific antibody format, including the exemplary bispecific antibody formats disclosed herein, may be adapted for use in the context of an antigen-binding fragment of an antibody of the present invention using routine techniques available in the art.

The antibodies of the present invention may function through complement-dependent cytotoxicity (CDC) or antibody-dependent cell-mediated cytotoxicity (ADCC). "Complement-dependent cytotoxicity" (CDC) refers to lysis of antigen-expressing cells by an antibody of the invention in the presence of complement. "Antibody-dependent cell-mediated cytotoxicity" (ADCC) refers to a cell-mediated reaction in which nonspecific cytotoxic cells that express Fc receptors (FcRs) (e.g., Natural Killer (NK) cells, neutrophils, and macrophages) recognize bound antibody on a target cell and thereby lead to lysis of the target cell. CDC and ADCC can be measured using assays that are well known and available in the art. (See, e.g., U.S. Pat. Nos. 5,500,362 and 5,821,337, and Clynes et al. (1998) Proc. Natl. Acad. Sci. (USA) 95:652-656). The constant region of an antibody is important in the ability of an antibody to fix complement and mediate cell-dependent cytotoxicity. Thus, the isotype of an antibody may be selected on the basis of whether it is desirable for the antibody to mediate cytotoxicity.

In certain embodiments of the invention, the anti-GITR antibodies of the invention are human antibodies. The term "human antibody", as used herein, is intended to include antibodies having variable and constant regions derived from human germline immunoglobulin sequences. The human antibodies of the invention may include amino acid residues not encoded by human germline immunoglobulin sequences (e.g., mutations introduced by random or site-specific mutagenesis in vitro or by somatic mutation in vivo), for example in the CDRs and in particular CDR3. However, the term "human antibody", as used herein, is not intended to include antibodies in which CDR sequences derived from the germline of another mammalian species, such as a mouse, have been grafted onto human framework sequences. The term "human antibody" does not include naturally occurring molecules that normally exist without modification or human intervention/manipulation, in a naturally occurring, unmodified living organism.

The antibodies of the invention may, in some embodiments, be recombinant human antibodies. The term "recombinant human antibody", as used herein, is intended to include all human antibodies that are prepared, expressed, created or isolated by recombinant means, such as antibodies expressed using a recombinant expression vector transfected into a host cell (described further below), antibodies isolated from a recombinant, combinatorial human antibody library (described further below), antibodies isolated from an animal (e.g., a mouse) that is transgenic for human immunoglobulin genes (see e.g., Taylor et al. (1992) Nucl. Acids Res. 20:6287-6295) or antibodies prepared, expressed, created or isolated by any other means that involves splicing of human immunoglobulin gene sequences to other DNA sequences. Such recombinant human antibodies have variable and constant regions derived from human germline immunoglobulin sequences. In certain embodiments, however, such recombinant human antibodies are subjected to in vitro mutagenesis (or, when an animal transgenic for human Ig sequences is used, in vivo somatic mutagenesis) and thus the amino acid sequences of the $V_H$ and $V_L$ regions of the recombinant antibodies are sequences that, while derived from and related to human germline $V_H$ and $V_L$ sequences, may not naturally exist within the human antibody germline repertoire in vivo.

Human antibodies can exist in two forms that are associated with hinge heterogeneity. In one form, an immunoglobulin molecule comprises a stable four chain construct of approximately 150-160 kDa in which the dimers are held together by an interchain heavy chain disulfide bond. In a second form, the dimers are not linked via inter-chain disulfide bonds and a molecule of about 75-80 kDa is formed composed of a covalently coupled light and heavy chain (half-antibody). These forms have been extremely difficult to separate, even after affinity purification.

The frequency of appearance of the second form in various intact IgG isotypes is due to, but not limited to, structural differences associated with the hinge region isotype of the antibody. A single amino acid substitution in the hinge region of the human IgG4 hinge can significantly reduce the appearance of the second form (Angal et al. (1993) Molecular Immunology 30:105) to levels typically observed using a human IgG1 hinge. The instant invention encompasses antibodies having one or more mutations in the hinge, $C_H2$ or $C_H3$ region which may be desirable, for example, in production, to improve the yield of the desired antibody form.

The antibodies of the invention may be isolated antibodies. An "isolated antibody," as used herein, means an antibody that has been identified and separated and/or recovered from at least one component of its natural environment. For example, an antibody that has been separated or removed from at least one component of an organism, or from a tissue or cell in which the antibody naturally exists or is naturally produced, is an "isolated antibody" for purposes of the present invention. An isolated antibody also includes an antibody in situ within a recombinant cell. Isolated antibodies are antibodies that have been subjected to at least one purification or isolation step. According to certain embodiments, an isolated antibody may be substantially free of other cellular material and/or chemicals.

The anti-GITR antibodies disclosed herein may comprise one or more amino acid substitutions, insertions and/or deletions in the framework and/or CDR regions of the heavy and light chain variable domains as compared to the corresponding germline sequences from which the antibodies were derived. Such mutations can be readily ascertained by comparing the amino acid sequences disclosed herein to germline sequences available from, for example, public antibody sequence databases. The present invention includes antibodies, and antigen-binding fragments thereof, which are derived from any of the amino acid sequences disclosed herein, wherein one or more amino acids within one or more framework and/or CDR regions are mutated to the corresponding residue(s) of the germline sequence from which the antibody was derived, or to the corresponding residue(s) of another human germline sequence, or to a conservative amino acid substitution of the corresponding germline residue(s) (such sequence changes are referred to herein collectively as "germline mutations"). A person of ordinary skill in the art, starting with the heavy and light chain variable region sequences disclosed herein, can easily produce numerous antibodies and antigen-binding fragments which comprise one or more individual germline mutations or combinations thereof. In certain embodiments, all of the framework and/or CDR residues within the $V_H$ and/or $V_L$ domains are mutated back to the residues found in the original germline sequence from which the antibody was derived. In other embodiments, only certain residues are mutated back to the original germline sequence, e.g., only the mutated residues found within the first 8 amino acids of FR1 or within the last 8 amino acids of FR4, or only the mutated residues found within CDR1, CDR2 or CDR3. In other embodiments, one or more of the framework and/or CDR residue(s) are mutated to the corresponding residue(s) of a different germline sequence (i.e., a germline sequence that is different from the germline sequence from which the antibody was originally derived). Furthermore, the antibodies of the present invention may contain any combination of two or more germline mutations within the framework and/or CDR regions, e.g., wherein certain individual residues are mutated to the corresponding residue of a particular germline sequence while certain other residues that differ from the original germline sequence are maintained or are mutated to the corresponding residue of a different germline sequence. Once obtained, antibodies and antigen-binding fragments that contain one or more germline mutations can be easily tested for one or more desired property such as, improved binding specificity, increased binding affinity, improved or enhanced antagonistic or agonistic biological properties (as the case may be), reduced immunogenicity, etc. Antibodies and antigen-binding fragments obtained in this general manner are encompassed within the present invention.

The present invention also includes anti-GITR antibodies comprising variants of any of the HCVR, LCVR, and/or CDR amino acid sequences disclosed herein having one or more conservative substitutions. For example, the present invention includes anti-GITR antibodies having HCVR, LCVR, and/or CDR amino acid sequences with, e.g., 10 or fewer, 8 or fewer, 6 or fewer, 4 or fewer, etc. conservative amino acid substitutions relative to any of the HCVR, LCVR, and/or CDR amino acid sequences set forth in Table 1 herein.

The term "epitope" refers to an antigenic determinant that interacts with a specific antigen-binding site in the variable region of an antibody molecule known as a paratope. A single antigen may have more than one epitope. Thus, different antibodies may bind to different areas on an antigen and may have different biological effects. Epitopes may be either conformational or linear. A conformational epitope is produced by spatially juxtaposed amino acids from different segments of the linear polypeptide chain. A linear epitope is one produced by adjacent amino acid residues in a polypeptide chain. In certain circumstance, an epitope may include moieties of saccharides, phosphoryl groups, or sulfonyl groups on the antigen.

The term "substantial identity" or "substantially identical," when referring to a nucleic acid or fragment thereof, indicates that, when optimally aligned with appropriate nucleotide insertions or deletions with another nucleic acid (or its complementary strand), there is nucleotide sequence identity in at least about 95%, and more preferably at least about 96%, 97%, 98% or 99% of the nucleotide bases, as measured by any well-known algorithm of sequence identity, such as FASTA, BLAST or Gap, as discussed below. A nucleic acid molecule having substantial identity to a reference nucleic acid molecule may, in certain instances, encode a polypeptide having the same or substantially similar amino acid sequence as the polypeptide encoded by the reference nucleic acid molecule.

As applied to polypeptides, the term "substantial similarity" or "substantially similar" means that two peptide sequences, when optimally aligned, such as by the programs GAP or BESTFIT using default gap weights, share at least 95% sequence identity, even more preferably at least 98% or 99% sequence identity. Preferably, residue positions which are not identical differ by conservative amino acid substitutions. A "conservative amino acid substitution" is one in which an amino acid residue is substituted by another amino acid residue having a side chain (R group) with similar chemical properties (e.g., charge or hydrophobicity). In general, a conservative amino acid substitution will not substantially change the functional properties of a protein. In cases where two or more amino acid sequences differ from each other by conservative substitutions, the percent sequence identity or degree of similarity may be adjusted upwards to correct for the conservative nature of the substitution. Means for making this adjustment are well-known to those of skill in the art. See, e.g., Pearson (1994) Methods Mol. Biol. 24: 307-331, herein incorporated by reference. Examples of groups of amino acids that have side chains with similar chemical properties include (1) aliphatic side chains: glycine, alanine, valine, leucine and isoleucine; (2) aliphatic-hydroxyl side chains: serine and threonine; (3) amide-containing side chains: asparagine and glutamine; (4) aromatic side chains: phenylalanine, tyrosine, and tryptophan; (5) basic side chains: lysine, arginine, and histidine; (6) acidic side chains: aspartate and glutamate, and (7) sulfur-containing side chains are cysteine and methionine. Preferred conservative amino acids substitution groups are: valine-leucine-isoleucine, phenylalanine-tyrosine, lysine-arginine, alanine-valine, glutamate-aspartate, and asparagine-glutamine. Alternatively, a conservative replacement is any change having a positive value in the PAM250 log-likelihood matrix disclosed in Gonnet et al. (1992) Science 256: 1443-1445, herein incorporated by reference. A "moderately conservative" replacement is any change having a nonnegative value in the PAM250 log-likelihood matrix.

Sequence similarity for polypeptides, which is also referred to as sequence identity, is typically measured using sequence analysis software. Protein analysis software matches similar sequences using measures of similarity assigned to various substitutions, deletions and other modifications, including conservative amino acid substitutions. For instance, GCG software contains programs such as Gap and Bestfit which can be used with default parameters to determine sequence homology or sequence identity between closely related polypeptides, such as homologous polypeptides from different species of organisms or between a wild type protein and a mutein thereof. See, e.g., GCG Version 6.1. Polypeptide sequences also can be compared using FASTA using default or recommended parameters, a program in GCG Version 6.1. FASTA (e.g., FASTA2 and FASTA3) provides alignments and percent sequence identity of the regions of the best overlap between the query and search sequences (Pearson (2000) supra). Another preferred algorithm when comparing a sequence of the invention to a database containing a large number of sequences from different organisms is the computer program BLAST, especially BLASTP or TBLASTN, using default parameters. See, e.g., Altschul et al. (1990) J. Mol. Biol. 215:403-410 and Altschul et al. (1997) Nucleic Acids Res. 25:3389-402, each herein incorporated by reference.

Anti-GITR Antibodies Comprising Fc Variants

According to certain embodiments of the present invention, anti-GITR antibodies are provided comprising an Fc domain comprising one or more mutations which enhance or diminish antibody binding to the FcRn receptor, e.g., at acidic pH as compared to neutral pH. For example, the present invention includes anti-GITR antibodies comprising a mutation in the $C_H2$ or a $C_H3$ region of the Fc domain, wherein the mutation(s) increases the affinity of the Fc domain to FcRn in an acidic environment (e.g., in an endosome where pH ranges from about 5.5 to about 6.0). Such mutations may result in an increase in serum half-life of the antibody when administered to an animal. Non-limiting examples of such Fc modifications include, e.g., a modification at position 250 (e.g., E or Q); 250 and 428 (e.g., L or F); 252 (e.g., L/Y/F/W or T), 254 (e.g., S or T), and 256 (e.g., S/R/Q/E/D or T); or a modification at position 428 and/or 433 (e.g., H/L/R/S/P/Q or K) and/or 434 (e.g., H/F or Y); or a modification at position 250 and/or 428; or a modification at position 307 or 308 (e.g., 308F, V308F), and 434. In one embodiment, the modification comprises a 428L (e.g., M428L) and 434S (e.g., N434S) modification; a 428L, 259I (e.g., V259I), and 308F (e.g., V308F) modification; a 433K (e.g., H433K) and a 434 (e.g., 434Y) modification; a 252, 254, and 256 (e.g., 252Y, 254T, and 256E) modification; a 250Q and 428L modification (e.g., T250Q and M428L); and a 307 and/or 308 modification (e.g., 308F or 308P).

For example, the present invention includes anti-GITR antibodies comprising an Fc domain comprising one or more pairs or groups of mutations selected from the group consisting of: 250Q and 248L (e.g., T250Q and M248L); 252Y, 254T and 256E (e.g., M252Y, S254T and T256E); 428L and 434S (e.g., M428L and N434S); and 433K and 434F (e.g., H433K and N434F). All possible combinations of the foregoing Fc domain mutations, and other mutations within the antibody variable domains disclosed herein, are contemplated within the scope of the present invention.

Biological Characteristics of the Anti-GITR Antibodies

The present invention includes antibodies and antigen-binding fragments thereof that bind monomeric human GITR with high affinity. For example, the present invention includes anti-GITR antibodies that bind monomeric human GITR (e.g., hGITR.mmh) with a $K_D$ of less than about 5.0 nM as measured by surface plasmon resonance at 37° C., e.g., using an assay format as defined in Example 3 herein, or a substantially similar assay. In some embodiments, anti-GITR antibodies are provided that bind monomeric human GITR at 37° C. with a $K_D$ of less than about 4 nM, less than about 3 nM, less than about 2 nM, or less than about 1.50 nM as measured by surface plasmon resonance, e.g., using an assay format as defined in Example 3 herein, or a substantially similar assay.

The present invention also includes antibodies and antigen-binding fragments thereof that bind monomeric human GITR (e.g., hGITR.mmh) with a dissociative half-life (t½) of greater than about 12 minutes as measured by surface plasmon resonance at 37° C., e.g., using an assay format as defined in Example 3 herein, or a substantially similar assay. According to certain embodiments, anti-GITR antibodies are provided that bind monomeric human GITR at 37° C. with a t½ of greater than about 12 minutes, greater than about 13 minutes, greater than about 14 minutes, greater than about 15 minutes, or longer, as measured by surface plasmon resonance, e.g., using an assay format as defined in Example 3 herein, or a substantially similar assay.

The present invention also includes antibodies and antigen-binding fragments thereof that bind dimeric human GITR (e.g., hGITR.mFc) with high affinity. For example, the present invention includes anti-GITR antibodies that bind dimeric human GITR with a $K_D$ of less than about 950 µM as measured by surface plasmon resonance at 37° C., e.g., using an assay format as defined in Example 3 herein, or a substantially similar assay. According to certain embodiments, anti-GITR antibodies are provided that bind dimeric human GITR at 37° C. with a $K_D$ of less than about 900 µM, less than about 850 µM, less than about 800 µM, less than about 700 µM, less than about 600 µM, less than about 500 µM, less than about 400 µM, less than about 300 µM, less than about 200 µM, or less than about 100 µM as measured by surface plasmon resonance, e.g., using an assay format as defined in Example 3 herein, or a substantially similar assay.

The present invention also includes antibodies and antigen-binding fragments thereof that bind dimeric human GITR (e.g., hGITR.mFc) with a dissociative half-life (t½) of greater than about 7 minutes as measured by surface plasmon resonance at 37° C., e.g., using an assay format as defined in Example 3 herein, or a substantially similar assay. According to certain embodiments, anti-GITR antibodies are provided that bind dimeric human GITR at 37° C. with a t½ of greater than about 10 minutes, greater than about 20 minutes, greater than about 30 minutes, greater than about 40 minutes, greater than about 50 minutes, greater than about 60 minutes, greater than about 70 minutes, greater than about 80 minutes, greater than about 90 minutes, greater than about 100 minutes, or longer, as measured by surface plasmon resonance, e.g., using an assay format as defined in Example 3 herein, or a substantially similar assay.

The present disclosure also includes antibodies and antigen-binding fragments thereof that bind cell-surface-expressed GITR. For example, antibodies that bind to human GITR transfected embryonic kidney 293 (HEK-293) D9 cells with high affinity are provided herein. For example, the instant disclosure includes anti-GITR antibodies that bind human GITR transfected embryonic kidney 293 (HEK-293) D9 cells with an $EC_{50}$ of less than about 260 µM as measured by electrochemiluminescence, e.g., using an assay format as defined in Example 4 herein, or a substantially similar assay. In certain embodiments, anti-GITR antibodies are provided that bind human GITR transfected embryonic kidney 293 (HEK-293) D9 cells with an $EC_{50}$ of less than about 250 µM, less than about 240 µM, less than about 230 µM, or less than about 220 µM as measured by electrochemiluminescence, e.g., using an assay format as defined in Example 4 herein, or a substantially similar assay.

The antibodies of the present invention may possess one or more of the aforementioned biological characteristics, or any combination thereof. The foregoing list of biological characteristics of the antibodies of the invention is not intended to be exhaustive. Other biological characteristics of the antibodies of the present invention will be evident to a person of ordinary skill in the art from a review of the present disclosure including the working Examples herein.

Fc Anchoring-Dependent and Anchoring-Independent GITR Activation and GITRL Blocking The present disclosure includes antibodies and antigen-binding fragments thereof that activate human GITR, e.g., as determined in the assay formats described in Example 5 and/or Example 6 herein, or in a substantially similar assay format. As used herein, "activates human GITR" refers to the activation of GITR via binding to its cognate ligand, GITR Ligand (GITRL) or to the binding of agonist anti-GITR antigen binding protein(s) to GITR. With regard to activation of GITR by agonist anti-GITR binding proteins, "activation" can be in the presence or absence of antigen-binding protein anchoring to Fc gamma receptors. Human GITR activation is manifested in the exhibition of certain biological activities, including but not limited to the induction or enhancement of GITR signaling in vitro or in vivo, the reduction of regulatory T cell suppression of effector T cell activity; the decrease of circulating T reg levels in vitro or in vivo, the decrease of intratumoral T regs in vivo, the activation of effector T cells in vitro or in vivo, the induction or enhancement of effector T cell proliferation in vitro or in vivo, or the inhibition or reduction of tumor growth in vivo.

GITR Activation in the Absence of Fc Anchoring

In some embodiments, the antibodies and antigen-binding fragments thereof provided herein activate human GITR in the absence of Fc anchoring, e.g., as determined in the assay formats described in Example 5 and/or Example 6 herein, or in a substantially similar assay format. As used herein, "in the absence of Fc anchoring" refers to the activation of GITR and GITR-mediated signaling or blocking of GITRL without the clustering of anti-GITR antibodies by different forms of the Fc gamma receptor and can be determined and quantified via, e.g., the activation of primary T-cells co-cultured in vitro in the absence of cell-surface bound Fc gamma receptor(s). In some embodiments, the antibody or antigen-binding fragment thereof activates human GITR at an activation percentage greater than about 25% at an $EC_{50}$ of less than about 3 nM in the absence of Fc anchoring, as determined by NFκB reporter assay, e.g., as described in Example 5 or substantially similar assay format. In some embodiments, the antibody or antigen-binding fragment thereof activates human GITR at an activation percentage greater than about 30%, greater than about 40%, greater than about 50%, greater than about 60%, or greater than about 65% at an $EC_{50}$ of less than about 3 nM in the absence of Fc anchoring as determined by NFκB reporter assay, e.g., as described in Example 5 or substantially similar assay format. In some embodiments, the antibody or antigen-binding fragment thereof activates human GITR at an activation percentage greater than about 30%, greater than about 40%, greater than about 50%, greater than about 60%, or greater than about 65% at an $EC_{50}$ of less than about 2 nM in the absence of Fc anchoring as determined by NFκB reporter assay, e.g., as described in Example 5 or substantially similar assay format. In some embodiments, the antibody or antigen-binding fragment thereof activates human GITR at an activation percentage greater than about 30%, greater than about 40%, greater than about 50%, greater than about 60%, or greater than about 65% at an $EC_{50}$ of less than about 1.5 nM in the absence of Fc anchoring as determined by NFκB reporter assay, e.g., as described in Example 5 or substantially similar assay format. In some embodiments, the antibody or antigen-binding fragment thereof activates human GITR at an activation percentage greater than about 30%, greater than about 40%, greater than about 50%, greater than about 60%, or greater than about 65% at an $EC_{50}$ of less than about 1.4 nM in the absence of Fc anchoring as determined by NFκB reporter assay, e.g., as described in Example 5 or substantially similar assay format. In some embodiments, the antibody or antigen-binding fragment thereof activates human GITR at an activation percentage greater than about 30%, greater than about 40%, greater than about 50%, greater than about 60%, or greater than about 65% at an $EC_{50}$ of less than about 1.3 nM in the absence of Fc anchoring as determined by NFκB reporter assay, e.g., as described in Example 5 or substantially similar assay format.

In some embodiments, the antibody or antigen-binding fragment thereof binds GITR and exhibits T-cell proliferative activity in the absence of Fc-anchoring as determined by naïve human CD4+ T-cell proliferation assay, e.g., as described in Example 6 or substantially similar assay format. In some embodiments, the antibody or antigen-binding fragment thereof binds GITR and exhibits T-cell proliferative activity in the absence of Fc anchoring with an $EC_{50}$ of about 8 nM or less as determined by naïve human CD4+ T-cell proliferation assay, e.g., as described in Example 6 or substantially similar assay format. In some embodiments, the antibody or antigen-binding fragment thereof binds GITR and exhibits T-cell proliferative activity in the absence of Fc anchoring at least 2, at least 3, at least 4, at least 5, at least 6, at least 7, at least 8, at least 9, at least 10, or at least 11 fold above background at about 22 nM antibody (or antigen-binding fragment) concentration as determined by naïve human CD4+ T-cell proliferation assay, e.g., as described in Example 6 or substantially similar assay format.

GITR Activation in the Presence of Fc Anchoring

In some embodiments, the antibodies or antigen-binding fragments thereof provided herein activate human GITR in the presence of Fc anchoring, e.g., as determined in the assay formats described in Example 5 and/or Example 6 herein, or in a substantially similar assay format. As used herein, "in the presence of Fc anchoring" refers to the activation of GITR and GITR mediated signaling or blocking of GITRL through the clustering of anti-GITR antibodies via the interaction of the Fc region of the antibodies with different forms of the Fc gamma receptor (FcgR), such as FcgRI, FcgRIIa or FcgRIIIa and can be determined and quantified via, e.g., the activation of T-cells co-cultured in vitro in the presence of cell-surface bound Fc gamma receptor(s).

In some embodiments, the antibody or antigen-binding fragment thereof exhibits T-cell proliferative activity in the presence of Fc anchoring at least about 2 fold above background at about 33 nM antibody (or antibody-binding fragment) concentration as determined by naïve human CD4+ T-cell proliferation assay, e.g., as described in Example 6 or substantially similar assay format. In some embodiments, the antibody or antigen-binding fragment thereof exhibits T-cell proliferative activity in the presence of Fc anchoring at least about 2 fold, at least about 3 fold, at least about 4 fold, or at least about 5 fold above background at about 33 nM antibody (or antigen-binding fragment) concentration as determined by naïve human CD4+ T-cell proliferation assay, e.g., as described in Example 6 or substantially similar assay format. In some embodiments, the antibody or antigen-binding fragment exhibits T-cell proliferative activity in the presence of Fc anchoring with an $EC_{50}$ of less than about 34 nM as determined by naïve human CD4+ T-cell proliferation assay, e.g., as described in Example 6 or substantially similar assay format. In some embodiments, the antibody or antigen-binding fragment exhibits T-cell proliferative activity in the presence of Fc anchoring with an $EC_{50}$ of less than about 30 nM, less than about 20 nM, less than about 10 nM, less than about 5 nM, or less than about 4 nM as determined by naïve human CD4+ T-cell proliferation assay, e.g., as described in Example 6 or substantially similar assay format.

Antibodies that Block GITR Ligand Mediated Receptor Stimulation

The present disclosure includes antibodies that block human GITR ligand (hGITRL)-mediated receptor stimulation, e.g., as determined in the assay format described in Example 5 herein. As used herein, "blocks human GITR ligand (hGITRL)-mediated receptor stimulation" refers to the ability of anti-GITR antigen binding proteins to block the binding of GITR to its cognate ligand, GITRL. The blocking of GITR ligand can restore the suppression of effector T-cell activity by regulatory T cells. The blocking of GITR ligand can be determined and quantified via a variety of methods known in the art, including, for example, the reduction in T-cell proliferation or cytokine secretion and an increase in the levels of circulating regulatory T cells.

In some embodiments, the antibodies provided herein block human GITR ligand (hGITRL)-mediated receptor stimulation in the absence of GITR anchoring, e.g., as determined in the assay format described in Example 5 herein. In some embodiments, the antibody or antibody-binding fragment thereof blocks human GITR ligand-mediated receptor stimulation in the absence of Fc anchoring with a blocking percentage greater than about 55% at an $IC_{50}$ less than about 4.0 nM as determined by NFκB reporter assay, e.g., as described in Example 5 or substantially similar assay format. In some embodiments, the antibody or antibody-binding fragment thereof blocks human GITR ligand-mediated receptor stimulation in the absence of Fc anchoring with a blocking percentage greater than about 60%, greater than about 70%, greater than about 80%, or greater than about 85% at an $IC_{50}$ less than about 4.0 nM, less than about 3.0 nM, less than about 2.0 nM, less than about 1.0 nM, less than about 0.9 nM, less than about 0.8 nM, or less than about 0.7 nM as determined by NFκB reporter assay, e.g., as described in Example 5 or substantially similar assay format.

In some embodiments, the antibodies or antigen binding fragments activates human GITR and blocks human GITR ligand-mediated receptor stimulation at a blocking percentage less than about 25% in the absence of Fc anchoring as determined by NFκB reporter assay, e.g., in the assay described in Example 5 or substantially similar assay. In some embodiments, the antibodies or antigen binding fragments activates human GITR and blocks human GITR ligand-mediated receptor stimulation at a blocking percentage less than about 54% in the absence of Fc anchoring as determined by NFκB reporter assay, e.g., in the assay described in Example 5 or substantially similar assay. In some embodiments, the antibodies or antigen binding fragments activates human GITR and blocks human GITR ligand-mediated receptor stimulation at a blocking percentage less than about 40%, less than about 30%, less than about 20%, less than about 10%, less than about 5%, or less than about 1% in the absence of Fc anchoring as determined by NFκB reporter assay, e.g., in the assay described in Example 5 or substantially similar assay. In some embodiments, the antibodies or antigen binding fragments activates human GITR at an activation percentage of at least about 50% and does not block hGITRL-mediated receptor stimulation at a blocking percentage of greater than about 50% in the absence of Fc anchoring as determined by NFκB reporter assay, e.g., in the assay described in Example 5 or substantially similar assay.

In some embodiments, the antibodies or antigen binding fragments both activate human GITR and block human GITR ligand (hGITRL)-mediated receptor stimulation.

In some embodiments, the antibodies both activate human GITR and block human GITR ligand (hGITRL)-mediated receptor stimulation in the absence of Fc anchoring, e.g., as determined in the assay format described in example 5 herein, or a substantially similar assay. In some embodiments, (A) the antibody or antigen-binding fragment possesses at least one of the properties selected from the group consisting of:

i. activates human GITR in the absence of Fc anchoring at an activation percentage greater than about 25% at an $EC_{50}$ less than about 3 nM as determined by NFκB reporter assay and
ii. activates human GITR in the absence of Fc anchoring with an $EC_{50}$ of less than about 1.0 nM as determined by NFκB reporter assay; and
(B) the antibody or antigen-binding fragment blocks hGITRL-mediated receptor stimulation in the absence of Fc anchoring at a blocking percentage greater than about 54% at an $IC_{50}$ of less than about 4.0 nM as determined by NFκB reporter assay.

In some embodiments,
(A) the antibody or antigen-binding fragment activates human GITR in the absence of Fc anchoring at an activation percentage greater than about 50% at an $EC_{50}$ less than about 1.5 nM as determined by NFκB reporter assay; and
(B) the antibody or antigen-binding fragment blocks hGITRL-mediated receptor stimulation in the absence of Fc anchoring at a blocking percentage greater than about 54% at an $IC_{50}$ of less than about 4.0 nM as determined by NFκB reporter assay; and Epitope Mapping and Related Technologies The epitope to which the antibodies of the present invention bind may consist of a single contiguous sequence of 3 or more (e.g., 3, 4, 5, 6, 7, 8, 9, 10, 11, 12, 13, 14, 15, 16, 17, 18, 19, 20 or more) amino acids of a GITR protein. Alternatively, the epitope may consist of a plurality of non-contiguous amino acids (or amino acid sequences) of GITR. In some embodiments, the epitope is located on or near the GITRL-binding domain of GITR. In other embodiments, the epitope is located outside of the GITRL-binding domain of GITR, e.g., at a location on the surface of GITR at which an antibody, when bound to such an epitope, does not interfere with GITRL binding to GITR.

Various techniques known to persons of ordinary skill in the art can be used to determine whether an antibody "interacts with one or more amino acids" within a polypeptide or protein. Exemplary techniques include, e.g., routine cross-blocking assay such as that described Antibodies, Harlow and Lane (Cold Spring Harbor Press, Cold Spring Harb., N.Y.), alanine scanning mutational analysis, peptide blots analysis (Reineke, 2004, Methods Mol Biol 248:443-463), and peptide cleavage analysis. In addition, methods such as epitope excision, epitope extraction and chemical modification of antigens can be employed (Tomer, 2000, Protein Science 9:487-496). Another method that can be used to identify the amino acids within a polypeptide with which an antibody interacts is hydrogen/deuterium exchange detected by mass spectrometry. In general terms, the hydrogen/deuterium exchange method involves deuterium-labeling the protein of interest, followed by binding the antibody to the deuterium-labeled protein. Next, the protein/antibody complex is transferred to water to allow hydrogen-deuterium exchange to occur at all residues except for the residues protected by the antibody (which remain deuterium-labeled). After dissociation of the antibody, the target protein is subjected to protease cleavage and mass spectrometry analysis, thereby revealing the deuterium-labeled residues which correspond to the specific amino acids with which the antibody interacts. See, e.g., Ehring (1999) *Analytical Biochemistry* 267(2):252-259; Engen and Smith (2001) *Anal. Chem.* 73:256A-265A.

The present invention further includes anti-GITR antibodies that bind to the same epitope as any of the specific exemplary antibodies described herein (e.g. antibodies comprising any of the amino acid sequences as set forth in Table 1 herein). Likewise, the present invention also includes anti-GITR antibodies that compete for binding to GITR with any of the specific exemplary antibodies described herein (e.g. antibodies comprising any of the amino acid sequences as set forth in Table 1 herein).

One can easily determine whether an antibody binds to the same epitope as, or competes for binding with, a reference anti-GITR antibody by using routine methods known in the art and exemplified herein. For example, to determine if a test antibody binds to the same epitope as a reference anti-GITR antibody of the invention, the reference antibody is allowed to bind to a GITR protein. Next, the ability of a test antibody to bind to the GITR molecule is assessed. If the test antibody is able to bind to GITR following saturation binding with the reference anti-GITR antibody, it can be concluded that the test antibody binds to a different epitope than the reference anti-GITR antibody. On the other hand, if the test antibody is not able to bind to the GITR molecule following saturation binding with the reference anti-GITR antibody, then the test antibody may bind to the same epitope as the epitope bound by the reference anti-GITR antibody of the invention. Additional routine experimentation (e.g., peptide mutation and binding analyses) can then be carried out to confirm whether the observed lack of binding of the test antibody is in fact due to binding to the same epitope as the reference antibody or if steric blocking (or another phenomenon) is responsible for the lack of observed binding. Experiments of this sort can be performed using ELISA, RIA, Biacore, flow cytometry or any other quantitative or qualitative antibody-binding assay available in the art. In accordance with certain embodiments of the present invention, two antibodies bind to the same (or overlapping) epitope if, e.g., a 1-, 5-, 10-, 20- or 100-fold excess of one antibody inhibits binding of the other by at least 50% but preferably 75%, 90% or even 99% as measured in a competitive binding assay (see, e.g., Junghans et al., Cancer Res. 1990:50:1495-1502). Alternatively, two antibodies are deemed to bind to the same epitope if essentially all amino acid mutations in the antigen that reduce or eliminate binding of one antibody reduce or eliminate binding of the other. Two antibodies are deemed to have "overlapping epitopes" if only a subset of the amino acid mutations that reduce or eliminate binding of one antibody reduce or eliminate binding of the other.

To determine if an antibody competes for binding (or cross-competes for binding) with a reference anti-GITR antibody, the above-described binding methodology is performed in two orientations: In a first orientation, the reference antibody is allowed to bind to a GITR protein under saturating conditions followed by assessment of binding of the test antibody to the GITR molecule. In a second orientation, the test antibody is allowed to bind to a GITR molecule under saturating conditions followed by assessment of binding of the reference antibody to the GITR molecule. If, in both orientations, only the first (saturating) antibody is capable of binding to the GITR molecule, then it is concluded that the test antibody and the reference antibody compete for binding to GITR. As will be appreciated by a person of ordinary skill in the art, an antibody that competes for binding with a reference antibody may not necessarily bind to the same epitope as the reference antibody, but may sterically block binding of the reference antibody by binding an overlapping or adjacent epitope.

Preparation of Human Antibodies

The anti-GITR antibodies of the present invention can be fully human antibodies. Methods for generating monoclonal antibodies, including fully human monoclonal antibodies are known in the art. Any such known methods can be used in the context of the present invention to make human antibodies that specifically bind to human GITR.

Using VELOCIMMUNE™ technology, for example, or any other similar known method for generating fully human monoclonal antibodies, high affinity chimeric antibodies to GITR are initially isolated having a human variable region and a mouse constant region. As in the experimental section below, the antibodies are characterized and selected for desirable characteristics, including affinity, ligand blocking activity, selectivity, epitope, etc. If necessary, mouse constant regions are replaced with a desired human constant region, for example wild-type or modified IgG1 or IgG4, to generate a fully human anti-GITR antibody. While the constant region selected may vary according to specific use, high affinity antigen-binding and target specificity characteristics reside in the variable region. In certain instances, fully human anti-GITR antibodies are isolated directly from antigen-positive B cells.

Bioequivalents

The anti-GITR antibodies and antibody fragments of the present invention encompass proteins having amino acid sequences that vary from those of the described antibodies but that retain the ability to bind human GITR. Such variant antibodies and antibody fragments comprise one or more additions, deletions, or substitutions of amino acids when compared to parent sequence, but exhibit biological activity that is essentially equivalent to that of the described antibodies. Likewise, the anti-GITR antibody-encoding DNA sequences of the present invention encompass sequences that comprise one or more additions, deletions, or substitutions of nucleotides when compared to the disclosed sequence, but that encode an anti-GITR antibody or antibody fragment that is essentially bioequivalent to an anti-GITR antibody or antibody fragment of the invention. Examples of such variant amino acid and DNA sequences are discussed above.

Two antigen-binding proteins, or antibodies, are considered bioequivalent if, for example, they are pharmaceutical equivalents or pharmaceutical alternatives whose rate and extent of absorption do not show a significant difference when administered at the same molar dose under similar experimental conditions, either single dose or multiple dose. Some antibodies will be considered equivalents or pharmaceutical alternatives if they are equivalent in the extent of their absorption but not in their rate of absorption and yet may be considered bioequivalent because such differences in the rate of absorption are intentional and are reflected in the labeling, are not essential to the attainment of effective body drug concentrations on, e.g., chronic use, and are considered medically insignificant for the particular drug product studied.

In one embodiment, two antigen-binding proteins are bioequivalent if there are no clinically meaningful differences in their safety, purity, and potency.

In one embodiment, two antigen-binding proteins are bioequivalent if a patient can be switched one or more times between the reference product and the biological product without an expected increase in the risk of adverse effects, including a clinically significant change in immunogenicity, or diminished effectiveness, as compared to continued therapy without such switching.

In one embodiment, two antigen-binding proteins are bioequivalent if they both act by a common mechanism or mechanisms of action for the condition or conditions of use, to the extent that such mechanisms are known.

Bioequivalence may be demonstrated by in vivo and in vitro methods. Bioequivalence measures include, e.g., (a) an in vivo test in humans or other mammals, in which the concentration of the antibody or its metabolites is measured in blood, plasma, serum, or other biological fluid as a function of time; (b) an in vitro test that has been correlated with and is reasonably predictive of human in vivo bioavailability data; (c) an in vivo test in humans or other mammals in which the appropriate acute pharmacological effect of the antibody (or its target) is measured as a function of time; and (d) in a well-controlled clinical trial that establishes safety, efficacy, or bioavailability or bioequivalence of an antibody.

Bioequivalent variants of anti-GITR antibodies of the invention may be constructed by, for example, making various substitutions of residues or sequences or deleting terminal or internal residues or sequences not needed for biological activity. For example, cysteine residues not essential for biological activity can be deleted or replaced with other amino acids to prevent formation of unnecessary or incorrect intramolecular disulfide bridges upon renaturation. In other contexts, bioequivalent antibodies may include anti-GITR antibody variants comprising amino acid changes which modify the glycosylation characteristics of the antibodies, e.g., mutations which eliminate or remove glycosylation.

Species Selectivity and Species Cross-Reactivity

The present invention, according to certain embodiments, provides anti-GITR antibodies that bind to human GITR but not to GITR from other species. The present invention also includes anti-GITR antibodies that bind to human GITR and to GITR from one or more non-human species. For example, the anti-GITR antibodies of the invention may bind to human GITR and may bind or not bind, as the case may be, to one or more of mouse, rat, guinea pig, hamster, gerbil, pig, cat, dog, rabbit, goat, sheep, cow, horse, camel, cynomolgous, marmoset, rhesus or chimpanzee GITR. According to certain exemplary embodiments of the present invention, anti-GITR antibodies are provided which specifically bind human GITR and cynomolgus monkey (e.g., *Macaca fascicularis*) GITR. Other anti-GITR antibodies of the invention bind human GITR but do not bind, or bind only weakly, to cynomolgus monkey GITR.

Multispecific Antibodies

The antibodies of the present invention may be monospecific or multispecific (e.g., bispecific). Multispecific antibodies may be specific for different epitopes of one target polypeptide or may contain antigen-binding domains specific for more than one target polypeptide. See, e.g., Tutt et al., 1991, J. Immunol. 147:60-69; Kufer et al., 2004, Trends Biotechnol. 22:238-244. The anti-GITR antibodies of the present invention can be linked to or co-expressed with another functional molecule, e.g., another peptide or protein. For example, an antibody or fragment thereof can be functionally linked (e.g., by chemical coupling, genetic fusion, noncovalent association or otherwise) to one or more other molecular entities, such as another antibody or antibody fragment to produce a bispecific or a multispecific antibody with a second binding specificity.

The present invention includes bispecific antibodies wherein one arm of an immunoglobulin binds human GITR, and the other arm of the immunoglobulin is specific for a second antigen. The GITR-binding arm can comprise any of the HCVR/LCVR or CDR amino acid sequences as set forth in Table 1 herein. In certain embodiments, the GITR-binding arm binds human GITR and blocks GITRL binding to GITR. In other embodiments, the GITR-binding arm binds human GITR but does not block GITRL binding to GITR. In some embodiments, the GITR binding arm binds human GITR and activates GITR signaling. In other embodiments, the GITR binding arm blocks GITRL mediated receptor stimulation. The present invention also includes bispecific antibodies wherein one arm of an antibody binds a first epitope of human GITR, and the other arm of said antibody binds a second distinct epitope of human GITR.

An exemplary bispecific antibody format that can be used in the context of the present invention involves the use of a first immunoglobulin (Ig) $C_H3$ domain and a second Ig $C_H3$ domain, wherein the first and second Ig $C_H3$ domains differ from one another by at least one amino acid, and wherein at least one amino acid difference reduces binding of the bispecific antibody to Protein A as compared to a bispecific antibody lacking the amino acid difference. In one embodiment, the first Ig $C_H3$ domain binds Protein A and the second Ig $C_H3$ domain contains a mutation that reduces or abolishes Protein A binding such as an H95R modification (by IMGT exon numbering; H435R by EU numbering). The second $C_H3$ may further comprise a Y96F modification (by IMGT; Y436F by EU). Further modifications that may be found within the second $C_H3$ include: D16E, L18M, N44S, K52N, V57M, and V821 (by IMGT; D356E, L358M, N384S, K392N, V397M, and V4221 by EU) in the case of IgG1 antibodies; N44S, K52N, and V821 (IMGT; N384S, K392N, and V4221 by EU) in the case of IgG2 antibodies; and Q15R, N44S, K52N, V57M, R69K, E79Q, and V821 (by IMGT; Q355R, N384S, K392N, V397M, R409K, E419Q, and V4221 by EU) in the case of IgG4 antibodies. Variations on the bispecific antibody format described above are contemplated within the scope of the present invention.

Other exemplary bispecific formats that can be used in the context of the present invention include, without limitation, e.g., scFv-based or diabody bispecific formats, IgG-scFv fusions, dual variable domain (DVD)-Ig, Quadroma, knobs-into-holes, common light chain (e.g., common light chain with knobs-into-holes, etc.), CrossMab, CrossFab, (SEED) body, leucine zipper, Duobody, IgG1/IgG2, dual acting Fab (DAF)-IgG, and Mab$^2$ bispecific formats (see, e.g., Klein et al. 2012, mAbs 4:6, 1-11, and references cited therein, for a review of the foregoing formats). Bispecific antibodies can also be constructed using peptide/nucleic acid conjugation, e.g., wherein unnatural amino acids with orthogonal chemical reactivity are used to generate site-specific antibody-oligonucleotide conjugates which then self-assemble into multimeric complexes with defined composition, valency and geometry. (See, e.g., Kazane et al., *J. Am. Chem. Soc.* [Epub: Dec. 4, 2012]).

Therapeutic Formulation and Administration

The invention provides pharmaceutical compositions comprising the anti-GITR antibodies or antigen-binding fragments thereof of the present invention. The pharmaceutical compositions of the invention are formulated with suitable carriers, excipients, and other agents that provide improved transfer, delivery, tolerance, and the like. A multitude of appropriate formulations can be found in the formulary known to all pharmaceutical chemists: Remington's Pharmaceutical Sciences, Mack Publishing Company, Easton, Pa. These formulations include, for example, powders, pastes, ointments, jellies, waxes, oils, lipids, lipid (cationic or anionic) containing vesicles (such as LIPOFECTIN™, Life Technologies, Carlsbad, Calif.), DNA conjugates, anhydrous absorption pastes, oil-in-water and water-in-oil emulsions, emulsions carbowax (polyethylene glycols of various molecular weights), semi-solid gels, and semi-solid mixtures containing carbowax. See also Powell et al. "Compendium of excipients for parenteral formulations" PDA (1998) J Pharm Sci Technol 52:238-311.

The dose of antibody administered to a patient may vary depending upon the age and the size of the patient, target disease, conditions, route of administration, and the like. The preferred dose is typically calculated according to body weight or body surface area. In an adult patient, it may be advantageous to intravenously administer the antibody of the present invention normally at a single dose of about 0.01 to about 20 mg/kg body weight, more preferably about 0.02 to about 7, about 0.03 to about 5, or about 0.05 to about 3 mg/kg body weight. Depending on the severity of the condition, the frequency and the duration of the treatment can be adjusted. Effective dosages and schedules for administering anti-GITR antibodies may be determined empirically; for example, patient progress can be monitored by periodic assessment, and the dose adjusted accordingly. Moreover, interspecies scaling of dosages can be performed using well-known methods in the art (e.g., Mordenti et al., 1991, *Pharmaceut. Res.* 8:1351).

Various delivery systems are known and can be used to administer the pharmaceutical composition of the invention, e.g., encapsulation in liposomes, microparticles, microcapsules, recombinant cells capable of expressing the mutant viruses, receptor mediated endocytosis (see, e.g., Wu et al., 1987, J. Biol. Chem. 262:4429-4432). Methods of introduction include, but are not limited to, intradermal, intramuscular, intraperitoneal, intravenous, subcutaneous, intranasal, epidural, and oral routes. The composition may be administered by any convenient route, for example by infusion or bolus injection, by absorption through epithelial or mucocutaneous linings (e.g., oral mucosa, rectal and intestinal mucosa, etc.) and may be administered together with other biologically active agents. Administration can be systemic or local.

A pharmaceutical composition of the present invention can be delivered subcutaneously or intravenously with a standard needle and syringe. In addition, with respect to subcutaneous delivery, a pen delivery device readily has applications in delivering a pharmaceutical composition of the present invention. Such a pen delivery device can be reusable or disposable. A reusable pen delivery device generally utilizes a replaceable cartridge that contains a pharmaceutical composition. Once all of the pharmaceutical composition within the cartridge has been administered and the cartridge is empty, the empty cartridge can readily be discarded and replaced with a new cartridge that contains the pharmaceutical composition. The pen delivery device can then be reused. In a disposable pen delivery device, there is no replaceable cartridge. Rather, the disposable pen delivery device comes prefilled with the pharmaceutical composition held in a reservoir within the device. Once the reservoir is emptied of the pharmaceutical composition, the entire device is discarded.

Numerous reusable pen and autoinjector delivery devices have applications in the subcutaneous delivery of a pharmaceutical composition of the present invention. Examples include, but are not limited to AUTOPEN™ (Owen Mumford, Inc., Woodstock, UK), DISETRONIC™ pen (Disetronic Medical Systems, Bergdorf, Switzerland), HUMALOG MIX 75/25™ pen, HUMALOG™ pen, HUMALIN 70/30™ pen (Eli Lilly and Co., Indianapolis, Ind.), NOVOPEN™ I, II and III (Novo Nordisk, Copenhagen, Denmark), NOVOPEN JUNIOR™ (Novo Nordisk, Copenhagen, Denmark), BD™ pen (Becton Dickinson, Franklin Lakes, N.J.), OPTIPEN™, OPTIPEN PRO™, OPTIPEN STARLET™, and OPTICLIK™ (sanofi-aventis, Frankfurt, Germany), to name only a few. Examples of disposable pen delivery devices having applications in subcutaneous delivery of a pharmaceutical composition of the present invention include, but are not limited to the SOLOSTAR™ pen (sanofi-aventis), the FLEXPEN™ (Novo Nordisk), and the KWIKPEN™ (Eli Lilly), the SURECLICK™ Autoinjector (Amgen, Thousand Oaks, Calif.), the PENLET™ (Haselmeier, Stuttgart, Germany), the EPIPEN (Dey, L.P.), and the HUMIRA™ Pen (Abbott Labs, Abbott Park Ill.), to name only a few.

In certain situations, the pharmaceutical composition can be delivered in a controlled release system. In one embodiment, a pump may be used (see Langer, supra; Sefton, 1987, CRC Crit. Ref. Biomed. Eng. 14:201). In another embodiment, polymeric materials can be used; see, Medical Applications of Controlled Release, Langer and Wise (eds.), 1974, CRC Pres., Boca Raton, Fla. In yet another embodiment, a controlled release system can be placed in proximity of the composition's target, thus requiring only a fraction of the systemic dose (see, e.g., Goodson, 1984, in Medical Applications of Controlled Release, supra, vol. 2, pp. 115-138). Other controlled release systems are discussed in the review by Langer, 1990, Science 249:1527-1533.

The injectable preparations may include dosage forms for intravenous, subcutaneous, intracutaneous and intramuscular injections, drip infusions, etc. These injectable preparations may be prepared by methods publicly known. For example, the injectable preparations may be prepared, e.g., by dissolving, suspending or emulsifying the antibody or its salt described above in a sterile aqueous medium or an oily medium conventionally used for injections. As the aqueous medium for injections, there are, for example, physiological saline, an isotonic solution containing glucose and other auxiliary agents, etc., which may be used in combination with an appropriate solubilizing agent such as an alcohol (e.g., ethanol), a polyalcohol (e.g., propylene glycol, polyethylene glycol), a nonionic surfactant [e.g., polysorbate 80, HCO-50 (polyoxyethylene (50 mol) adduct of hydrogenated castor oil)], etc. As the oily medium, there are employed, e.g., sesame oil, soybean oil, etc., which may be used in combination with a solubilizing agent such as benzyl benzoate, benzyl alcohol, etc. The injection thus prepared is preferably filled in an appropriate ampoule.

Advantageously, the pharmaceutical compositions for oral or parenteral use described above are prepared into dosage forms in a unit dose suited to fit a dose of the active ingredients. Such dosage forms in a unit dose include, for example, tablets, pills, capsules, injections (ampoules), suppositories, etc. The amount of the aforesaid antibody contained is generally about 5 to about 500 mg per dosage form in a unit dose; especially in the form of injection, it is preferred that the aforesaid antibody is contained in about 5 to about 100 mg and in about 10 to about 250 mg for the other dosage forms.

Therapeutic Uses of the Antibodies

The present invention includes methods comprising administering to a subject in need thereof a therapeutic composition comprising an anti-GITR antibody (e.g., an anti-GITR antibody comprising any of the HCVR/LCVR or CDR sequences as set forth in Table 1 herein). The therapeutic composition can comprise any of the anti-GITR antibodies, antigen-binding fragments thereof, or ADCs disclosed herein, and a pharmaceutically acceptable carrier or diluent.

The antibodies of the invention are useful, inter alia, for the treatment, prevention and/or amelioration of any disease or disorder associated with or mediated by GITR expression or activity, or treatable by blocking the interaction between GITR and GITRL, and/or inhibiting or stimulating GITR activity and/or signaling. For example, the antibodies and antigen-binding fragments of the present disclosure can be used to treat immune and proliferative diseases or disorders, e.g., cancer, by modulating the immune response, though, e.g., GITR activation.

The antibodies and antigen-binding fragments of the instant disclosure can be used to treat a disease or disorder by enhancing an immune response. The instant disclosure includes methods of modulating anti-tumor immune response in a subject comprising administering to the subject an anti-GITR antibody or antigen-binding fragment described herein. In certain embodiments, the antibody or antigen-binding fragment reduces the suppressive activity of T effector cells by T regulatory cells. In some embodiments, the antibody or antigen-binding fragment of the instant disclosure enhances intra-tumoral T effector/T regulatory cell ratio conducive for therapeutic benefit. In some embodiments, the antibody or antigen-binding fragment of the instant disclosure promotes T cell survival.

Exemplary diseases or disorders that can be treated by the antibodies and antigen-binding fragments include immune and proliferative diseases or disorders, e.g., cancer. The antibodies and antigen-binding fragments of the present invention can be used to treat primary and/or metastatic tumors arising in the brain and meninges, oropharynx, lung and bronchial tree, gastrointestinal tract, male and female reproductive tract, muscle, bone, skin and appendages, connective tissue, spleen, immune system, blood forming cells and bone marrow, liver and urinary tract, and special sensory organs such as the eye. In some embodiments, the antibodies and antigen-binding fragments of the instant disclosure are used to treat solid or blood-borne tumors. In certain embodiments, the antibodies of the instant disclosure are used to treat one or more of the following cancers: renal cell carcinoma, pancreatic carcinoma, head and neck cancer, prostate cancer, malignant gliomas, osteosarcoma, colorectal cancer, gastric cancer (e.g., gastric cancer with MET amplification), malignant mesothelioma, multiple myeloma, ovarian cancer, cervical cancer, small cell lung cancer, non-small cell lung cancer, synovial sarcoma, thyroid cancer, breast cancer, melanoma, testicular, kidney, esophageal cancer, uterine cancer, endometrial cancer, or liver cancer.

In certain embodiments, the antibodies of the invention are useful for treating an autoimmune disease, including but not limited to, alopecia areata, autoimmune hepatitis, celiac disease, Graves' disease, Guillain-Barre syndrome, Hashimoto's disease, hemolytic anemia, inflammatory bowel disease, inflammatory myopathies, multiple sclerosis, primary biliary cirrhosis, psoriasis, rheumatoid arthritis, scleroderma, Sjögren's syndrome, systemic lupus erthyematosus, vitiligo, autoimmune pancreatitis, autoimmune urticaria, autoimmune thrombocytopenic purpura, Crohn's disease, diabetes type I, eosinophilic fasciitis, eosinophilic enterogastritis, Goodpasture's syndrome, myasthenia gravis, psoriatic arthritis, rheumatic fever, ulcerative colitis, vasculitis and Wegener's granulomatosis.

In the context of the methods of treatment described herein, the anti-GITR antibody may be administered as a monotherapy (i.e., as the only therapeutic agent) or in combination with one or more additional therapeutic agents (examples of which are described elsewhere herein).

Combination Therapies and Formulations

Provided herein are also combination therapies utilizing an anti-GITR antibody of the present disclosure and any additional therapeutic agent that may be advantageously combined with an antibody of the instant disclosure or antigen-binding fragment thereof.

The present invention includes compositions and therapeutic formulations comprising any of the anti-GITR antibodies described herein in combination with one or more additional therapeutically active components, and methods of treatment comprising administering such combinations to subjects in need thereof.

The antibodies of the present invention may be combined synergistically with one or more anti-cancer drugs or therapy used to treat cancer, including, for example, renal cell carcinoma, colorectal cancer, glioblastoma multiforme, squamous cell carcinoma of head and neck, non-small-cell lung cancer, colon cancer, ovarian cancer, adenocarcinoma, prostate cancer, glioma, and melanoma. It is contemplated herein to use anti-GITR antibodies of the invention in combination with immunostimulatory and/or immunosupportive therapies to inhibit tumor growth, and/or enhance survival of cancer patients. The immunostimulatory therapies include direct immunostimulatory therapies to augment immune cell activity by either "releasing the brake" on suppressed immune cells or "stepping on the gas" to activate an immune response. Examples include targeting other checkpoint receptors, vaccination and adjuvants. The immunosupportive modalities may increase antigenicity of the tumor by promoting immunogenic cell death, inflammation or have other indirect effects that promote an anti-tumor immune response. Examples include radiation, chemotherapy, anti-angiogenic agents, and surgery.

The instant disclosure includes methods of modulating anti-tumor immune response in a subject comprising administering to the subject an anti-GITR antibody in combination with one or more agonistic antibodies against activating receptors and one or more blocking antibodies against inhibitory receptors that enhance T-cell stimulation to promote tumor destruction.

The instant disclosure includes methods of modulating anti-tumor immune response in a subject comprising administering to the subject an anti-GITR antibody or antigen-binding fragment described herein in combination with one or more isolated antibody or antigen-binding fragment thereof that binds to a second T-cell activating receptor (i.e., other than GITR). In some embodiments, the second T-cell activating receptor is CD28, OX40, CD137, CD27, or VEM. The instant disclosure also includes formulations comprising an anti-GITR antibody or antigen binding fragment thereof provided herein and an antibody or antigen-binding fragment that binds said second T-cell activating receptor.

In various embodiments, one or more antibodies of the present invention may be used in combination with an antibody to PD-L1, an antibody to PD-1 (e.g., nivolumab), a LAG-3 inhibitor, a CTLA-4 inhibitor (e.g., ipilimumab), a TIM3 inhibitor, a BTLA inhibitor, a TIGIT inhibitor, a CD47 inhibitor, an antagonist of another T-cell co-inhibitor or ligand (e.g., an antibody to CD-28, 2B4, LY108, LAIR1, ICOS, CD160 or VISTA), an indoleamine-2,3-dioxygenase (IDO) inhibitor, a vascular endothelial growth factor (VEGF) antagonist [e.g., a "VEGF-Trap" such as aflibercept or other VEGF-inhibiting fusion protein as set forth in U.S. Pat. No. 7,087,411, or an anti-VEGF antibody or antigen binding fragment thereof (e.g., bevacizumab, or ranibizumab) or a small molecule kinase inhibitor of VEGF receptor (e.g., sunitinib, sorafenib, or pazopanib)], an Ang2 inhibitor (e.g., nesvacumab), a transforming growth factor beta (TGFβ) inhibitor, an epidermal growth factor receptor (EGFR) inhibitor (e.g., erlotinib, cetuximab), an agonist to a co-stimulatory receptor (e.g., an agonist to glucocorticoid-induced TNFR-related protein), an antibody to a tumor-specific antigen (e.g., CA9, CA125, melanoma-associated antigen 3 (MAGE3), carcinoembryonic antigen (CEA), vimentin, tumor-M2-PK, prostate-specific antigen (PSA), mucin-1, MART-1, and CA19-9), a vaccine (e.g., *Bacillus* Calmette-Guerin, a cancer vaccine), an adjuvant to increase antigen presentation (e.g., granulocyte-macrophage colony-stimulating factor), a bispecific antibody (e.g., CD3×CD20 bispecific antibody, PSMAxCD3 bispecific antibody), a cytotoxin, a chemotherapeutic agent (e.g., dacarbazine, temozolomide, cyclophosphamide, docetaxel, doxorubicin, daunorubicin, cisplatin, carboplatin, gemcitabine, methotrexate, mitoxantrone, oxaliplatin, paclitaxel, and vincristine), cyclophosphamide, radiotherapy, an IL-6R inhibitor (e.g., sarilumab), an IL-4R inhibitor (e.g., dupilumab), an IL-10 inhibitor, a cytokine such as IL-2, IL-7, IL-21, and IL-15, an antibody-drug conjugate (ADC) (e.g., anti-CD19-DM4 ADC, and anti-DS6-DM4 ADC), an anti-inflammatory drug (e.g., corticosteroids, and non-steroidal anti-inflammatory drugs), a dietary supplement such as anti-oxidants or any palliative care to treat cancer. In certain embodiments, the anti-GITR antibodies of the present invention may be used in combination with cancer vaccines including dendritic cell vaccines, oncolytic viruses, tumor cell vaccines, etc. to augment the anti-tumor response. Examples of cancer vaccines that can be used in combination with anti-GITR antibodies of the present invention include MAGE3 vaccine for melanoma and bladder cancer, MUC1 vaccine for breast cancer, EGFRv3 (e.g., Rindopepimut) for brain cancer (including glioblastoma multiforme), or ALVAC-CEA (for CEA+ cancers).

In some embodiments, one or more anti-GITR antibodies described herein are administered in combination with one or more anti-PD1 antibodies, including but not limited to those described in U.S. Patent Publication No. 2015/0203579, which is incorporated herein by reference in its entirety. In some embodiments, the anti-GITR antibody is H1H14536P2 or H2aM14536P2. In some embodiments, the anti-PD1 antibody is REGN 2810 (also known as H4H7798N as disclosed in U.S. Patent Publication No. 2015/0203579), pembrolizumab, or nivolumab.

In certain embodiments, the anti-GITR antibodies of the invention may be administered in combination with radiation therapy in methods to generate long-term durable anti-tumor responses and/or enhance survival of patients with cancer. In some embodiments, the anti-GITR antibodies of the invention may be administered prior to, concomitantly or after administering radiation therapy to a cancer patient. For example, radiation therapy may be administered in one or more doses to tumor lesions followed by administration of one or more doses of anti-GITR antibodies of the invention. In some embodiments, radiation therapy may be administered locally to a tumor lesion to enhance the local immunogenicity of a patient's tumor (adjuvinating radiation) and/or to kill tumor cells (ablative radiation) followed by systemic administration of an anti-GITR antibody of the invention. For example, intracranial radiation may be administered to a patient with brain cancer (e.g., glioblastoma multiforme) in combination with systemic administration of an anti-GITR antibody of the invention. In certain embodiments, the anti-GITR antibodies of the invention may be administered in combination with radiation therapy and a chemotherapeutic agent (e.g., temozolomide) or a VEGF antagonist (e.g., aflibercept).

In certain embodiments, the anti-GITR antibodies of the invention may be administered in combination with one or more anti-viral drugs to treat chronic viral infection caused by LCMV, HIV, HPV, HBV or HCV. Examples of anti-viral drugs include, but are not limited to, zidovudine, lamivudine, abacavir, ribavirin, lopinavir, efavirenz, cobicistat, tenofovir, rilpivirine and corticosteroids. In some embodiments, the anti-GITR antibodies of the invention may be administered in combination with a LAG3 inhibitor, a CTLA-4 inhibitor or any antagonist of another T-cell co-inhibitor to treat chronic viral infection.

In certain embodiments, the anti-GITR antibodies of the invention may be combined with an antibody to a Fc receptor on immune cells for the treatment of an autoimmune disease. In one embodiment, an antibody or fragment thereof of the invention is administered in combination with an antibody or antigen-binding protein targeted to an antigen specific to autoimmune tissue. In certain embodiments, an antibody or antigen-binding fragment thereof of the invention is administered in combination with an antibody or antigen-binding protein targeted to a T-cell receptor or a B-cell receptor, including but not limited to, Fcα (e.g., CD89), Fc gamma (e.g., CD64, CD32, CD16a, and CD16b), CD19, etc. The antibodies of fragments thereof of the invention may be used in combination with any drug or therapy known in the art (e.g., corticosteroids and other immunosuppressants) to treat an autoimmune disease or disorder including, but not limited to alopecia areata, autoimmune hepatitis, celiac disease, Graves' disease, Guillain-Barre syndrome, Hashimoto's disease, hemolytic anemia, inflammatory bowel disease, inflammatory myopathies, multiple sclerosis, primary biliary cirrhosis, psoriasis, rheumatoid arthritis, scleroderma, Sjögren's syndrome, systemic lupus erthyematosus, vitiligo, autoimmune pancreatitis, autoimmune urticaria, autoimmune thrombocytopenic purpura, Crohn's disease, diabetes type I, eosinophilic fasciitis, eosinophilic enterogastritis, Goodpasture's syndrome, myasthenia gravis, psoriatic arthritis, rheumatic fever, ulcerative colitis, vasculitis and Wegener's granulomatosis.

The instant disclosure also includes methods of modulating anti-tumor immune response in a subject comprising administering to the subject an anti-GITR antibody or antigen-binding fragment described herein in combination with one or more isolated antibody or antigen-binding fragment thereof that binds to a T-cell inhibitory receptor. In some embodiments, the T-cell inhibitory receptor is CTLA-4, PD-1, TIM-3, BTLA, VISTA, or LAG-3. The instant disclosure also includes formulations comprising an anti-GITR antibody or antigen-binding fragment thereof provided herein and an antibody or antigen-binding fragment that binds said T-cell inhibitory receptor.

The instant disclosure also includes methods of treating cancer by administering an antibody or antigen-binding fragment thereof or formulation described herein to a subject in conjunction with radiation or chemotherapy.

In some embodiments, the anti-GITR antibodies of the present invention are co-formulated with and/or administered in combination with one or more additional therapeutically active component(s) selected from the group consisting of: an EGFR antagonist (e.g., an anti-EGFR antibody [e.g., cetuximab or panitumumab] or small molecule inhibitor of EGFR [e.g., gefitinib or erlotinib]), an antagonist of another EGFR family member such as Her2/ErbB2, ErbB3 or ErbB4 (e.g., anti-ErbB2 [e.g., trastuzumab or T-DM1 {KADCYLA®}], anti-ErbB3 or anti-ErbB4 antibody or small molecule inhibitor of ErbB2, ErbB3 or ErbB4 activity), an antagonist of EGFRvIII (e.g., an antibody that specifically binds EGFRvIII), a cMET anagonist (e.g., an anti-cMET antibody), an IGF1R antagonist (e.g., an anti-IGF1R antibody), a B-raf inhibitor (e.g., vemurafenib, sorafenib, GDC-0879, PLX-4720), a PDGFR-α inhibitor (e.g., an anti-PDGFR-α antibody), a PDGFRβ inhibitor (e.g., an anti-PDGFRβ antibody or small molecule kinase inhibitor such as, e.g., imatinib mesylate or sunitinib malate), a PDGF ligand inhibitor (e.g., anti-PDGF-A, -B, -C, or -D antibody, aptamer, siRNA, etc.), a VEGF antagonist (e.g., a VEGF-Trap such as aflibercept, see, e.g., U.S. Pat. No. 7,087,411 (also referred to herein as a "VEGF-inhibiting fusion protein"), anti-VEGF antibody (e.g., bevacizumab), a small molecule kinase inhibitor of VEGF receptor (e.g., sunitinib, sorafenib or pazopanib)), a DLL4 antagonist (e.g., an anti-DLL4 antibody disclosed in US 2009/0142354 such as REGN421), an Ang2 antagonist (e.g., an anti-Ang2 antibody disclosed in US 2011/0027286 such as H1 H685P), a FOLH1 antagonist (e.g., an anti-FOLH1 antibody), a STEAP1 or STEAP2 antagonist (e.g., an anti-STEAP1 antibody or an anti-STEAP2 antibody), a TMPRSS2 antagonist (e.g., an anti-TMPRSS2 antibody), a MSLN antagonist (e.g., an anti-MSLN antibody), a CA9 antagonist (e.g., an anti-CA9 antibody), a uroplakin antagonist (e.g., an anti-uroplakin [e.g., anti-UPK3A] antibody), a MUC16 antagonist (e.g., an anti-MUC16 antibody), a Tn antigen antagonist (e.g., an anti-Tn antibody), a CLEC12A antagonist (e.g., an anti-CLEC12A antibody), a TNFRSF17 antagonist (e.g., an anti-TNFRSF17 antibody), a LGRS antagonist (e.g., an anti-LGRS antibody), a monovalent CD20 antagonist (e.g., a monovalent anti-CD20 antibody such as rituximab), etc. Other agents that may be beneficially administered in combination with antibodies of the invention include, e.g., tamoxifen, aromatase inhibitors, and cytokine inhibitors, including small-molecule cytokine inhibitors and antibodies that bind to cytokines such as IL-1, IL-2, IL-3, IL-4, IL-5, IL-6, IL-8, IL-9, IL-11, IL-12, IL-13, IL-17, IL-18, or to their respective receptors.

The present invention includes compositions and therapeutic formulations comprising any of the anti-GITR antibodies described herein in combination with one or more chemotherapeutic agents. Examples of chemotherapeutic agents include alkylating agents such as thiotepa and cyclosphosphamide (Cytoxan™); alkyl sulfonates such as busulfan, improsulfan and piposulfan; aziridines such as benzodopa, carboquone, meturedopa, and uredopa; ethylenimines and methylamelamines including altretamine, triethylenemelamine, trietylenephosphoramide, triethylenethiophosphaoramide and trimethylolomelamine; nitrogen mustards such as chlorambucil, chlornaphazine, cholophosphamide, estramustine, ifosfamide, mechlorethamine, mechlorethamine oxide hydrochloride, melphalan, novembichin, phenesterine, prednimustine, trofosfamide, uracil mustard; nitrosureas such as carmustine, chlorozotocin, fotemustine, lomustine, nimustine, ranimustine; antibiotics such as aclacinomysins, actinomycin, authramycin, azaserine, bleomycins, cactinomycin, calicheamicin, carabicin, carminomycin, carzinophilin, chromomycins, dactinomycin, daunorubicin, detorubicin, 6-diazo-5-oxo-L-norleucine, doxorubicin, epirubicin, esorubicin, idarubicin, marcellomycin, mitomycins, mycophenolic acid, nogalamycin, olivomycins, peplomycin, potfiromycin, puromycin, quelamycin, rodorubicin, streptonigrin, streptozocin, tubercidin, ubenimex, zinostatin, zorubicin; anti-metabolites such as methotrexate and 5-fluorouracil (5-FU); folic acid analogues such as denopterin, methotrexate, pteropterin, trimetrexate; purine analogs such as fludarabine, 6-mercaptopurine, thiamiprine, thioguanine; pyrimidine analogs such as ancitabine, azacitidine, 6-azauridine, carmofur, cytarabine, dideoxyuridine, doxifluridine, enocitabine, floxuridine; androgens such as calusterone, dromostanolone propionate, epitiostanol, mepitiostane, testolactone; anti-adrenals such as aminoglutethimide, mitotane, trilostane; folic acid replenisher such as frolinic acid; aceglatone; aldophosphamide glycoside; aminolevulinic acid; amsacrine; bestrabucil; bisantrene; edatraxate; defofamine; demecolcine; diaziquone; elfornithine; elliptinium acetate; etoglucid; gallium nitrate; hydroxyurea; lentinan; lonidamine; mitoguazone; mitoxantrone; mopidamol; nitracrine; pentostatin; phenamet; pirarubicin; podophyllinic acid; 2-ethylhydrazide; procarbazine; PSK™; razoxane; sizofiran; spirogermanium; tenuazonic acid; triaziquone; 2,2',2"-trichlorotriethylamine; urethan; vindesine; dacarbazine; mannomustine; mitobronitol; mitolactol; pipobroman; gacytosine; arabinoside ("Ara-C"); cyclophosphamide; thiotepa; taxanes, e.g. paclitaxel (Taxol™, Bristol-Myers Squibb Oncology, Princeton, N.J.) and docetaxel (Taxotere™; Aventis Antony, France); chlorambucil; gemcitabine; 6-thioguanine; mercaptopurine; methotrexate; platinum analogs such as cisplatin and carboplatin; vinblastine; platinum; etoposide (VP-16); ifosfamide; mitomycin C; mitoxantrone; vincristine; vinorelbine; navelbine; novantrone; teniposide; daunomycin; aminopterin; xeloda; ibandronate; CPT-11; topoisomerase inhibitor RFS 2000; difluoromethylornithine (DMFO); retinoic acid; esperamicins; capecitabine; and pharmaceutically acceptable salts, acids or derivatives of any of the above. Also included in this definition are anti-hormonal agents that act to regulate or inhibit hormone action on tumors such as anti-estrogens including for example tamoxifen, raloxifene, aromatase inhibiting 4(5)-imidazoles, 4-hydroxytamoxifen, trioxifene, keoxifene, LY 117018, onapristone, and toremifene (Fareston); and anti-androgens such as flutamide, nilutamide, bicalutamide, leuprolide, and goserelin; and pharmaceutically acceptable salts, acids or derivatives of any of the above.

The anti-GITR antibodies of the invention may also be administered and/or co-formulated in combination with antivirals, antibiotics, analgesics, corticosteroids, steroids, oxygen, antioxidants, COX inhibitors, cardioprotectants, metal chelators, IFN-gamma, and/or NSAIDs.

The additional therapeutically active component(s), e.g., any of the agents listed above or derivatives thereof, may be administered just prior to, concurrent with, or shortly after the administration of an anti-GITR antibody of the present invention; (for purposes of the present disclosure, such administration regimens are considered the administration of an anti-GITR antibody "in combination with" an additional therapeutically active component). The present invention includes pharmaceutical compositions in which an anti-GITR antibody of the present invention is co-formulated with one or more of the additional therapeutically active component(s) as described elsewhere herein.

The additional therapeutically active component(s) may be administered to a subject prior to administration of an anti-GITR antibody of the present invention. For example, a first component may be deemed to be administered "prior to" a second component if the first component is administered 1 week before, 72 hours before, 60 hours before, 48 hours before, 36 hours before, 24 hours before, 12 hours before, 6 hours before, 5 hours before, 4 hours before, 3 hours before, 2 hours before, 1 hour before, 30 minutes before, 15 minutes before, 10 minutes before, 5 minutes before, or less than 1 minute before administration of the second component. In other embodiments, the additional therapeutically active component(s) may be administered to a subject after administration of an anti-GITR antibody of the present invention. For example, a first component may be deemed to be administered "after" a second component if the first component is administered 1 minute after, 5 minutes after, 10 minutes after, 15 minutes after, 30 minutes after, 1 hour after, 2 hours after, 3 hours after, 4 hours after, 5 hours after, 6 hours after, 12 hours after, 24 hours after, 36 hours after, 48 hours after, 60 hours after, 72 hours after administration of the second component. In yet other embodiments, the additional therapeutically active component(s) may be administered to a subject concurrent with administration of an anti-GITR antibody of the present invention. "Concurrent" administration, for purposes of the present invention, includes, e.g., administration of an anti-GITR antibody and an additional therapeutically active component to a subject in a single dosage form (e.g., co-formulated), or in separate dosage forms administered to the subject within about 30 minutes or less of each other. If administered in separate dosage forms, each dosage form may be administered via the same route (e.g., both the anti-GITR antibody and the additional therapeutically active component may be administered intravenously, subcutaneously, etc.); alternatively, each dosage form may be administered via a different route (e.g., the anti-GITR antibody may be administered intravenously, and the additional therapeutically active component may be administered subcutaneously). In any event, administering the components in a single dosage from, in separate dosage forms by the same route, or in separate dosage forms by different routes are all considered "concurrent administration," for purposes of the present disclosure. For purposes of the present disclosure, administration of an anti-GITR antibody "prior to", "concurrent with," or "after" (as those terms are defined herein above) administration of an additional therapeutically active component is considered administration of an anti-GITR antibody "in combination with" an additional therapeutically active component).

The present invention includes pharmaceutical compositions in which an anti-GITR antibody of the present invention is co-formulated with one or more of the additional therapeutically active component(s) as described elsewhere herein using a variety of dosage combinations.

In exemplary embodiments in which an anti-GITR antibody of the invention is administered in combination with a VEGF antagonist (e.g., a VEGF trap such as aflibercept), including administration of co-formulations comprising an anti-GITR antibody and a VEGF antagonist, the individual components may be administered to a subject and/or co-formulated using a variety of dosage combinations. For example, the anti-GITR antibody may be administered to a subject and/or contained in a co-formulation in an amount selected from the group consisting of 0.01 mg, 0.02 mg, 0.03 mg, 0.04 mg, 0.05 mg, 0.1 mg, 0.2 mg, 0.3 mg, 0.4 mg, 0.5 mg, 0.6 mg, 0.7 mg, 0.8 mg, 0.9 mg, 1.0 mg, 1.5 mg, 2.0 mg, 2.5 mg, 3.0 mg, 3.5 mg, 4.0 mg, 4.5 mg, 5.0 mg, 6.0 mg, 7.0 mg, 8.0 mg, 9.0 mg, and 10.0 mg; and the VEGF antagonist (e.g., a VEGF trap such as aflibercept) may be administered to the subject and/or contained in a co-formulation in an amount selected from the group consisting of 0.1 mg, 0.2 mg, 0.3 mg, 0.4 mg, 0.5 mg, 0.6 mg, 0.7 mg, 0.8 mg, 0.9 mg, 1.0 mg, 1.1 mg, 1.2 mg, 1.3 mg, 1.4 mg, 1.5 mg, 1.6 mg, 1.7 mg, 1.8 mg, 1.9 mg, 2.0 mg, 2.1 mg, 2.2 mg, 2.3 mg, 2.4 mg, 2.5 mg, 2.6 mg, 2.7 mg, 2.8 mg, 2.9 mg and 3.0 mg. The combinations/co-formulations may be administered to a subject according to any of the administration regimens disclosed elsewhere herein, including, e.g., twice a week, once every week, once every 2 weeks, once every 3 weeks, once every month, once every 2 months, once every 3 months, once every 4 months, once every 5 months, once every 6 months, etc.

Administration Regimens

According to certain embodiments of the present invention, multiple doses of an anti-GITR antibody (or a pharmaceutical composition comprising a combination of an anti-GITR antibody and any of the additional therapeutically active agents mentioned herein) may be administered to a subject over a defined time course. The methods according to this aspect of the invention comprise sequentially administering to a subject multiple doses of an anti-GITR antibody of the invention. As used herein, "sequentially administering" means that each dose of anti-GITR antibody is administered to the subject at a different point in time, e.g., on different days separated by a predetermined interval (e.g., hours, days, weeks or months). The present invention includes methods which comprise sequentially administering to the patient a single initial dose of an anti-GITR antibody, followed by one or more secondary doses of the anti-GITR antibody, and optionally followed by one or more tertiary doses of the anti-GITR antibody.

The terms "initial dose," "secondary doses," and "tertiary doses," refer to the temporal sequence of administration of the anti-GITR antibody of the invention. Thus, the "initial dose" is the dose which is administered at the beginning of the treatment regimen (also referred to as the "baseline dose"); the "secondary doses" are the doses which are administered after the initial dose; and the "tertiary doses" are the doses which are administered after the secondary doses. The initial, secondary, and tertiary doses may all contain the same amount of anti-GITR antibody, but generally may differ from one another in terms of frequency of administration. In certain embodiments, however, the amount of anti-GITR antibody contained in the initial, secondary and/or tertiary doses varies from one another (e.g., adjusted up or down as appropriate) during the course of treatment. In certain embodiments, two or more (e.g., 2, 3, 4, or 5) doses are administered at the beginning of the treatment regimen as "loading doses" followed by subsequent doses that are administered on a less frequent basis (e.g., "maintenance doses").

In certain exemplary embodiments of the present invention, each secondary and/or tertiary dose is administered 1 to 26 (e.g., 1, 1½, 2, 2½, 3, 3½, 4, 4½, 5, 5½, 6, 6½, 7, 7½, 8, 8½, 9, 9½, 10, 10½, 11, 11½, 12, 12½, 13, 13½, 14, 14½, 15, 15½, 16, 16½, 17, 17½, 18, 18½, 19, 19½, 20, 20½, 21, 21½, 22, 22½, 23, 23½, 24, 24½, 25, 25½, 26, 26½, or more) weeks after the immediately preceding dose. The phrase "the immediately preceding dose," as used herein, means, in a sequence of multiple administrations, the dose of anti-GITR antibody which is administered to a patient prior to the administration of the very next dose in the sequence with no intervening doses.

The methods according to this aspect of the invention may comprise administering to a patient any number of secondary and/or tertiary doses of an anti-GITR antibody. For example, in certain embodiments, only a single secondary dose is administered to the patient. In other embodiments, two or more (e.g., 2, 3, 4, 5, 6, 7, 8, or more) secondary doses are administered to the patient. Likewise, in certain embodiments, only a single tertiary dose is administered to the patient. In other embodiments, two or more (e.g., 2, 3, 4, 5, 6, 7, 8, or more) tertiary doses are administered to the patient. The administration regimen may be carried out indefinitely over the lifetime of a particular subject, or until such treatment is no longer therapeutically needed or advantageous.

In embodiments involving multiple secondary doses, each secondary dose may be administered at the same frequency as the other secondary doses. For example, each secondary dose may be administered to the patient 1 to 2 weeks or 1 to 2 months after the immediately preceding dose. Similarly, in embodiments involving multiple tertiary doses, each tertiary dose may be administered at the same frequency as the other tertiary doses. For example, each tertiary dose may be administered to the patient 2 to 12 weeks after the immediately preceding dose. In certain embodiments of the invention, the frequency at which the secondary and/or tertiary doses are administered to a patient can vary over the course of the treatment regimen. The frequency of administration may also be adjusted during the course of treatment by a physician depending on the needs of the individual patient following clinical examination.

The present invention includes administration regimens in which 2 to 6 loading doses are administered to a patient at a first frequency (e.g., once a week, once every two weeks, once every three weeks, once a month, once every two months, etc.), followed by administration of two or more maintenance doses to the patient on a less frequent basis. For example, according to this aspect of the invention, if the loading doses are administered at a frequency of once a month, then the maintenance doses may be administered to the patient once every six weeks, once every two months, once every three months, etc.

Diagnostic Uses of the Antibodies

The anti-GITR antibodies of the present invention may also be used to detect and/or measure GITR, or GITR-expressing cells in a sample, e.g., for diagnostic purposes. For example, an anti-GITR antibody, or fragment thereof, may be used to diagnose a condition or disease characterized by aberrant expression (e.g., over-expression, under-expression, lack of expression, etc.) of GITR. Exemplary diagnostic assays for GITR may comprise, e.g., contacting a sample, obtained from a patient, with an anti-GITR antibody of the invention, wherein the anti-GITR antibody is labeled with a detectable label or reporter molecule. Alternatively, an unlabeled anti-GITR antibody can be used in diagnostic applications in combination with a secondary antibody which is itself detectably labeled. The detectable label or reporter molecule can be a radioisotope, such as $^3$H, $^{14}$C, $^{32}$P, $^{35}$S, or $^{125}$I; a fluorescent or chemiluminescent moiety such as fluorescein, or rhodamine; or an enzyme such as alkaline phosphatase, beta-galactosidase, horseradish peroxidase, or luciferase. Specific exemplary assays that can be used to detect or measure GITR in a sample include enzyme-linked immunosorbent assay (ELISA), radioimmunoassay (RIA), immuno-PET (e.g., $^{89}$Zr, $^{64}$Cu, etc.), and fluorescence-activated cell sorting (FACS).

Samples that can be used in GITR diagnostic assays according to the present invention include any tissue or fluid sample obtainable from a patient which contains detectable quantities of GITR protein, or fragments thereof, under normal or pathological conditions. Generally, levels of GITR in a particular sample obtained from a healthy patient (e.g., a patient not afflicted with a disease or condition associated with abnormal GITR levels or activity) will be measured to initially establish a baseline, or standard, level of GITR. This baseline level of GITR can then be compared against the levels of GITR measured in samples obtained from individuals suspected of having a GITR related disease or condition.

EXAMPLES

The following examples are put forth so as to provide those of ordinary skill in the art with a complete disclosure and description of how to make and use the methods and compositions of the invention, and are not intended to limit the scope of what the inventors regard as their invention. Efforts have been made to ensure accuracy with respect to numbers used (e.g., amounts, temperature, etc.) but some experimental errors and deviations should be accounted for. Unless indicated otherwise, parts are parts by weight, molecular weight is average molecular weight, temperature is in degrees Centigrade, and pressure is at or near atmospheric.

Example 1. Generation of Anti-GITR Antibodies

Anti-GITR antibodies were obtained by immunizing a VELOCIMMUNE® mouse (i.e., an engineered mouse comprising DNA encoding human immunoglobulin heavy and kappa light chain variable regions) with an immunogen comprising a soluble dimeric ecto domain of human GITR. The antibody immune response was monitored by a GITR-specific immunoassay. Several fully human anti-GITR antibodies were isolated directly from antigen-positive B cells without fusion to myeloma cells, as described in US 2007/0280945A1.

Certain biological properties of the exemplary anti-GITR antibodies generated in accordance with the methods of this Example are described in detail in the Examples set forth below.

Example 2. Heavy and Light Chain Variable Region Amino Acid and Nucleic Acid Sequences Table 1 sets forth the amino acid sequence identifiers of the heavy and light chain variable regions and CDRs of selected anti-GITR antibodies of the invention. The corresponding nucleic acid sequence identifiers are set forth in Table 2.

TABLE 1

Amino Acid Sequence Identifiers

| Antibody Designation | SEQ ID NOs: | | | | | | | |
|---|---|---|---|---|---|---|---|---|
| | HCVR | HCDR1 | HCDR2 | HCDR3 | LCVR | LCDR1 | LCDR2 | LCDR3 |
| H1H14474P | 2 | 4 | 6 | 8 | 10 | 12 | 14 | 16 |
| H1H14486P | 18 | 20 | 22 | 24 | 26 | 28 | 30 | 32 |
| H1H14491P | 34 | 36 | 38 | 40 | 42 | 44 | 46 | 48 |
| H1H14493P | 50 | 52 | 54 | 56 | 58 | 60 | 62 | 64 |
| H1H14495P | 66 | 68 | 70 | 72 | 74 | 76 | 78 | 80 |
| H1H14503P | 82 | 84 | 86 | 88 | 90 | 92 | 94 | 96 |
| H1H14512P | 98 | 100 | 102 | 104 | 106 | 108 | 110 | 112 |
| H1H14520P | 114 | 116 | 118 | 120 | 122 | 124 | 126 | 128 |
| H1H14523P | 130 | 132 | 134 | 136 | 138 | 140 | 142 | 144 |
| H1H14524P | 146 | 148 | 150 | 152 | 154 | 156 | 158 | 160 |
| H4H14469P | 162 | 164 | 166 | 168 | 170 | 172 | 174 | 176 |
| H4H14470P | 178 | 180 | 182 | 184 | 186 | 188 | 190 | 192 |
| H4H14475P | 194 | 196 | 198 | 200 | 202 | 204 | 206 | 208 |
| H4H14476P | 210 | 212 | 214 | 216 | 218 | 220 | 222 | 224 |
| H4H14508P | 226 | 228 | 230 | 232 | 234 | 236 | 238 | 240 |
| H4H14516P | 242 | 244 | 246 | 248 | 250 | 252 | 254 | 256 |
| H4H14521P | 258 | 260 | 262 | 264 | 266 | 268 | 270 | 272 |
| H4H14525P | 274 | 276 | 278 | 280 | 282 | 284 | 286 | 288 |
| H4H14528P | 290 | 292 | 294 | 296 | 298 | 300 | 302 | 304 |
| H4H14530P | 306 | 308 | 310 | 312 | 314 | 316 | 318 | 320 |
| H4H14531P2 | 322 | 324 | 326 | 328 | 402 | 404 | 406 | 408 |
| H4H14532P2 | 330 | 332 | 334 | 336 | 402 | 404 | 406 | 408 |
| H4H14536P2 | 338 | 340 | 342 | 344 | 402 | 404 | 406 | 408 |
| H4H14539P2 | 346 | 348 | 350 | 352 | 402 | 404 | 406 | 408 |
| H4H14541P2 | 354 | 356 | 358 | 360 | 402 | 404 | 406 | 408 |
| H4H15736P2 | 362 | 364 | 366 | 368 | 402 | 404 | 406 | 408 |
| H4H15740P2 | 370 | 372 | 374 | 376 | 402 | 404 | 406 | 408 |
| H4H15744P2 | 378 | 380 | 382 | 384 | 402 | 404 | 406 | 408 |
| H4H15745P2 | 386 | 388 | 390 | 392 | 402 | 404 | 406 | 408 |
| H4H15753P2 | 394 | 396 | 398 | 400 | 402 | 404 | 406 | 408 |

TABLE 2

Nucleic Acid Sequence Identifiers

| Antibody Designation | SEQ ID NOs: | | | | | | | |
|---|---|---|---|---|---|---|---|---|
| | HCVR | HCDR1 | HCDR2 | HCDR3 | LCVR | LCDR1 | LCDR2 | LCDR3 |
| H1H14474P | 1 | 3 | 5 | 7 | 9 | 11 | 13 | 15 |
| H1H14486P | 17 | 19 | 21 | 23 | 25 | 27 | 29 | 31 |
| H1H14491P | 33 | 35 | 37 | 39 | 41 | 43 | 45 | 47 |
| H1H14493P | 49 | 51 | 53 | 55 | 57 | 59 | 61 | 63 |
| H1H14495P | 65 | 67 | 69 | 71 | 73 | 75 | 77 | 79 |
| H1H14503P | 81 | 83 | 85 | 87 | 89 | 91 | 93 | 95 |
| H1H14512P | 97 | 99 | 101 | 103 | 105 | 107 | 109 | 111 |
| H1H14520P | 113 | 115 | 117 | 119 | 121 | 123 | 125 | 127 |
| H1H14523P | 129 | 131 | 133 | 135 | 137 | 139 | 141 | 143 |
| H1H14524P | 145 | 147 | 149 | 151 | 153 | 155 | 157 | 159 |
| H4H14469P | 161 | 163 | 165 | 167 | 169 | 171 | 173 | 175 |
| H4H14470P | 177 | 179 | 181 | 183 | 185 | 187 | 189 | 191 |
| H4H14475P | 193 | 195 | 197 | 199 | 201 | 203 | 205 | 207 |

TABLE 2-continued

| Nucleic Acid Sequence Identifiers | | | | | | | | |
|---|---|---|---|---|---|---|---|---|
| Antibody | SEQ ID NOs: | | | | | | | |
| Designation | HCVR | HCDR1 | HCDR2 | HCDR3 | LCVR | LCDR1 | LCDR2 | LCDR3 |
| H4H14476P | 209 | 211 | 213 | 215 | 217 | 219 | 221 | 223 |
| H4H14508P | 225 | 227 | 229 | 231 | 233 | 235 | 237 | 239 |
| H4H14516P | 241 | 243 | 245 | 247 | 249 | 251 | 253 | 255 |
| H4H14521P | 257 | 259 | 261 | 263 | 265 | 267 | 269 | 271 |
| H4H14525P | 273 | 275 | 277 | 279 | 281 | 283 | 285 | 287 |
| H4H14528P | 289 | 291 | 293 | 295 | 297 | 299 | 301 | 303 |
| H4H14530P | 305 | 307 | 309 | 311 | 313 | 315 | 317 | 319 |
| H4H14531P2 | 321 | 323 | 325 | 327 | 401 | 403 | 405 | 407 |
| H4H14532P2 | 329 | 331 | 333 | 335 | 401 | 403 | 405 | 407 |
| H4H14536P2 | 337 | 339 | 341 | 343 | 401 | 403 | 405 | 407 |
| H4H14539P2 | 345 | 347 | 349 | 351 | 401 | 403 | 405 | 407 |
| H4H14541P2 | 353 | 355 | 357 | 359 | 401 | 403 | 405 | 407 |
| H4H15736P2 | 361 | 363 | 365 | 367 | 401 | 403 | 405 | 407 |
| H4H15740P2 | 369 | 371 | 373 | 375 | 401 | 403 | 405 | 407 |
| H4H15744P2 | 377 | 379 | 381 | 383 | 401 | 403 | 405 | 407 |
| H4H15745P2 | 385 | 387 | 389 | 391 | 401 | 403 | 405 | 407 |
| H4H15753P2 | 393 | 395 | 397 | 399 | 401 | 403 | 405 | 407 |

Antibodies are typically referred to herein according to the following nomenclature: Fc prefix (e.g. "H1H," "H4H," etc.), followed by a numerical identifier (e.g. "14493," "14495," etc.), followed by a "P" or "P2" suffix, as shown in Tables 1 and 2. Thus, according to this nomenclature, an antibody may be referred to herein as, e.g., "H1H14486P," "H4H14531P2," etc. The H1H, and H4H prefixes on the antibody designations used herein indicate the particular Fc region isotype of the antibody. For example, an "H1H" antibody has a human IgG1 Fc, an "H4H" antibody has a human IgG4 Fc, and an H2M has a mouse IgG2 Fc (all variable regions are fully human as denoted by the first 'H' in the antibody designation). As will be appreciated by a person of ordinary skill in the art, an antibody having a particular Fc isotype can be converted to an antibody with a different Fc isotype, but in any event, the variable domains (including the CDRs)—which are indicated by the numerical identifiers shown in Tables 1 and 2—will remain the same, and the binding properties are expected to be identical or substantially similar regardless of the nature of the Fc domain.

Control Constructs Used in the Following Examples

Control constructs were included in the following experiments for comparative purposes: Anti-GITR Control Ab I: a mouse anti-human GITR hybridoma with variable heavy and light chain domains having the amino acid sequences of the corresponding domains of "clone 6C8" as set forth in WO 2006/105021 A2; produced with mIgG1 and mIgG2a constant regions in the following examples; and Anti-GITR Control Ab II: a human anti-GITR antibody with variable heavy and light chain domains having the amino acid sequences of the corresponding domains of "36E5" as set forth in U.S. Pat. No. 8,709,424 B2.

Example 3. Surface Plasmon Resonance Derived Binding Affinities and Kinetic Constants of Human Monoclonal Anti-TNFRSF18 (GITR) Antibodies Binding affinities and kinetic constants of human anti-GITR antibodies were determined by surface plasmon resonance (Biacore 4000 or T-200) at 37° C. (Table 3). Antibodies, expressed as human IgG1 or IgG4 (i.e., "H1H" or "H4H" designations), were captured onto a mouse anti-human Fc CM5 Biacore sensor surface (mAb-capture format) and soluble monomeric (human (h) GITR.mmh; SEQ ID NO: 409 and *Macaca* fasicularis (mf) GITR.mmh; SEQ ID NO: 412) or dimeric (hGITR.hFc; SEQ ID NO: 411 and hGITRmFc; SEQ ID NO: 410). GITR proteins were injected over the sensor surface at a flow rate of 30 µL/minute. All Biacore binding studies were performed in a buffer composed of 0.01M HEPES pH 7.4, 0.15M NaCl, 3 mM EDTA, 0.05% v/v Surfactant P20 (HBS-ET running buffer). Antibody-reagent association was monitored for 4 minutes while dissociation in HBS-ET running buffer (10 mM HEPES, 150 mM NaCl, 3 mM EDTA, 0.05% (v/v) Surfactant P20, pH 7.4) was monitored for 10 minutes. Kinetic association ($k_a$) and dissociation ($k_d$) rate constants were determined by fitting the real-time sensorgrams to a 1:1 binding model using Scrubber 2.0c curve fitting software. Binding dissociation equilibrium constants ($K_D$) and dissociative half-lives (t½) were calculated from the kinetic rate constants as: $K_D [M] = k_d/k_a$; and t½ (min) = (ln2/(60*$k_d$)). Results are summarized in Table 3.

TABLE 3

| Biacore Binding Affinities of Human Fc mAbs at 37° C. | | | | | |
|---|---|---|---|---|---|
| | | Binding at 37° C./Antibody Capture Format | | | |
| Antibody | Analyte | ka ($Ms^{-1}$) | Kd ($s^{-1}$) | $K_D$ (Molar) | t½ (min) |
| H1H14503P | hGITR.mmh | 5.32E+05 | 7.39E−04 | 1.39E−09 | 15.6 |
| | hGITR.mFc | 1.12E+06 | 1.54E−04 | 1.37E−10 | 75.0 |
| | mfGITR.mmh | 2.68E+05 | 5.60E−03 | 2.09E−08 | 2.1 |

TABLE 3-continued

Biacore Binding Affinities of Human Fc mAbs at 37° C.

Binding at 37° C./Antibody Capture Format

| Antibody | Analyte | ka ($Ms^{-1}$) | Kd ($s^{-1}$) | $K_D$ (Molar) | $t^{1/2}$ (min) |
|---|---|---|---|---|---|
| H1H14474P | hGITR.mmh | 5.91E+05 | 1.16E-03 | 1.96E-09 | 9.9 |
|  | hGITR.mFc | 1.21E+06 | 1.30E-04 | 1.07E-10 | 89.2 |
|  | mfGITR.mmh | 3.39E+05 | 9.51E-03 | 2.80E-08 | 1.2 |
| H1H14495P | hGITR.mmh | 5.17E+05 | 1.27E-03 | 2.45E-09 | 9.1 |
|  | hGITR.mFc | 1.14E+06 | 1.10E-04 | 9.68E-11 | 105.0 |
|  | mfGITR.mmh | 2.96E+05 | 7.23E-03 | 2.45E-08 | 1.6 |
| H1H14486P | hGITR.mmh | 4.39E+05 | 1.23E-03 | 2.79E-09 | 9.4 |
|  | hGITR.mFc | 9.65E+05 | 1.53E-04 | 1.59E-10 | 75.5 |
|  | mfGITR.mmh | 1.37E+05 | 1.66E-02 | 1.22E-07 | 0.7 |
| H1H14524P | hGITR.mmh | 4.05E+05 | 1.47E-03 | 3.62E-09 | 7.9 |
|  | hGITR.mFc | 9.22E+05 | 1.35E-04 | 1.46E-10 | 85.6 |
|  | mfGITR.mmh | 1.20E+05 | 1.89E-02 | 1.58E-07 | 0.6 |
| H4H14530P | hGITR.mmh | 2.72E+05 | 1.38E-03 | 5.06E-09 | 8.4 |
|  | hGITR.mFc | 2.93E+05 | 1.85E-04 | 6.30E-10 | 62.6 |
|  | mfGITR.mmh | 2.40E+05 | 6.11E-04 | 2.55E-09 | 18.9 |
| H1H14491P | hGITR.mmh | 3.19E+05 | 1.62E-03 | 5.06E-09 | 7.2 |
|  | hGITR.mFc | 8.42E+05 | 1.69E-04 | 2.01E-10 | 68.3 |
|  | mfGITR.mmh | 1.18E+05 | 8.89E-03 | 7.53E-08 | 1.3 |
| H1H14523P | hGITR.mmh | 2.16E+05 | 1.86E-03 | 8.63E-09 | 6.2 |
|  | hGITR.mFc | 5.55E+05 | 1.20E-04 | 2.16E-10 | 96.3 |
|  | mfGITR.mmh | 1.23E+05 | 1.09E-02 | 8.85E-08 | 1.1 |
| H1H14493P | hGITR.mmh | 1.86E+05 | 2.50E-03 | 1.34E-08 | 4.6 |
|  | hGITR.mFc | 5.24E+05 | 1.91E-04 | 3.65E-10 | 60.4 |
|  | mfGITR.mmh | 1.00E+04 | 1.40E-02 | 1.40E-06 | 0.8 |
| H4H14532P2 | hGITR.mmh | 3.48E+05 | 6.45E-03 | 1.85E-08 | 1.8 |
|  | hGITR.mFc | 7.20E+05 | 2.69E-04 | 3.73E-10 | 42.9 |
|  | mfGITR.mmh | 2.60E+05 | 6.48E-03 | 2.49E-08 | 1.8 |
| H4H14521P | hGITR.mmh | 3.45E+05 | 7.84E-03 | 2.27E-08 | 1.5 |
|  | hGITR.mFc | 1.23E+06 | 4.79E-04 | 3.89E-10 | 24.1 |
|  | mfGITR.mmh | 1.66E+05 | 3.34E-03 | 2.01E-08 | 3.5 |
| H4H14536P2 | hGITR.mmh | 4.24E+05 | 9.76E-03 | 2.30E-08 | 1.2 |
|  | hGITR.mFc | 1.26E+06 | 2.19E-04 | 1.73E-10 | 52.7 |
|  | mfGITR.mmh | 1.04E+05 | 1.47E-02 | 1.42E-07 | 0.8 |
| H4H14476P | hGITR.mmh | 3.92E+05 | 1.23E-02 | 3.14E-08 | 0.9 |
|  | hGITR.mFc | 9.06E+05 | 2.69E-04 | 2.97E-10 | 42.9 |
|  | mfGITR.mmh | 1.91E+05 | 1.07E-02 | 5.58E-08 | 1.1 |
| H4H14516P | hGITR.mmh | 2.25E+05 | 7.38E-03 | 3.27E-08 | 1.6 |
|  | hGITR.mFc | 1.68E+06 | 1.81E-03 | 1.08E-09 | 6.4 |
|  | mfGITR.mmh | 1.90E+05 | 1.12E-02 | 5.87E-08 | 1.0 |
| H4H14508P | hGITR.mmh | 2.55E+05 | 9.35E-03 | 3.66E-08 | 1.2 |
|  | hGITR.mFc | 1.21E+06 | 7.19E-04 | 5.97E-10 | 16.1 |
|  | mfGITR.mmh | 1.29E+05 | 5.07E-03 | 3.93E-08 | 2.3 |
| H4H14469P | hGITR.mmh | 2.84E+05 | 1.22E-02 | 4.30E-08 | 0.9 |
|  | hGITR.mFc | 1.20E+06 | 4.01E-04 | 3.35E-10 | 28.8 |
|  | mfGITR.mmh | 5.91E+04 | 2.43E-03 | 4.11E-08 | 4.7 |
| H4H14475P | hGITR.mmh | 3.07E+05 | 1.40E-02 | 4.57E-08 | 0.8 |
|  | hGITR.mFc | 1.60E+06 | 1.35E-03 | 8.47E-10 | 8.5 |
|  | mfGITR.mmh | 1.83E+05 | 7.65E-03 | 4.17E-08 | 1.5 |
| H4H14528P | hGITR.mmh | 1.02E+05 | 5.23E-03 | 5.13E-08 | 2.2 |
|  | hGITR.mFc | 1.58E+06 | 1.77E-03 | 1.12E-09 | 6.5 |
|  | mfGITR.mmh | NB | NB | NB | NB |
| H4H14525P | hGITR.mmh | 3.17E+05 | 1.66E-02 | 5.24E-08 | 0.7 |
|  | hGITR.mFc | 7.91E+05 | 3.38E-04 | 4.27E-10 | 34.2 |
|  | mfGITR.mmh | 1.33E+05 | 2.05E-02 | 1.55E-07 | 0.6 |
| H1H14520P | hGITR.mmh | 2.66E+05 | 1.67E-02 | 6.30E-08 | 0.7 |
|  | hGITR.mFc | 1.09E+06 | 5.83E-04 | 5.37E-10 | 19.8 |
|  | mfGITR.mmh | 1.99E+05 | 1.71E-02 | 8.59E-08 | 0.7 |
| H4H14470P | hGITR.mmh | 2.21E+05 | 1.43E-02 | 6.47E-08 | 0.8 |
|  | hGITR.mFc | 9.04E+05 | 1.04E-03 | 1.15E-09 | 11.1 |
|  | mfGITR.mmh | NB | NB | NB | NB |
| H4H14539P2 | hGITR.mmh | 2.14E+05 | 1.77E-02 | 8.25E-08 | 0.7 |
|  | hGITR.mFc | 8.53E+05 | 4.72E-04 | 5.54E-10 | 24.5 |
|  | mfGITR.mmh | 7.23E+04 | 1.65E-03 | 2.28E-08 | 7.0 |
| Anti-GITR Control Ab I-mIgG1 | hGITR.mmh | 2.16E+05 | 2.63E-02 | 1.22E-07 | 0.4 |
|  | hGITR.hFc | 3.82E+05 | 7.80E-03 | 2.04E-08 | 1.5 |
|  | mfGITR.mmh | 2.18E+05 | 4.64E-02 | 2.13E-07 | 0.2 |
| Anti-GITR Control Ab II-hIgG1 | hGITR.mmh | 1.94E+05 | 9.67E-04 | 4.99E-09 | 11.9 |
|  | hGITR.mFc | 1.83E+06 | 1.73E-03 | 9.48E-10 | 6.7 |
|  | mfGITR.mmh | 2.31E+05 | 8.63E-03 | 3.74E-08 | 1.3 |

NB = No binding observed under conditions used

As shown in Table 3, all the anti-GITR antibodies of this invention bound to human GITR, with several antibodies displaying sub-nanomolar affinities to dimeric human GITR protein. Additionally, a majority of the anti-GITR antibodies also displayed cross reactivity to cynomolgus GITR protein. Cross reactivity to rodent GITR proteins was not observed (data not shown).

Example 4. Anti-GITR Antibodies Bind Specifically and Potently to Human GITR Expressing Cells In this example, the ability of anti-GITR antibodies to bind specifically to a human GITR-expressing cell line was determined using electrochemiluminescence (ECL) based detection.

Briefly, human embryonic kidney (HEK)-293-D9 cells were stably transfected with human GITR (amino acids M1-V241, NCBI Accession #NP_004186.1, SEQ ID: 413) via Lipofectamine 2000-mediated methodology. Transfectants were selected for at least two weeks in complete growth media+G418.

For cell binding studies, approximately $1 \times 10^5$ hGITR/HEK293-D9 or parental HEK293-D9 cells, which do not express human GITR, were seeded onto 96-well carbon electrode plates (MULTI-ARRAY, MSD) for 1 h at 37° C. Nonspecific binding sites were blocked with 2% BSA (w/v)+PBS for 1 h at room temperature (RT). Next, serial dilutions of anti-GITR antibodies, ranging from 1.7 μM to 100 nM, were added to cells for 1 h at RT. Plates were then washed to remove unbound antibodies (AquaMax2000 plate washer, MSD Analytical Technologies) and plate-bound antibodies were detected with a SULFO-TAG™ conjugated anti-human kappa light chain IgG antibody (Jackson lmmunoresearch) for 1 h at RT.

Following washes, luminescent signals were recorded with a SECTOR Imager 6000 (MSD) instrument. Direct binding signals (relative light units, RLU) were analyzed as a function of the antibody concentration and data were fitted with a sigmoidal (four-parameter logistic) dose-response model using GraphPad Prism™ software. The $EC_{50}$ for binding hGITR/HEK293-D9 cells, defined as the concentration of antibody at which 50% of the maximal binding signal is detected, was determined to indicate binding potency of each antibody. The signal detected with 100 nM antibody binding to the hGITR expressing cells versus parental cells was recorded as an indication of intensity and specificity of GITR binding. Results are summarized in Table 4.

As summarized in Table 4, most of the anti-GITR antibodies of this invention bound specifically to human GITR expressing cells versus parental HEK293 with $EC_{50}$s ranging from 210 μM to 85 nM. A majority of the antibodies bound to human GITR-expressing cells with sub-nanomolar $EC_{50}$ values. The isotype control antibody did not display binding to hGITR-expressing or parental cell lines.

TABLE 4

Anti-GITR antibody binding $EC_{50}$ and binding intensity at 100 nM on human GITR expressing cells

| Antibody | Binding to hGITR/HEK293-D9 cells EC50 (M) | Binding to hGITR/HEK293-D9 cells (at 100 nM) Average Signal (RLU) | Binding to HEK293-D9 Cells (at 100 nM) Average Signal (RLU) |
|---|---|---|---|
| H1H14474P | 2.80E−10 | 6230 | 680 |
| H1H14486P | 4.30E−10 | 5830 | 280 |
| H1H14491P | 4.00E−10 | 6840 | 300 |
| H1H14493P | 3.00E−10 | 7220 | 790 |
| H1H14495P | 4.30E−10 | 6470 | 340 |
| H1H14503P | 2.10E−10 | 5880 | 330 |
| H1H14512P | 2.50E−10 | 4620 | 180 |
| H1H14520P | 2.40E−10 | 6450 | 1130 |
| H1H14523P | 4.00E−10 | 6350 | 530 |
| H1H14524P | 2.10E−10 | 5740 | 500 |
| H4H14469P | 2.30E−10 | 5230 | 260 |
| H4H14470P | 1.40E−09 | 8390 | 1580 |
| H4H14475P | 8.00E−09 | 7500 | 1580 |
| H4H14476P | 5.70E−10 | 8120 | 1770 |
| H4H14508P | 4.50E−10 | 6870 | 580 |
| H4H14516P | 7.00E−10 | 10330 | 2560 |
| H4H14521P | 4.30E−10 | 10080 | 600 |
| H4H14525P | 6.00E−10 | 8840 | 1490 |
| H4H14528P | 4.50E−10 | 7310 | 420 |
| H4H14530P | 8.50E−08 | 4200 | 520 |
| H4H14532P2 | 4.30E−10 | 5740 | 300 |
| H4H14536P2 | 3.60E−10 | 8960 | 330 |
| H4H14539P2 | 3.00E−10 | 4910 | 300 |
| Anti-GITR Control Ab II-hIgG1 | 2.60E−10 | 13750 | 10240 |
| Isotype Control Ab-hIgG4 | NB | 750 | 650 |

In summary, this example demonstrates that the anti-GITR antibodies of this invention display specific and potent binding to human GITR-expressing cell lines.

Example 5. Anti-GITR Antibodies are Partial Blockers and Partial Activators in NF-κB/Luciferase Reporter Assay in the Presence or Absence of Fc Gamma R Antibody Anchoring In this example, the ability of anti-GITR antibodies to activate hGITR or block hGITR ligand (hGITRL)-mediated receptor stimulation in the presence or absence of antibody anchoring to Fc gamma receptors (Fc gamma Rs) was assessed via luciferase-based reporter assays.

Briefly, a Jurkat cell line with stable incorporation of hGITR and NF-κB-dependent luciferase reporter was engineered (hGITR/Jurkat/NF-κBLuc). The NF-κB Luciferase reporter was introduced into Jurkat Cells using the Cignal Lenti Reporter system (SABiosciences). Lentiviruses expressing hGITR were generated in HEK293/T17 utilizing the Lenti-X Lentiviral Expression System (Clontech). Jurkat/NF-κB-Luc cells were transduced with the hGITR-expressing lentivirus via polybrene-mediated transduction and selected in 500 ug/ml G418 for 2 weeks. For antibody anchoring studies, HEK293 cells were transduced with the Fc gamma RI-expressing lentivirus, as described above.

First, the activation and blocking properties of anti-hGITR antibodies in the absence of Fc gamma R anchoring (non-anchored bioassay format) was assessed. Approximately $4 \times 10^4$ Jurkat/NF-κBLuc/hGITR cells were seeded overnight (ON) in PDL coated 96 well plates in OptiMEM+0.5% FBS.

To determine antibody activation ability, cells were incubated for 6 h at 37° C. with serially diluted anti hGITR antibodies or hGITRL with concentrations ranging from 0.5 µM to 100 nM. To assess antibody blocking of hGITRL mediated receptor stimulation, cells were pre-incubated for 30 min with serially diluted anti hGITR antibodies (0.5 µM to 100 nM) followed by a constant dose of 10 nM hGITRL for 6 h.

Next, the activation and blocking properties of selected anti-hGITR antibodies in the presence of Fc gamma R anchoring (anchored bioassay format) was determined. Similar to the above, $2.5 \times 10^4$ Jurkat/NfkBLuc/hGITR cells were seeded in PDL coated 96 well plates in complete growth media.

To assess antibody activation, cells were pre-incubated for 1 h at 37° C. with serially diluted anti-hGITR mAbs or hGITRL (0.5 µM to 100 nM). Then, $1 \times 10^4$ hFc gamma R1/HEK293 cells were immediately added to the wells followed by a 6 h incubation. To assess blocking, hGITR/Jurkat/NfkBLuc cells were pre-incubated for 1 h with serially diluted anti-hGITR antibodies (0.5 µM to 100 nM). $1 \times 10^4$ hFcγR1/HEK293 cells were added to the wells followed by the addition of a constant dose of 10 nM hGITRL.

For both anchored and non-anchored bioassay formats, Luciferase activity was measured with One glow reagent (Promega) and relative light units (RLUs) were measured on a Victor luminometer (Perkin Elmer). The $EC_{50}/IC_{50}$ values were determined from a four-parameter logistic equation over a 12-point response curve using GraphPad Prism. Results are summarized in Table 5 and Table 6. To determine % blocking, background RLU (relative light units) from untreated wells are subtracted from treated wells, and the percent blocking is calculated according to the following formula: [100−(antibody RLU at max dose/constant ligand dose RLU)]*100]. % activation is calculated according the following formula: (normalized mAb RLU/max GITR ligand response)*100; normalized mAb RLU is determined by subtracting the RLU from untreated wells from treated wells. Mean fold activation is calculated as: RLU at maximum Antibody dose/background RLU from untreated wells.

TABLE 5

Blocking and activation properties of anti-GITR antibodies in the absence of Fc gamma R anchoring

| Antibody | $IC_{50}$ (nM) | % Blocking- | $EC_{50}$ (nM) | % Activation |
|---|---|---|---|---|
| H4H14475P | ND | −2 | 1.0 | 70 |
| H1H14491P | 0.60 | 90 | 2.0 | 60 |
| H4H14521P | 3.80 | 60 | 0.4 | 50 |
| H1H14503P | 0.60 | 90 | 1.4 | 50 |
| H4H14469P | 0.70 | 90 | 2.3 | 50 |
| H4H14516P | 2.30 | 70 | 0.8 | 45 |
| H1H14523P | 0.90 | 70 | 2.5 | 40 |
| H1H14524P | 0.70 | 80 | 2.2 | 40 |
| H4H14528P | 3.40 | 90 | 1.1 | 30 |
| H1H14495P | 0.70 | 80 | 1.3 | 30 |
| H1H14474P | 0.80 | 80 | 1.2 | 30 |
| H4H14508P | 0.90 | 40 | 1.2 | 30 |
| H4H14532P2 | 1.00 | 90 | 1.2 | 30 |
| H1H14486P | 1.10 | 50 | 1.2 | 30 |
| H1H14493P | 0.60 | 90 | 1.2 | 25 |
| H1H14512P | 0.70 | 100 | 1.2 | 20 |
| H4H14525P | 1.40 | 70 | 1.1 | 20 |
| H4H14539P2 | 1.20 | 30 | 1.3 | 20 |
| H4H14536P2 | 2.00 | 90 | 1.1 | 20 |
| H4H14470P | 0.90 | 80 | 1.2 | 20 |
| H4H14476P | 2.60 | 90 | 1.0 | 10 |

TABLE 5-continued

Blocking and activation properties of anti-GITR antibodies in the absence of Fc gamma R anchoring

| Antibody | $IC_{50}$ (nM) | % Blocking- | $EC_{50}$ (nM) | % Activation |
|---|---|---|---|---|
| H1H14520P | 0.90 | 80 | 1.1 | 10 |
| Anti-GITR Control Ab I-mIgG1 | 0.10 | 54 | 1.02 | 25 |
| Isotype Control- IgG1 | No-blocking (NB) | NB | (No-activating) NA | NA |
| Isotype Control- IgG4 | NB | NB | NA | NA |

As summarized in the Table 5 above and Table 6 below, the antibodies tested displayed partial activating and partial-blocking properties in both the non-anchored and anchored bioassay formats. In the non-anchored format, antibodies mediated receptor stimulation with $EC_{50}$s ranging from 0.4 nM to 2.5 nM. Several antibodies, such as H4H14475P and H4H14491P were potent activators of the GITR receptor displaying 70 and 60 percent activation respectively. A majority of the antibodies tested also displayed blocking of hGITRL mediated receptor stimulation, with $IC_{50}$s ranging from 0.6 nM to 3.8 nM. Several exemplary antibodies, such as H1 H14512P and H4H14536P2 displayed potent blocking activity of 100% and 90% respectively. H4H14475P, the most potent activator, displayed the least activity in the blocking assay (percent blocking: −2%).

TABLE 6

Blocking and activation properties of anti-GITR antibodies in the presence of Fc gamma R anchoring

| Antibody | $IC_{50}$ (nM) | % Blocking | $EC_{50}$ (nM) | Fold Activation over basal signal |
|---|---|---|---|---|
| H1H14512P | 0.10 | 64 | 0.02 | 7.0 |
| H4H14475P | 0.20 | 43 | 0.04 | 8.0 |
| H4H14536P2 | 0.20 | 73 | 0.01 | 5.0 |
| Anti-GITR Control Ab I-mIgG1 | 0.20 | 60 | 0.10 | 6.0 |
| Anti-GITR Control Ab I-mIgG2a | 0.01 | 74 | 0.20 | 5.0 |
| Anti-GITR Control Ab II-hIgG1 | 0.20 | 70 | 0.01 | 8.0 |

Selected antibodies tested in the Fc gamma R-anchoring bioassay format also displayed a range of activation and blocking properties. H4H14475P, the strongest activator in the non-anchored format also potently activated hGITR in the anchored bioassay with a fold activation of 8.0 above the basal signal. Strong blockers in the non-anchored blocking format, such as H1H14512P and H4H14536P2, also displayed potent blocking in the anchored assay (% Blocking: 60% and 70%).

In summary, the results demonstrate that the anti-GITR antibodies of this invention display potent GITR activating properties as well as the ability to block GITRL mediated receptor stimulation in the absence of Fc gamma R anchoring in an engineered bioassay. Exemplary antibodies, such as H4H14775P and H4H1536P2 also maintain their activating and blocking properties, respectively, in the presence of Fc gamma R anchoring.

Example 6. Anti-GITR Antibody H4H14536P2 Demonstrates Potent Activity in a Naïve Human CD4+ T-Cell Proliferation Assay in the Presence and Absence of Fc Gamma R Anchoring As described above, anti-GITR antibodies were tested in an engineered bioassay for their ability to activate hGITR in the presence or absence of anchoring Fc gamma receptors (Fc gamma R). In this example, the effect of antibody anchoring on hGITR activation was assessed in a naïve human CD4+ T-cell proliferation primary bioassay. The human CD4+ T-cell system has the advantage that GITR copy number is at endogenous levels, whereas the engineered system utilizes cells with a higher GITR copy number.

First, anti-GITR antibodies were tested for CD4+ T-cell proliferative ability in the presence of plate-bound anti-CD3. Briefly, Human CD4+ T cells were isolated from healthy donor leukopacks using Human CD4+ T cell Enrichment Cocktail (Stemcell Technologies). Naïve T cells were further enriched by depletion of CD45RO+ cells by MACS (Miltenyi Biotech). Approximately $5\times10^4$ T cells were plated onto 96-well U-bottomed polystyrene plates pre-coated with a suboptimal amount of the anti-CD3 mAb OKT3 (30 ng/mL) and titrated amounts of anti-GITR antibodies or controls. Three days after stimulation, tritiated thymidine (1 µCi per well, Perkin Elmer Health Sciences NET027001) was added to each microwell and pulsed for 18 hours. Cells were harvested onto filter plates (Unifilter-96 GF/C 6005174) using a Filtermate Harvester (Perkin Elmer Health Sciences D961962). Scintillation fluid (Perkin Elmer Health Sciences Microscint20 6013621) was added to filter plates and radioactive counts were measured using a plate reader (Perkin Elmer Health Sciences Topcount NXT). T-cell proliferation relative to control, given as the mean fold activation at 10.6 nM of antibody concentration, is presented in Table 7. In this assay format, 10.6 nM represented the point at which T-cell proliferation reached a plateau on the dose response curve.

TABLE 7

T-cell proliferative activity (Fold activation) of plate-bound anti-GITR antibodies at 10.6 nM in the presence of plate-bound anti-CD3 Ab

| Antibody | Donor 1 | 2 | 3 | 4 | 5 | 6 | 7 | 8 | Mean Fold Activation |
|---|---|---|---|---|---|---|---|---|---|
| H4H14536P2 | 3 | 24 | 24 | 25 | 24 | 47 | 26 | 16 | 23 |
| H4H14508P | 10 | 4 | 4 | 7 | 4 | 11 | 3 | 2 | 5 |
| H4H14525P | 6 | 1 | 1 | 2 | 1 | 3 | 2 | 1 | 2 |
| H4H14469P | 3 | 12 | 12 | 15 | 12 | 17 | 11 | 11 | 12 |
| H4H14532P2 | 2 | 6 | 6 | 12 | 6 | 19 | 7 | 2 | 8 |
| H4H14470P | 0 | 3 | 3 | 4 | 3 | 6 | 4 | 1 | 3 |
| H4H14475P | 0 | 2 | 2 | 2 | 2 | 12 | 1 | 0 | 3 |
| H4H14528P | 2 | 8 | 8 | 4 | 8 | 31 | 5 | 4 | 8 |
| H4H14539P2 | 2 | 12 | 12 | 13 | 12 | 39 | 11 | 6 | 13 |
| H4H14516P | 1 | 4 | 4 | 12 | 4 | 14 | 4 | 1 | 5 |
| H4H14521P | 1 | 4 | 4 | 5 | 4 | 12 | 3 | 2 | 4 |
| Anti-GITR Control Ab 1-mIgG1 | 6 | 23 | 23 | 40 | 23 | 66 | 25 | 11 | 27 |
| Isotype Control | 1 | 1 | 1 | 1 | 1 | 1 | 1 | 1 | 1 |

As the results in Table 7 show, the anti-GITR antibodies tested demonstrated T-cell proliferative ability when plate-bound in the presence of plate-bound anti-CD3. The Anti-GITR Control Ab I demonstrated proliferative activity 27-fold above the isotype control. The majority of the anti-GITR antibodies of this invention displayed activation 2-8 fold above the isotype control, with several exemplary antibodies, H4H14469P, H4H14539P2, and H4H14536P2 demonstrating activation 12, 13 and 23 fold above the control, respectively. In summary, the results demonstrate that the anti-GITR antibodies tested demonstrate T-cell proliferative activity in this classical format.

Next, additional assay formats were employed to test the ability of anti-GITR antibodies to activate T-cells in the presence or absence of cell-surface bound Fc gamma R.

To assess anti-GITR antibody ability to activate T cells in the presence of Fc gamma R1 anchoring, HEK293 cells were engineered to express the high affinity hFc gamma R1 receptor, as described above. HEK293/Fc gamma RI cells were treated with 50 ug/mL Mitomycin C for 30 min at 37° C. to inhibit proliferation. After subsequent washes to remove traces of Mitomycin C, cells were coated with 300 ng/mL anti-CD3 antibody OKT3 to stimulate T cell activation. HEK293/Fc gamma RI cells were co-cultured with human naïve CD4+ T cells in a 1:2 ratio and titrated amounts of anti-GITR antibodies or controls were added to the co-culture medium.

T cell proliferation was assessed by measurement of the levels of tritiated thymidine incorporation. 72 h after stimulation, tritiated thymidine (0.5 µCi per well, Perkin Elmer Health Sciences) was added to each microwell for an additional 18 h at 37° C. Cells were harvested onto filter plates (Unifilter-96 GF/C 6005174) using a Filtermate Harvester (Perkin Elmer Health Sciences D961962). Scintillation fluid (Perkin Elmer Health Sciences Microscint20 6013621) was added to filter plates and radioactive counts were measured using a plate reader (Perkin Elmer Health Sciences Topcount NXT). T-cell proliferation relative to control, given as the mean fold activation at a 33 nM concentration of antibody is presented in Table 8. In this assay format, 33 nM represented the point at which T-cell proliferation reached a plateau on the dose response curve.

TABLE 8

T-cell proliferative activity (Fold activation) of anti-GITR antibodies at 33 nM in the presence of Fc gamma R anchoring

| Antibody | Donor 1 | 2 | 3 | 4 | 5 | Mean Fold Activation |
|---|---|---|---|---|---|---|
| H4H14536P2 | 1.3 | 6.3 | 1.5 | 2.7 | 15.7 | 5.5 |
| H4H14508P | 1.0 | 0.7 | 1.1 | 1.8 | 1.3 | 1.2 |
| H4H14525P | 1.2 | 0.8 | 1.0 | 1.5 | 1.5 | 1.2 |
| H4H14469P | 0.70 | 1.0 | 0.9 | 1.5 | 1.5 | 1.1 |
| H4H14532P2 | 0.80 | 0.9 | 1.0 | 1.7 | 2.1 | 1.3 |
| H4H14470P | 1.8 | 1.0 | 1.4 | 1.5 | 2.0 | 1.5 |
| H4H14475P | 1.0 | 1.3 | 1.3 | 1.6 | 1.5 | 1.3 |
| H4H14528P | 0.9 | 1.5 | 1.1 | 1.9 | 1.7 | 1.4 |
| H4H14539P2 | 0.9 | 0.7 | 1.1 | 1.5 | 1.5 | 1.1 |
| H4H14516P | 1.2 | 0.9 | 1.2 | 1.3 | 1.1 | 1.1 |
| H4H14521P | 1.5 | 1.1 | 1.1 | 1.7 | 0.9 | 1.2 |
| H4H14476P | 0.6 | 0.20 | 0.8 | 0.8 | 0.1 | 0.5 |
| Anti-GITR Control mAbs | | | | | | |
| Control I-mIgG1 | 2.8 | 2.8 | 1.4 | 1.1 | 1.7 | 2.0 |
| Control I-mIgG2a | 1.1 | 0.1 | 1.0 | 1.0 | 1.2 | 1.3 |
| Control II-hIgG1 | 0.1 | 0.6 | 1.3 | 0.2 | 1.2 | 0.7 |
| Isotype Control-hIgG4 | 1.0 | 1.0 | 1.0 | 1.0 | 1.0 | 1.0 |

TABLE 9

T-cell proliferative activity ($EC_{50}$) of anti-GITR antibodies at 33 nM in the presence of Fc gamma R anchoring

| Antibody | Donor | | | | | Mean $EC_{50}$ (nM) |
|---|---|---|---|---|---|---|
| | 1 | 2 | 3 | 4 | 5 | |
| H4H14536P2 | 1.2 | 0.5 | 1.3 | 11.2 | 1.6 | 3.2 |
| Control I-mIgG1 | 37.2 | NA | 42.9 | 3.5 | 52.7 | 34.1 |

As the results in Table 8 summarize, several antibodies showed activation above controls with levels ranging from 1-2 fold. However, one exemplary antibody, H4H14536P2, demonstrated potent T-cell proliferation activity in the anchored setting. With a mean fold activation of 5.5, H4H14536P2 stimulated greater T-cell activation compared to the anti-GITR comparator antibodies (mean fold activation range: 0.7-2.0). H4H14536P2 had a mean $EC_{50}$ of T-cell proliferation of 3.2 nM compared with 34.1 nM for the most potent anti-GITR control Ab, Control 1-m IgG (Table 9). Furthermore, in this assay format, H4H14475P, a potent activator in the engineered bioassay described above, demonstrated modest proliferative activity in this primary bioassay setting.

Next, antibodies were tested for T-cell proliferation activity in the absence of Fc gamma R anchoring. Human CD4+ T cells were isolated as described above, and plated onto 96-well U-bottomed polystyrene plates pre-coated with 30 ng/mL of the anti-CD3 antibody, OKT3. Similar to above, titrated concentrations of anti-GITR antibodies or controls were added to the culture medium. T cell proliferation was measured by tritiated thymidine incorporation. T-cell proliferation observed in four donors at 22 nM antibody concentration is presented as the fold activation compared to isotype control in Table 10. The EC50 (nM) of H4H14536P2 is shown in Table 11.

As observed in the anchored assay format, H4H14536P2 again displayed potent T cell proliferative activity at 22 nM in the non-anchored format. H4H14536P2 activated T cells with a mean fold activation of 11.0 and an $EC_{50}$ of 8.3 nM. In this assay format, control anti-GITR antibody I exhibited no T-cell proliferation capability.

TABLE 10

T-cell proliferative activity (Fold activation) of anti-GITR antibodies at 22 nM in the absence of Fc gamma R anchoring

| Antibody | Donor | | | | Mean Fold Activation |
|---|---|---|---|---|---|
| | 1 | 2 | 3 | 4 | |
| H4H14536P2 | 6.2 | 4.2 | 10.1 | 23.4 | 11.0 |
| H4H14508P | 0.7 | 0.9 | 0.9 | 1.4 | 1.0 |
| H4H14525P | 0.7 | 1.0 | 0.9 | 1.0 | 0.9 |
| H4H14469P | 0.9 | 0.8 | 1.0 | 0.9 | 0.9 |
| H4H14532P2 | 0.7 | 0.8 | 1.0 | 1.1 | 0.9 |
| H4H14470P | 0.7 | 0.9 | 1.0 | 1.7 | 1.1 |
| H4H14475P | 0.7 | 1.1 | 0.8 | 0.8 | 0.9 |
| H4H14528P | 0.6 | 0.8 | 0.9 | 1.0 | 0.8 |
| H4H14539P2 | 0.5 | 0.8 | 1.1 | 0.8 | 0.8 |
| H4H14516P | 0.7 | 1.2 | 1.0 | 0.9 | 0.9 |
| H4H14521P | 0.5 | 1.2 | 0.8 | 1.0 | 0.9 |
| H4H14476P | 0.7 | 0.9 | 0.9 | 0.8 | 0.8 |
| Anti-GITR Control Ab Control I- mIgG1 | 0.7 | 0.8 | 1.0 | 1.0 | 0.9 |
| Isotype Control | 1.0 | 1.0 | 1.0 | 1.0 | 1.0 |

TABLE 11

| EC50 (nM) of H4H14536P2 | | | | | |
|---|---|---|---|---|---|
| Donor: | 1 | 2 | 3 | 4 | Average |
| H4H14536P2 $EC_{50}$ (nM): | 12.2 | 6.4 | 9.0 | 5.7 | 8.3 |

In summary, this example demonstrates that one exemplary anti-GITR antibody, H4H14536P2, displays potent T-cell proliferative activity in the presence and absence of hFc gamma R1 anchoring, while the anti-GITR comparative antibody Control I displayed no T-cell proliferative activity in the non-anchored setting. Thus, the ability of H4H14536P2 to activate T cells in the absence of hFc gamma R1 anchoring is a unique property, implying that the antibody may not have to compete with endogenous IgG binding to Fc gamma receptors in vivo to retain activity. This unique property of H4H14536P2 may confer an advantage in a therapeutic setting.

Example 7. Administration of Anti-GITR Antibodies in Combination with Anti-PD1 Antibodies Synergistically Controls and Eradicates Tumors As assessment of the effect of administering anti-GITR antibodies in combination with anti-PD1 antibodies on tumor growth was performed using the following methods. The results of the assessment are summarized below.

Tumor Implantation, Treatment Regimen and Growth Measurement

MC38 colorectal cancer cells (obtained from ATCC) were implanted subcutaneously in C57BL/6 mice ($3 \times 10^5$ cells/mouse) (defined as day 0). On day 6 (i.e., 6 days post tumor implantation), mice were segregated into 4 groups (5 mice per group) and each group was treated intra-peritoneally (IP) with: (1) rat IgG2a (2A3, Bio X cell, Cat. #BE0089) (isotype control)+rat IgG2b (LTF2, Bio X cell, Cat. #BE0090) (isotype control) (2) anti-GITR monoclonal antibody DTA1 (rat anti-mouse GITR, Bio X cell, Cat. #BE0063)+rat IgG2a (control) (3) anti-PD-1 monoclonal antibody RPM1-14 (rat anti-mouse PD-1, Bio X cell, Cat. #BE0146)+rat IgG2b (control) or (4) anti-GITR antibody DTA1+anti-PD-1 antibody RPM1-14. Antibody injection(s) were then administrated again on day 13. Antibody treatments were dosed at 5 mg/kg of each antibody. Tumors were measured two dimensionally (length×width) and tumor volume was calculated (length×width$^2$×0.5). Mice were euthanized when the tumor reached a designated tumor end-point (tumor volume>2000 mm$^3$ or tumor ulceration).

Tumor Re-Challenge Assessment

Mice treated with the combination of anti-PD-1 antibody and anti-GITR antibody that remained tumor free for over 80 days were re-challenged with $3 \times 10^5$ of the syngeneic tumor (MC38) in the right flank and $2.5 \times 10^5$ of an allogeneic (B16F10.9) tumor cell line (melanoma cell line, ATCC) in the left flank. Tumors were monitored as described above.

Antibody Depletion Experiments

Mice injected with different depleting mAbs (anti-CD4, anti-CD8, anti-CD25) starting at one day prior of tumor challenge and given at twice weekly for total eight doses, were treated with the combination therapy or the isotype control IgG. The depletion efficiency was confirmed by FACS analysis of peripheral blood samples.

Flow Cytometry (FACS) Analysis of Intratumoral Lymphocytes

Mice were treated as described above. Five days after antibody treatment, tumor and spleen were collected. Tumors were minced with scissors and dissociated to single cell suspension with Liberase TL/DNAse I mix. Spleens were dissociated with gentleMACS Octo Dissociator. Cells were stained with panels of FACS antibodies against mouse CD45, CD3, CD4, CD8, CD25 and FoxP3, as well as activation markers (PD1, GITR, Ki67, CD160, CTLA4, ICOS, TIM3, LAGS, KLRG1 and CD44). Cells were acquired on BD Fortessa X20 or LSR II and analyzed by FlowJo software.

Figure 2:
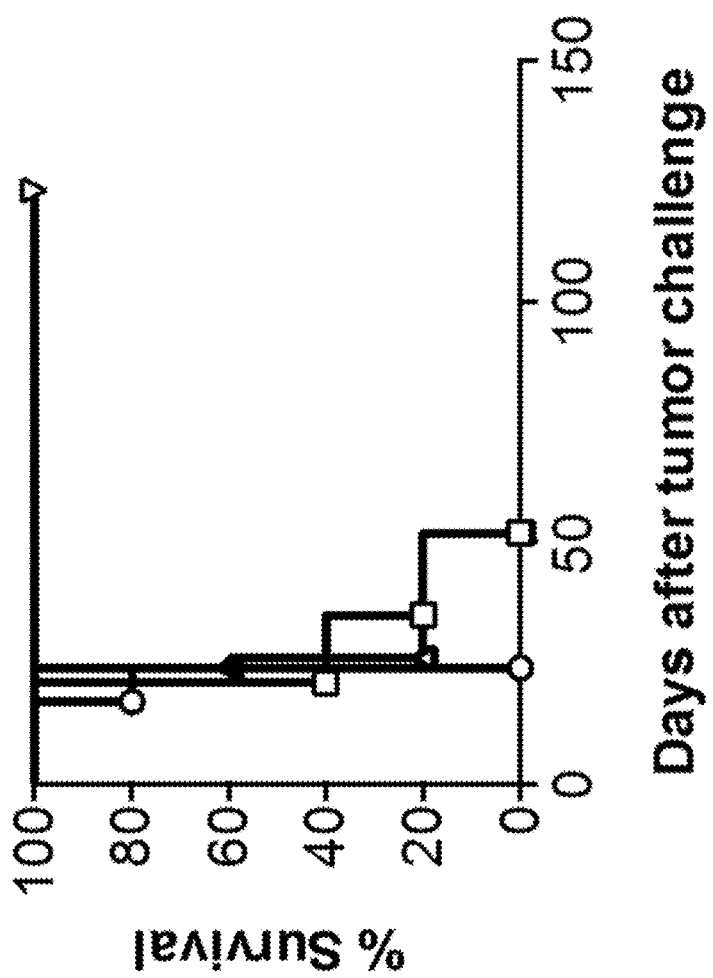
FIG. 2 depicts survival analysis of MC38 bearing mice treated with the combination of an anti-mouse GITR and anti-mouse-PD1 antibody as described in Example 7. Mice were treated with either isotype antibody (open circles, ○), anti-PD-1 antibody (open squares, □), anti-GITR antibody (open pyramids, Δ), or a combination of anti-PD-1 and anti-GITR (open inverted pyramids, ∇).

Administration of Anti-Mouse GITR Antibodies in Combination with Anti-Mouse PD1 Antibodies Significantly Induces Tumor Regression and Provides Long-Term Tumor Remission in MC38 Bearing Mice Using the methods described above, the efficacy of administering an anti-mouse GITR antibody (clone DTA-1, Bio X cell, Cat. #BE0063) in combination with an anti-mouse PD-1 antibody (clone RMP1-14, Bio X cell, Cat. #BE0146) in the control of subcutaneous MC38 tumors was assessed. As shown in FIG. 1 and Tables 12 and 13, combination treatment of PD1 blockade and anti-GITR (DTA-1) antibody significantly induced tumor regression in MC38 tumor bearing mice, in comparison to anti-PD-1 or anti-GITR mAb alone or isotype control treated mice. Furthermore, mice treated with combination therapy showed long-term tumor remission, as 100% of the mice remained tumor free for over 120 days (FIG. 2, Tables 14, 15).

Figure 3:
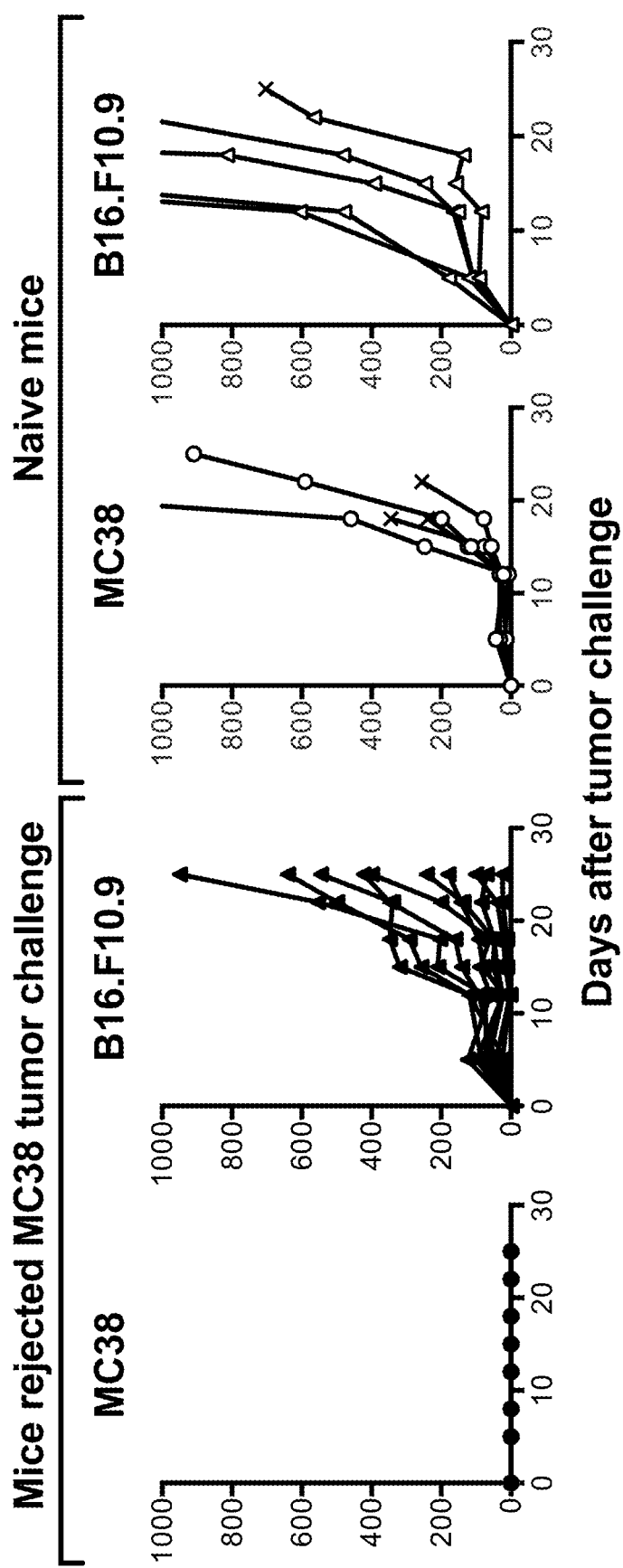
FIG. 3 depicts the individual tumor growth curve of tumor-free or naïve control mice challenged with MC38 or B16.F10.9 tumor cells as described in Example 7.

MC38 colon carcinoma cells in the right flank and $2.5 \times 10^5$ of allogeneic melanoma cell line B16F10.9 in the left flank. It was found that MC38 tumors did not grow in mice treated with the anti-PD1 antibody and anti-GITR antibody combination, while the same tumors grew in naive control mice (without any previous treatment) (FIG. 3). In contrast, the allogeneic tumor (melanoma) did not grow in both groups, demonstrating that the combined administration of anti-PD-1 and anti GITR antibodies induced tumor-antigen specific immunologic memory response capable of controlling the second challenge with the same type of tumor.

TABLE 14

Survival Proportions (percentage)

| Days | Isotype | Anti-PD-1 | Anti-GITR | Anti-PD-1 + Anti-GITR |
|---|---|---|---|---|
| 0 | 100 | 100 | 100 | 100 |
| 17 | 80 | | | |
| 21 | | 40 | | |
| 24 | 0 | | 60 | |
| 26 | | | 20 | |
| 35 | | 20 | | |
| 52 | | 0 | 0 | |
| 123 | | | | 100 |

Immune Population Study

Mice were treated with CD4, CD8 and CD25 depleting mAbs prior to anti-PD-1 antibody and anti-GITR antibody combination treatment. It was found that depletion of CD8+

TABLE 12

Average tumor volumes for each treatment group (mm³ ± SEM) and tumor free mice following anti-GITR and/or anti-PD-1 Ab treatment

| Treatment Group | Tumor Volume (mm3) Mean (SEM) | | | | | Tumor Free mice |
|---|---|---|---|---|---|---|
| | Day 10 | Day 13 | Day 17 | Day 19 | Day 21 | Day 21 |
| Isotype (Rat IgG2a + Rat IgG2b) | 196 (44) | 232 (46) | 802 (869) | NA | NA | 0/5 |
| Anti-PD1 + Rat IgG2b | 181 (37) | 259 (103) | 551 (199) | 880 (335) | 1550 (616) | 0/5 |
| Anti-GITR + Rat IgG2a | 172 (9) | 262 (72) | 407 (112) | 741 (269) | 882 (307) | 0/5 |
| Anti-GITR + Anti-PD1 | 130 (29) | 41 (13) | 0 (0) | 0 (0) | 0 (0) | 5/5 |

TABLE 13

Summary of tumor free mice of three independent experiments following anti-GITR and/or anti-PD1 Ab treatment

| Treatment Group | Tumor Free mice Day 21 |
|---|---|
| Isotype (Rat IgG2a + Rat IgG2b) | 0/15 |
| Anti-PD1 + Rat IgG2b | 0/15 |
| Anti-GITR + Rat IgG2a | 1/15 |
| Anti-GITR + Anti-PD1 | 10/15 |

Figure 4:
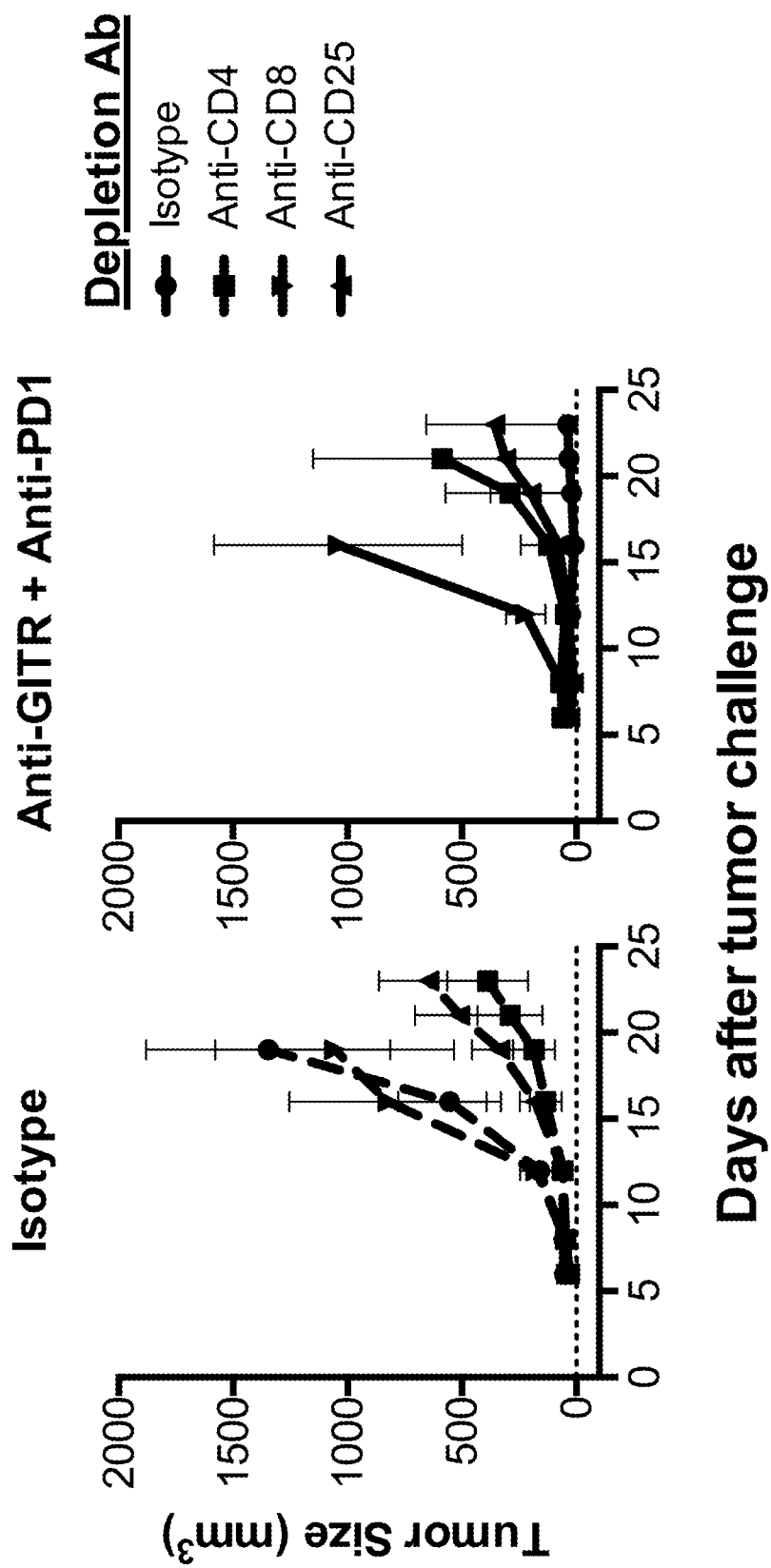
FIG. 4 depicts average tumor volumes for mice treated with different depletion antibodies as described in Example 7.

Administration of Anti-Mouse GITR Antibodies in Combination with Anti-Mouse PD1 Antibodies Induces Tumor/Antigen-Specific Immunologic Memory Response To determine whether mice treated with the combined administration of anti-PD-1 and anti-GITR antibodies developed a tumor/antigen-specific memory response, survival tumor-free mice were re-challenged with $3 \times 10^5$ of syngeneic cells fully abrogated the anti-tumoral effect (MC38 tumors), while depletion of CD4 or CD25 T cells showed partial inhibition (FIG. 4, Table 15). Thus, the anti-tumor effect of the combination therapy in MC38 tumors appears predominantly dependent on CD8+ T cells.

Figure 5:
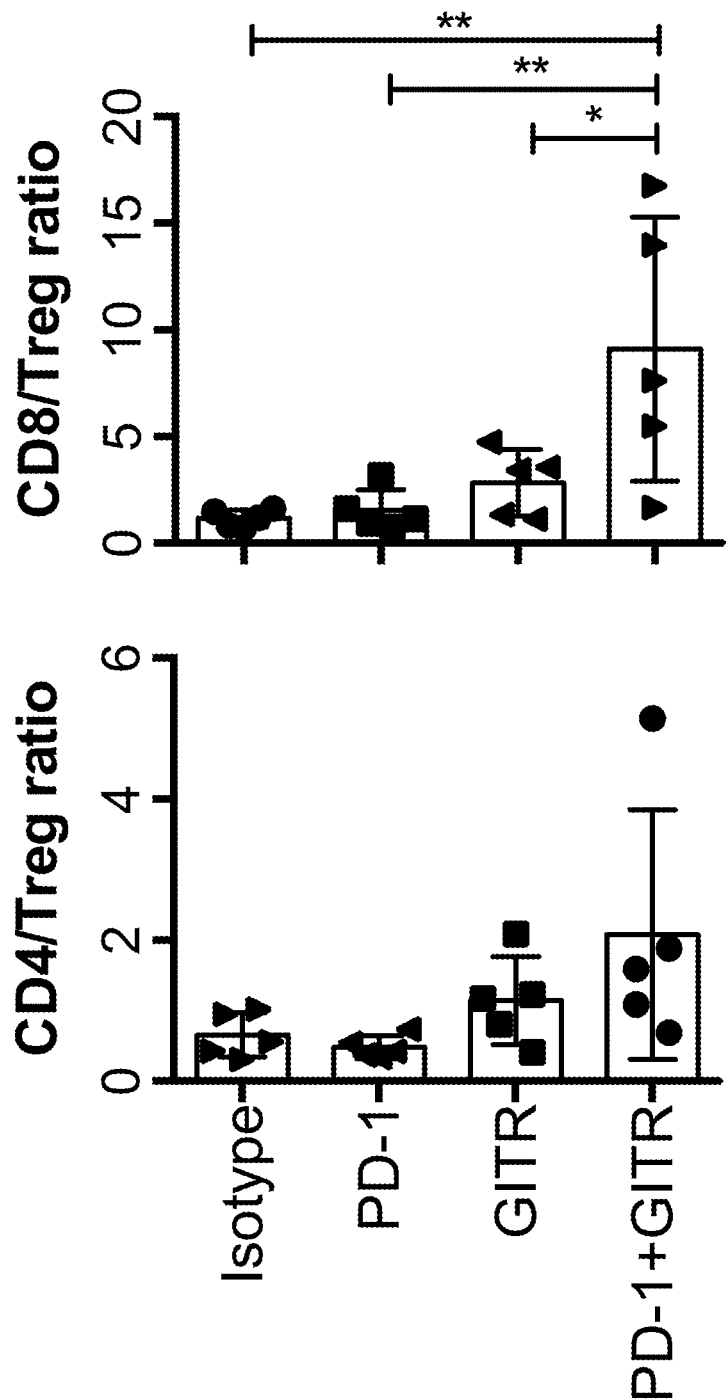
FIG. 5 depicts FACS analysis result of intratumoral CD8/Treg, CD4 Teff/Treg ratio as described in Example 7.
Figure 6:
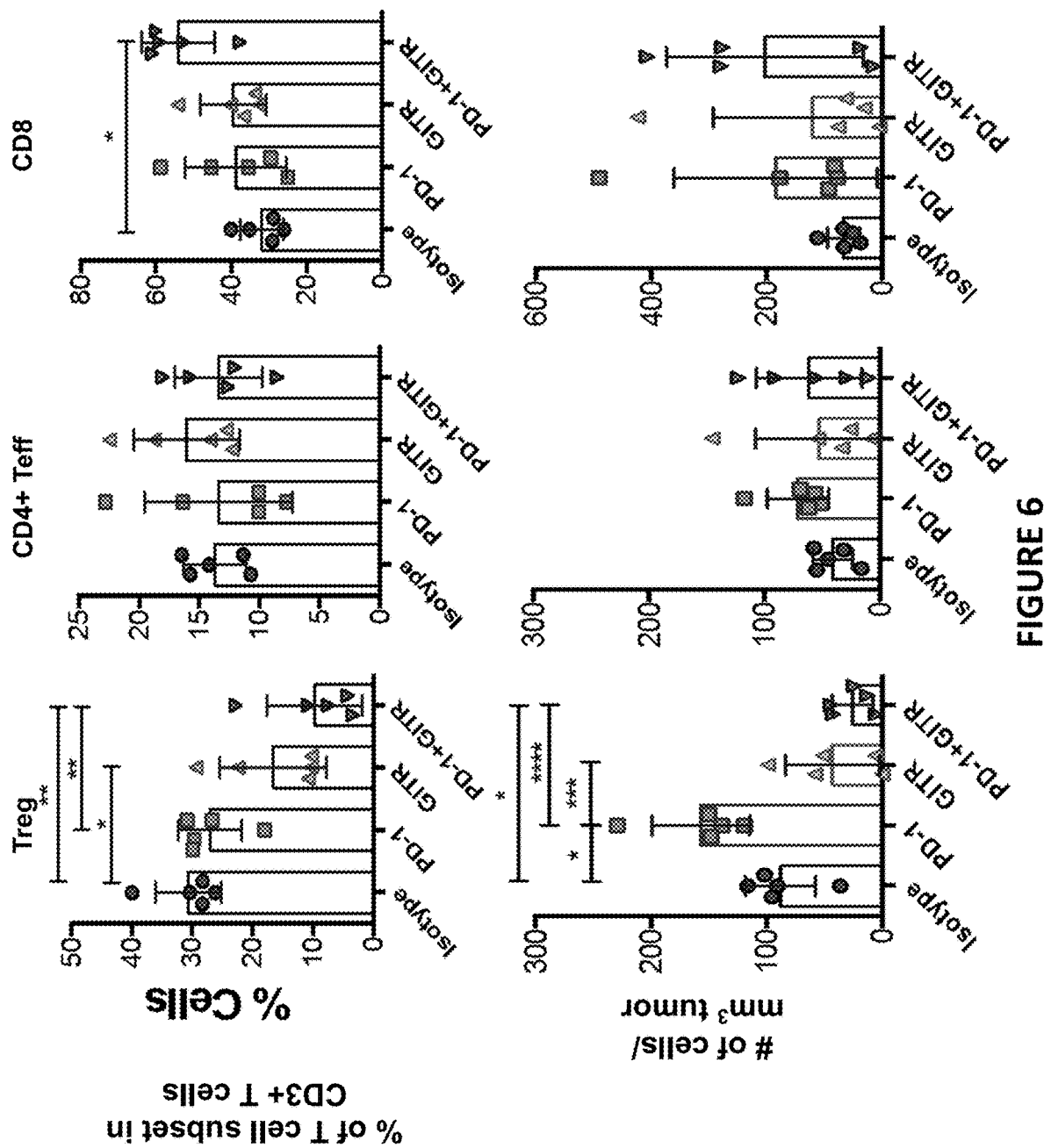
FIG. 6 depicts percentage and cell number/$mm^3$ tumor of T cell subsets in tumor as described in Example 7.

The effect of anti-GITR and anti-PD1 combination treatment on tumor infiltrating lymphocytes (TILs) was assessed. It was found that the combination treatment induced a significant increase in the CD8/Treg ratio in comparison to mono-therapy treatment (anti-PD-1 or anti-GITR) or isotype control (FIG. 5). The effect of the combination treatment on CD4/Treg ratio was found to be less pronounced. Anti-PD-1 and anti-GITR combination treatment decreased the percentage of intra-tumoral Tregs while it increased the CD8 T cells (FIG. 6). Further, anti-PD-1 treatment alone induced expansion of the Treg cell number, while the anti-PD-1/anti-GITR combination treatment significantly reduced it in comparison to the isotype control treated mice.

TABLE 15

Anti-tumor efficacy after CD4, CD8, or CD25 depletion

| Immunotherapy | Depletion Antibody | Tumor size (mm³) Mean (SEM) | | |
|---|---|---|---|---|
| | | Day 8 | Day 12 | Day 16 |
| Isotype control | Isotype control | 55 (12) | 161 (60) | 555 (224) |
| | Anti-CD4 | 48 (17) | 60 (22) | 135 (71) |
| | Anti-CD8 | 49 (17) | 176 (431) | 825 (431) |
| | Anti-CD25 | 59 (16) | 61 (21) | 182 (68) |
| Anti-GITR + Anti-PD1 | Isotype control | 43 (19) | 26 (16) | 11 (7) |
| | Anti-CD4 | 68 (21) | 50 (32) | 123 (122) |
| | Anti-CD8 | 67 (23) | 222 (86) | 1041 (543) |
| | Anti-CD25 | 14 (6) | 35 (30) | 80 (64) |

Figure 7:
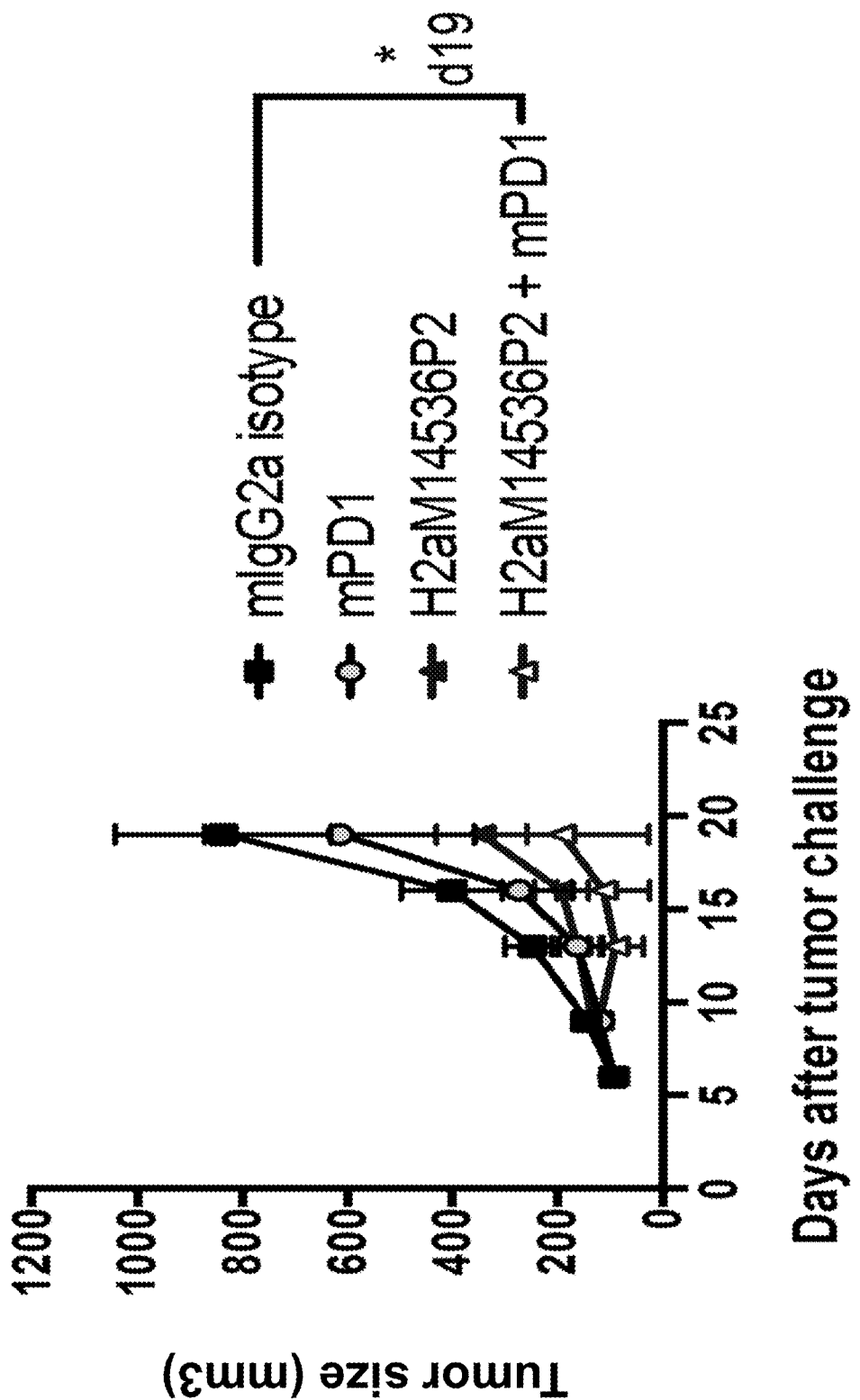
FIG. 7 depicts average tumor volumes for each treatment group ($mm^3 \pm SEM$) plotted against days after tumor challenge as depicted in Example 7.
Figure 8:
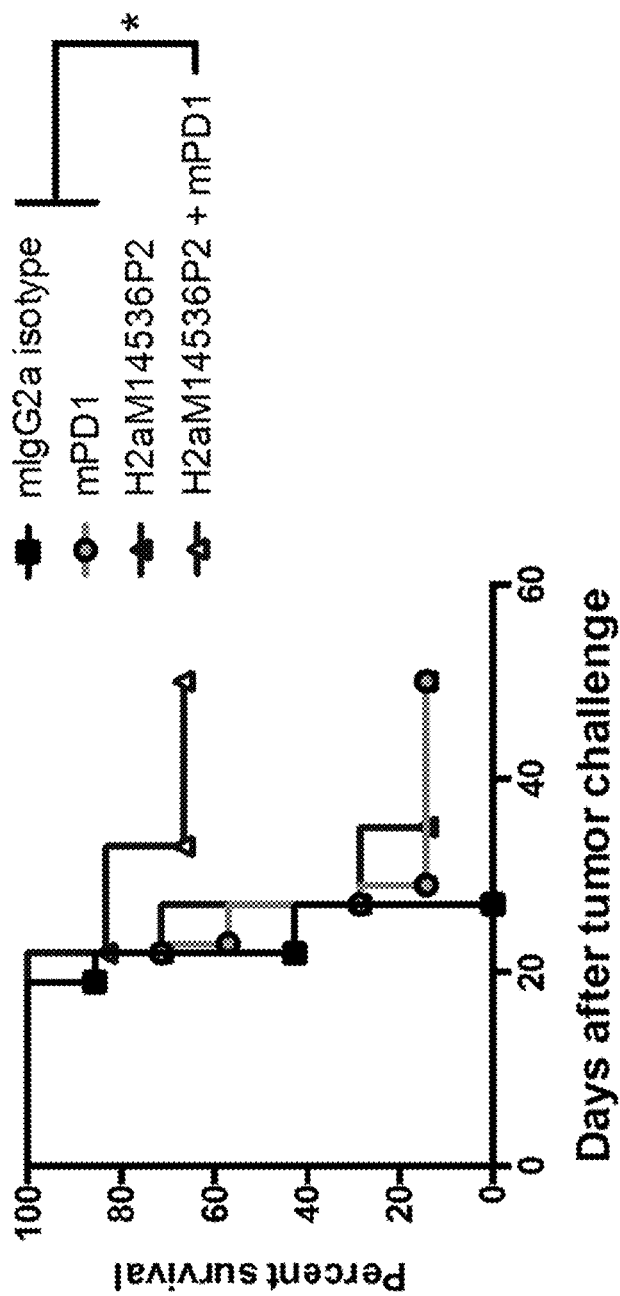
FIG. 8 depicts survival analysis of MC38 bearing GITR/GIRL humanized mice treated with the combination of an anti-human GITR- and anti-mouse PD1-antibody as described in Example 7.

Administration of Anti-Human GITR Antibodies in Combination with Anti-Mouse PD1 Antibodies Significantly Induces Tumor Regression and Provides Long-Term Tumor Remission in MC38 Bearing GITR/GITRL Humanized Mice The efficacy of administering an anti-human GITR antibody (H2aM14536P2) in combination with an anti-mouse PD-1 antibody (clone RMP1-14 Bio X cell, Cat. #BE0146) in the control of subcutaneous MC38 tumors was assessed in GITR/GITRL humanized mice. It was found that anti-mouse PD-1 blockade synergized with the anti-human GITR antibody and significantly induced tumor regression (4/6 mice) in MC38 tumor bearing mice, in comparison to anti-PD1 (1/7) or anti-GITR (1/7) mAb alone or isotype control (0/7) treated mice, as shown in the average tumor growth curves (FIG. 7, Table 16). Further, mice treated with the combination therapy showed long-term tumor remission, as over 60% of the mice remain tumor free at day 50, in comparison to 0% for the isotype control and 10% for the anti-PD-1 or the anti-GITR treatment groups (FIG. 8, Table 16).

Anti-Human GITR Antibodies Increase Intra-Tumoral CD8/Treg Ratio

Figure 9:
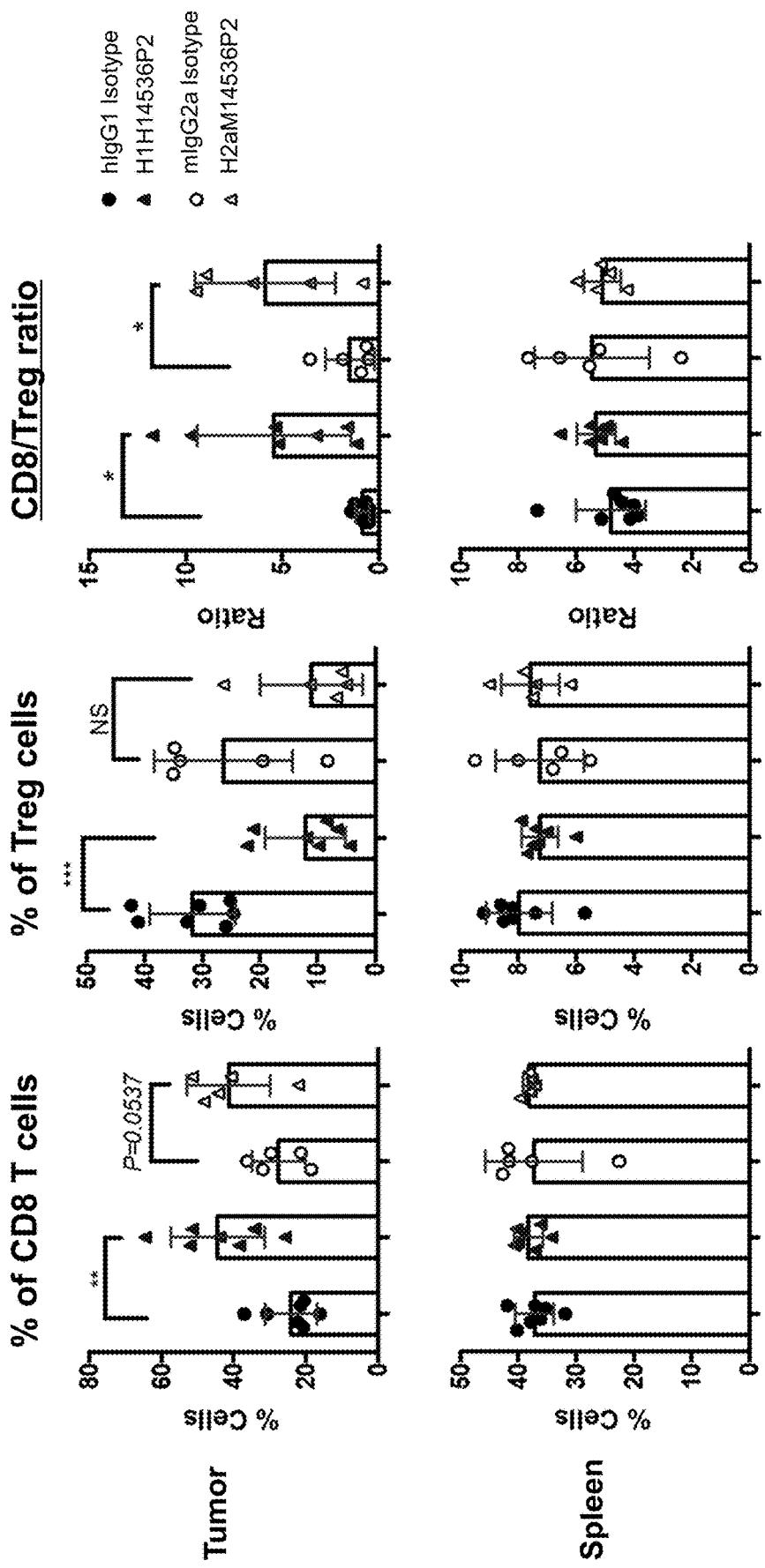
FIG. 9 depicts FACS analysis of intratumoral and spleen percentage of CD8 T cells, percentage of Treg cells, and CD8/Treg ratio as described in Example 7.

The effect of anti-human GITR antibodies on intra-tumoral and splenic T cell populations was assessed. Anti-human GITR antibodies H2aM14536P2 and H1 H14536P2 were evaluated. It was found that both anti-human GITR antibody isotypes (mIg2a and hIgG1) induced a significant increase in the intra-tumoral CD8/Treg ratio (FIG. 9). The same treatment had no effect on peripheral spleen T cell subsets. Human IgG1 and mouse IgG2a isotype IgG were used in the assay for controls.

TABLE 16

Anti-tumor efficacy mediated by anti-human GITR antibody and anti-mouse PD1 antibody treatment

| Treatment Group | Tumor size (mm³) Mean (SEM) | | | | Tumor Free Mice |
|---|---|---|---|---|---|
| | Day 9 | Day 13 | Day 16 | Day 19 | Day 51 |
| Isotype control | 146 (26) | 248 (53) | 402 (97) | 838 (205) | 0/7 (0%) |
| Anti-mPD1 | 120 (23) | 163 (50) | 275 (103) | 617 (257) | 1/7 (14%) |
| H2aM14536P2 | 134 (28) | 162 (51) | 194 (51) | 346 (87) | 1/7 (14%) |
| H2aH14536P2 + Anti-PD-1 | 122 (18) | 90 (54) | 114 (88) | 192 (165) | 4/6 (67%) |

TABLE 17

Anti-tumor efficacy mediated by anti-mouse GITR + anti-human PD1 Ab treatment

| Treatment Group | Tumor size (mm3) Mean (SEM) | | | |
|---|---|---|---|---|
| | Day 13 | Day 17 | Day 20 | Day 24 |
| Isotype control | 301 (38) | 742 (81) | 1392 (104) | 2790 (366) |
| Anti-PD1 (REGN2810) | 184 (21) | 354 (143) | 589 (201) | 937 (324) |
| Anti-GITR | 362 (99) | 713 (360) | 1199 (563) | NA |
| Anti-GITR + Anti-PD-1 | 212 (117) | 120 (60) | 127 (62) | 167 (98) |

Figure 10:
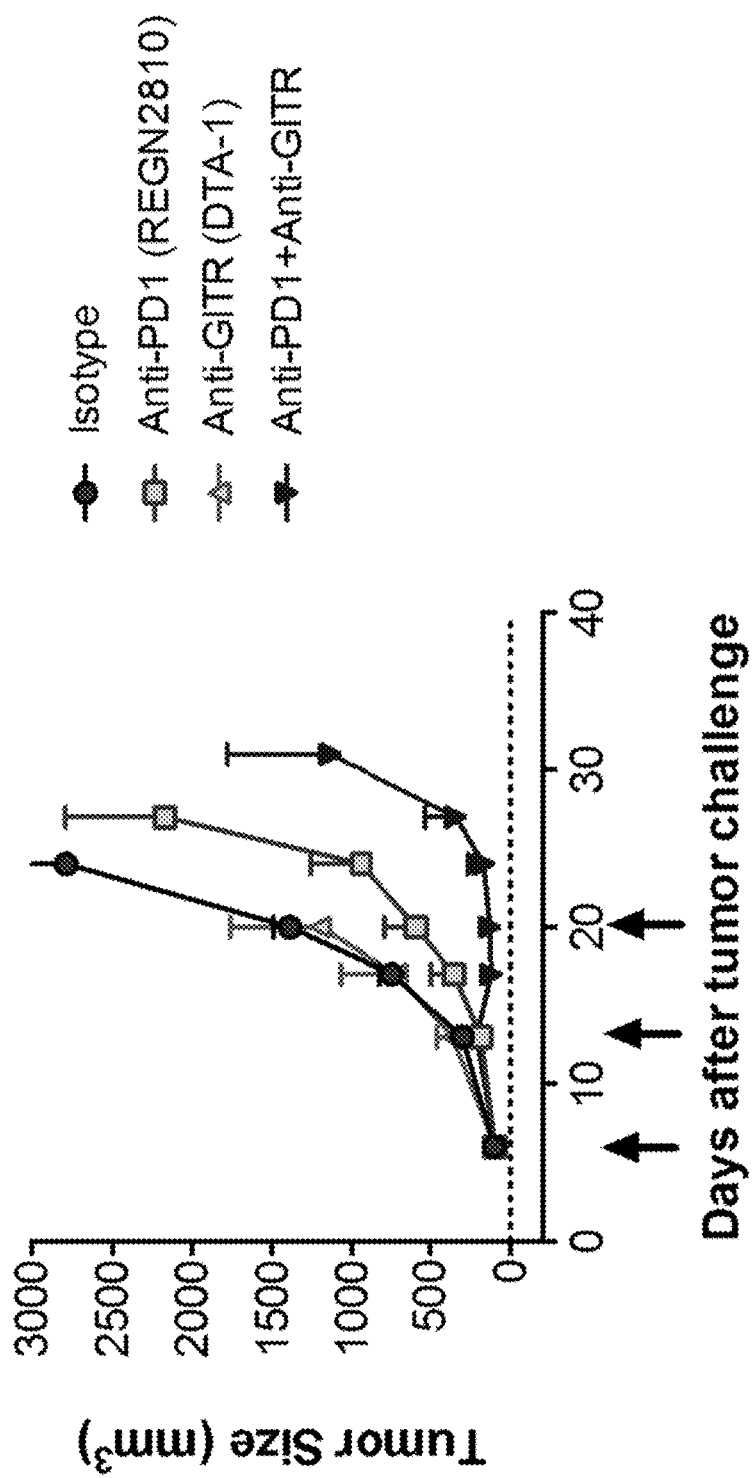
FIG. 10 depicts average tumor volumes for each treatment group ($mm^3 \pm SEM$) plotted against days after tumor challenge as described in Example 7.
Figure 11:
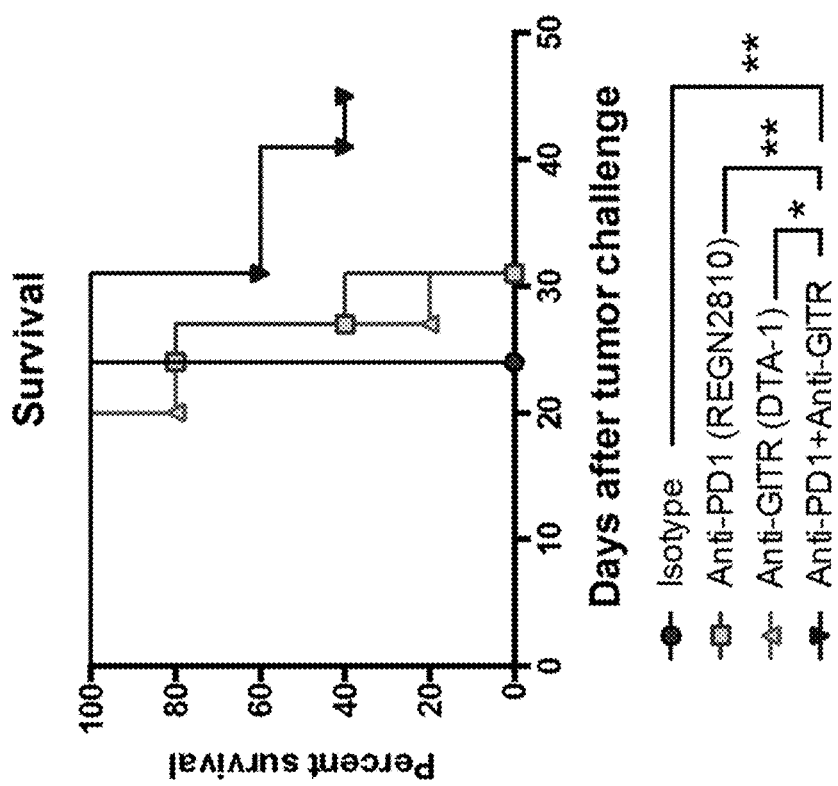
FIG. 11 depicts survival analysis of MC38 bearing PD1/PDL1 humanized mice treated with the combination of an anti-mouse GITR- and anti-human PD1-antibody as described in Example 7.

Administration of Anti-Mouse GITR Antibodies in Combination with Anti-Human PD1 Antibodies Significantly Induces Tumor Regression and Provides Long-Term Tumor Remission in MC38 Bearing PD1/PDL1 Humanized Mice The efficacy of administering an anti-mouse GITR antibody (DTA-1) in combination with an anti-human PD-1 antibody (REGN2810, also known as H4H7798N as disclosed in US Patent Publication No. 2015/0203579) in the control of subcutaneous MC38 tumors was assessed in PD1/PDL1 humanized mice. It was found that anti-human PD-1 blockade synergized with the anti-mouse GITR antibody and induced tumor growth delay in MC38 tumor bearing mice, in comparison to anti PD1 or anti GITR mAb alone or isotype control treated mice as shown in the average tumor growth curves (FIG. 10, Table 17). Further, mice treated with the combination therapy showed long-term tumor remission as over 40% of the mice remained tumor free at day 45, in comparison to 0% for the isotype control, the anti-PD-1 or the anti-GITR treatment groups (FIG. 11).

Example 8. RNA Extraction and Analysis

Single-Cell Sorting RNA-Seq Analysis

On day 8 and 11 post tumor challenge, single cell suspension of tumor was prepared by mouse tumor dissociation kit (Miltenyi Biotec, Bergisch Gladbach, Del.) and spleens were dissociated with gentleMACS™ Octo Dissociator (Miltenyi Biotec). Tumors and spleens from the same treatment group were pooled and viable CD8+ T cells were sorted by FACS. FACS sorted T cells were mixed with C1 Cell Suspension Reagent (Fluidigm, South San Francisco, Calif.) before loading onto a 5- to 10-μm C1 Integrated Fluidic Circuit (IFC; Fluidigm). LIVE/DEAD staining solution was prepared by adding 2.5 μL ethidium homodimer-1 and 0.625 μL calcein AM (Life Technologies, Carlsbad, Calif.) to 1.25 mL C1 Cell Wash Buffer (Fluidigm) and 20

µL was loaded onto the C1 IFC. Each capture site was carefully examined under a Zeiss microscope in bright field, GFP, and Texas Red channels for cell doublets and viability. Cell lysing, reverse transcription, and cDNA amplification were performed on the C1 Single-Cell Auto Prep IFC, as specified by the manufacturer (protocol 100-7168 E1). The SMARTer™ Ultra Low RNA Kit (Clontech, Mountain View, Calif.) was used for cDNA synthesis from the single cells. Illumina NGS libraries were constructed using the NEXTERA XT DNA Sample Prep kit (Illumina), according to the manufacturer's recommendations (protocol 100-7168 E1). A total of 2,222 single cells were sequenced on Illumina NextSeq (Illumina, San Diego, Calif.) by multiplexed single-read run with 75 cycles. Raw sequence data (BCL files) were converted to FASTQ format via Illumina CASAVA 1.8.2. Reads were decoded based on their barcodes. Read quality was evaluated using FastQC (www.bioinformatics.babraham.ac.uk/projects/fastqc/).

Example 9. Role of CD226 and TIGIT in Combination Treatment

Genetic inactivation or pharmacological inhibition of CD226 reversed the tumor regression mediated by anti-GITR/anti-PD1 combination treatment in some experiments, while inhibition of other TNF-receptor or B7 superfamily members had no effect.
CD226 Blocking Experiment 0.5 mg of anti-CD226 (10E5, eBioscience, San Diego, Calif.) or rat IgG2b isotype control IgG (LTF2, Bio X Cell, West Lebanon, N.H.) were injected intraperitoneally (i.p.) on day 5 post tumor challenge and one day prior to immunotherapy. Perpendicular tumor diameters were measured blindly 2-3 times per weeks using digital calipers (VWR, Radnor, Pa.). Volume was calculated using the formula L×W×0.5, where L is the longest dimension and W is the perpendicular dimension. Differences in survival were determined for each group by the Kaplan-Meier method and the overall P value was calculated by the log-rank testing using survival analysis by PRISM version 6 (GraphPad Software Inc., La Jolla, Calif.). An event was defined as death when tumor burden reached the protocol-specified size of 2000 mm$^3$ in maximum tumor volume to minimize morbidity.

Figure 12:
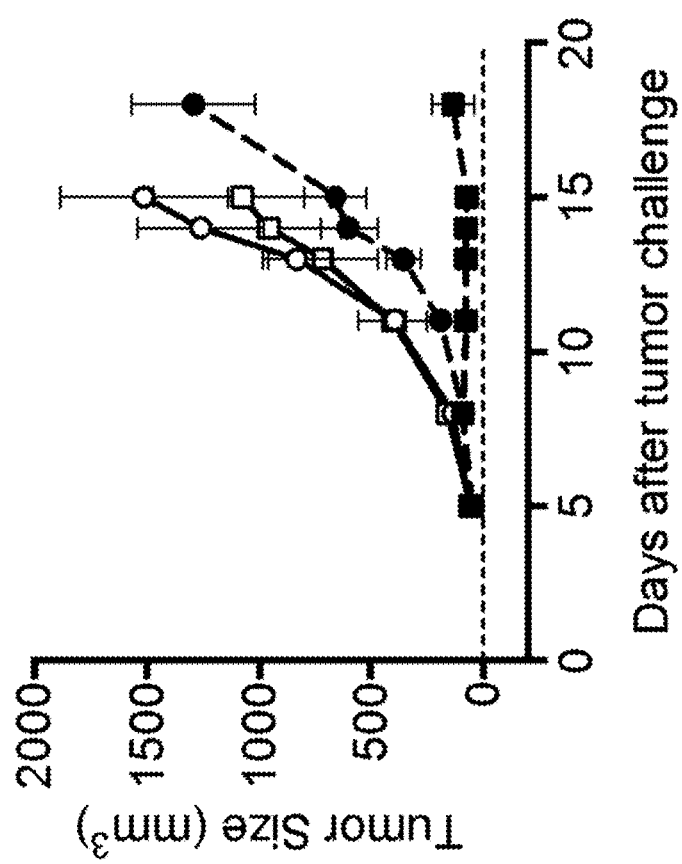
FIG. 12 depicts a tumor growth curve of MC38-bearing mice as described in Example 7. The Y-axis depicts tumor volume in cubic millimeters and the X-axis depicts time in days post tumor challenge. Open symbols (□, ○) represent mice first treated with an isotype antibody (control). Filled symbols (■, ●) represent mice first treated with an anti-CD226 antibody. Those mice then treated with the isotype antibody are represented by circles (○, ●) and solid lines. Those mice then treated with the anti-GITR and anti-PD-1 combination are represented by squares (□, ■) and dotted lines.
Figure 13:
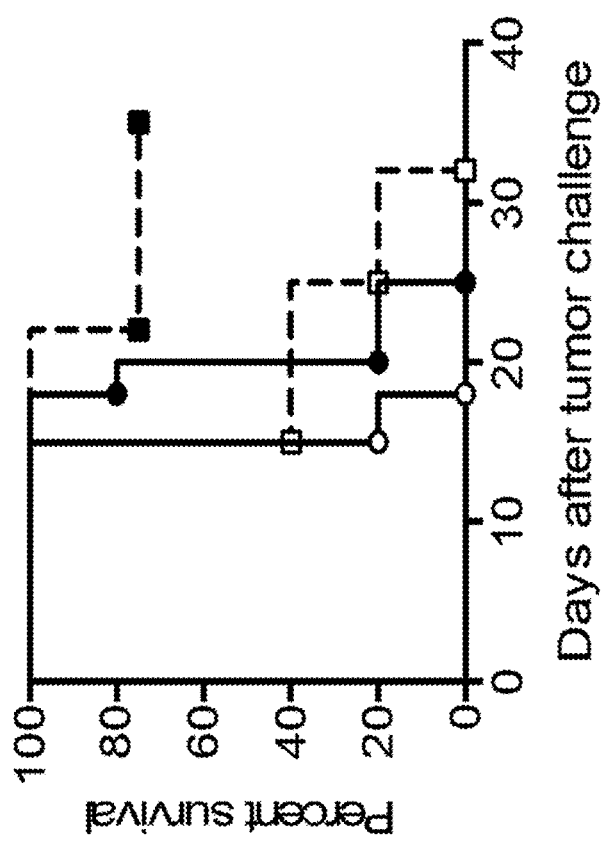
FIG. 13 depicts a survival curve of MC38-bearing mice as described in Example 7. The Y-axis depicts percent survival and the X-axis depicts time in days post tumor challenge. Open symbols (□, ○) represent mice first treated with an isotype antibody (control). Filled symbols (■, ●) represent mice first treated with an anti-CD226 antibody. Those mice then treated with the isotype antibody are represented by circles (○, ●) and solid lines. Those mice then treated with the anti-GITR and anti-PD-1 combination are represented by squares (□, ■) and dotted lines.

As shown in FIGS. 12 and 13, MC38 tumor bearing mice were treated with either CD226 blocking Ab or isotype Ab (control IgG) 1d prior to immunotherapy with anti-GITR+anti-PD-1 or isotype Abs. Average tumor growth curve (FIG. 12) and survival curves (FIG. 13) are shown. Data are representative of three experiments, n=5 mice per group, survival analysis by Log-rank test.

Figure 14:
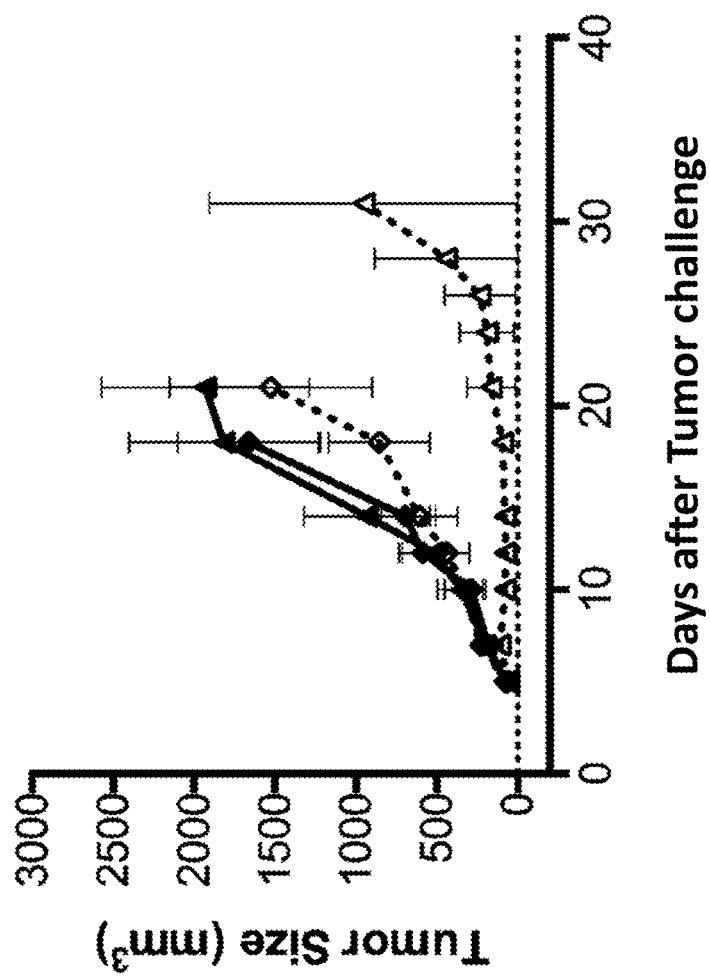
FIG. 14 depicts a tumor growth curve of MC38-bearing wild type mice (represented by diamonds [◇◆]) or TIGIT knock-out mice (represented by triangles [△▲]) treated with isotype IgGs as described in Example 7. The Y-axis depicts tumor volume in cubic millimeters and the X-axis depicts time in days post tumor challenge. Open symbols and dotted lines represent mice first treated with an isotype antibody (control). Filled symbols and solid lines represent mice first treated with an anti-CD226 antibody.
Figure 15:
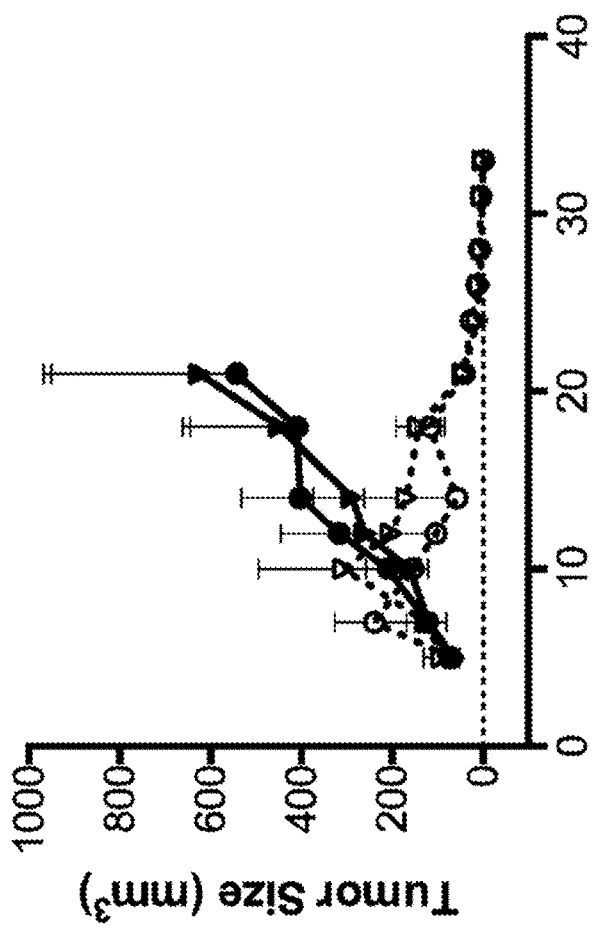
FIG. 15 depicts a tumor growth curve of MC38-bearing wild type mice (represented by circles [○, ●]) or TIGIT knock-out mice (represented by inverted triangles [▽▼]) treated with isotype IgGs as described in Example 7. The Y-axis depicts tumor volume in cubic millimeters and the X-axis depicts time in days post tumor challenge. Open symbols and dotted lines represent mice first treated with an isotype antibody (control). Filled symbols and solid lines represent mice first treated with an anti-CD226 antibody.

Wild type or TIGIT KO mice were challenged with MC38 tumors, treated with anti-CD226 or control IgG and either received isotype control (FIG. 14) or anti-GITR+anti-PD-1 combination therapy (FIG. 15). Data shown are average tumor growth curves representative of two experiments (n=4-5 mice per group).

Using the CD226 blocking mAb, it was shown that co-stimulatory signaling through CD226 is required for the anti-tumor immunity mediated by combination treatment. Furthermore, the CD226 signaling pathway was required for enhanced tumor surveillance in TIGIT KO mice (FIGS. 14 and 15).
RNA Signatures in CD8+ T Cells from Combination Treatment Samples To identify unique gene signatures in clonally expanded CD8+ T cells (tumors harvested at day 11) from combination treatment samples, comprehensive comparisons across different treatment groups were performed. Genes upregulated in clonally expanded CD8+ T cells from combination therapy were compared to upregulated genes of CD8+ T cells from isotype treatment or non-expanded CD8+ T cells with combination treatment. Heat mapping analysis identified thirty genes overlapping within the comparison. An RNA signature change of 2-fold (p<0.01) was observed within the expanded CD8 T cell population for the 30 genes after the anti-GITR/anti-PD1 combination treatment of tumors. Those 30 genes include Id2, S100a11, Ndufb3, Serinc3, Ctsd, S100a4, Ppp1ca, Lbr, Peli1, Lcp2, Ube2h, Cd226, Mapkapk3, Racgap1, Arf3, Mki67, Ergic2, Azi2, Dync1i2, Sik1, Pde4d, Ppp3cc, Nek7, Emc4, Vav1, Dock10, Tmem173, Fam3c, Ppp1cc, and Glud1.

Figure 16A:
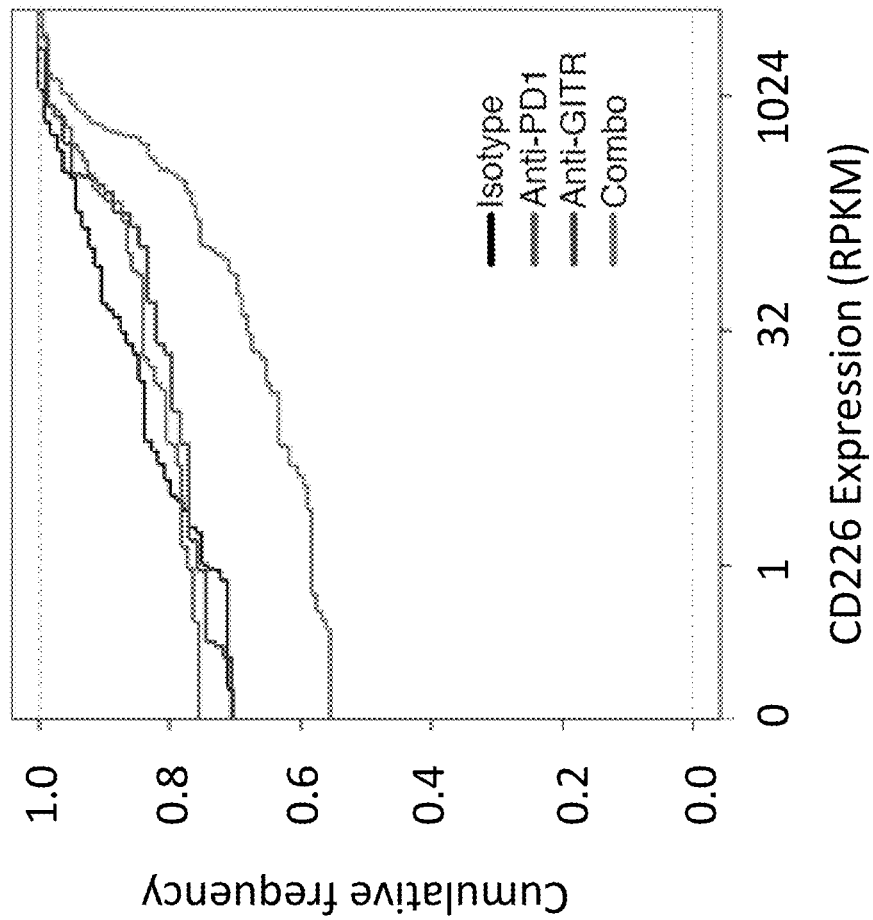
FIG. 16A is a cumulative distribution function (CDF) plot depicting the upregulated expression of CD226 by combination treatment in total CD8+ T cells. The X-axis depicts CD226 expression in log 2(RPKM) (Reads Per Kilobase of transcript per Million mapped reads) and the Y-axis depicts cumulative frequency. The red line represents the anti-GITR/anti-PD1 treatment; the black line represents isotype antibody treatment; the blue line represents anti-GITR treatment; and the purple line represents anti-PD1 treatment.
Figure 16B:
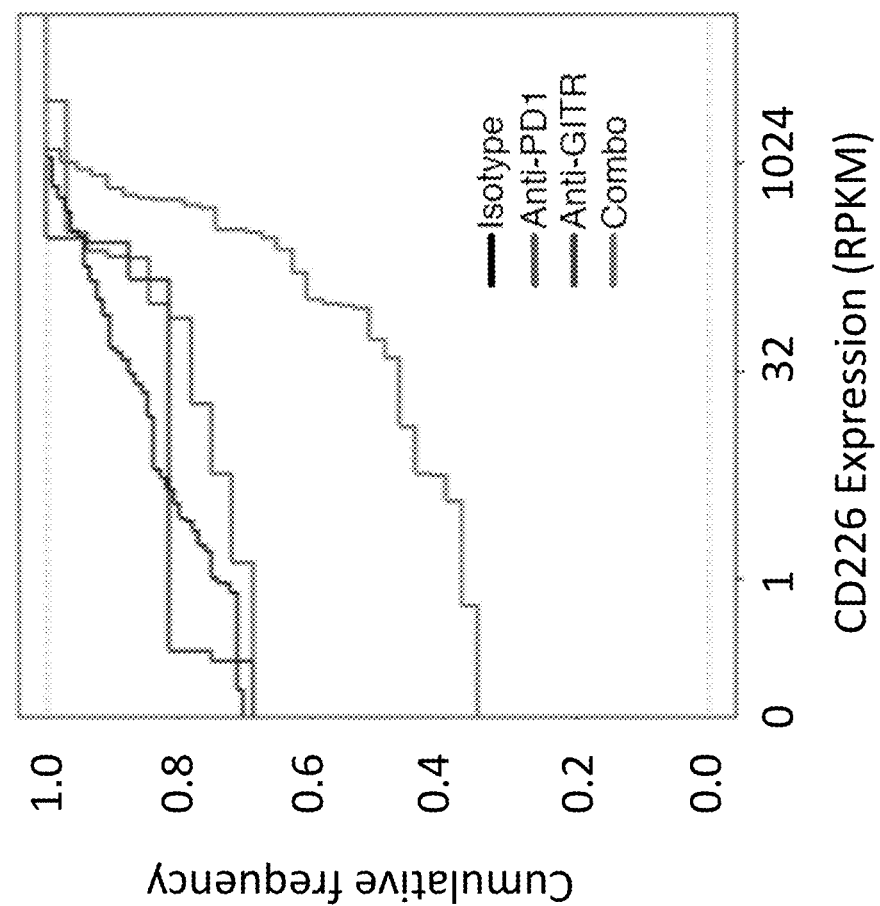
FIG. 16B is a cumulative distribution function (CDF) plot depicting the upregulated expression of CD226 by combination treatment in clonal expanded CD8+ T cells. The X-axis depicts CD226 expression in log 2(RPKM) (Reads Per Kilobase of transcript per Million mapped reads) and the Y-axis depicts cumulative frequency. The red line represents the anti-GITR/anti-PD1 treatment; the black line represents isotype antibody treatment; the blue line represents anti-GITR treatment; and the purple line represents anti-PD1 treatment.
Figure 16C:
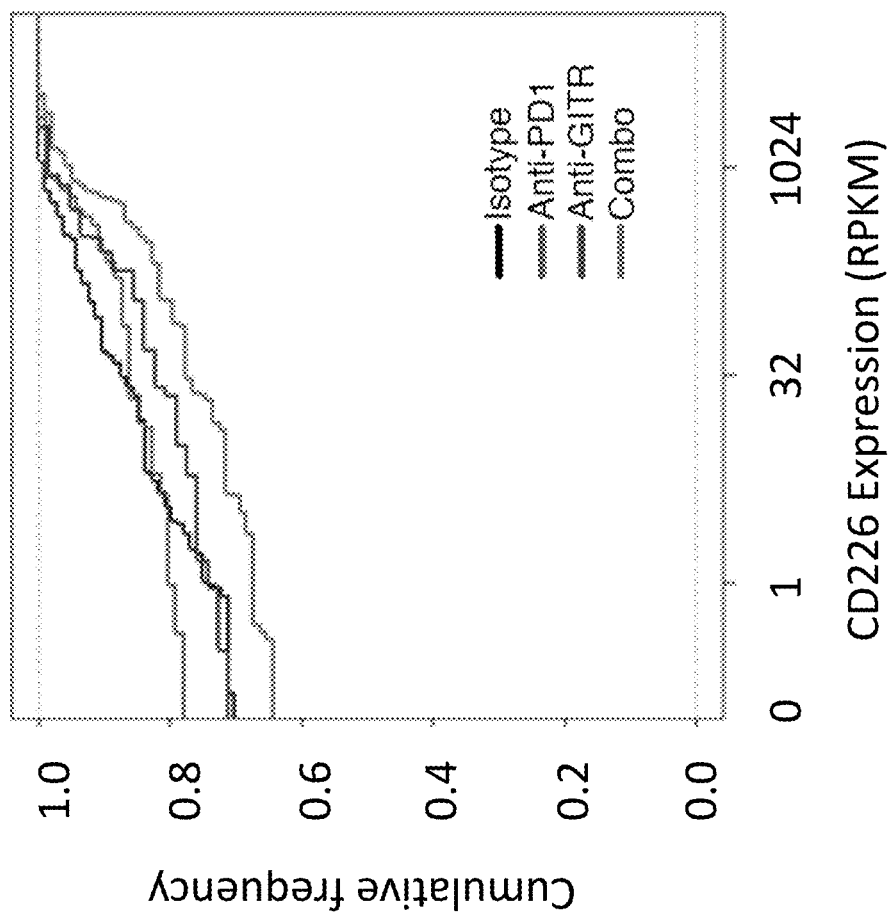
FIG. 16C is a cumulative distribution function (CDF) plot depicting the upregulated expression of CD226 by combination treatment in non-expanded CD8+ T cells. The X-axis depicts CD226 expression in log 2(RPKM) (Reads Per Kilobase of transcript per Million mapped reads) and the Y-axis depicts cumulative frequency. The red line represents the anti-GITR/anti-PD1 treatment; the black line represents isotype antibody treatment; the blue line represents anti-GITR treatment; and the purple line represents anti-PD1 treatment.

A four-way comparison across all five groups (i.e., (i) isotype treatment, (ii) anti-GITR expanded CD8, (iii) anti-GITR/anti-PD1 combination expanded CD8, (iv) anti-PD1 expanded CD8, and (v) anti-GITR/anti-PD1 combination non-expanded CD8) was next performed to identify genes specifically regulated upon combination therapy versus monotherapy treatment. Two overlapping upregulated genes (p<0.01, ≥2 fold change in expression) were identified in the four-way analysis. CD226, which is a costimulatory molecule that plays an important role in anti-tumor response, was identified as one of the two genes shared across different comparison pairs. Expression analysis of different subsets of intratumoral CD8+ T cells ((a) total, (b) clonally expanded, or (c) non-expanded) across treatment groups (i.e., (i) isotype, (ii) anti-GITR, (iii) anti-PD1, and (iv) anti-GITR/anti-PD1 combination) revealed that CD226 mRNA levels were significantly increased by combination treatment on clonally expanded T cells (fold change=10.7), while this difference was diluted in bulk (fold change=3.5) and non-expanded CD8+ T cells (not significant). Further, CD226 mRNA levels were significantly increased by combination treatment on clonally expanded CD8 T cells in comparison to anti-PD-1 (fold change=6.5) and anti-GITR (fold change=9.2) (FIG. 16).
Association Between PD1 and CD226

Figure 17:
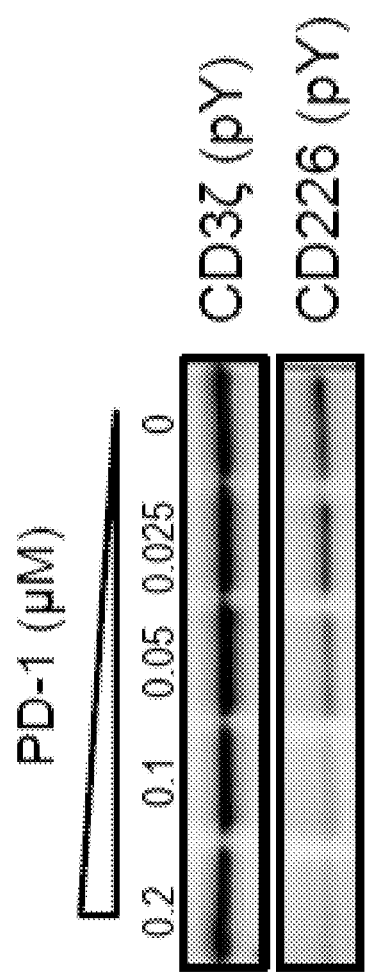
FIG. 17 is a Western blot depicting the relative expression of phospho-CD3ζ and phospho-CD226 as a function of PD-1 concentration.
Figure 18A:
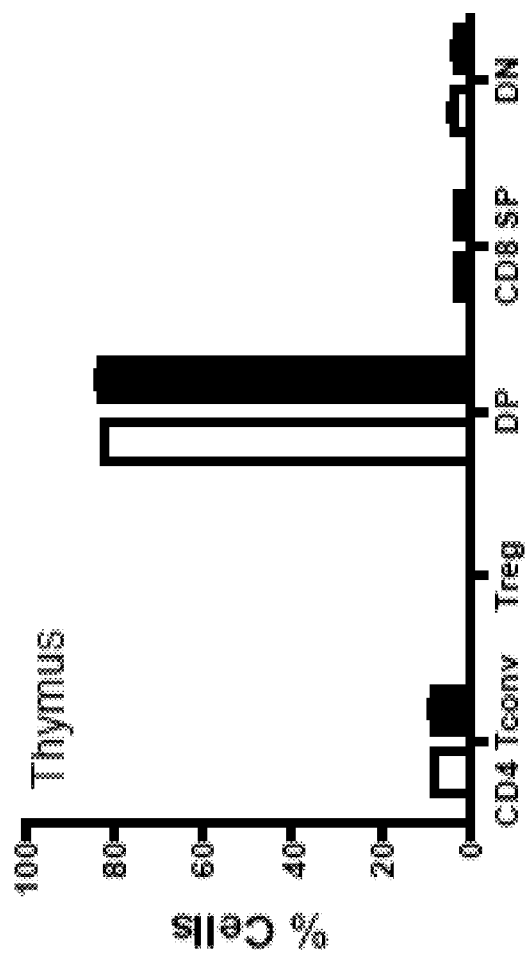
FIG. 18A is a bar chart depicting FACS analysis (number of cells) of T cell development in thymus (Tconv, conventional T cells; DP, CD4/CD8 double positive; SP, single positive; DN, CD4/CD8 double negative). Open bars represent wildtype (CD226$^+$) mice. Solid filled bars represent CD226 knock out (CD226$^{-/-}$) mice.
Figure 18B:
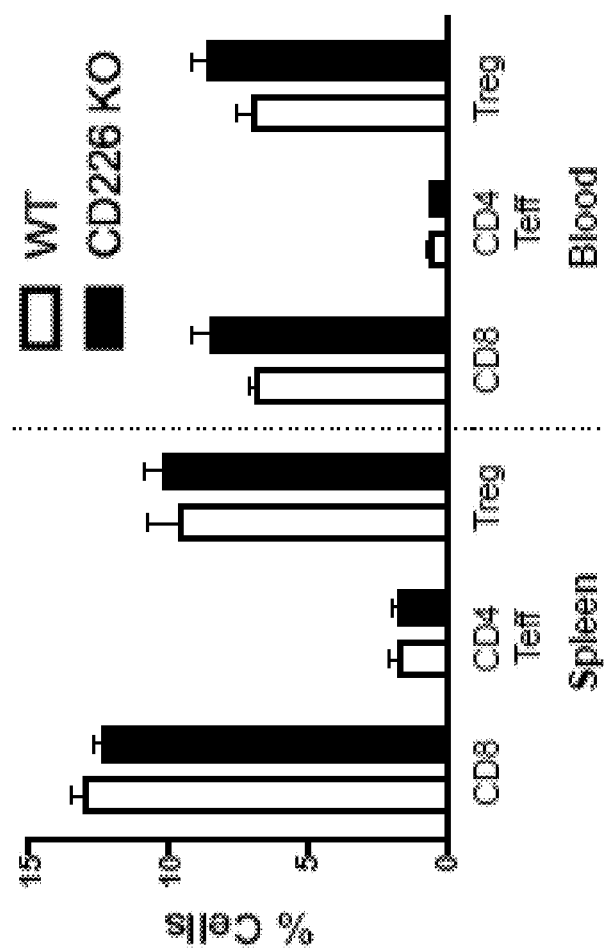
FIG. 18B is a bar chart depicting FACS validation (number of cells) of the population of T cell subsets in spleen and blood in wildtype and CD226$^{-/-}$ animals. Open bars represent wildtype (CD226$^+$) mice. Solid filled bars represent CD226 knock out (CD226$^{-/-}$) mice.
Figure 18C:
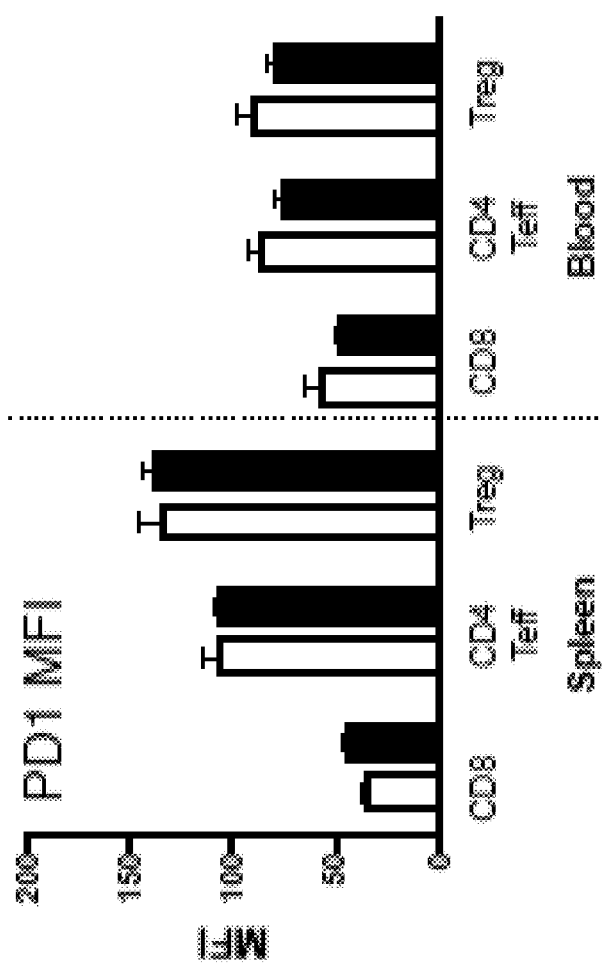
FIG. 18C is a bar chart depicting FACS analysis (MFI, mean fluorescence intensity) of T cell subsets in spleen and blood that express PD1. Open bars represent wildtype (CD226$^+$) mice. Solid filled bars represent CD226 knock out (CD226$^{-/-}$) mice.
Figure 18D:
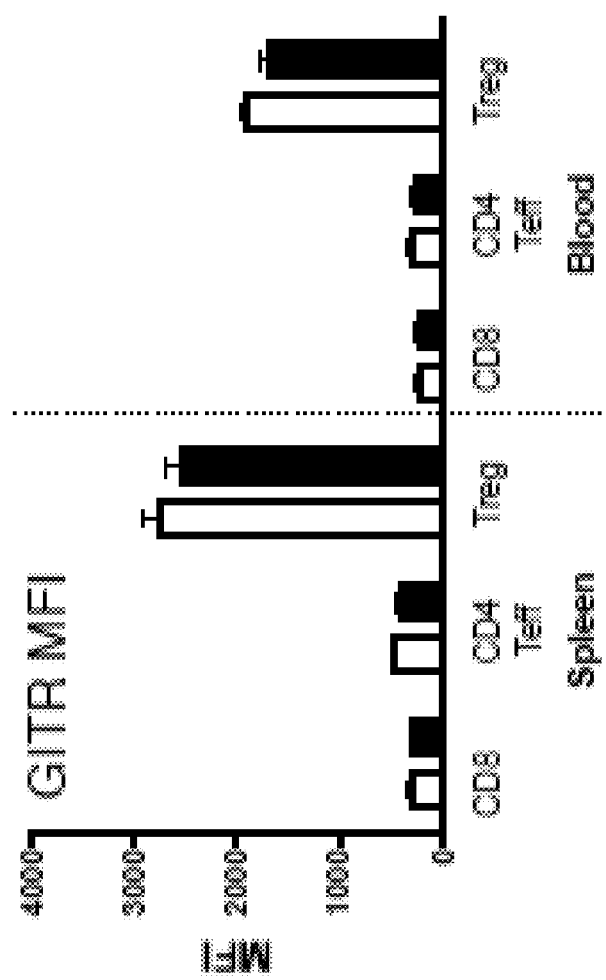
FIG. 18D is a bar chart depicting FACS analysis (MFI) of T cell subsets in spleen and blood that express GITR. Open bars represent wildtype (CD226$^+$) mice. Solid filled bars represent CD226 knock out (CD226$^{-/-}$) mice.
Figures 18E, 18F:
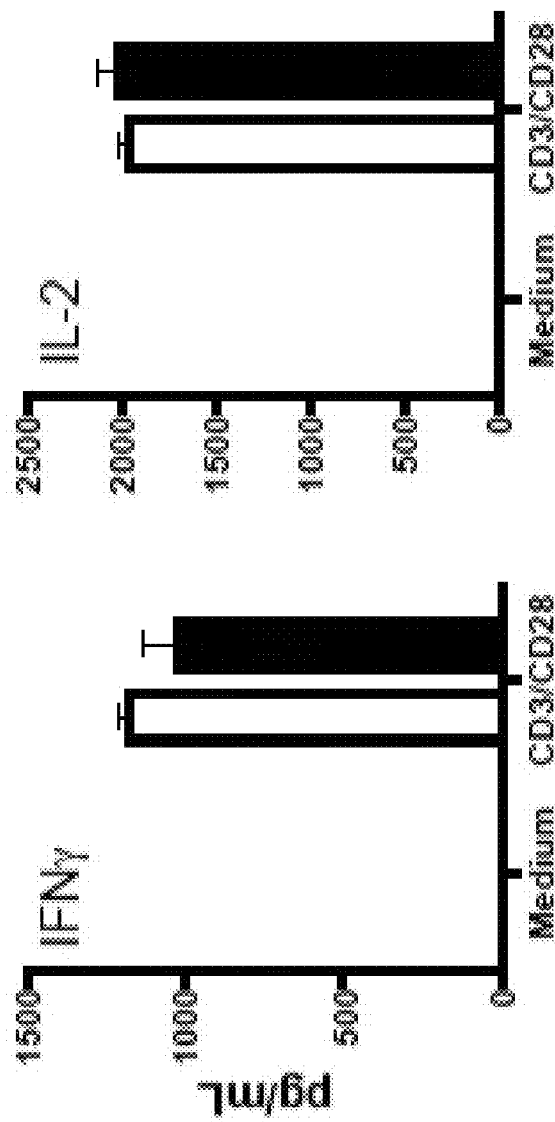
FIG. 18 E is a bar chart depicting IFN-γ secretion in picograms per milliliter upon ex vivo TCR stimulation of splenocytes with anti-CD3+anti-CD28 Ab for 16 hours. Splenocytes from CD226−/− (solid bars) or wild type (WT) (open bars) mice were stimulated with anti-CD3+ anti-CD28 Ab for 16 hours.
Figures 18G, 18H, 18I:
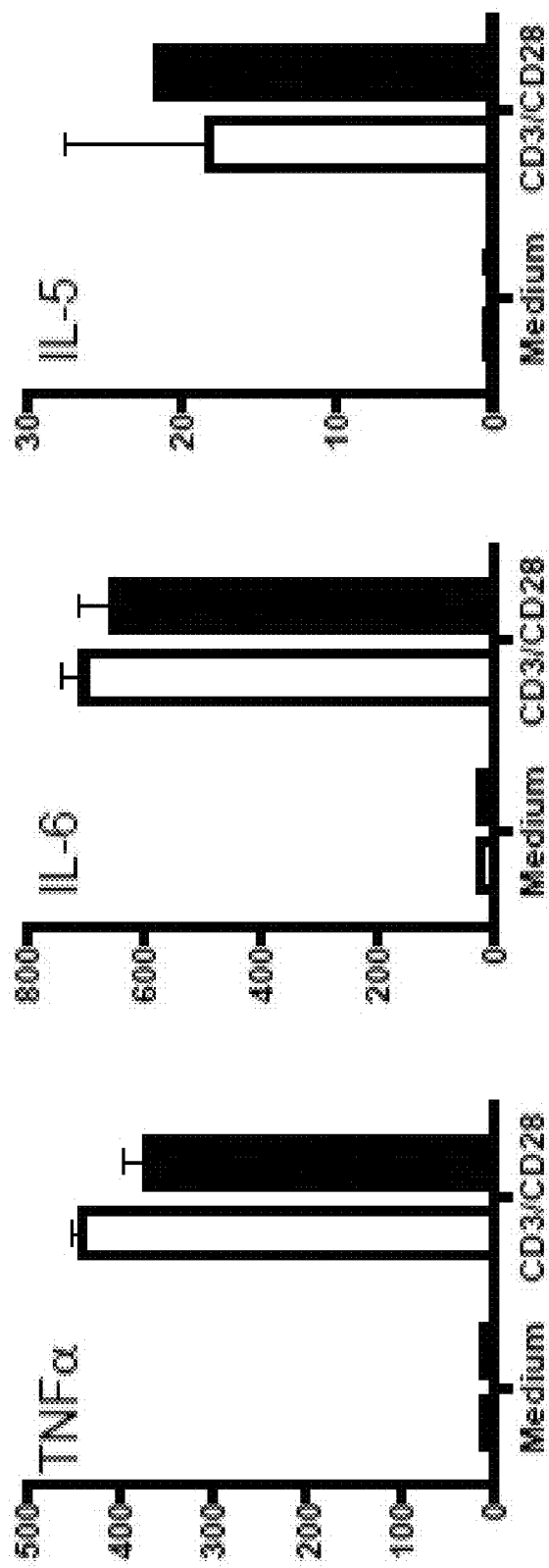
Figure 19B:
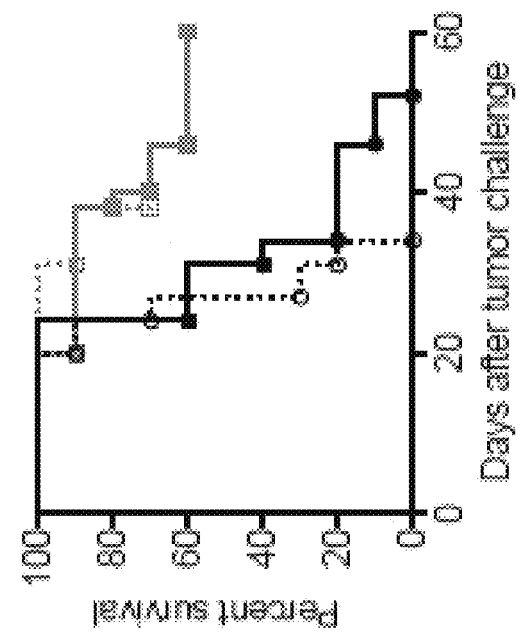
FIG. 19A, FIG. 19B, FIG. 19C, and FIG. 19D are line graphs depicting percent animal survival as a function of time in days post tumor challenge.
Figure 19A:
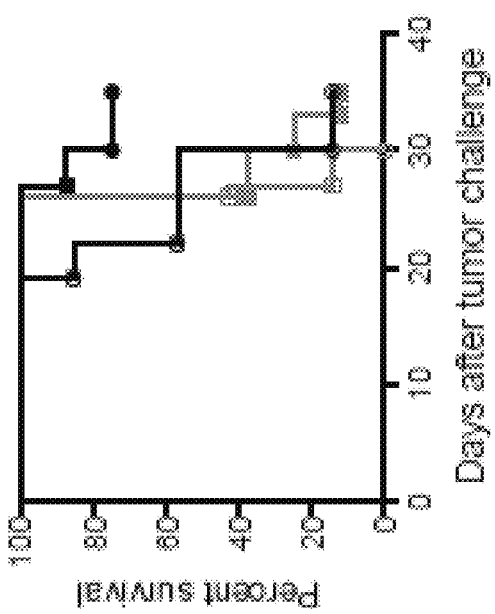
Figure 19D:
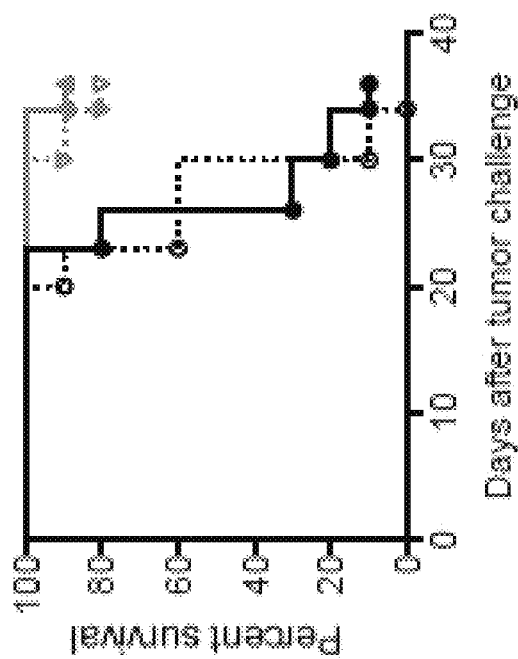
Figure 19C:
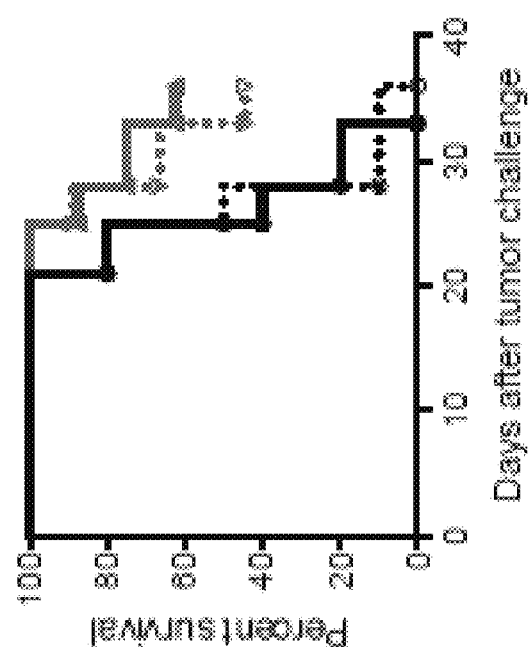

The potential association between PD1 and CD226 molecules was next investigated. To examine if CD226 is a target for desphosphorylation by the PD1-Shp2 complex, we reconstituted different components involved in T cell signaling in a cell-free large unilamellar vesicle (LUV) system (i.e., CD3, CD226, cytosolic tyrosine kinase Lck, Zap70, SLP76 52, and PI3K (p85a). The sensitivity of each component in response to PD-1 titration on the LUVs was measured by phosphotyrosine (pY) immunoblotting (FIG. 17). We confirmed that TCR/CD3ζ was not a target of desphosphorylation by PD-1-Shp2, whereas CD226 was efficiently dephosphorylated by PD1-Shp2 in a dose dependent manner after 30 minutes of treatment (FIG. 17). This data demonstrated an association between PD-1 and CD226.

Figure 22:
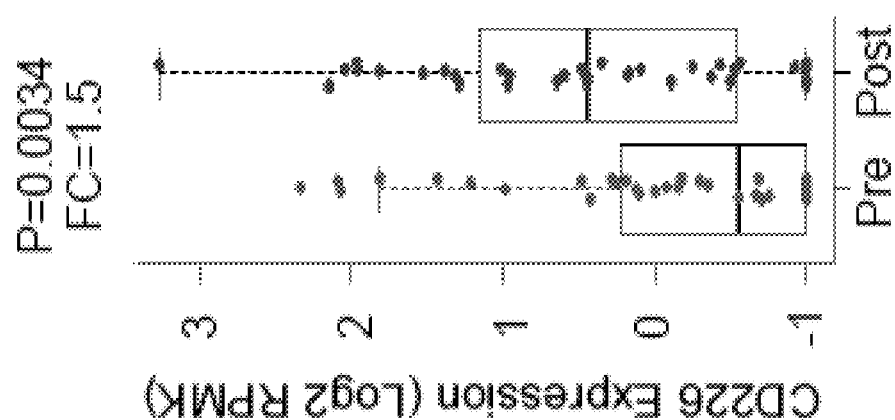
FIG. 22 depicts a dot plot RNA-seq analysis of cancer patient tumor biopsies showing CD226 RNA expression (in log 2[RPKM]) as a function of anti-PD-1 Ab treatment.

Next, the relationship between PD-1 inhibition and CD226 expression was investigated in a clinical setting. RNA-seq analysis was performed on tumor biopsies collected from 43 advanced cancer patients pre- and post-PD-1 targeted treatment. CD226 expression was significantly increased after two doses of anti-hPD-1 treatment in cancer patients (FIG. 22). Further, clinical data from The Cancer Genome Atlas (TCGA) was interrogated to examine if CD226 expression level correlates with the overall T cell activation strength and may be predictive of a better prognosis in cancer patients. Indeed, patients with high baseline CD226 expression have significantly higher survival probabilities in five (skin cutaneous melanoma, lung adenocarcinoma, head and neck squamous carcinoma, uterine corpus endometrial carcinoma and sarcoma) out of twenty different types of cancer evaluated (skin cutaneous melanoma, lung adenocarcinoma, head and neck squamous carcinoma, uterine corpus endometrial carcinoma, sarcoma, rectum adenocarcinoma, breast invasive carcinoma, kidney renal clear cell carcinoma, cervical squamous cell carcinoma and endocervical adenocarcinoma, glioblastoma multiforme, colon adenocarcinoma, stomach adenocarcinoma, bladder urothelial carcinoma, thyroid carcinoma, prostate adenocarcinoma, pancreatic adenocarcinoma, brain lower grade glioma, lung squamous cell carcinoma, kidney renal papillary cell carcinoma, and ovarian serous cystadenocarcinoma. Overall, these results support an immunotherapy strategy that boosts CD226 signaling while simultaneously blocking TIGIT (e.g., via anti-GITR treatment) for maximum T cell activation.

Genetic Inactivation of CD226

Using a CD226 blocking mAb, we showed that costimulatory signaling through CD226 was required for the anti-tumor immunity mediated by combination treatment (FIGS. 12, 13). Since CD226 Ab could possibly have a potential depleting effect on subset of CD8 T cells, CD226 was genetically inactivated in C57BL/6 background mice to confirm that result. CD226−/− mice showed no defect on T cell (CD4+, CD8+, Tregs) homeostasis (FIG. 18, panels A-D) and responded similarly to wild-type mice to TCR activation (FIG. 18, panels E-I). We observed that the combination treatment no longer conferred the anti-tumor effect or survival benefit in CD226−/− mice, suggesting that CD226 was essential for the observed anti-tumor effects of the combination (FIG. 19, panel A). The effect of CD226 is specific, since the inhibition of other members of the TNF receptor superfamily (OX40L or 4-1 BBL) or blockade of the B7 costimulatory molecule (CD28) using CTLA4-Ig preserved the anti-tumor effect mediated by the combination therapy (FIG. 19, panels B-D).

Requirement for CD226 in TIGIT Null Animals

Overall single-cell sorting RNA-seq and FACS phenotyping data showed that anti-PD-1 favored the expression of CD226, while anti-GITR treatment down-regulated surface expression of TIGIT, synergistically restoring the homeostatic T cell function.

Figures 20A, 20B:
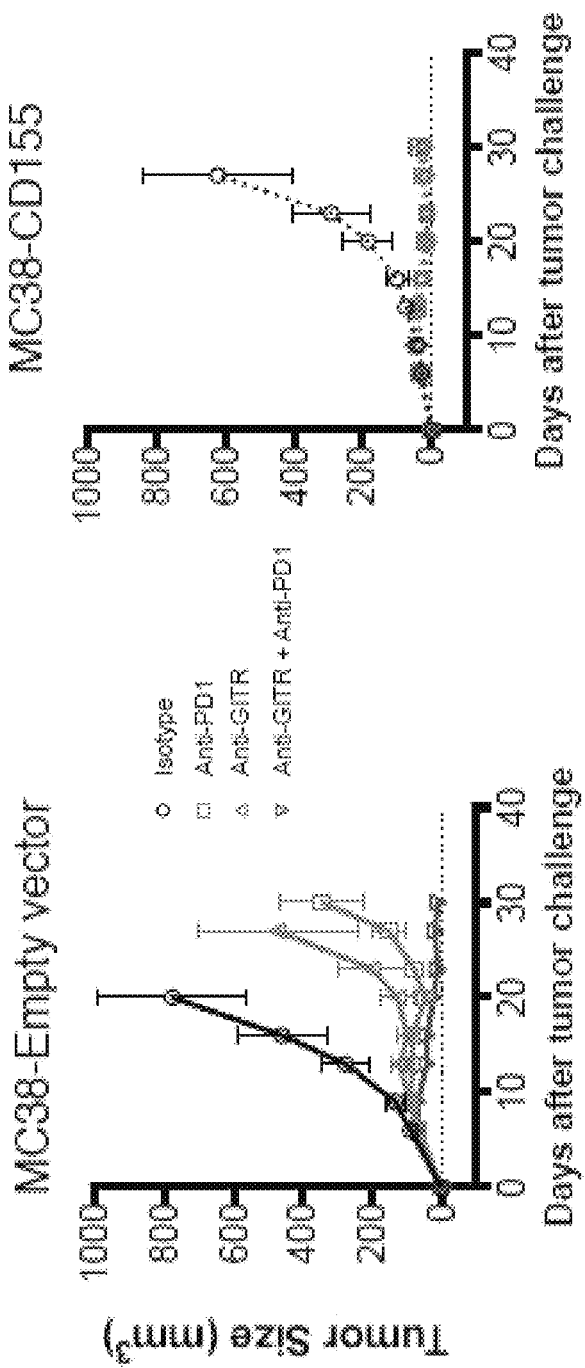
FIG. 20A is a line graph depicting tumor size (in cubic millimeters) as a function of days after tumor challenge for mice treated with isotype (open circles and black line), anti-PD1 (open squares, red line), anti-GITR (open upright pyramids and green line), and anti-GITR/anti-PD1 combination therapy (open inverted pyramids and blue lines). The tumors depicted in FIG. 20A are MC38 tumors that do not express CD155.
FIG. 20B is a line graph depicting tumor size (in cubic millimeters) as a function of days after tumor challenge for mice treated with isotype (open circles and black line), anti-PD1 (open squares, red line), anti-GITR (open upright pyramids and green line), and anti-GITR/anti-PD1 combination therapy (open inverted pyramids and blue lines). The tumors depicted in FIG. 20B are MC38 tumors that express CD155.
Figure 21A:
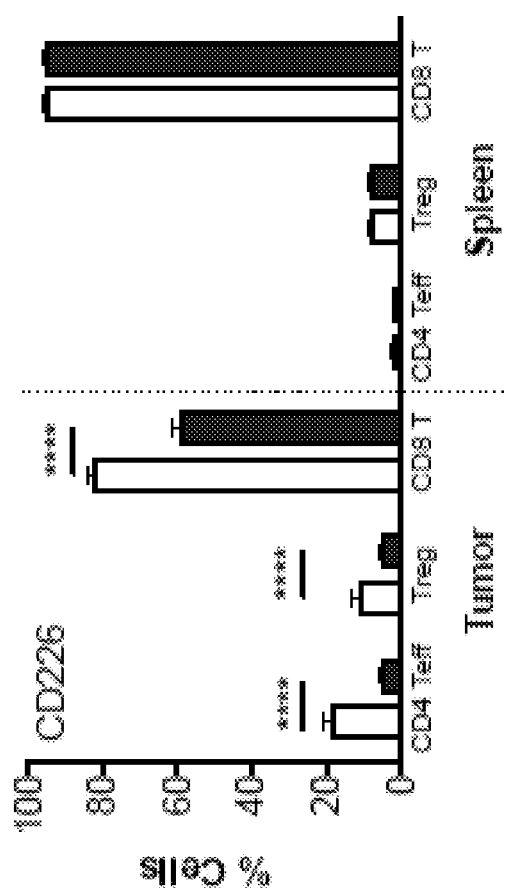
FIG. 21A is a bar chart depicting the number of cells expressing CD226 from animals challenged with MC38 tumor cells over expressing CD155 (filled bars) and MC38 tumor cells that do not express CD155 (open bars).
Figure 21B:
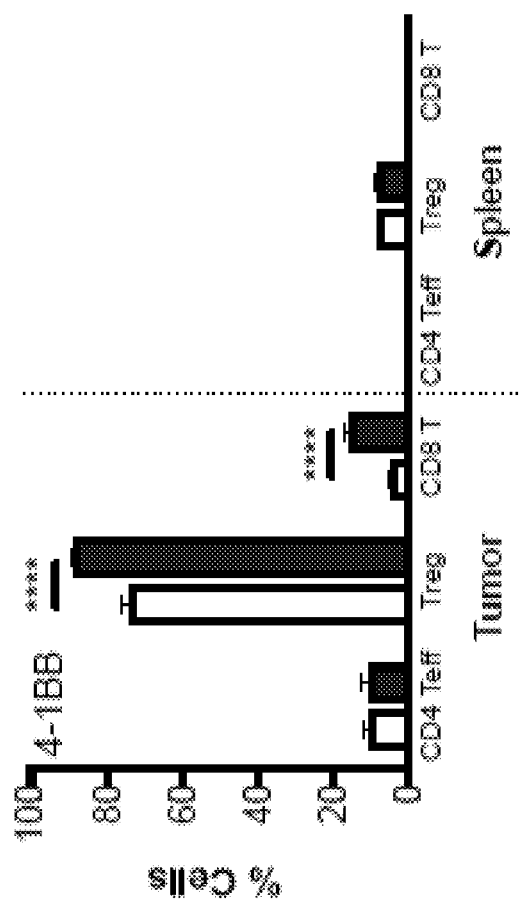
FIG. 21 B is a bar chart depicting the number of cells expressing 4-1 BB from animals challenged with MC38 tumor cells over expressing CD155 (filled bars) and MC38 tumor cells that do not express CD155 (open bars).
FIG. 21C is a bar chart depicting the number of cells expressing IFN-γ (Panel C) from animals challenged with MC38 tumor cells over expressing CD155 (filled bars) and MC38 tumor cells that do not express CD155 (open bars).
Figure 21C:
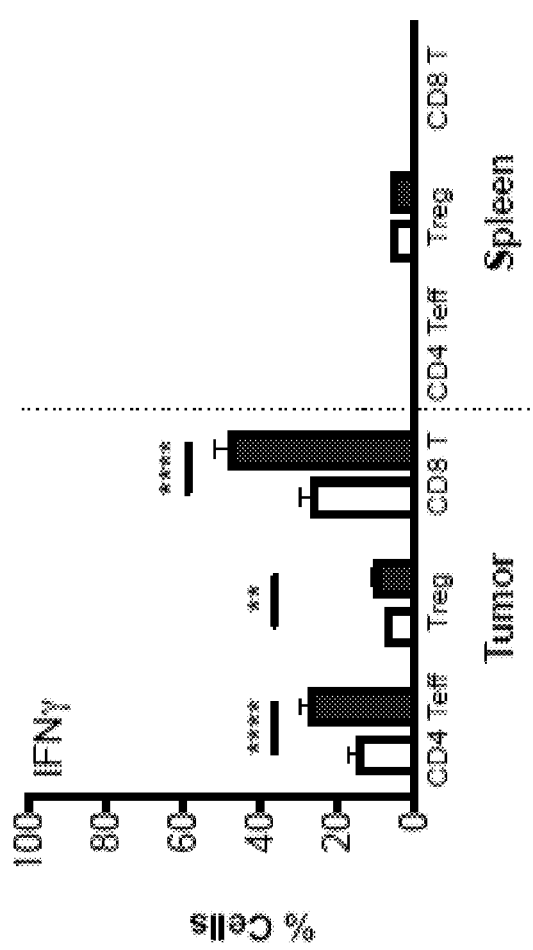

We showed that the CD226 signaling pathway was required for enhanced tumor surveillance in TIGIT−/− mice (FIGS. 14, 15). Additionally, mice bearing MC38 tumor cells overexpressing CD155/PVR6, which is the major ligand for CD226, showed significant delay of tumor growth upon anti-PD-1 or anti-GITR or combination therapy in comparison to MC38-empty vector (MC38-EV) tumor cells or mice treated with isotype control (FIG. 20). Immune profiling analysis of mice transplanted with MC38-CD155 confirmed sustained higher CD155 expression level on MC38-CD155 cells over M38-EV (empty vector) post-implantation. We found that CD155 over-expression on MC38 tumor cells was associated with decreased detectable CD226 expression on CD4+, CD8+ T and Tregs cells (FIG. 21A), while it boosted T cell activation as indicated by enhanced IFNγ (FIG. 21 B) and 4-1 BB (FIG. 21C) expression on intra-tumoral T cells. No effect was observed in the periphery.

Without being bound by any theory, it is hypothesized that CD226 expression level should correlate with the overall T cell activation strength and may be predictive of a better prognosis in cancer patients. Indeed, patients with high CD226 expression have significantly higher survival probabilities in three types of cancer (skin cutaneous melanoma, lung adenocarcinoma and sarcoma). These data support an immunotherapy strategy that boosts CD226 signaling while simultaneously blocking TIGIT for maximum T cell activation.

The forgoing experiments demonstrate the synergistic effect of administering an anti-GITR antibody in combination with an anti-PD1 antibody. In particular, among other things, the experiments above demonstrate that the combined administration of an anti-GITR antibody and anti-PD1 antibody induces tumor regression, provides long-term tumor remission, and induces tumor/antigen-specific immunologic memory response.

Example 10. TCR Analysis

For TCR analysis, we developed a new bioinformatic pipeline rpsTCR for reconstructing and extracting TCR sequences, especially TCR-CDR3 sequences from random priming short RNA sequencing reads. The rpsTCR took paired- and single-end short reads and maps these reads to mouse or human genomes and transcriptomes, but not TCR gene loci and transcripts using TopHat (Bioinformatics 25, 1105-1111 (2009)) with default parameters. Mapped reads were discarded and unmapped reads are recycled for extraction of TCR sequences. Low quality nucleotides in the unmapped reads were trimmed. Then reads with length less than 35 bp were filtered out using HTQC toolkit (Bioinformatics 14, 33 (2013). QC passed short reads was assembled into longer reads using iSSAKE (Bioinformatics 25, 458-464 (2009)) default setting. TCRklass (J Immunol 194, 446-454 (2015)) was used to identify CDR3 sequences with Scr (conserved residue support score) set from default 1.7 to 2. A targeted TCR-seq data from a healthy human PBMC samples was used as a positive control to evaluate whether the extra steps introduced to the pipeline resulted in higher false positive or false negative rates comparing to TCRklass alone.

The majority of unique CDR3 sequences from TCRB (64,031) or TCRA (51,448) were detected by both rpsTCR and TCRklass. The squared correlations between rpsTCR and TCRklass were 0.9999 and 0.9365 for TCRB-CDR3 and TCRA-CDR3, respectively. Six TCR-negative cancer or non-cancer cell lines were used as negative controls. No CDR3 sequences were detected by rpsTCR, whereas some CDR sequences were extracted by TCRklass from some TCR-negative cancer cell lines.

To further validate the performance of the subject pipeline, we sequenced a heathy mouse PBMC sample using both targeted TCR-seq and random priming RNA-seq approaches (200M, 2×100 bp). Although the number of CDR3 sequences assembled from RNA-seq data was much smaller than that from the targeted TCR-seq approach, about 45% of the CDR3 sequences identified from RNA-seq data using rpsTCR were also observed among CDR3 sequences from targeted TCR-seq. Because of the technique limitation of targeted TCR-seq, it is not surprising that a fraction of the CDR3 sequences we extracted from RNA-seq data were not present in the TCR-seq results. For example, the efficiency of 5' race adapter used for targeted TCR-seq is generally low and the multiply PCR tends to amplify high frequency TCRs, thus only a small portion of TCRs can be targeted. As expected, much higher percentage (~70%) of the CDR3 sequences identified from RNA-seq data using rpsTCR were also observed among high frequency CDR3 sequences (>=0.1%) from targeted TCR-seq, while only about 40% extracted using TCRklass alone. Moreover, we cut the 100 bp read length in 50 bp segments and randomly selected 200M reads. Among the top 10 CDR3 sequences ranked by targeted TCR-seq approach, 8 CDR3 sequences were detected by our rpsTCR, while only 3 were detected by TCRklass. We then applied our rpsTCR pipeline to extracting CDR3 sequences from the single cell RNA-seq data generated from intratumoral CD8 T cells of MC38 treated with different antibodies. Our CDR3_beta and CDR3_alpha sequence detection rates were comparable to published data using targeted TCR-seq approach to detect TCR sequences from single cell sequencing of T cells The present invention is not to be limited in scope by the specific embodiments described herein. Indeed, various modifications of the invention in addition to those described herein will become apparent to those skilled in the art from the foregoing description and the accompanying figures. Such modifications are intended to fall within the scope of the appended claims.

What is claimed is:

1. An isolated nucleic acid molecule comprising a nucleic acid sequence encoding a heavy chain immunoglobulin variable domain region (HCVR) of an antibody that binds glucocorticoid-induced tumor necrosis factor receptor (GITR), wherein the HCVR comprises a heavy chain CDR1 (HCDR1) comprising SEQ ID NO: 340, a heavy chain CDR2 (HCDR2) comprising SEQ ID NO: 342, and a heavy chain CDR3 (HCDR3) comprising SEQ ID NO: 344.

2. The nucleic acid molecule of claim 1, wherein the HCVR comprises the amino acid sequence of SEQ ID NO: 338.

3. The nucleic acid molecule of claim 1, wherein the nucleic acid molecule comprises the nucleotide sequence of SEQ ID NO: 337 or a nucleotide sequence that is at least 95% identical to the nucleotide sequence of SEQ ID NO: 337.

4. The nucleic acid molecule of claim 1, wherein the nucleic acid molecule comprises the nucleotide sequence of SEQ ID NO: 337.

5. An expression vector comprising:
(a) a nucleic acid molecule comprising a nucleic acid sequence encoding a heavy chain immunoglobulin variable domain region (HCVR) of an antibody that binds GITR, wherein the HCVR comprises a heavy chain CDR1 (HCDR1) comprising SEQ ID NO: 340, a heavy chain CDR2 (HCDR2) comprising SEQ ID NO: 342, and a heavy chain CDR3 (HCDR3) comprising SEQ ID NO: 344.

6. An isolated host cell comprising the expression vector of claim 5.

7. The host cell of claim 6, wherein the host cell is a mammalian cell or a prokaryotic cell.

8. The host cell of claim 6, wherein the host cell is a Chinese Hamster Ovary (CHO) cell or an *Escherichia coli* (*E. coli*) cell.

9. A composition comprising a first nucleic acid molecule and a second nucleic acid molecule;
wherein the first nucleic acid molecule comprises a nucleic acid sequence encoding a heavy chain immunoglobulin variable domain region (HCVR) of an antibody that specifically binds to GITR that comprises a heavy chain CDR1 (HCDR1) comprising SEQ ID NO: 340, a heavy chain CDR2 (HCDR2) comprising SEQ ID NO: 342, and a heavy chain CDR3 (HCDR3) comprising SEQ ID NO: 344; and
wherein the second nucleic acid molecule comprises a nucleic acid sequence encoding a light chain immunoglobulin variable domain region (LCVR) of an antibody that specifically binds to GITR that comprises a light chain CDR1 (LCDR1) comprising SEQ ID NO: 404, a light chain CDR2 (LCDR2) comprising SEQ ID NO: 406, and a light chain CDR3 (LCDR3) comprising SEQ ID NO: 408.

10. The composition of claim 9, wherein the HCVR comprises SEQ ID NO: 338, and wherein the LCVR comprises SEQ ID NO: 402.

11. An isolated nucleic acid molecule encoding an antibody or antigen-binding fragment thereof, which specifically binds GITR, wherein the antibody or antigen-binding fragment comprises a heavy chain variable region (HCVR) comprising three heavy chain CDRs (HCDR1, HCDR2, and HCDR3) from SEQ ID NO: 338, and a light chain variable region (LCVR) comprising three light chain CDRs (LCDR1, LCDR2, and LCDR3) from SEQ ID NO: 402, wherein:
(a) the HCDR1 comprises SEQ ID NO: 340;
(b) the HCDR2 comprises SEQ ID NO: 342;
(c) the HCDR3 comprises SEQ ID NO: 344;
(d) the LCDR1 comprises SEQ ID NO: 404;
(e) the LCDR2 comprises SEQ ID NO: 406;
(f) the LCDR3 comprises SEQ ID NO: 408.

12. The nucleic acid molecule of claim 11, wherein the HCVR comprises SEQ ID NO: 338.

13. The nucleic acid molecule of claim 11, wherein the LCVR comprises SEQ ID NO: 402.

14. The nucleic acid molecule of claim 11, wherein the HCVR comprises SEQ ID NO: 338 and the LCVR comprises SEQ ID NO: 402.

15. An expression vector comprising the nucleic acid molecule of claim 11.

16. An isolated host cell comprising the expression vector of claim 15.

17. The host cell of claim 16, wherein the host cell is a mammalian cell or a prokaryotic cell.

18. The host cell of claim 16, wherein the host cell is a Chinese Hamster Ovary (CHO) cell or an *Escherichia coli* (*E. coli*) cell.

19. A method of producing an anti-human GITR antibody or antigen binding fragment thereof, comprising growing the host cell of claim 16 under conditions permitting production of the antibody or fragment, and recovering the antibody or fragment so produced.

20. The method of claim 19, further comprising formulating the antibody or antigen-binding fragment thereof as a pharmaceutical composition comprising an acceptable carrier.

21. An expression vector comprising:
(a) a nucleic acid molecule comprising a nucleic acid sequence encoding a heavy chain immunoglobulin variable domain region (HCVR) of an antibody that binds GITR, wherein the HCVR comprises a heavy chain CDR1 (HCDR1) comprising SEQ ID NO: 340, a heavy chain CDR2 (HCDR2) comprising SEQ ID NO: 342, and a heavy chain CDR3 (HCDR3) comprising SEQ ID NO: 344; and
(b) a nucleic acid molecule comprising a nucleic acid sequence encoding a light chain immunoglobulin variable domain region (LCVR) of an antibody that binds GITR, wherein the HCVR comprises a light chain CDR1 (LCDR1) comprising SEQ ID NO: 404, a light chain CDR2 (LCDR2) comprising SEQ ID NO: 406, and a light chain CDR3 (LCDR3) comprising SEQ ID NO: 408.

22. An isolated host cell comprising the expression vector of claim 21.

23. The host cell of claim 22, wherein the host cell is a mammalian cell or a prokaryotic cell.

24. The host cell of claim 22, wherein the host cell is a Chinese Hamster Ovary (CHO) cell or an *Escherichia coli* (*E. coli*) cell.

25. A method of producing an anti-human GITR antibody or antigen-binding fragment thereof, the method comprising growing the host cell of claim 22 under conditions permitting production of the antibody or antigen-binding fragment thereof, wherein said host cell comprises both a nucleic acid molecule comprising a nucleic acid sequence encoding said HCVR and a nucleic acid molecule comprising a nucleic acid sequence encoding said LCVR.

26. The method of claim 25, further comprising formulating the antibody or antigen-binding fragment thereof as a pharmaceutical composition comprising an acceptable carrier.

* * * * *

SEQUENCE LISTING

<160> NUMBER OF SEQ ID NOS: 413

<210> SEQ ID NO 1
<211> LENGTH: 369
<212> TYPE: DNA
<213> ORGANISM: Artificial Sequence
<220> FEATURE:
<223> OTHER INFORMATION: synthetic

<400> SEQUENCE: 1

```
caggtgcagc tggtggagtc tgggggaggc gtggtccagc ctgggaggtc cctgagactc        60
tcctgtgcag cgtctggatt caccttcagt agttatggca tggactgggt ccgccaggct       120
ccaggcaagg gctggagtg gtggcagtt atatggtatc ctggaagtaa taaatactat        180
gcagactccg tgaagggccg attcaccgtc tccagagaca attccaagaa cacgctgtat       240
ctgcaaatga acagcctgag agccgaggac acggctgtgt attactgtgc gagagacgga       300
gaactgggac tggactacta ctccggcatg gacgtctggg gccaagggac cacggtcacc       360
gtctcctca                                                              369
```

<210> SEQ ID NO 2
<211> LENGTH: 123
<212> TYPE: PRT
<213> ORGANISM: Artificial Sequence
<220> FEATURE:
<223> OTHER INFORMATION: synthetic

<400> SEQUENCE: 2

Gln Val Gln Leu Val Glu Ser Gly Gly Gly Val Val Gln Pro Gly Arg
1               5                   10                  15

Ser Leu Arg Leu Ser Cys Ala Ala Ser Gly Phe Thr Phe Ser Ser Tyr
            20                  25                  30

Gly Met Asp Trp Val Arg Gln Ala Pro Gly Lys Gly Leu Glu Trp Val
        35                  40                  45

Ala Val Ile Trp Tyr Pro Gly Ser Asn Lys Tyr Tyr Ala Asp Ser Val
    50                  55                  60

Lys Gly Arg Phe Thr Val Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Asp Gly Glu Leu Gly Leu Asp Tyr Tyr Ser Gly Met Asp Val
            100                 105                 110

Trp Gly Gln Gly Thr Thr Val Thr Val Ser Ser
        115                 120

<210> SEQ ID NO 3
<211> LENGTH: 24
<212> TYPE: DNA
<213> ORGANISM: Artificial Sequence
<220> FEATURE:
<223> OTHER INFORMATION: synthetic

<400> SEQUENCE: 3

```
ggattcacct tcagtagtta tggc                                              24
```

<210> SEQ ID NO 4
<211> LENGTH: 8
<212> TYPE: PRT
<213> ORGANISM: Artificial Sequence
<220> FEATURE:
<223> OTHER INFORMATION: synthetic

<400> SEQUENCE: 4

Gly Phe Thr Phe Ser Ser Tyr Gly
1               5

<210> SEQ ID NO 5
<211> LENGTH: 24
<212> TYPE: DNA
<213> ORGANISM: Artificial Sequence
<220> FEATURE:
<223> OTHER INFORMATION: synthetic

<400> SEQUENCE: 5
atatggtatc ctggaagtaa taaa                                          24

<210> SEQ ID NO 6
<211> LENGTH: 8
<212> TYPE: PRT
<213> ORGANISM: Artificial Sequence
<220> FEATURE:
<223> OTHER INFORMATION: synthetic

<400> SEQUENCE: 6

Ile Trp Tyr Pro Gly Ser Asn Lys
1               5

<210> SEQ ID NO 7
<211> LENGTH: 48
<212> TYPE: DNA
<213> ORGANISM: Artificial Sequence
<220> FEATURE:
<223> OTHER INFORMATION: synthetic

<400> SEQUENCE: 7
gcgagagacg gagaactggg actggactac tactccggca tggacgtc                48

<210> SEQ ID NO 8
<211> LENGTH: 16
<212> TYPE: PRT
<213> ORGANISM: Artificial Sequence
<220> FEATURE:
<223> OTHER INFORMATION: synthetic

<400> SEQUENCE: 8

Ala Arg Asp Gly Glu Leu Gly Leu Asp Tyr Tyr Ser Gly Met Asp Val
1               5                   10                  15

<210> SEQ ID NO 9
<211> LENGTH: 321
<212> TYPE: DNA
<213> ORGANISM: Artificial Sequence
<220> FEATURE:
<223> OTHER INFORMATION: synthetic

<400> SEQUENCE: 9
gacatccaga tgacccagtc tccatcctcc ctgtctgcat ctgtaggaga cagagtcacc    60
atcacttgcc gggcaagtca gggcattaga aatgatttaa actggtatca gcagaaacca   120
gggaaagccc ctaagcgcct gatcaatggt gcatccagtt tgcaaagtgg ggtcccatca   180
aggttcagcg gcagtggatc tgggacagaa ttcactctca caatcagcag cctgcagcct   240
gaagattttg caacttatta ctgtctacaa cttaatagtt accctcggac gttcggccaa   300
gggaccaagg tggaaatcaa a                                             321

```
<210> SEQ ID NO 10
<211> LENGTH: 107
<212> TYPE: PRT
<213> ORGANISM: Artificial Sequence
<220> FEATURE:
<223> OTHER INFORMATION: synthetic

<400> SEQUENCE: 10
```

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Gly Ile Arg Asn Asp
            20                  25                  30

Leu Asn Trp Tyr Gln Gln Lys Pro Gly Lys Ala Pro Lys Arg Leu Ile
        35                  40                  45

Asn Gly Ala Ser Ser Leu Gln Ser Gly Val Pro Ser Arg Phe Ser Gly
    50                  55                  60

Ser Gly Ser Gly Thr Glu Phe Thr Leu Thr Ile Ser Ser Leu Gln Pro
65                  70                  75                  80

Glu Asp Phe Ala Thr Tyr Tyr Cys Leu Gln Leu Asn Ser Tyr Pro Arg
                85                  90                  95

Thr Phe Gly Gln Gly Thr Lys Val Glu Ile Lys
            100                 105

```
<210> SEQ ID NO 11
<211> LENGTH: 18
<212> TYPE: DNA
<213> ORGANISM: Artificial Sequence
<220> FEATURE:
<223> OTHER INFORMATION: synthetic

<400> SEQUENCE: 11
cagggcatta gaaatgat                                                      18

<210> SEQ ID NO 12
<211> LENGTH: 6
<212> TYPE: PRT
<213> ORGANISM: Artificial Sequence
<220> FEATURE:
<223> OTHER INFORMATION: synthetic

<400> SEQUENCE: 12
```

Gln Gly Ile Arg Asn Asp
1               5

```
<210> SEQ ID NO 13
<211> LENGTH: 9
<212> TYPE: DNA
<213> ORGANISM: Artificial Sequence
<220> FEATURE:
<223> OTHER INFORMATION: synthetic

<400> SEQUENCE: 13 ggtgcatcc                                                                 9

<210> SEQ ID NO 14
<211> LENGTH: 3
<212> TYPE: PRT
<213> ORGANISM: Artificial Sequence
<220> FEATURE:
<223> OTHER INFORMATION: synthetic

<400> SEQUENCE: 14
```

Gly Ala Ser
1

<210> SEQ ID NO 15
<211> LENGTH: 27
<212> TYPE: DNA
<213> ORGANISM: Artificial Sequence
<220> FEATURE:
<223> OTHER INFORMATION: synthetic

<400> SEQUENCE: 15
ctacaactta atagttaccc tcggacg                                          27

<210> SEQ ID NO 16
<211> LENGTH: 9
<212> TYPE: PRT
<213> ORGANISM: Artificial Sequence
<220> FEATURE:
<223> OTHER INFORMATION: synthetic

<400> SEQUENCE: 16

Leu Gln Leu Asn Ser Tyr Pro Arg Thr
1               5

<210> SEQ ID NO 17
<211> LENGTH: 369
<212> TYPE: DNA
<213> ORGANISM: Artificial Sequence
<220> FEATURE:
<223> OTHER INFORMATION: synthetic

<400> SEQUENCE: 17
caggtgcagc tggtggagtc tgggggaggc gtggtccagc ctggggaggtc cctgagactc      60 tcctgtgcag cgtctggatt caccttcagc aactatggca tgcactgggt ccgccaggct     120
ccaggcaagg ggctggagtg gtggcagtt atatggtatc ctggaagtaa taagttctat      180
acagactccg tggagggccg attcaccatc tccagagaca attccaagaa cacggtatat     240
ctacaaatgg acagcctgag agccgaagac acggctgtgt attactgtgc gagagggggg     300
gcactggggg tagactatta ctacggtatg gacgtctggg gccaagggac cacggtcacc     360
gtctcctca                                                             369

<210> SEQ ID NO 18
<211> LENGTH: 123
<212> TYPE: PRT
<213> ORGANISM: Artificial Sequence
<220> FEATURE:
<223> OTHER INFORMATION: synthetic

<400> SEQUENCE: 18

Gln Val Gln Leu Val Glu Ser Gly Gly Gly Val Val Gln Pro Gly Arg
1               5                   10                  15

Ser Leu Arg Leu Ser Cys Ala Ala Ser Gly Phe Thr Phe Ser Asn Tyr
            20                  25                  30

Gly Met His Trp Val Arg Gln Ala Pro Gly Lys Gly Leu Glu Trp Val
        35                  40                  45

Ala Val Ile Trp Tyr Pro Gly Ser Asn Lys Phe Tyr Thr Asp Ser Val
    50                  55                  60

Glu Gly Arg Phe Thr Ile Ser Arg Asp Asn Ser Lys Asn Thr Val Tyr
65                  70                  75                  80

Leu Gln Met Asp Ser Leu Arg Ala Glu Asp Thr Ala Val Tyr Tyr Cys
                85                  90                  95

Ala Arg Gly Gly Ala Leu Gly Val Asp Tyr Tyr Tyr Gly Met Asp Val

```
              100                 105                 110
Trp Gly Gln Gly Thr Thr Val Thr Val Ser Ser
        115                 120
```

<210> SEQ ID NO 19
<211> LENGTH: 24
<212> TYPE: DNA
<213> ORGANISM: Artificial Sequence
<220> FEATURE:
<223> OTHER INFORMATION: synthetic

<400> SEQUENCE: 19
ggattcacct tcagcaacta tggc                                        24

<210> SEQ ID NO 20
<211> LENGTH: 8
<212> TYPE: PRT
<213> ORGANISM: Artificial Sequence
<220> FEATURE:
<223> OTHER INFORMATION: synthetic

<400> SEQUENCE: 20

```
Gly Phe Thr Phe Ser Asn Tyr Gly
1               5
```

<210> SEQ ID NO 21
<211> LENGTH: 24
<212> TYPE: DNA
<213> ORGANISM: Artificial Sequence
<220> FEATURE:
<223> OTHER INFORMATION: synthetic

<400> SEQUENCE: 21
atatggtatc ctggaagtaa taag                                        24

<210> SEQ ID NO 22
<211> LENGTH: 8
<212> TYPE: PRT
<213> ORGANISM: Artificial Sequence
<220> FEATURE:
<223> OTHER INFORMATION: synthetic

<400> SEQUENCE: 22

```
Ile Trp Tyr Pro Gly Ser Asn Lys
1               5
```

<210> SEQ ID NO 23
<211> LENGTH: 48
<212> TYPE: DNA
<213> ORGANISM: Artificial Sequence
<220> FEATURE:
<223> OTHER INFORMATION: synthetic

<400> SEQUENCE: 23
gcgagagggg gggcactggg ggtagactat tactacggta tggacgtc              48

<210> SEQ ID NO 24
<211> LENGTH: 16
<212> TYPE: PRT
<213> ORGANISM: Artificial Sequence
<220> FEATURE:
<223> OTHER INFORMATION: synthetic

<400> SEQUENCE: 24

```
Ala Arg Gly Gly Ala Leu Gly Val Asp Tyr Tyr Tyr Gly Met Asp Val
1               5                   10                  15
```

<210> SEQ ID NO 25
<211> LENGTH: 321
<212> TYPE: DNA
<213> ORGANISM: Artificial Sequence
<220> FEATURE:
<223> OTHER INFORMATION: synthetic

<400> SEQUENCE: 25

```
gccatccaga tgacccagtc tccatcctcc ctgtctgcat ctgtaggaga cagagtcacc    60
ctcacttgcc gggcaagtca gggcattaga aatgatttag ctggtatca gcagaaacca   120
gggaaagccc ctaatttcct gatctattct gcatccagtt tacaaagtgg ggtcccatca   180
aggttcagcg gcagtggatc tggcacagat ttcactctca ccatcagcag cctacagcct   240
gaggattttg caacttatta ctgtctacaa aattacaatt acccgtggac gttcggccaa   300
gggaccaagg tggaaatcaa a                                             321
```

<210> SEQ ID NO 26
<211> LENGTH: 107
<212> TYPE: PRT
<213> ORGANISM: Artificial Sequence
<220> FEATURE:
<223> OTHER INFORMATION: synthetic

<400> SEQUENCE: 26

```
Ala Ile Gln Met Thr Gln Ser Pro Ser Ser Leu Ser Ala Ser Val Gly
1               5                   10                  15

Asp Arg Val Thr Leu Thr Cys Arg Ala Ser Gln Gly Ile Arg Asn Asp
            20                  25                  30

Leu Gly Trp Tyr Gln Gln Lys Pro Gly Lys Ala Pro Asn Phe Leu Ile
        35                  40                  45

Tyr Ser Ala Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Leu Gln Asn Tyr Asn Tyr Pro Trp
                85                  90                  95

Thr Phe Gly Gln Gly Thr Lys Val Glu Ile Lys
            100                 105
```

<210> SEQ ID NO 27
<211> LENGTH: 18
<212> TYPE: DNA
<213> ORGANISM: Artificial Sequence
<220> FEATURE:
<223> OTHER INFORMATION: synthetic

<400> SEQUENCE: 27

```
cagggcatta gaaatgat                                                  18
```

<210> SEQ ID NO 28
<211> LENGTH: 6
<212> TYPE: PRT
<213> ORGANISM: Artificial Sequence
<220> FEATURE:
<223> OTHER INFORMATION: synthetic

<400> SEQUENCE: 28

```
Gln Gly Ile Arg Asn Asp
1               5
```

<210> SEQ ID NO 29
<211> LENGTH: 9
<212> TYPE: DNA
<213> ORGANISM: Artificial Sequence
<220> FEATURE:
<223> OTHER INFORMATION: synthetic

<400> SEQUENCE: 29 tctgcatcc                                                                 9

<210> SEQ ID NO 30
<211> LENGTH: 3
<212> TYPE: PRT
<213> ORGANISM: Artificial Sequence
<220> FEATURE:
<223> OTHER INFORMATION: synthetic

<400> SEQUENCE: 30

Ser Ala Ser
1

<210> SEQ ID NO 31
<211> LENGTH: 27
<212> TYPE: DNA
<213> ORGANISM: Artificial Sequence
<220> FEATURE:
<223> OTHER INFORMATION: synthetic

<400> SEQUENCE: 31
ctacaaaatt acaattaccc gtggacg                                            27

<210> SEQ ID NO 32
<211> LENGTH: 9
<212> TYPE: PRT
<213> ORGANISM: Artificial Sequence
<220> FEATURE:
<223> OTHER INFORMATION: synthetic

<400> SEQUENCE: 32

Leu Gln Asn Tyr Asn Tyr Pro Trp Thr
1               5

<210> SEQ ID NO 33
<211> LENGTH: 372
<212> TYPE: DNA
<213> ORGANISM: Artificial Sequence
<220> FEATURE:
<223> OTHER INFORMATION: synthetic

<400> SEQUENCE: 33
caggtgcagc tggtggagtc tgggggaggc gtggtccagc ctggggaggtc cctgagactc        60 tcctgtgttg cgtctggatt caccttcagt gactatggca tgcactgggt ccgccaggct       120
ccaggcaagg ggctagagtg ggtggcagtt atatggtatg aaggaagtaa taaatattat       180
gcagactccg tgacgggccg attcaccatc tccagagaca attccaagaa cacgctgttt       240
ctgcaaatga acagtctgaa agccgaagac acggctgagt attattgtgc gaaagatggg       300
gggcagctcg cctaccagta ttactacggc atggacgtct ggggccaagg gaccacggtc       360
accgtctcct ca                                                          372

<210> SEQ ID NO 34
<211> LENGTH: 124
<212> TYPE: PRT
<213> ORGANISM: Artificial Sequence
<220> FEATURE:
<223> OTHER INFORMATION: synthetic

<400> SEQUENCE: 34

Gln Val Gln Leu Val Glu Ser Gly Gly Gly Val Val Gln Pro Gly Arg
1               5                   10                  15

Ser Leu Arg Leu Ser Cys Val Ala Ser Gly Phe Thr Phe Ser Asp Tyr
            20                  25                  30

Gly Met His Trp Val Arg Gln Ala Pro Gly Lys Gly Leu Glu Trp Val
        35                  40                  45

Ala Val Ile Trp Tyr Glu Gly Ser Asn Lys Tyr Tyr Ala Asp Ser Val
    50                  55                  60

Thr Gly Arg Phe Thr Ile Ser Arg Asp Asn Ser Lys Asn Thr Leu Phe
65                  70                  75                  80

Leu Gln Met Asn Ser Leu Lys Ala Glu Asp Thr Ala Glu Tyr Tyr Cys
                85                  90                  95

Ala Lys Asp Gly Gly Gln Leu Ala Tyr Gln Tyr Tyr Tyr Gly Met Asp
            100                 105                 110

Val Trp Gly Gln Gly Thr Thr Val Thr Val Ser Ser
        115                 120

<210> SEQ ID NO 35
<211> LENGTH: 24
<212> TYPE: DNA
<213> ORGANISM: Artificial Sequence
<220> FEATURE:
<223> OTHER INFORMATION: synthetic

<400> SEQUENCE: 35
ggattcacct tcagtgacta tggc                                         24

<210> SEQ ID NO 36
<211> LENGTH: 8
<212> TYPE: PRT
<213> ORGANISM: Artificial Sequence
<220> FEATURE:
<223> OTHER INFORMATION: synthetic

<400> SEQUENCE: 36

Gly Phe Thr Phe Ser Asp Tyr Gly
1               5

<210> SEQ ID NO 37
<211> LENGTH: 24
<212> TYPE: DNA
<213> ORGANISM: Artificial Sequence
<220> FEATURE:
<223> OTHER INFORMATION: synthetic

<400> SEQUENCE: 37
atatggtatg aaggaagtaa taaa                                         24

<210> SEQ ID NO 38
<211> LENGTH: 8
<212> TYPE: PRT
<213> ORGANISM: Artificial Sequence
<220> FEATURE:
<223> OTHER INFORMATION: synthetic

<400> SEQUENCE: 38

Ile Trp Tyr Glu Gly Ser Asn Lys
1               5

<210> SEQ ID NO 39
<211> LENGTH: 51
<212> TYPE: DNA
<213> ORGANISM: Artificial Sequence
<220> FEATURE:
<223> OTHER INFORMATION: synthetic

<400> SEQUENCE: 39
gcgaaagatg gggggcagct cgcctaccag tattactacg gcatggacgt c    51

<210> SEQ ID NO 40
<211> LENGTH: 17
<212> TYPE: PRT
<213> ORGANISM: Artificial Sequence
<220> FEATURE:
<223> OTHER INFORMATION: synthetic

<400> SEQUENCE: 40

Ala Lys Asp Gly Gly Gln Leu Ala Tyr Gln Tyr Tyr Tyr Gly Met Asp
1               5                   10                  15
Val

<210> SEQ ID NO 41
<211> LENGTH: 321
<212> TYPE: DNA
<213> ORGANISM: Artificial Sequence
<220> FEATURE:
<223> OTHER INFORMATION: synthetic

<400> SEQUENCE: 41
gccatccaga tgacccagtc tccatcctcc ctgtctgcat ctgtaggaga cagagtcacc     60
ctcacttgcc gggcaagtca gggcattaga aatgatttag ctggtatca gcagaaacca    120 ggaaaagccc ctaagagcct gatctatgct gcttccaatt tacaaagtgg agtcccttca    180
aggttcagcg gcagtggatc tggcacagat ttcactctca ccatcagcag cctgcagcct    240
gaggattctg caacttatta ctgtctacaa gactacaatt accctcggac gttcggccaa    300
gggaccaagg tggaaatcaa a                                              321

<210> SEQ ID NO 42
<211> LENGTH: 107
<212> TYPE: PRT
<213> ORGANISM: Artificial Sequence
<220> FEATURE:
<223> OTHER INFORMATION: synthetic

<400> SEQUENCE: 42

Ala Ile Gln Met Thr Gln Ser Pro Ser Ser Leu Ser Ala Ser Val Gly
1               5                   10                  15
Asp Arg Val Thr Leu Thr Cys Arg Ala Ser Gln Gly Ile Arg Asn Asp
            20                  25                  30
Leu Gly Trp Tyr Gln Gln Lys Pro Gly Lys Ala Pro Lys Ser Leu Ile
        35                  40                  45
Tyr Ala Ala Ser Asn Leu Gln Ser Gly Val Pro Ser Arg Phe Ser Gly
    50                  55                  60
Ser Gly Ser Gly Thr Asp Phe Thr Leu Thr Ile Ser Ser Leu Gln Pro
65                  70                  75                  80
Glu Asp Ser Ala Thr Tyr Tyr Cys Leu Gln Asp Tyr Asn Tyr Pro Arg
                85                  90                  95
Thr Phe Gly Gln Gly Thr Lys Val Glu Ile Lys
            100                 105

<210> SEQ ID NO 43
<211> LENGTH: 18
<212> TYPE: DNA
<213> ORGANISM: Artificial Sequence
<220> FEATURE:
<223> OTHER INFORMATION: synthetic

<400> SEQUENCE: 43
cagggcatta gaaatgat                                                 18

<210> SEQ ID NO 44
<211> LENGTH: 6
<212> TYPE: PRT
<213> ORGANISM: Artificial Sequence
<220> FEATURE:
<223> OTHER INFORMATION: synthetic

<400> SEQUENCE: 44

Gln Gly Ile Arg Asn Asp
1               5

<210> SEQ ID NO 45
<211> LENGTH: 9
<212> TYPE: DNA
<213> ORGANISM: Artificial Sequence
<220> FEATURE:
<223> OTHER INFORMATION: synthetic

<400> SEQUENCE: 45 gctgcttcc                                                            9

<210> SEQ ID NO 46
<211> LENGTH: 3
<212> TYPE: PRT
<213> ORGANISM: Artificial Sequence
<220> FEATURE:
<223> OTHER INFORMATION: synthetic

<400> SEQUENCE: 46

Ala Ala Ser
1

<210> SEQ ID NO 47
<211> LENGTH: 27
<212> TYPE: DNA
<213> ORGANISM: Artificial Sequence
<220> FEATURE:
<223> OTHER INFORMATION: synthetic

<400> SEQUENCE: 47
ctacaagact acaattaccc tcggacg                                       27

<210> SEQ ID NO 48
<211> LENGTH: 9
<212> TYPE: PRT
<213> ORGANISM: Artificial Sequence
<220> FEATURE:
<223> OTHER INFORMATION: synthetic

<400> SEQUENCE: 48

Leu Gln Asp Tyr Asn Tyr Pro Arg Thr
1               5

<210> SEQ ID NO 49
<211> LENGTH: 369

```
<212> TYPE: DNA
<213> ORGANISM: Artificial Sequence
<220> FEATURE:
<223> OTHER INFORMATION: synthetic

<400> SEQUENCE: 49
caggtgcagc tggtggagtc tgggggaggc gtggtccagc ctgggaggtc cctgagactc      60
tcctgtgcag cgtctggatt caacttcagg agctatggca tgcactgggt ccgccaggct     120
ccaggcaagg ggctggagtg gtggcagtt atatggtatg atggaagtaa taaatattat      180
gcagactccg tgaagggccg attcaccatc tccagagaca gttccaggga cacgctgttt     240
ctgcaaatga acagcctgag agccggggac acggctgtgt attactgtgc gagaggaggt     300
atgttgggac gggactacta ctacggtatg gacgtctggg gccaagggac cacggtcacc     360
gtctcctca                                                              369

<210> SEQ ID NO 50
<211> LENGTH: 123
<212> TYPE: PRT
<213> ORGANISM: Artificial Sequence
<220> FEATURE:
<223> OTHER INFORMATION: synthetic

<400> SEQUENCE: 50

Gln Val Gln Leu Val Glu Ser Gly Gly Gly Val Val Gln Pro Gly Arg
1               5                   10                  15

Ser Leu Arg Leu Ser Cys Ala Ala Ser Gly Phe Asn Phe Arg Ser Tyr
                20                  25                  30

Gly Met His Trp Val Arg Gln Ala Pro Gly Lys Gly Leu Glu Trp Val
            35                  40                  45

Ala Val Ile Trp Tyr Asp Gly Ser Asn Lys Tyr Tyr Ala Asp Ser Val
        50                  55                  60

Lys Gly Arg Phe Thr Ile Ser Arg Asp Ser Ser Arg Asp Thr Leu Phe
65                  70                  75                  80

Leu Gln Met Asn Ser Leu Arg Ala Gly Asp Thr Ala Val Tyr Tyr Cys
                85                  90                  95

Ala Arg Gly Gly Met Leu Gly Arg Asp Tyr Tyr Tyr Gly Met Asp Val
            100                 105                 110

Trp Gly Gln Gly Thr Thr Val Thr Val Ser Ser
        115                 120

<210> SEQ ID NO 51
<211> LENGTH: 24
<212> TYPE: DNA
<213> ORGANISM: Artificial Sequence
<220> FEATURE:
<223> OTHER INFORMATION: synthetic

<400> SEQUENCE: 51
ggattcaact tcaggagcta tggc                                              24

<210> SEQ ID NO 52
<211> LENGTH: 8
<212> TYPE: PRT
<213> ORGANISM: Artificial Sequence
<220> FEATURE:
<223> OTHER INFORMATION: synthetic

<400> SEQUENCE: 52

Gly Phe Asn Phe Arg Ser Tyr Gly
1               5
```

<210> SEQ ID NO 53
<211> LENGTH: 24
<212> TYPE: DNA
<213> ORGANISM: Artificial Sequence
<220> FEATURE:
<223> OTHER INFORMATION: synthetic

<400> SEQUENCE: 53
atatggtatg atggaagtaa taaa						24

<210> SEQ ID NO 54
<211> LENGTH: 8
<212> TYPE: PRT
<213> ORGANISM: Artificial Sequence
<220> FEATURE:
<223> OTHER INFORMATION: synthetic

<400> SEQUENCE: 54

Ile Trp Tyr Asp Gly Ser Asn Lys
1               5

<210> SEQ ID NO 55
<211> LENGTH: 48
<212> TYPE: DNA
<213> ORGANISM: Artificial Sequence
<220> FEATURE:
<223> OTHER INFORMATION: synthetic

<400> SEQUENCE: 55
gcgagaggag gtatgttggg acgggactac tactacggta tggacgtc				48

<210> SEQ ID NO 56
<211> LENGTH: 16
<212> TYPE: PRT
<213> ORGANISM: Artificial Sequence
<220> FEATURE:
<223> OTHER INFORMATION: synthetic

<400> SEQUENCE: 56

Ala Arg Gly Gly Met Leu Gly Arg Asp Tyr Tyr Tyr Gly Met Asp Val
1               5                   10                  15

<210> SEQ ID NO 57
<211> LENGTH: 321
<212> TYPE: DNA
<213> ORGANISM: Artificial Sequence
<220> FEATURE:
<223> OTHER INFORMATION: synthetic

<400> SEQUENCE: 57
gacatccaga tgacccagtc tccatcctcc ctgtctgcat ctgtaggaga cagagtcacc     60
atcacttgcc gggcaagtca gggcattaga aatgatttag ctggtatca gcagaaacca    120 gggaaagccc ctaagcgcct gatctatgct gcatccagtt tgcaaagtgg ggtcccatca   180
aggttcagcg gcagtggatc tgggacagaa ttcactctca caatcagcag cctgcagcct   240
gaagattttg caacttatta ctgtctacaa cataatagtt acccgaacac ttttggccag   300
gggaccaagc tggagatcaa a                                              321

<210> SEQ ID NO 58
<211> LENGTH: 107
<212> TYPE: PRT
<213> ORGANISM: Artificial Sequence
<220> FEATURE:

<223> OTHER INFORMATION: synthetic

<400> SEQUENCE: 58

Asp Ile Gln Met Thr Gln Ser Pro Ser Ser Leu Ser Ala Ser Val Gly
1               5                   10                  15
Asp Arg Val Thr Ile Thr Cys Arg Ala Ser Gln Gly Ile Arg Asn Asp
            20                  25                  30
Leu Gly Trp Tyr Gln Gln Lys Pro Gly Lys Ala Pro Lys Arg Leu Ile
        35                  40                  45
Tyr Ala Ala Ser Ser Leu Gln Ser Gly Val Pro Ser Arg Phe Ser Gly
    50                  55                  60
Ser Gly Ser Gly Thr Glu Phe Thr Leu Thr Ile Ser Ser Leu Gln Pro
65                  70                  75                  80
Glu Asp Phe Ala Thr Tyr Tyr Cys Leu Gln His Asn Ser Tyr Pro Asn
                85                  90                  95
Thr Phe Gly Gln Gly Thr Lys Leu Glu Ile Lys
            100                 105

<210> SEQ ID NO 59
<211> LENGTH: 18
<212> TYPE: DNA
<213> ORGANISM: Artificial Sequence
<220> FEATURE:
<223> OTHER INFORMATION: synthetic

<400> SEQUENCE: 59
cagggcatta gaaatgat                                                 18

<210> SEQ ID NO 60
<211> LENGTH: 6
<212> TYPE: PRT
<213> ORGANISM: Artificial Sequence
<220> FEATURE:
<223> OTHER INFORMATION: synthetic

<400> SEQUENCE: 60

Gln Gly Ile Arg Asn Asp
1               5

<210> SEQ ID NO 61
<211> LENGTH: 9
<212> TYPE: DNA
<213> ORGANISM: Artificial Sequence
<220> FEATURE:
<223> OTHER INFORMATION: synthetic

<400> SEQUENCE: 61 gctgcatcc                                                            9

<210> SEQ ID NO 62
<211> LENGTH: 3
<212> TYPE: PRT
<213> ORGANISM: Artificial Sequence
<220> FEATURE:
<223> OTHER INFORMATION: synthetic

<400> SEQUENCE: 62

Ala Ala Ser
1

<210> SEQ ID NO 63
<211> LENGTH: 27
<212> TYPE: DNA

<210> SEQ ID NO 64
<211> LENGTH: 9
<212> TYPE: PRT
<213> ORGANISM: Artificial Sequence
<220> FEATURE:
<223> OTHER INFORMATION: synthetic

<400> SEQUENCE: 63
ctacaacata atagttaccc gaacact                                              27

<210> SEQ ID NO 64
<211> LENGTH: 9
<212> TYPE: PRT
<213> ORGANISM: Artificial Sequence
<220> FEATURE:
<223> OTHER INFORMATION: synthetic

<400> SEQUENCE: 64

Leu Gln His Asn Ser Tyr Pro Asn Thr
1               5

<210> SEQ ID NO 65
<211> LENGTH: 369
<212> TYPE: DNA
<213> ORGANISM: Artificial Sequence
<220> FEATURE:
<223> OTHER INFORMATION: synthetic

<400> SEQUENCE: 65
caggtgcagc tggtggagtc tgggggaggc gcggtccagc ctgggacgtc cctgagactc          60
tcctgcgcgg cgtctggatt caccttcagt agttttggca tgcactgggt ccgccaggct         120
ccaggcaagg ggctggagtg ggtgtcagtt atatggtatg agggagtaa taaatattat          180 gcagattcag tgaagggccg attcaccatc tccagagaca attccagaaa cacgctgagt         240
ctgcaaatgg acagcctgag agtcgaggac acggctgtgt attactgtgc gagaggtggg         300
gaactgggag tcaactacta ttacgatatg gacgtctggg gccaagggac cacggtcacc         360
gtctcctca                                                                369

<210> SEQ ID NO 66
<211> LENGTH: 123
<212> TYPE: PRT
<213> ORGANISM: Artificial Sequence
<220> FEATURE:
<223> OTHER INFORMATION: synthetic

<400> SEQUENCE: 66

Gln Val Gln Leu Val Glu Ser Gly Gly Gly Ala Val Gln Pro Gly Thr
1               5                   10                  15

Ser Leu Arg Leu Ser Cys Ala Ala Ser Gly Phe Thr Phe Ser Ser Phe
            20                  25                  30

Gly Met His Trp Val Arg Gln Ala Pro Gly Lys Gly Leu Glu Trp Val
        35                  40                  45

Ser Val Ile Trp Tyr Glu Gly Ser Asn Lys Tyr Tyr Ala Asp Ser Val
    50                  55                  60

Lys Gly Arg Phe Thr Ile Ser Arg Asp Asn Ser Arg Asn Thr Leu Ser
65                  70                  75                  80

Leu Gln Met Asp Ser Leu Arg Val Glu Asp Thr Ala Val Tyr Tyr Cys
                85                  90                  95

Ala Arg Gly Gly Glu Leu Gly Val Asn Tyr Tyr Tyr Asp Met Asp Val
            100                 105                 110

Trp Gly Gln Gly Thr Thr Val Thr Val Ser Ser
        115                 120

<210> SEQ ID NO 67
<211> LENGTH: 24
<212> TYPE: DNA
<213> ORGANISM: Artificial Sequence
<220> FEATURE:
<223> OTHER INFORMATION: synthetic

<400> SEQUENCE: 67
ggattcacct tcagtagttt tggc                                              24

<210> SEQ ID NO 68
<211> LENGTH: 8
<212> TYPE: PRT
<213> ORGANISM: Artificial Sequence
<220> FEATURE:
<223> OTHER INFORMATION: synthetic

<400> SEQUENCE: 68

Gly Phe Thr Phe Ser Ser Phe Gly
1               5

<210> SEQ ID NO 69
<211> LENGTH: 24
<212> TYPE: DNA
<213> ORGANISM: Artificial Sequence
<220> FEATURE:
<223> OTHER INFORMATION: synthetic

<400> SEQUENCE: 69
atatggtatg aggggagtaa taaa                                              24

<210> SEQ ID NO 70
<211> LENGTH: 8
<212> TYPE: PRT
<213> ORGANISM: Artificial Sequence
<220> FEATURE:
<223> OTHER INFORMATION: synthetic

<400> SEQUENCE: 70

Ile Trp Tyr Glu Gly Ser Asn Lys
1               5

<210> SEQ ID NO 71
<211> LENGTH: 48
<212> TYPE: DNA
<213> ORGANISM: Artificial Sequence
<220> FEATURE:
<223> OTHER INFORMATION: synthetic

<400> SEQUENCE: 71
gcgagaggtg gggaactggg agtcaactac tattacgata tggacgtc                    48

<210> SEQ ID NO 72
<211> LENGTH: 16
<212> TYPE: PRT
<213> ORGANISM: Artificial Sequence
<220> FEATURE:
<223> OTHER INFORMATION: synthetic

<400> SEQUENCE: 72

Ala Arg Gly Gly Glu Leu Gly Val Asn Tyr Tyr Tyr Asp Met Asp Val
1               5                   10                  15

<210> SEQ ID NO 73
<211> LENGTH: 321
<212> TYPE: DNA

<213> ORGANISM: Artificial Sequence
<220> FEATURE:
<223> OTHER INFORMATION: synthetic

<400> SEQUENCE: 73

```
gacatccaga tgacccagtc tccatcctcc ctgtctgcat ctgtaggaga cagagtcacc    60
atcacttgcc gggcaagtca ggacattaaa aatgatttag gctggtttca gcagaaggca   120
ggtaaagccc ctaagcgcct gttctatgct acatccagtt tgcaaagtgg ggtcccatca   180
cggttcagcg gcagtggatc tgggacagaa ttcactctca caatcagcag cctgcagcct   240
gaagattttg caacttatta ctgtctacag gttcatagtt accctcggac gttcggccaa   300
gggaccaagg tggaaatcaa a                                             321
```

<210> SEQ ID NO 74
<211> LENGTH: 107
<212> TYPE: PRT
<213> ORGANISM: Artificial Sequence
<220> FEATURE:
<223> OTHER INFORMATION: synthetic

<400> SEQUENCE: 74

```
Asp Ile Gln Met Thr Gln Ser Pro Ser Ser Leu Ser Ala Ser Val Gly
1               5                   10                  15
Asp Arg Val Thr Ile Thr Cys Arg Ala Ser Gln Asp Ile Lys Asn Asp
            20                  25                  30
Leu Gly Trp Phe Gln Gln Lys Ala Gly Lys Ala Pro Lys Arg Leu Phe
        35                  40                  45
Tyr Ala Thr Ser Ser Leu Gln Ser Gly Val Pro Ser Arg Phe Ser Gly
    50                  55                  60
Ser Gly Ser Gly Thr Glu Phe Thr Leu Thr Ile Ser Ser Leu Gln Pro
65                  70                  75                  80
Glu Asp Phe Ala Thr Tyr Tyr Cys Leu Gln Val His Ser Tyr Pro Arg
                85                  90                  95
Thr Phe Gly Gln Gly Thr Lys Val Glu Ile Lys
            100                 105
```

<210> SEQ ID NO 75
<211> LENGTH: 18
<212> TYPE: DNA
<213> ORGANISM: Artificial Sequence
<220> FEATURE:
<223> OTHER INFORMATION: synthetic

<400> SEQUENCE: 75

```
caggacatta aaaatgat                                                  18
```

<210> SEQ ID NO 76
<211> LENGTH: 6
<212> TYPE: PRT
<213> ORGANISM: Artificial Sequence
<220> FEATURE:
<223> OTHER INFORMATION: synthetic

<400> SEQUENCE: 76

```
Gln Asp Ile Lys Asn Asp
1               5
```

<210> SEQ ID NO 77
<211> LENGTH: 9
<212> TYPE: DNA
<213> ORGANISM: Artificial Sequence
<220> FEATURE:
<223> OTHER INFORMATION: synthetic

<400> SEQUENCE: 77 gctacatcc                                                              9

<210> SEQ ID NO 78
<211> LENGTH: 3
<212> TYPE: PRT
<213> ORGANISM: Artificial Sequence
<220> FEATURE:
<223> OTHER INFORMATION: synthetic

<400> SEQUENCE: 78

Ala Thr Ser
1

<210> SEQ ID NO 79
<211> LENGTH: 27
<212> TYPE: DNA
<213> ORGANISM: Artificial Sequence
<220> FEATURE:
<223> OTHER INFORMATION: synthetic

<400> SEQUENCE: 79
ctacaggttc atagttaccc tcggacg                                         27

<210> SEQ ID NO 80
<211> LENGTH: 9
<212> TYPE: PRT
<213> ORGANISM: Artificial Sequence
<220> FEATURE:
<223> OTHER INFORMATION: synthetic

<400> SEQUENCE: 80

Leu Gln Val His Ser Tyr Pro Arg Thr
1               5

<210> SEQ ID NO 81
<211> LENGTH: 369
<212> TYPE: DNA
<213> ORGANISM: Artificial Sequence
<220> FEATURE:
<223> OTHER INFORMATION: synthetic

<400> SEQUENCE: 81
caggtgcagc tggtggagtc tgggggaggc gtggtccagc ctggggaggtc cctgagactc     60 tcctgtgaag cgtctggatt caccttcagc aactatggct ttcactgggt ccgccaggct    120
ccaggcaagg ggctggattg ggtggcagtt atatggtatg ctggaagtaa taagttctat    180
gtagactccg tgcagggccg attcaccatc tccagagaca attccaaaca atatattgttt   240 cttcaaatga acagcctgag agccgaggac tcggctgttt attactgtgt gagagggggg    300
atactgggca tagactacta ctccggtatg gacgtctggg gccaagggac cacggtcacc    360
gtctcctca                                                            369

<210> SEQ ID NO 82
<211> LENGTH: 123
<212> TYPE: PRT
<213> ORGANISM: Artificial Sequence
<220> FEATURE:
<223> OTHER INFORMATION: synthetic

<400> SEQUENCE: 82

Gln Val Gln Leu Val Glu Ser Gly Gly Val Val Gln Pro Gly Arg
1               5                   10                  15

Ser Leu Arg Leu Ser Cys Glu Ala Ser Gly Phe Thr Phe Ser Asn Tyr
            20                  25                  30

Gly Phe His Trp Val Arg Gln Ala Pro Gly Lys Gly Leu Asp Trp Val
        35                  40                  45

Ala Val Ile Trp Tyr Ala Gly Ser Asn Lys Phe Tyr Val Asp Ser Val
    50                  55                  60

Gln Gly Arg Phe Thr Ile Ser Arg Asp Asn Ser Lys Gln Ile Leu Phe
65                  70                  75                  80

Leu Gln Met Asn Ser Leu Arg Ala Glu Asp Ser Ala Val Tyr Tyr Cys
                85                  90                  95

Val Arg Gly Gly Ile Leu Gly Ile Asp Tyr Tyr Ser Gly Met Asp Val
            100                 105                 110

Trp Gly Gln Gly Thr Thr Val Thr Val Ser Ser
        115                 120

<210> SEQ ID NO 83
<211> LENGTH: 24
<212> TYPE: DNA
<213> ORGANISM: Artificial Sequence
<220> FEATURE:
<223> OTHER INFORMATION: synthetic

<400> SEQUENCE: 83
ggattcacct tcagcaacta tggc                                          24

<210> SEQ ID NO 84
<211> LENGTH: 8
<212> TYPE: PRT
<213> ORGANISM: Artificial Sequence
<220> FEATURE:
<223> OTHER INFORMATION: synthetic

<400> SEQUENCE: 84

Gly Phe Thr Phe Ser Asn Tyr Gly
1               5

<210> SEQ ID NO 85
<211> LENGTH: 24
<212> TYPE: DNA
<213> ORGANISM: Artificial Sequence
<220> FEATURE:
<223> OTHER INFORMATION: synthetic

<400> SEQUENCE: 85
atatggtatg ctggaagtaa taag                                          24

<210> SEQ ID NO 86
<211> LENGTH: 8
<212> TYPE: PRT
<213> ORGANISM: Artificial Sequence
<220> FEATURE:
<223> OTHER INFORMATION: synthetic

<400> SEQUENCE: 86

Ile Trp Tyr Ala Gly Ser Asn Lys
1               5

<210> SEQ ID NO 87
<211> LENGTH: 48
<212> TYPE: DNA
<213> ORGANISM: Artificial Sequence
<220> FEATURE:
<223> OTHER INFORMATION: synthetic

<400> SEQUENCE: 87
gtgagagggg ggatactggg catagactac tactccggta tggacgtc                48

<210> SEQ ID NO 88
<211> LENGTH: 16
<212> TYPE: PRT
<213> ORGANISM: Artificial Sequence
<220> FEATURE:
<223> OTHER INFORMATION: synthetic

<400> SEQUENCE: 88

Val Arg Gly Gly Ile Leu Gly Ile Asp Tyr Tyr Ser Gly Met Asp Val
1               5                   10                  15

<210> SEQ ID NO 89
<211> LENGTH: 321
<212> TYPE: DNA
<213> ORGANISM: Artificial Sequence
<220> FEATURE:
<223> OTHER INFORMATION: synthetic

<400> SEQUENCE: 89
gccatccaga tgacccagtc accatcctcc ctgtctgcat ctgtaggaga cagagtcacc     60
atcacttgcc gggcaagtca ggacattaga aatgatttag ctggtatca gcagagacca    120 gggaaggccc ctaagttcct gatctattct acatccagtt tacaaagtgg ggtcccatca   180
agattcagcg gcagtggatc tggcacagat ttcattctca ccatcagcag cctgcagcct   240
gaggattttg ccacttatta ctgtctacaa agtcacaatt atccgtggac gttcggccac   300
gggaccaagg tggaaatcaa a                                              321

<210> SEQ ID NO 90
<211> LENGTH: 107
<212> TYPE: PRT
<213> ORGANISM: Artificial Sequence
<220> FEATURE:
<223> OTHER INFORMATION: synthetic

<400> SEQUENCE: 90

Ala Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Ile Arg Asn Asp
                20                  25                  30

Leu Gly Trp Tyr Gln Gln Arg Pro Gly Lys Ala Pro Lys Phe Leu Ile
            35                  40                  45

Tyr Ser Thr Ser Ser Leu Gln Ser Gly Val Pro Ser Arg Phe Ser Gly
        50                  55                  60

Ser Gly Ser Gly Thr Asp Phe Ile Leu Thr Ile Ser Ser Leu Gln Pro
65                  70                  75                  80

Glu Asp Phe Ala Thr Tyr Tyr Cys Leu Gln Ser His Asn Tyr Pro Trp
                85                  90                  95

Thr Phe Gly His Gly Thr Lys Val Glu Ile Lys
            100                 105

<210> SEQ ID NO 91
<211> LENGTH: 18
<212> TYPE: DNA
<213> ORGANISM: Artificial Sequence
<220> FEATURE:

<223> OTHER INFORMATION: synthetic

<400> SEQUENCE: 91
caggacatta gaaatgat                                                      18

<210> SEQ ID NO 92
<211> LENGTH: 6
<212> TYPE: PRT
<213> ORGANISM: Artificial Sequence
<220> FEATURE:
<223> OTHER INFORMATION: synthetic

<400> SEQUENCE: 92

Gln Asp Ile Arg Asn Asp
1               5

<210> SEQ ID NO 93
<211> LENGTH: 9
<212> TYPE: DNA
<213> ORGANISM: Artificial Sequence
<220> FEATURE:
<223> OTHER INFORMATION: synthetic

<400> SEQUENCE: 93 tctacatcc                                                                 9

<210> SEQ ID NO 94
<211> LENGTH: 3
<212> TYPE: PRT
<213> ORGANISM: Artificial Sequence
<220> FEATURE:
<223> OTHER INFORMATION: synthetic

<400> SEQUENCE: 94

Ser Thr Ser
1

<210> SEQ ID NO 95
<211> LENGTH: 27
<212> TYPE: DNA
<213> ORGANISM: Artificial Sequence
<220> FEATURE:
<223> OTHER INFORMATION: synthetic

<400> SEQUENCE: 95
ctacaaagtc acaattatcc gtggacg                                            27

<210> SEQ ID NO 96
<211> LENGTH: 9
<212> TYPE: PRT
<213> ORGANISM: Artificial Sequence
<220> FEATURE:
<223> OTHER INFORMATION: synthetic

<400> SEQUENCE: 96

Leu Gln Ser His Asn Tyr Pro Trp Thr
1               5

<210> SEQ ID NO 97
<211> LENGTH: 369
<212> TYPE: DNA
<213> ORGANISM: Artificial Sequence
<220> FEATURE:
<223> OTHER INFORMATION: synthetic

<400> SEQUENCE: 97

```
caggtgcagc tggtggagtc tggggaggc gtggtccagc ctgggaggtc cctgagactc    60
tcctgtgcag tgtctggatt caccctcagt agttatggca tggactgggt ccgccaggct   120
ccaggcaagg ggctggagtg ggtggcagtt atatggtatg acggaagtaa taaatactat   180
tcagactccg tgaagggccg attcaccatc tccagagaca attccaagaa cacactgttt   240
ctgcaaatga acagcctgag agccgacgac acggctgtgt attattgtgc gagagacggg   300
gaactgggac tggactacta ctccggtatg gacgtctggg gccaagggac cacggtcacc   360
gtctcctca                                                            369
```

<210> SEQ ID NO 98
<211> LENGTH: 123
<212> TYPE: PRT
<213> ORGANISM: Artificial Sequence
<220> FEATURE:
<223> OTHER INFORMATION: synthetic

<400> SEQUENCE: 98

```
Gln Val Gln Leu Val Glu Ser Gly Gly Gly Val Val Gln Pro Gly Arg
1               5                   10                  15

Ser Leu Arg Leu Ser Cys Ala Val Ser Gly Phe Thr Leu Ser Ser Tyr
            20                  25                  30

Gly Met Asp Trp Val Arg Gln Ala Pro Gly Lys Gly Leu Glu Trp Val
        35                  40                  45

Ala Val Ile Trp Tyr Asp Gly Ser Asn Lys Tyr Tyr Ser Asp Ser Val
    50                  55                  60

Lys Gly Arg Phe Thr Ile Ser Arg Asp Asn Ser Lys Asn Thr Leu Phe
65                  70                  75                  80

Leu Gln Met Asn Ser Leu Arg Ala Asp Asp Thr Ala Val Tyr Tyr Cys
                85                  90                  95

Ala Arg Asp Gly Glu Leu Gly Leu Asp Tyr Tyr Ser Gly Met Asp Val
            100                 105                 110

Trp Gly Gln Gly Thr Thr Val Thr Val Ser Ser
        115                 120
```

<210> SEQ ID NO 99
<211> LENGTH: 24
<212> TYPE: DNA
<213> ORGANISM: Artificial Sequence
<220> FEATURE:
<223> OTHER INFORMATION: synthetic

<400> SEQUENCE: 99

```
ggattcaccc tcagtagtta tggc                                            24
```

<210> SEQ ID NO 100
<211> LENGTH: 8
<212> TYPE: PRT
<213> ORGANISM: Artificial Sequence
<220> FEATURE:
<223> OTHER INFORMATION: synthetic

<400> SEQUENCE: 100

```
Gly Phe Thr Leu Ser Ser Tyr Gly
1               5
```

<210> SEQ ID NO 101
<211> LENGTH: 24
<212> TYPE: DNA
<213> ORGANISM: Artificial Sequence
<220> FEATURE:

<223> OTHER INFORMATION: synthetic

<400> SEQUENCE: 101
atatggtatg acggaagtaa taaa                                          24

<210> SEQ ID NO 102
<211> LENGTH: 8
<212> TYPE: PRT
<213> ORGANISM: Artificial Sequence
<220> FEATURE:
<223> OTHER INFORMATION: synthetic

<400> SEQUENCE: 102

Ile Trp Tyr Asp Gly Ser Asn Lys
1               5

<210> SEQ ID NO 103
<211> LENGTH: 48
<212> TYPE: DNA
<213> ORGANISM: Artificial Sequence
<220> FEATURE:
<223> OTHER INFORMATION: synthetic

<400> SEQUENCE: 103
gcgagagacg gggaactggg actggactac tactccggta tggacgtc               48

<210> SEQ ID NO 104
<211> LENGTH: 16
<212> TYPE: PRT
<213> ORGANISM: Artificial Sequence
<220> FEATURE:
<223> OTHER INFORMATION: synthetic

<400> SEQUENCE: 104

Ala Arg Asp Gly Glu Leu Gly Leu Asp Tyr Tyr Ser Gly Met Asp Val
1               5                   10                  15

<210> SEQ ID NO 105
<211> LENGTH: 321
<212> TYPE: DNA
<213> ORGANISM: Artificial Sequence
<220> FEATURE:
<223> OTHER INFORMATION: synthetic

<400> SEQUENCE: 105
gacatccaga tgacccagtc tccatcctcc ctgtctgcat ctgtaggaga cagagtcacc    60
atcacttgcc gggcaagtca ggacattaga aatgatttag ctggtatca gcagaaacca   120 gggaaagccc ctaagcgcct gatctatggt gcatccagtt tgcaaagtgg tgtcccatca   180
aggttcagcg gcagtggatc tgggacagag ttcactctca caatcagcag cctgcagcct   240
gaagattttg caacttatta ttgtctacag cttaatagtt accctcggac gttcggccaa   300
gggaccaagg tggaaatcaa a                                            321

<210> SEQ ID NO 106
<211> LENGTH: 107
<212> TYPE: PRT
<213> ORGANISM: Artificial Sequence
<220> FEATURE:
<223> OTHER INFORMATION: synthetic

<400> SEQUENCE: 106

Asp Ile Gln Met Thr Gln Ser Pro Ser Ser Leu Ser Ala Ser Val Gly
1               5                   10                  15

```
Asp Arg Val Thr Ile Thr Cys Arg Ala Ser Gln Asp Ile Arg Asn Asp
            20                  25                  30

Leu Gly Trp Tyr Gln Gln Lys Pro Gly Lys Ala Pro Lys Arg Leu Ile
        35                  40                  45

Tyr Gly Ala Ser Ser Leu Gln Ser Gly Val Pro Ser Arg Phe Ser Gly
    50                  55                  60

Ser Gly Ser Gly Thr Glu Phe Thr Leu Thr Ile Ser Ser Leu Gln Pro
65                  70                  75                  80

Glu Asp Phe Ala Thr Tyr Tyr Cys Leu Gln Leu Asn Ser Tyr Pro Arg
                85                  90                  95

Thr Phe Gly Gln Gly Thr Lys Val Glu Ile Lys
            100                 105
```

<210> SEQ ID NO 107
<211> LENGTH: 18
<212> TYPE: DNA
<213> ORGANISM: Artificial Sequence
<220> FEATURE:
<223> OTHER INFORMATION: synthetic

<400> SEQUENCE: 107
caggacatta gaaatgat        18

<210> SEQ ID NO 108
<211> LENGTH: 6
<212> TYPE: PRT
<213> ORGANISM: Artificial Sequence
<220> FEATURE:
<223> OTHER INFORMATION: synthetic

<400> SEQUENCE: 108

Gln Asp Ile Arg Asn Asp
1               5

<210> SEQ ID NO 109
<211> LENGTH: 9
<212> TYPE: DNA
<213> ORGANISM: Artificial Sequence
<220> FEATURE:
<223> OTHER INFORMATION: synthetic

<400> SEQUENCE: 109 ggtgcatcc        9

<210> SEQ ID NO 110
<211> LENGTH: 3
<212> TYPE: PRT
<213> ORGANISM: Artificial Sequence
<220> FEATURE:
<223> OTHER INFORMATION: synthetic

<400> SEQUENCE: 110

Gly Ala Ser
1

<210> SEQ ID NO 111
<211> LENGTH: 27
<212> TYPE: DNA
<213> ORGANISM: Artificial Sequence
<220> FEATURE:
<223> OTHER INFORMATION: synthetic

<400> SEQUENCE: 111
ctacagctta atagttaccc tcggacg        27

<210> SEQ ID NO 112
<211> LENGTH: 9
<212> TYPE: PRT
<213> ORGANISM: Artificial Sequence
<220> FEATURE:
<223> OTHER INFORMATION: synthetic

<400> SEQUENCE: 112

Leu Gln Leu Asn Ser Tyr Pro Arg Thr
1               5

<210> SEQ ID NO 113
<211> LENGTH: 354
<212> TYPE: DNA
<213> ORGANISM: Artificial Sequence
<220> FEATURE:
<223> OTHER INFORMATION: synthetic

<400> SEQUENCE: 113
caggtgcagc tggtggagtc tgggggaggc gtggtccagc ctggagggtc cctgagactc       60
tcctgtgcag cctctggatt caccttcagt agctttggca tgcactgggt ccgccaggct      120
ccaggcaagg ggctggagtg ggtggcagtg atatcatatg atggaagaaa tagatactat      180
gcagactccg tgaagggccg attcaccatc tccagagaca attccaagaa cacgctgtat      240
ctgcaaatga acagtctgag cgctgaggac acggctatgt tttactgtgc gaaagatggc      300
tttggcaact cttttgacta ctggggccag ggaaccctgg tcaccgtctc ctca            354

<210> SEQ ID NO 114
<211> LENGTH: 118
<212> TYPE: PRT
<213> ORGANISM: Artificial Sequence
<220> FEATURE:
<223> OTHER INFORMATION: synthetic

<400> SEQUENCE: 114

Gln Val Gln Leu Val Glu Ser Gly Gly Gly Val Val Gln Pro Gly Arg
1               5                   10                  15

Ser Leu Arg Leu Ser Cys Ala Ala Ser Gly Phe Thr Phe Ser Ser Phe
            20                  25                  30

Gly Met His Trp Val Arg Gln Ala Pro Gly Lys Gly Leu Glu Trp Val
        35                  40                  45

Ala Val Ile Ser Tyr Asp Gly Arg Asn Arg Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Ser Ala Glu Asp Thr Ala Met Phe Tyr Cys
                85                  90                  95

Ala Lys Asp Gly Phe Gly Asn Ser Phe Asp Tyr Trp Gly Gln Gly Thr
            100                 105                 110

Leu Val Thr Val Ser Ser
        115

<210> SEQ ID NO 115
<211> LENGTH: 24
<212> TYPE: DNA
<213> ORGANISM: Artificial Sequence
<220> FEATURE:
<223> OTHER INFORMATION: synthetic

<400> SEQUENCE: 115

```
ggattcacct tcagtagctt tggc                                                24
```

<210> SEQ ID NO 116
<211> LENGTH: 8
<212> TYPE: PRT
<213> ORGANISM: Artificial Sequence
<220> FEATURE:
<223> OTHER INFORMATION: synthetic

<400> SEQUENCE: 116

```
Gly Phe Thr Phe Ser Ser Phe Gly
1               5
```

<210> SEQ ID NO 117
<211> LENGTH: 24
<212> TYPE: DNA
<213> ORGANISM: Artificial Sequence
<220> FEATURE:
<223> OTHER INFORMATION: synthetic

<400> SEQUENCE: 117

```
atatcatatg atggaagaaa taga                                                24
```

<210> SEQ ID NO 118
<211> LENGTH: 8
<212> TYPE: PRT
<213> ORGANISM: Artificial Sequence
<220> FEATURE:
<223> OTHER INFORMATION: synthetic

<400> SEQUENCE: 118

```
Ile Ser Tyr Asp Gly Arg Asn Arg
1               5
```

<210> SEQ ID NO 119
<211> LENGTH: 33
<212> TYPE: DNA
<213> ORGANISM: Artificial Sequence
<220> FEATURE:
<223> OTHER INFORMATION: synthetic

<400> SEQUENCE: 119

```
gcgaaagatg gctttggcaa ctcttttgac tac                                      33
```

<210> SEQ ID NO 120
<211> LENGTH: 11
<212> TYPE: PRT
<213> ORGANISM: Artificial Sequence
<220> FEATURE:
<223> OTHER INFORMATION: synthetic

<400> SEQUENCE: 120

```
Ala Lys Asp Gly Phe Gly Asn Ser Phe Asp Tyr
1               5                   10
```

<210> SEQ ID NO 121
<211> LENGTH: 336
<212> TYPE: DNA
<213> ORGANISM: Artificial Sequence
<220> FEATURE:
<223> OTHER INFORMATION: synthetic

<400> SEQUENCE: 121

```
gatgttgtga tgactcagtc tccactctcc ctgcccgtca cccttggaca gccggcctcc         60
atctcctgca ggtctagtca aagcctccta tacagtgatg gaaatacccta cttgacttgg       120
```

-continued

```
tttcagcaga ggccaggcca atctccaagg cgcctaattt ataaggtttc taaccgggac    180
tctggggtcc cagacagatt cagcggcagt gggtcaggca ctgatttcac actgacaatc    240
agcagggtgg aggctgagga tgttgggatt tattactgca tgcaaggcac acactggccg    300
tggacgtttg gccagggac caaggtggaa atcaaa                               336
```

<210> SEQ ID NO 122
<211> LENGTH: 112
<212> TYPE: PRT
<213> ORGANISM: Artificial Sequence
<220> FEATURE:
<223> OTHER INFORMATION: synthetic

<400> SEQUENCE: 122

```
Asp Val Val Met Thr Gln Ser Pro Leu Ser Leu Pro Val Thr Leu Gly
1               5                   10                  15

Gln Pro Ala Ser Ile Ser Cys Arg Ser Ser Gln Ser Leu Leu Tyr Ser
            20                  25                  30

Asp Gly Asn Thr Tyr Leu Thr Trp Phe Gln Gln Arg Pro Gly Gln Ser
        35                  40                  45

Pro Arg Arg Leu Ile Tyr Lys Val Ser Asn Arg Asp Ser Gly Val Pro
    50                  55                  60

Asp Arg Phe Ser Gly Ser Gly Ser Gly Thr Asp Phe Thr Leu Thr Ile
65                  70                  75                  80

Ser Arg Val Glu Ala Glu Asp Val Gly Ile Tyr Tyr Cys Met Gln Gly
                85                  90                  95

Thr His Trp Pro Trp Thr Phe Gly Gln Gly Thr Lys Val Glu Ile Lys
            100                 105                 110
```

<210> SEQ ID NO 123
<211> LENGTH: 33
<212> TYPE: DNA
<213> ORGANISM: Artificial Sequence
<220> FEATURE:
<223> OTHER INFORMATION: synthetic

<400> SEQUENCE: 123

```
caaagcctcc tatacagtga tggaaatacc tac                                 33
```

<210> SEQ ID NO 124
<211> LENGTH: 11
<212> TYPE: PRT
<213> ORGANISM: Artificial Sequence
<220> FEATURE:
<223> OTHER INFORMATION: synthetic

<400> SEQUENCE: 124

```
Gln Ser Leu Leu Tyr Ser Asp Gly Asn Thr Tyr
1               5                   10
```

<210> SEQ ID NO 125
<211> LENGTH: 9
<212> TYPE: DNA
<213> ORGANISM: Artificial Sequence
<220> FEATURE:
<223> OTHER INFORMATION: synthetic

<400> SEQUENCE: 125

```
aaggtttct                                                             9
```

<210> SEQ ID NO 126

<211> LENGTH: 3
<212> TYPE: PRT
<213> ORGANISM: Artificial Sequence
<220> FEATURE:
<223> OTHER INFORMATION: synthetic

<400> SEQUENCE: 126

Lys Val Ser
1

<210> SEQ ID NO 127
<211> LENGTH: 27
<212> TYPE: DNA
<213> ORGANISM: Artificial Sequence
<220> FEATURE:
<223> OTHER INFORMATION: synthetic

<400> SEQUENCE: 127
atgcaaggca cacactggcc gtggacg                                        27

<210> SEQ ID NO 128
<211> LENGTH: 9
<212> TYPE: PRT
<213> ORGANISM: Artificial Sequence
<220> FEATURE:
<223> OTHER INFORMATION: synthetic

<400> SEQUENCE: 128

Met Gln Gly Thr His Trp Pro Trp Thr
1               5

<210> SEQ ID NO 129
<211> LENGTH: 369
<212> TYPE: DNA
<213> ORGANISM: Artificial Sequence
<220> FEATURE:
<223> OTHER INFORMATION: synthetic

<400> SEQUENCE: 129
caggtgcagc tggtggagtc tgggggaggc gtggtccagc ctggggaggtc cctgagactc    60 tcctgtgaag cgtctggatt caccttcagt agctatggca tgcactgggt ccgccaggct   120
ccaggcaagg ggctggagtg ggtggcagtt atatggtaca gtgaaagtaa taaatactat   180
acagactcca tgaagggccg actcaccatc tccagagaca attccaagaa cacgctgtat   240
ttgcaaatga acagcctgag agccgaggac acggctgtgt attattgtgc gagagggggg   300
ctcctgggga agtactacta ctacggtatg gacgtctggg gccaagggac cacggtcacc   360
gtctcctca                                                           369

<210> SEQ ID NO 130
<211> LENGTH: 123
<212> TYPE: PRT
<213> ORGANISM: Artificial Sequence
<220> FEATURE:
<223> OTHER INFORMATION: synthetic

<400> SEQUENCE: 130

Gln Val Gln Leu Val Glu Ser Gly Gly Gly Val Val Gln Pro Gly Arg
1               5                   10                  15

Ser Leu Arg Leu Ser Cys Glu Ala Ser Gly Phe Thr Phe Ser Ser Tyr
            20                  25                  30

Gly Met His Trp Val Arg Gln Ala Pro Gly Lys Gly Leu Glu Trp Val
        35                  40                  45

Ala Val Ile Trp Tyr Ser Glu Ser Asn Lys Tyr Tyr Thr Asp Ser Met
 50                  55                  60

Lys Gly Arg Leu Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
                 85                  90                  95

Ala Arg Gly Gly Leu Leu Gly Lys Tyr Tyr Tyr Gly Met Asp Val
            100                 105                 110

Trp Gly Gln Gly Thr Thr Val Thr Val Ser Ser
        115                 120

<210> SEQ ID NO 131
<211> LENGTH: 24
<212> TYPE: DNA
<213> ORGANISM: Artificial Sequence
<220> FEATURE:
<223> OTHER INFORMATION: synthetic

<400> SEQUENCE: 131
ggattcacct tcagtagcta tggc					24

<210> SEQ ID NO 132
<211> LENGTH: 8
<212> TYPE: PRT
<213> ORGANISM: Artificial Sequence
<220> FEATURE:
<223> OTHER INFORMATION: synthetic

<400> SEQUENCE: 132

Gly Phe Thr Phe Ser Ser Tyr Gly
1               5

<210> SEQ ID NO 133
<211> LENGTH: 24
<212> TYPE: DNA
<213> ORGANISM: Artificial Sequence
<220> FEATURE:
<223> OTHER INFORMATION: synthetic

<400> SEQUENCE: 133
atatggtaca gtgaaagtaa taaa					24

<210> SEQ ID NO 134
<211> LENGTH: 8
<212> TYPE: PRT
<213> ORGANISM: Artificial Sequence
<220> FEATURE:
<223> OTHER INFORMATION: synthetic

<400> SEQUENCE: 134

Ile Trp Tyr Ser Glu Ser Asn Lys
1               5

<210> SEQ ID NO 135
<211> LENGTH: 48
<212> TYPE: DNA
<213> ORGANISM: Artificial Sequence
<220> FEATURE:
<223> OTHER INFORMATION: synthetic

<400> SEQUENCE: 135
gcgagagggg ggctcctggg gaagtactac tactacggta tggacgtc					48

<210> SEQ ID NO 136

```
<211> LENGTH: 16
<212> TYPE: PRT
<213> ORGANISM: Artificial Sequence
<220> FEATURE:
<223> OTHER INFORMATION: synthetic

<400> SEQUENCE: 136

Ala Arg Gly Gly Leu Leu Gly Lys Tyr Tyr Tyr Tyr Gly Met Asp Val
1               5                   10                  15

<210> SEQ ID NO 137
<211> LENGTH: 321
<212> TYPE: DNA
<213> ORGANISM: Artificial Sequence
<220> FEATURE:
<223> OTHER INFORMATION: synthetic

<400> SEQUENCE: 137
gacatccaga tgacccagtc tccatcctcc ctgtctgcat ctgtaggaga cagagtcatt      60
atcacttgcc gggcaagtca ggacattaga aatgatttag ctggtatca gcagaaacca     120 gggaaagccc ctaagcgcct gatctatgct gcatccagtt tgcaaagtgg ggtcccatca     180
aggttcagcg gcagtggatc tgggacagaa ttcactctca caatcagcag cctgcagcct     240
gaagattttg caacttttta ctgtctacag cttaatagtt acccgtacac ttttggccag     300
gggaccaagc tggagatcaa a                                               321

<210> SEQ ID NO 138
<211> LENGTH: 107
<212> TYPE: PRT
<213> ORGANISM: Artificial Sequence
<220> FEATURE:
<223> OTHER INFORMATION: synthetic

<400> SEQUENCE: 138

Asp Ile Gln Met Thr Gln Ser Pro Ser Ser Leu Ser Ala Ser Val Gly
1               5                   10                  15

Asp Arg Val Ile Ile Thr Cys Arg Ala Ser Gln Asp Ile Arg Asn Asp
            20                  25                  30

Leu Gly Trp Tyr Gln Gln Lys Pro Gly Lys Ala Pro Lys Arg Leu Ile
        35                  40                  45

Tyr Ala Ala Ser Ser Leu Gln Ser Gly Val Pro Ser Arg Phe Ser Gly
    50                  55                  60

Ser Gly Ser Gly Thr Glu Phe Thr Leu Thr Ile Ser Ser Leu Gln Pro
65                  70                  75                  80

Glu Asp Phe Ala Thr Phe Tyr Cys Leu Gln Leu Asn Ser Tyr Pro Tyr
                85                  90                  95

Thr Phe Gly Gln Gly Thr Lys Leu Glu Ile Lys
            100                 105

<210> SEQ ID NO 139
<211> LENGTH: 18
<212> TYPE: DNA
<213> ORGANISM: Artificial Sequence
<220> FEATURE:
<223> OTHER INFORMATION: synthetic

<400> SEQUENCE: 139
caggacatta gaaatgat                                                    18

<210> SEQ ID NO 140
<211> LENGTH: 6
```

```
<212> TYPE: PRT
<213> ORGANISM: Artificial Sequence
<220> FEATURE:
<223> OTHER INFORMATION: synthetic

<400> SEQUENCE: 140

Gln Asp Ile Arg Asn Asp
1               5

<210> SEQ ID NO 141
<211> LENGTH: 9
<212> TYPE: DNA
<213> ORGANISM: Artificial Sequence
<220> FEATURE:
<223> OTHER INFORMATION: synthetic

<400> SEQUENCE: 141 gctgcatcc                                                            9

<210> SEQ ID NO 142
<211> LENGTH: 3
<212> TYPE: PRT
<213> ORGANISM: Artificial Sequence
<220> FEATURE:
<223> OTHER INFORMATION: synthetic

<400> SEQUENCE: 142

Ala Ala Ser
1

<210> SEQ ID NO 143
<211> LENGTH: 27
<212> TYPE: DNA
<213> ORGANISM: Artificial Sequence
<220> FEATURE:
<223> OTHER INFORMATION: synthetic

<400> SEQUENCE: 143
ctacagctta atagttaccc gtacact                                       27

<210> SEQ ID NO 144
<211> LENGTH: 9
<212> TYPE: PRT
<213> ORGANISM: Artificial Sequence
<220> FEATURE:
<223> OTHER INFORMATION: synthetic

<400> SEQUENCE: 144

Leu Gln Leu Asn Ser Tyr Pro Tyr Thr
1               5

<210> SEQ ID NO 145
<211> LENGTH: 369
<212> TYPE: DNA
<213> ORGANISM: Artificial Sequence
<220> FEATURE:
<223> OTHER INFORMATION: synthetic

<400> SEQUENCE: 145
caggtgcagc tggtggagtc tgggggaggc gtggcccagc ctggggaggtc cctgagcctc    60 tcctgtgcag cgtctggatt caccttcagt gactatggca tgcactgggt ccgccaggct   120
ccaggcaagg ggctggagtg ggtggcggtt atttggtatg ctggaagtaa taaatattat   180
gcagactctg tgaaggaccg atttaccatc tccagagaca attccaagaa cacgctgtat   240
ctgcagatgc gcagcctgag agtcgaggac acggctgtat attactgtgc gagagggggg   300
```

```
gaattgcgtc ttgactacta ctccggtttg gacgtctggg gccaagggac cacggtcacc    360
gtctcctca                                                            369
```

<210> SEQ ID NO 146
<211> LENGTH: 123
<212> TYPE: PRT
<213> ORGANISM: Artificial Sequence
<220> FEATURE:
<223> OTHER INFORMATION: synthetic

<400> SEQUENCE: 146

```
Gln Val Gln Leu Val Glu Ser Gly Gly Gly Val Ala Gln Pro Gly Arg
1               5                   10                  15

Ser Leu Ser Leu Ser Cys Ala Ala Ser Gly Phe Thr Phe Ser Asp Tyr
            20                  25                  30

Gly Met His Trp Val Arg Gln Ala Pro Gly Lys Gly Leu Glu Trp Val
        35                  40                  45

Ala Val Ile Trp Tyr Ala Gly Ser Asn Lys Tyr Tyr Ala Asp Ser Val
    50                  55                  60

Lys Asp Arg Phe Thr Ile Ser Arg Asp Asn Ser Lys Asn Thr Leu Tyr
65                  70                  75                  80

Leu Gln Met Arg Ser Leu Arg Val Glu Asp Thr Ala Val Tyr Tyr Cys
                85                  90                  95

Ala Arg Gly Gly Glu Leu Arg Leu Asp Tyr Tyr Ser Gly Leu Asp Val
            100                 105                 110

Trp Gly Gln Gly Thr Thr Val Thr Val Ser Ser
        115                 120
```

<210> SEQ ID NO 147
<211> LENGTH: 24
<212> TYPE: DNA
<213> ORGANISM: Artificial Sequence
<220> FEATURE:
<223> OTHER INFORMATION: synthetic

<400> SEQUENCE: 147

```
ggattcacct tcagtgacta tggc                                           24
```

<210> SEQ ID NO 148
<211> LENGTH: 8
<212> TYPE: PRT
<213> ORGANISM: Artificial Sequence
<220> FEATURE:
<223> OTHER INFORMATION: synthetic

<400> SEQUENCE: 148

```
Gly Phe Thr Phe Ser Asp Tyr Gly
1               5
```

<210> SEQ ID NO 149
<211> LENGTH: 24
<212> TYPE: DNA
<213> ORGANISM: Artificial Sequence
<220> FEATURE:
<223> OTHER INFORMATION: synthetic

<400> SEQUENCE: 149

```
atttggtatg ctggaagtaa taaa                                           24
```

<210> SEQ ID NO 150
<211> LENGTH: 8

```
<212> TYPE: PRT
<213> ORGANISM: Artificial Sequence
<220> FEATURE:
<223> OTHER INFORMATION: synthetic

<400> SEQUENCE: 150

Ile Trp Tyr Ala Gly Ser Asn Lys
1               5

<210> SEQ ID NO 151
<211> LENGTH: 48
<212> TYPE: DNA
<213> ORGANISM: Artificial Sequence
<220> FEATURE:
<223> OTHER INFORMATION: synthetic

<400> SEQUENCE: 151
gcgagagggg gggaattgcg tcttgactac tactccggtt tggacgtc                    48

<210> SEQ ID NO 152
<211> LENGTH: 16
<212> TYPE: PRT
<213> ORGANISM: Artificial Sequence
<220> FEATURE:
<223> OTHER INFORMATION: synthetic

<400> SEQUENCE: 152

Ala Arg Gly Gly Glu Leu Arg Leu Asp Tyr Tyr Ser Gly Leu Asp Val
1               5                   10                  15

<210> SEQ ID NO 153
<211> LENGTH: 321
<212> TYPE: DNA
<213> ORGANISM: Artificial Sequence
<220> FEATURE:
<223> OTHER INFORMATION: synthetic

<400> SEQUENCE: 153
gacatccaga tgacccagtc tccatcctcc ctgtctgcat ctgtaggaga cagagtcacc        60
gtcacttgcc gggcaagtca gggcattaga agtgatttag ctggtatca gcagaaacca      120 ggaaaagccc ctaagcgcct gatctatgct gcatccagtt tccaaagtgg ggtcccatca      180
aggttcagcg gcagtggatc tgggacagaa ttcactctca caatcagcag cctgcaccct      240
gaagattttg ctacttatta ctgtctacag tctaataatt acccgtggac gttcggccaa      300
gggaccaagg tggaaatcaa a                                                 321

<210> SEQ ID NO 154
<211> LENGTH: 107
<212> TYPE: PRT
<213> ORGANISM: Artificial Sequence
<220> FEATURE:
<223> OTHER INFORMATION: synthetic

<400> SEQUENCE: 154

Asp Ile Gln Met Thr Gln Ser Pro Ser Ser Leu Ser Ala Ser Val Gly
1               5                   10                  15

Asp Arg Val Thr Val Thr Cys Arg Ala Ser Gln Gly Ile Arg Ser Asp
                20                  25                  30

Leu Gly Trp Tyr Gln Gln Lys Pro Gly Lys Ala Pro Lys Arg Leu Ile
            35                  40                  45

Tyr Ala Ala Ser Ser Phe Gln Ser Gly Val Pro Ser Arg Phe Ser Gly
        50                  55                  60
```

Ser Gly Ser Gly Thr Glu Phe Thr Leu Thr Ile Ser Ser Leu His Pro
65                  70                  75                  80

Glu Asp Phe Ala Thr Tyr Tyr Cys Leu Gln Ser Asn Asn Tyr Pro Trp
                85                  90                  95

Thr Phe Gly Gln Gly Thr Lys Val Glu Ile Lys
            100                 105

<210> SEQ ID NO 155
<211> LENGTH: 18
<212> TYPE: DNA
<213> ORGANISM: Artificial Sequence
<220> FEATURE:
<223> OTHER INFORMATION: synthetic

<400> SEQUENCE: 155
cagggcatta gaagtgat                                                18

<210> SEQ ID NO 156
<211> LENGTH: 6
<212> TYPE: PRT
<213> ORGANISM: Artificial Sequence
<220> FEATURE:
<223> OTHER INFORMATION: synthetic

<400> SEQUENCE: 156

Gln Gly Ile Arg Ser Asp
1               5

<210> SEQ ID NO 157
<211> LENGTH: 9
<212> TYPE: DNA
<213> ORGANISM: Artificial Sequence
<220> FEATURE:
<223> OTHER INFORMATION: synthetic

<400> SEQUENCE: 157 gctgcatcc                                                          9

<210> SEQ ID NO 158
<211> LENGTH: 3
<212> TYPE: PRT
<213> ORGANISM: Artificial Sequence
<220> FEATURE:
<223> OTHER INFORMATION: synthetic

<400> SEQUENCE: 158

Ala Ala Ser
1

<210> SEQ ID NO 159
<211> LENGTH: 27
<212> TYPE: DNA
<213> ORGANISM: Artificial Sequence
<220> FEATURE:
<223> OTHER INFORMATION: synthetic

<400> SEQUENCE: 159
ctacagtcta ataattaccc gtggacg                                      27

<210> SEQ ID NO 160
<211> LENGTH: 9
<212> TYPE: PRT
<213> ORGANISM: Artificial Sequence
<220> FEATURE:
<223> OTHER INFORMATION: synthetic

<400> SEQUENCE: 160

Leu Gln Ser Asn Asn Tyr Pro Trp Thr
1               5

<210> SEQ ID NO 161
<211> LENGTH: 372
<212> TYPE: DNA
<213> ORGANISM: Artificial Sequence
<220> FEATURE:
<223> OTHER INFORMATION: synthetic

<400> SEQUENCE: 161
caggtgcagc tggtggagtc tgggggaggc gtggtccagc cggggggggtc ccttagactc      60 tcctgtgcag tgtctggatt caccttcagt gactatggca tgcactgggt ccgccaggtt     120
ccaggcgcgg ggctggagtg gtggcagtt atttactatg aaggaagtaa caaatactat     180
gcagactccg tgaagggccg attcaccatc tccagagaca attccaagaa cacgctgtat     240
ctgcaaatga acagcctgag agtcgaggac acgtctatgt atttctgtgc gagaggcccc     300
cttctcggcg ggaacttcta ctcttacctt atggacgtct ggggccaggg gaccacggtc     360
accgtctcct ca                                                        372

<210> SEQ ID NO 162
<211> LENGTH: 124
<212> TYPE: PRT
<213> ORGANISM: Artificial Sequence
<220> FEATURE:
<223> OTHER INFORMATION: synthetic

<400> SEQUENCE: 162

Gln Val Gln Leu Val Glu Ser Gly Gly Gly Val Val Gln Pro Gly Gly
1               5                   10                  15

Ser Leu Arg Leu Ser Cys Ala Val Ser Gly Phe Thr Phe Ser Asp Tyr
            20                  25                  30

Gly Met His Trp Val Arg Gln Val Pro Gly Ala Gly Leu Glu Trp Val
        35                  40                  45

Ala Val Ile Tyr Tyr Glu Gly Ser Asn Lys Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Val Glu Asp Thr Ser Met Tyr Phe Cys
                85                  90                  95

Ala Arg Gly Pro Leu Leu Gly Gly Asn Phe Tyr Ser Tyr Leu Met Asp
            100                 105                 110

Val Trp Gly Gln Gly Thr Thr Val Thr Val Ser Ser
        115                 120

<210> SEQ ID NO 163
<211> LENGTH: 24
<212> TYPE: DNA
<213> ORGANISM: Artificial Sequence
<220> FEATURE:
<223> OTHER INFORMATION: synthetic

<400> SEQUENCE: 163
ggattcacct tcagtgacta tggc                                            24

<210> SEQ ID NO 164
<211> LENGTH: 8
<212> TYPE: PRT

```
<213> ORGANISM: Artificial Sequence
<220> FEATURE:
<223> OTHER INFORMATION: synthetic

<400> SEQUENCE: 164

Gly Phe Thr Phe Ser Asp Tyr Gly
1               5

<210> SEQ ID NO 165
<211> LENGTH: 24
<212> TYPE: DNA
<213> ORGANISM: Artificial Sequence
<220> FEATURE:
<223> OTHER INFORMATION: synthetic

<400> SEQUENCE: 165
atttactatg aaggaagtaa caaa                                           24

<210> SEQ ID NO 166
<211> LENGTH: 8
<212> TYPE: PRT
<213> ORGANISM: Artificial Sequence
<220> FEATURE:
<223> OTHER INFORMATION: synthetic

<400> SEQUENCE: 166

Ile Tyr Tyr Glu Gly Ser Asn Lys
1               5

<210> SEQ ID NO 167
<211> LENGTH: 51
<212> TYPE: DNA
<213> ORGANISM: Artificial Sequence
<220> FEATURE:
<223> OTHER INFORMATION: synthetic

<400> SEQUENCE: 167
gcgagaggcc cccttctcgg cgggaacttc tactcttacc ttatggacgt c            51

<210> SEQ ID NO 168
<211> LENGTH: 17
<212> TYPE: PRT
<213> ORGANISM: Artificial Sequence
<220> FEATURE:
<223> OTHER INFORMATION: synthetic

<400> SEQUENCE: 168

Ala Arg Gly Pro Leu Leu Gly Gly Asn Phe Tyr Ser Tyr Leu Met Asp
1               5                   10                  15

Val

<210> SEQ ID NO 169
<211> LENGTH: 321
<212> TYPE: DNA
<213> ORGANISM: Artificial Sequence
<220> FEATURE:
<223> OTHER INFORMATION: synthetic

<400> SEQUENCE: 169
gccatccaga tgacccagtc tccatcctcc ctgtctgcat ctgtaggaga cagagtcacc    60
atcacttgcc gggcaagtca gggcattaga aatggtttag ctggtatca gcagaaacca   120 gggaaagccc ctaaactcct gatctatact gcatccagtt tacaaagtgg agtcccatca   180
agattcagcg gcagtggatc tggcacagac ttcactctca ccatcagcag cctgcagcct   240
```

```
gaagattttg caacttatta ctgtctacaa gattacaatt acccttttcag tttcggccct    300 gggaccaaag tggatatcaa a                                               321
```

<210> SEQ ID NO 170
<211> LENGTH: 107
<212> TYPE: PRT
<213> ORGANISM: Artificial Sequence
<220> FEATURE:
<223> OTHER INFORMATION: synthetic

<400> SEQUENCE: 170

```
Ala Ile Gln Met Thr Gln Ser Pro Ser Leu Ser Ala Ser Val Gly
1               5                   10                  15

Asp Arg Val Thr Ile Thr Cys Arg Ala Ser Gln Gly Ile Arg Asn Gly
            20                  25                  30

Leu Gly Trp Tyr Gln Gln Lys Pro Gly Lys Ala Pro Lys Leu Leu Ile
        35                  40                  45

Tyr Thr Ala Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Leu Gln Asp Tyr Asn Tyr Pro Phe
                85                  90                  95

Ser Phe Gly Pro Gly Thr Lys Val Asp Ile Lys
            100                 105
```

<210> SEQ ID NO 171
<211> LENGTH: 18
<212> TYPE: DNA
<213> ORGANISM: Artificial Sequence
<220> FEATURE:
<223> OTHER INFORMATION: synthetic

<400> SEQUENCE: 171

```
cagggcatta gaaatggt                                                   18
```

<210> SEQ ID NO 172
<211> LENGTH: 6
<212> TYPE: PRT
<213> ORGANISM: Artificial Sequence
<220> FEATURE:
<223> OTHER INFORMATION: synthetic

<400> SEQUENCE: 172

```
Gln Gly Ile Arg Asn Gly
1               5
```

<210> SEQ ID NO 173
<211> LENGTH: 9
<212> TYPE: DNA
<213> ORGANISM: Artificial Sequence
<220> FEATURE:
<223> OTHER INFORMATION: synthetic

<400> SEQUENCE: 173

```
actgcatcc                                                             9
```

<210> SEQ ID NO 174
<211> LENGTH: 3
<212> TYPE: PRT
<213> ORGANISM: Artificial Sequence
<220> FEATURE:
<223> OTHER INFORMATION: synthetic

<400> SEQUENCE: 174

Thr Ala Ser
1

<210> SEQ ID NO 175
<211> LENGTH: 27
<212> TYPE: DNA
<213> ORGANISM: Artificial Sequence
<220> FEATURE:
<223> OTHER INFORMATION: synthetic

<400> SEQUENCE: 175
ctacaagatt acaattaccc tttcagt                                          27

<210> SEQ ID NO 176
<211> LENGTH: 9
<212> TYPE: PRT
<213> ORGANISM: Artificial Sequence
<220> FEATURE:
<223> OTHER INFORMATION: synthetic

<400> SEQUENCE: 176

Leu Gln Asp Tyr Asn Tyr Pro Phe Ser
1               5

<210> SEQ ID NO 177
<211> LENGTH: 372
<212> TYPE: DNA
<213> ORGANISM: Artificial Sequence
<220> FEATURE:
<223> OTHER INFORMATION: synthetic

<400> SEQUENCE: 177
caggtgcagc tggtggagtc tgggggaggc gtggtccagc ctggagggtc cctgagactc      60
tcctgtgcag cgtctggatt taccgtcaga aactatggca tgcactgggt ccgccaggct     120
ccaggcaagg ggctggagtg ggtggcagtt atatggtatg atggaagtaa taaatactat     180
gcagactccg tgaagggccg attcaccatc tccagagaca attccaagaa cacgctgttt     240
ctgcaaatga acagcctgag agccgaggac acggctgtgt attactgtgc gagaggggga     300
gagctggtac gtggggacta ctactacggt atggacgtct ggggccaagg gaccacggtc     360
accgtctcct ca                                                        372

<210> SEQ ID NO 178
<211> LENGTH: 124
<212> TYPE: PRT
<213> ORGANISM: Artificial Sequence
<220> FEATURE:
<223> OTHER INFORMATION: synthetic

<400> SEQUENCE: 178

Gln Val Gln Leu Val Glu Ser Gly Gly Gly Val Val Gln Pro Gly Arg
1               5                   10                  15

Ser Leu Arg Leu Ser Cys Ala Ala Ser Gly Phe Thr Val Arg Asn Tyr
            20                  25                  30

Gly Met His Trp Val Arg Gln Ala Pro Gly Lys Gly Leu Glu Trp Val
        35                  40                  45

Ala Val Ile Trp Tyr Asp Gly Ser Asn Lys Tyr Tyr Ala Asp Ser Val
    50                  55                  60

Lys Gly Arg Phe Thr Ile Ser Arg Asp Asn Ser Lys Asn Thr Leu Phe
65                  70                  75                  80

Leu Gln Met Asn Ser Leu Arg Ala Glu Asp Thr Ala Val Tyr Tyr Cys
            85                  90                  95

Ala Arg Gly Gly Glu Leu Val Arg Gly Asp Tyr Tyr Gly Met Asp
        100                 105                 110

Val Trp Gly Gln Gly Thr Thr Val Thr Val Ser Ser
        115                 120

<210> SEQ ID NO 179
<211> LENGTH: 24
<212> TYPE: DNA
<213> ORGANISM: Artificial Sequence
<220> FEATURE:
<223> OTHER INFORMATION: synthetic

<400> SEQUENCE: 179
ggatttaccg tcagaaacta tggc                                          24

<210> SEQ ID NO 180
<211> LENGTH: 8
<212> TYPE: PRT
<213> ORGANISM: Artificial Sequence
<220> FEATURE:
<223> OTHER INFORMATION: synthetic

<400> SEQUENCE: 180

Gly Phe Thr Val Arg Asn Tyr Gly
1               5

<210> SEQ ID NO 181
<211> LENGTH: 24
<212> TYPE: DNA
<213> ORGANISM: Artificial Sequence
<220> FEATURE:
<223> OTHER INFORMATION: synthetic

<400> SEQUENCE: 181
atatggtatg atggaagtaa taaa                                          24

<210> SEQ ID NO 182
<211> LENGTH: 8
<212> TYPE: PRT
<213> ORGANISM: Artificial Sequence
<220> FEATURE:
<223> OTHER INFORMATION: synthetic

<400> SEQUENCE: 182

Ile Trp Tyr Asp Gly Ser Asn Lys
1               5

<210> SEQ ID NO 183
<211> LENGTH: 51
<212> TYPE: DNA
<213> ORGANISM: Artificial Sequence
<220> FEATURE:
<223> OTHER INFORMATION: synthetic

<400> SEQUENCE: 183
gcgagagggg gagagctggt acgtggggac tactactacg gtatggacgt c            51

<210> SEQ ID NO 184
<211> LENGTH: 17
<212> TYPE: PRT
<213> ORGANISM: Artificial Sequence
<220> FEATURE:
<223> OTHER INFORMATION: synthetic

<400> SEQUENCE: 184

Ala Arg Gly Gly Glu Leu Val Arg Gly Asp Tyr Tyr Tyr Gly Met Asp
1               5                   10                  15
Val

<210> SEQ ID NO 185
<211> LENGTH: 321
<212> TYPE: DNA
<213> ORGANISM: Artificial Sequence
<220> FEATURE:
<223> OTHER INFORMATION: synthetic

<400> SEQUENCE: 185
gacatccaga tgacccagtc tccatcctcc ctgtctgcat ctgtaggaga cagagtcacc      60
atcacttgcc gggcaagtca gggcattaga aatgatttag gctggtatca gcagaaacca     120
gggaaagccc ctaagcgcct gatctatggt gcatccagtt tgcaaagtgg ggtcccatca     180
aggttcagcg gcagtggatc tgggacagaa ttcactctca caatcagcag cctgcagcct     240
gaagattttg caacttatta ctgtctacag cataatagtt acccgtacac ttttggccag     300
gggaccaagc tggagatcaa a                                                321

<210> SEQ ID NO 186
<211> LENGTH: 107
<212> TYPE: PRT
<213> ORGANISM: Artificial Sequence
<220> FEATURE:
<223> OTHER INFORMATION: synthetic

<400> SEQUENCE: 186

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Gly Ile Arg Asn Asp
            20                  25                  30

Leu Gly Trp Tyr Gln Gln Lys Pro Gly Lys Ala Pro Lys Arg Leu Ile
        35                  40                  45

Tyr Gly Ala Ser Ser Leu Gln Ser Gly Val Pro Ser Arg Phe Ser Gly
    50                  55                  60

Ser Gly Ser Gly Thr Glu Phe Thr Leu Thr Ile Ser Ser Leu Gln Pro
65                  70                  75                  80

Glu Asp Phe Ala Thr Tyr Tyr Cys Leu Gln His Asn Ser Tyr Pro Tyr
                85                  90                  95

Thr Phe Gly Gln Gly Thr Lys Leu Glu Ile Lys
            100                 105

<210> SEQ ID NO 187
<211> LENGTH: 18
<212> TYPE: DNA
<213> ORGANISM: Artificial Sequence
<220> FEATURE:
<223> OTHER INFORMATION: synthetic

<400> SEQUENCE: 187
cagggcatta gaaatgat                                                     18

<210> SEQ ID NO 188
<211> LENGTH: 6
<212> TYPE: PRT
<213> ORGANISM: Artificial Sequence
<220> FEATURE:

<223> OTHER INFORMATION: synthetic

<400> SEQUENCE: 188

Gln Gly Ile Arg Asn Asp
1               5

<210> SEQ ID NO 189
<211> LENGTH: 9
<212> TYPE: DNA
<213> ORGANISM: Artificial Sequence
<220> FEATURE:
<223> OTHER INFORMATION: synthetic

<400> SEQUENCE: 189 ggtgcatcc                                                                  9

<210> SEQ ID NO 190
<211> LENGTH: 3
<212> TYPE: PRT
<213> ORGANISM: Artificial Sequence
<220> FEATURE:
<223> OTHER INFORMATION: synthetic

<400> SEQUENCE: 190

Gly Ala Ser
1

<210> SEQ ID NO 191
<211> LENGTH: 27
<212> TYPE: DNA
<213> ORGANISM: Artificial Sequence
<220> FEATURE:
<223> OTHER INFORMATION: synthetic

<400> SEQUENCE: 191
ctacagcata atagttaccc gtacact                                              27

<210> SEQ ID NO 192
<211> LENGTH: 9
<212> TYPE: PRT
<213> ORGANISM: Artificial Sequence
<220> FEATURE:
<223> OTHER INFORMATION: synthetic

<400> SEQUENCE: 192

Leu Gln His Asn Ser Tyr Pro Tyr Thr
1               5

<210> SEQ ID NO 193
<211> LENGTH: 351
<212> TYPE: DNA
<213> ORGANISM: Artificial Sequence
<220> FEATURE:
<223> OTHER INFORMATION: synthetic

<400> SEQUENCE: 193
caggtgcagc tggtggagtc tgggggcggc gtggtccagc ctggggaggtc cctgagactc          60 tcctgtgcag cctctggaac tatcttcagt acccatggca tgcactgggt ccgccaggct         120
ccaggcaagg ggctggagtg gtggcagtt atatcatatg atggaaataa gaagtactat         180
gcaggctccg tgaagggccg attcaccatc tccagagaca attccaagaa cacgctgtat         240
ctgcaaatga acgacgttag atctgaggac acggctgttt atcactgtac gacagatatt         300
actggaatca cggactactg gggccaggga accctggtca ccgtctcctc a                  351

<210> SEQ ID NO 194
<211> LENGTH: 117
<212> TYPE: PRT
<213> ORGANISM: Artificial Sequence
<220> FEATURE:
<223> OTHER INFORMATION: synthetic

<400> SEQUENCE: 194

```
Gln Val Gln Leu Val Glu Ser Gly Gly Val Val Gln Pro Gly Arg
1               5                   10                  15

Ser Leu Arg Leu Ser Cys Ala Ala Ser Gly Thr Ile Phe Ser Thr His
                20                  25                  30

Gly Met His Trp Val Arg Gln Ala Pro Gly Lys Gly Leu Glu Trp Val
            35                  40                  45

Ala Val Ile Ser Tyr Asp Gly Asn Lys Lys Tyr Tyr Ala Gly Ser Val
        50                  55                  60

Lys Gly Arg Phe Thr Ile Ser Arg Asp Asn Ser Lys Asn Thr Leu Tyr
65                  70                  75                  80

Leu Gln Met Asn Asp Val Arg Ser Glu Asp Thr Ala Val Tyr His Cys
                85                  90                  95

Thr Thr Asp Ile Thr Gly Ile Thr Asp Tyr Trp Gly Gln Gly Thr Leu
            100                 105                 110

Val Thr Val Ser Ser
        115
```

<210> SEQ ID NO 195
<211> LENGTH: 24
<212> TYPE: DNA
<213> ORGANISM: Artificial Sequence
<220> FEATURE:
<223> OTHER INFORMATION: synthetic

<400> SEQUENCE: 195
ggaactatct tcagtaccca tggc                                          24

<210> SEQ ID NO 196
<211> LENGTH: 8
<212> TYPE: PRT
<213> ORGANISM: Artificial Sequence
<220> FEATURE:
<223> OTHER INFORMATION: synthetic

<400> SEQUENCE: 196

```
Gly Thr Ile Phe Ser Thr His Gly
1               5
```

<210> SEQ ID NO 197
<211> LENGTH: 24
<212> TYPE: DNA
<213> ORGANISM: Artificial Sequence
<220> FEATURE:
<223> OTHER INFORMATION: synthetic

<400> SEQUENCE: 197
atatcatatg atggaaataa gaag                                          24

<210> SEQ ID NO 198
<211> LENGTH: 8
<212> TYPE: PRT
<213> ORGANISM: Artificial Sequence
<220> FEATURE:
<223> OTHER INFORMATION: synthetic

<400> SEQUENCE: 198

Ile Ser Tyr Asp Gly Asn Lys Lys
1               5

<210> SEQ ID NO 199
<211> LENGTH: 30
<212> TYPE: DNA
<213> ORGANISM: Artificial Sequence
<220> FEATURE:
<223> OTHER INFORMATION: synthetic

<400> SEQUENCE: 199
acgacagata ttactggaat cacggactac                                   30

<210> SEQ ID NO 200
<211> LENGTH: 10
<212> TYPE: PRT
<213> ORGANISM: Artificial Sequence
<220> FEATURE:
<223> OTHER INFORMATION: synthetic

<400> SEQUENCE: 200

Thr Thr Asp Ile Thr Gly Ile Thr Asp Tyr
1               5                   10

<210> SEQ ID NO 201
<211> LENGTH: 318
<212> TYPE: DNA
<213> ORGANISM: Artificial Sequence
<220> FEATURE:
<223> OTHER INFORMATION: synthetic

<400> SEQUENCE: 201
gacatccaga tgacccagtc tccatcctcc ctgtctgcat ctgtaggaga cagagtcacc    60
atcacttgcc gggcaagtca gggcattgga aatgatttag ctggtatca gcagaaacta   120 gggaaggccc ctaagcgcct gatctatgct gcatccagtt tggagagtgg ggtcccatca   180
aggttcagcg gcagtggatc cgggacagaa ttcattctca caatcagcag cctgcaggct   240
gaagattttg caacttacta ctgtctacag cataatggtt tcccgacgtt cggccaaggg   300
accaaggtgg aaatcaaa                                                 318

<210> SEQ ID NO 202
<211> LENGTH: 106
<212> TYPE: PRT
<213> ORGANISM: Artificial Sequence
<220> FEATURE:
<223> OTHER INFORMATION: synthetic

<400> SEQUENCE: 202

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Gly Ile Gly Asn Asp
            20                  25                  30

Leu Gly Trp Tyr Gln Gln Lys Leu Gly Lys Ala Pro Lys Arg Leu Ile
        35                  40                  45

Tyr Ala Ala Ser Ser Leu Glu Ser Gly Val Pro Ser Arg Phe Ser Gly
    50                  55                  60

Ser Gly Ser Gly Thr Glu Phe Ile Leu Thr Ile Ser Ser Leu Gln Ala
65                  70                  75                  80

Glu Asp Phe Ala Thr Tyr Tyr Cys Leu Gln His Asn Gly Phe Pro Thr
                85                  90                  95

Phe Gly Gln Gly Thr Lys Val Glu Ile Lys
            100                 105

<210> SEQ ID NO 203
<211> LENGTH: 18
<212> TYPE: DNA
<213> ORGANISM: Artificial Sequence
<220> FEATURE:
<223> OTHER INFORMATION: synthetic

<400> SEQUENCE: 203
cagggcattg gaaatgat                                                   18

<210> SEQ ID NO 204
<211> LENGTH: 6
<212> TYPE: PRT
<213> ORGANISM: Artificial Sequence
<220> FEATURE:
<223> OTHER INFORMATION: synthetic

<400> SEQUENCE: 204

Gln Gly Ile Gly Asn Asp
1               5

<210> SEQ ID NO 205
<211> LENGTH: 9
<212> TYPE: DNA
<213> ORGANISM: Artificial Sequence
<220> FEATURE:
<223> OTHER INFORMATION: synthetic

<400> SEQUENCE: 205 gctgcatcc                                                              9

<210> SEQ ID NO 206
<211> LENGTH: 3
<212> TYPE: PRT
<213> ORGANISM: Artificial Sequence
<220> FEATURE:
<223> OTHER INFORMATION: synthetic

<400> SEQUENCE: 206

Ala Ala Ser
1

<210> SEQ ID NO 207
<211> LENGTH: 24
<212> TYPE: DNA
<213> ORGANISM: Artificial Sequence
<220> FEATURE:
<223> OTHER INFORMATION: synthetic

<400> SEQUENCE: 207
ctacagcata atggtttccc gacg                                            24

<210> SEQ ID NO 208
<211> LENGTH: 8
<212> TYPE: PRT
<213> ORGANISM: Artificial Sequence
<220> FEATURE:
<223> OTHER INFORMATION: synthetic

<400> SEQUENCE: 208

Leu Gln His Asn Gly Phe Pro Thr
1               5

<210> SEQ ID NO 209
<211> LENGTH: 363
<212> TYPE: DNA
<213> ORGANISM: Artificial Sequence
<220> FEATURE:
<223> OTHER INFORMATION: synthetic

<400> SEQUENCE: 209

```
caggtgcagc tggtggagtc tgggggaggc gtggtccagc ctgggaggtc cctgagactc      60
tcctgtgcag cgtctggatt caccttcagt aactatggca ttcactgggt ccgccagcct     120
ccaggccagg gcctggagtg gtggcagtt atatggtatg ctggaagtaa taagttttat     180
gcagattccg tgaagggccg attcaccatc tccagagaca attccaagaa ctcggcgtat     240
ctgcaaatga acagcctgag agccgaggat acgctgtgt attactgtgc gagagccccc     300
ctgggttatt actactacgg tatggacgtc tggggccaag gaccacggt caccgtctcc     360 tca                                                                   363
```

<210> SEQ ID NO 210
<211> LENGTH: 121
<212> TYPE: PRT
<213> ORGANISM: Artificial Sequence
<220> FEATURE:
<223> OTHER INFORMATION: synthetic

<400> SEQUENCE: 210

Gln Val Gln Leu Val Glu Ser Gly Gly Gly Val Val Gln Pro Gly Arg
1               5                   10                  15

Ser Leu Arg Leu Ser Cys Ala Ala Ser Gly Phe Thr Phe Ser Asn Tyr
            20                  25                  30

Gly Ile His Trp Val Arg Gln Pro Pro Gly Gln Gly Leu Glu Trp Val
        35                  40                  45

Ala Val Ile Trp Tyr Ala Gly Ser Asn Lys Phe Tyr Ala Asp Ser Val
    50                  55                  60

Lys Gly Arg Phe Thr Ile Ser Arg Asp Asn Ser Lys Asn Ser Ala Tyr
65                  70                  75                  80

Leu Gln Met Asn Ser Leu Arg Ala Glu Asp Thr Ala Val Tyr Tyr Cys
                85                  90                  95

Ala Arg Ala Pro Leu Gly Tyr Tyr Tyr Tyr Gly Met Asp Val Trp Gly
            100                 105                 110

Gln Gly Thr Thr Val Thr Val Ser Ser
        115                 120

<210> SEQ ID NO 211
<211> LENGTH: 24
<212> TYPE: DNA
<213> ORGANISM: Artificial Sequence
<220> FEATURE:
<223> OTHER INFORMATION: synthetic

<400> SEQUENCE: 211

```
ggattcacct tcagtaacta tggc                                             24
```

<210> SEQ ID NO 212
<211> LENGTH: 8
<212> TYPE: PRT
<213> ORGANISM: Artificial Sequence
<220> FEATURE:
<223> OTHER INFORMATION: synthetic

<400> SEQUENCE: 212

```
<210> SEQ ID NO 213
<211> LENGTH: 24
<212> TYPE: DNA
<213> ORGANISM: Artificial Sequence
<220> FEATURE:
<223> OTHER INFORMATION: synthetic

<400> SEQUENCE: 213
atatggtatg ctggaagtaa taag                                           24

<210> SEQ ID NO 214
<211> LENGTH: 8
<212> TYPE: PRT
<213> ORGANISM: Artificial Sequence
<220> FEATURE:
<223> OTHER INFORMATION: synthetic

<400> SEQUENCE: 214

Ile Trp Tyr Ala Gly Ser Asn Lys
1               5

<210> SEQ ID NO 215
<211> LENGTH: 42
<212> TYPE: DNA
<213> ORGANISM: Artificial Sequence
<220> FEATURE:
<223> OTHER INFORMATION: synthetic

<400> SEQUENCE: 215
gcgagagccc ccctgggtta ttactactac ggtatggacg tc                       42

<210> SEQ ID NO 216
<211> LENGTH: 14
<212> TYPE: PRT
<213> ORGANISM: Artificial Sequence
<220> FEATURE:
<223> OTHER INFORMATION: synthetic

<400> SEQUENCE: 216

Ala Arg Ala Pro Leu Gly Tyr Tyr Tyr Tyr Gly Met Asp Val
1               5                   10

<210> SEQ ID NO 217
<211> LENGTH: 321
<212> TYPE: DNA
<213> ORGANISM: Artificial Sequence
<220> FEATURE:
<223> OTHER INFORMATION: synthetic

<400> SEQUENCE: 217
gacatccaga tgacccagtc tccatcctcc ctgtctgcat ctgtaggaga cagagtcacc    60
atcacttgcc gggcaagtca gggcattaga aatgatttag ctggtatca gcagaaacca   120 gggaaagccc ctaagcgcct gatctatgat gcatccagtt tggaaagtgg ggtcccatca   180
aggttcagcg gcagtggatc tgggacagaa ttcactctca caatcagcag cctgcagcct   240
gaagattttg caacttatta ctgtctacag cataatagtt acccgtggac gttcggccaa   300
gggaccaagg tggaaatcaa a                                             321

<210> SEQ ID NO 218
<211> LENGTH: 107
```

Gly Phe Thr Phe Ser Asn Tyr Gly
1               5

```
<212> TYPE: PRT
<213> ORGANISM: Artificial Sequence
<220> FEATURE:
<223> OTHER INFORMATION: synthetic

<400> SEQUENCE: 218

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Gly Ile Arg Asn Asp
            20                  25                  30

Leu Gly Trp Tyr Gln Gln Lys Pro Gly Lys Ala Pro Lys Arg Leu Ile
        35                  40                  45

Tyr Asp Ala Ser Ser Leu Glu Ser Gly Val Pro Ser Arg Phe Ser Gly
    50                  55                  60

Ser Gly Ser Gly Thr Glu Phe Thr Leu Thr Ile Ser Ser Leu Gln Pro
65                  70                  75                  80

Glu Asp Phe Ala Thr Tyr Tyr Cys Leu Gln His Asn Ser Tyr Pro Trp
                85                  90                  95

Thr Phe Gly Gln Gly Thr Lys Val Glu Ile Lys
            100                 105

<210> SEQ ID NO 219
<211> LENGTH: 18
<212> TYPE: DNA
<213> ORGANISM: Artificial Sequence
<220> FEATURE:
<223> OTHER INFORMATION: synthetic

<400> SEQUENCE: 219
cagggcatta gaaatgat                                                        18

<210> SEQ ID NO 220
<211> LENGTH: 6
<212> TYPE: PRT
<213> ORGANISM: Artificial Sequence
<220> FEATURE:
<223> OTHER INFORMATION: synthetic

<400> SEQUENCE: 220

Gln Gly Ile Arg Asn Asp
1               5

<210> SEQ ID NO 221
<211> LENGTH: 9
<212> TYPE: DNA
<213> ORGANISM: Artificial Sequence
<220> FEATURE:
<223> OTHER INFORMATION: synthetic

<400> SEQUENCE: 221 gatgcatcc                                                                   9

<210> SEQ ID NO 222
<211> LENGTH: 3
<212> TYPE: PRT
<213> ORGANISM: Artificial Sequence
<220> FEATURE:
<223> OTHER INFORMATION: synthetic

<400> SEQUENCE: 222

Asp Ala Ser
1
```

```
<210> SEQ ID NO 223
<211> LENGTH: 27
<212> TYPE: DNA
<213> ORGANISM: Artificial Sequence
<220> FEATURE:
<223> OTHER INFORMATION: synthetic

<400> SEQUENCE: 223
ctacagcata atagttaccc gtggacg                                               27

<210> SEQ ID NO 224
<211> LENGTH: 9
<212> TYPE: PRT
<213> ORGANISM: Artificial Sequence
<220> FEATURE:
<223> OTHER INFORMATION: synthetic

<400> SEQUENCE: 224

Leu Gln His Asn Ser Tyr Pro Trp Thr
1               5

<210> SEQ ID NO 225
<211> LENGTH: 375
<212> TYPE: DNA
<213> ORGANISM: Artificial Sequence
<220> FEATURE:
<223> OTHER INFORMATION: synthetic

<400> SEQUENCE: 225
caggtgcagc tggtggagtc tgggggaggc gtggtccagc ctgggaggtc cctgagactc       60
tcctgtgcag cgtctggact caccgtcagt agttatgtca tgcactgggt ccgccaggct      120
ccaggcaagg ggctggagtg ggtggcaatt atatggtatg atggaagtaa taatactat       180 ggagactccg tgaagggccg attcaccatc tccagagaca attccaagaa aacgctgtat      240
ctgcaaatga acagcctgag agccgaggac acggctgtgt attactgtgc gagaggccgc      300
cccctgtcta gtagttcgtc cgattattac ggttttggacg tctggggcca agggaccacg      360
gtcaccgtct cctca                                                       375

<210> SEQ ID NO 226
<211> LENGTH: 125
<212> TYPE: PRT
<213> ORGANISM: Artificial Sequence
<220> FEATURE:
<223> OTHER INFORMATION: synthetic

<400> SEQUENCE: 226

Gln Val Gln Leu Val Glu Ser Gly Gly Gly Val Val Gln Pro Gly Arg
1               5                   10                  15

Ser Leu Arg Leu Ser Cys Ala Ala Ser Gly Leu Thr Val Ser Ser Tyr
            20                  25                  30

Val Met His Trp Val Arg Gln Ala Pro Gly Lys Gly Leu Glu Trp Val
        35                  40                  45

Ala Ile Ile Trp Tyr Asp Gly Ser Asn Lys Tyr Tyr Gly Asp Ser Val
    50                  55                  60

Lys Gly Arg Phe Thr Ile Ser Arg Asp Asn Ser Lys Lys Thr Leu Tyr
65                  70                  75                  80

Leu Gln Met Asn Ser Leu Arg Ala Glu Asp Thr Ala Val Tyr Tyr Cys
                85                  90                  95

Ala Arg Gly Arg Pro Leu Ser Ser Ser Ser Asp Tyr Tyr Gly Leu
            100                 105                 110
```

Asp Val Trp Gly Gln Gly Thr Thr Val Thr Val Ser Ser
            115                 120                 125

<210> SEQ ID NO 227
<211> LENGTH: 24
<212> TYPE: DNA
<213> ORGANISM: Artificial Sequence
<220> FEATURE:
<223> OTHER INFORMATION: synthetic

<400> SEQUENCE: 227
ggactcaccg tcagtagtta tgtc                                          24

<210> SEQ ID NO 228
<211> LENGTH: 8
<212> TYPE: PRT
<213> ORGANISM: Artificial Sequence
<220> FEATURE:
<223> OTHER INFORMATION: synthetic

<400> SEQUENCE: 228

Gly Leu Thr Val Ser Ser Tyr Val
1               5

<210> SEQ ID NO 229
<211> LENGTH: 24
<212> TYPE: DNA
<213> ORGANISM: Artificial Sequence
<220> FEATURE:
<223> OTHER INFORMATION: synthetic

<400> SEQUENCE: 229
atatggtatg atggaagtaa taaa                                          24

<210> SEQ ID NO 230
<211> LENGTH: 8
<212> TYPE: PRT
<213> ORGANISM: Artificial Sequence
<220> FEATURE:
<223> OTHER INFORMATION: synthetic

<400> SEQUENCE: 230

Ile Trp Tyr Asp Gly Ser Asn Lys
1               5

<210> SEQ ID NO 231
<211> LENGTH: 54
<212> TYPE: DNA
<213> ORGANISM: Artificial Sequence
<220> FEATURE:
<223> OTHER INFORMATION: synthetic

<400> SEQUENCE: 231
gcgagaggcc gccccctgtc tagtagttcg tccgattatt acggtttgga cgtc         54

<210> SEQ ID NO 232
<211> LENGTH: 18
<212> TYPE: PRT
<213> ORGANISM: Artificial Sequence
<220> FEATURE:
<223> OTHER INFORMATION: synthetic

<400> SEQUENCE: 232

Ala Arg Gly Arg Pro Leu Ser Ser Ser Ser Asp Tyr Tyr Gly Leu
1               5                   10                  15

Asp Val

<210> SEQ ID NO 233
<211> LENGTH: 321
<212> TYPE: DNA
<213> ORGANISM: Artificial Sequence
<220> FEATURE:
<223> OTHER INFORMATION: synthetic

<400> SEQUENCE: 233

```
gccatccaga tgacccagtc tccatcctcc ctgtctgcat ctgtaggaga cagagtcacc    60
atcatttgcc gggcaagtca gggcattaga aatgatttag ctggtatca gcagaaacca   120
gggaaagccc ctaacctcct gatctatgct gcatccagtt tacaaagtgg ggtcccatca   180
aggttcagcg gcagtggatc tggcacagat ttcactctca ccatcagcag cctgcagcct   240
gaagattttg caacttatta ctgtctacaa gattacaatt atccgtggac gttcggccaa   300
gggaccaagg tggaaatcaa a                                             321
```

<210> SEQ ID NO 234
<211> LENGTH: 107
<212> TYPE: PRT
<213> ORGANISM: Artificial Sequence
<220> FEATURE:
<223> OTHER INFORMATION: synthetic

<400> SEQUENCE: 234

```
Ala Ile Gln Met Thr Gln Ser Pro Ser Ser Leu Ser Ala Ser Val Gly
1               5                   10                  15

Asp Arg Val Thr Ile Ile Cys Arg Ala Ser Gln Gly Ile Arg Asn Asp
            20                  25                  30

Leu Gly Trp Tyr Gln Gln Lys Pro Gly Lys Ala Pro Asn Leu Leu Ile
        35                  40                  45

Tyr Ala Ala Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Leu Gln Asp Tyr Asn Tyr Pro Trp
                85                  90                  95

Thr Phe Gly Gln Gly Thr Lys Val Glu Ile Lys
            100                 105
```

<210> SEQ ID NO 235
<211> LENGTH: 18
<212> TYPE: DNA
<213> ORGANISM: Artificial Sequence
<220> FEATURE:
<223> OTHER INFORMATION: synthetic

<400> SEQUENCE: 235

```
cagggcatta gaaatgat                                                  18
```

<210> SEQ ID NO 236
<211> LENGTH: 6
<212> TYPE: PRT
<213> ORGANISM: Artificial Sequence
<220> FEATURE:
<223> OTHER INFORMATION: synthetic

<400> SEQUENCE: 236

```
Gln Gly Ile Arg Asn Asp
1               5
```

<210> SEQ ID NO 237
<211> LENGTH: 9
<212> TYPE: DNA
<213> ORGANISM: Artificial Sequence
<220> FEATURE:
<223> OTHER INFORMATION: synthetic

<400> SEQUENCE: 237 gctgcatcc                                                                                    9

<210> SEQ ID NO 238
<211> LENGTH: 3
<212> TYPE: PRT
<213> ORGANISM: Artificial Sequence
<220> FEATURE:
<223> OTHER INFORMATION: synthetic

<400> SEQUENCE: 238

Ala Ala Ser
1

<210> SEQ ID NO 239
<211> LENGTH: 27
<212> TYPE: DNA
<213> ORGANISM: Artificial Sequence
<220> FEATURE:
<223> OTHER INFORMATION: synthetic

<400> SEQUENCE: 239
ctacaagatt acaattatcc gtggacg                                                                27

<210> SEQ ID NO 240
<211> LENGTH: 9
<212> TYPE: PRT
<213> ORGANISM: Artificial Sequence
<220> FEATURE:
<223> OTHER INFORMATION: synthetic

<400> SEQUENCE: 240

Leu Gln Asp Tyr Asn Tyr Pro Trp Thr
1               5

<210> SEQ ID NO 241
<211> LENGTH: 360
<212> TYPE: DNA
<213> ORGANISM: Artificial Sequence
<220> FEATURE:
<223> OTHER INFORMATION: synthetic

<400> SEQUENCE: 241
gaggtgcagc tggtggagtc tgggggaggc ctggtacagc ctggagggtc cctgagactc      60
tcctgtgcag cctctggatt caccttcagt aattatgaaa tgtattgggt ccgccaggct     120
ccagggaagg ggctggaatg ggtttcatac attagtagta gtggtactac catatactac     180
gcagactctg tgaagggccg attcagtgtc tccagagaaa acgccaggag ctcactgtat     240
ctgcaaatga acagtctgag agtcgaggac tcggctgttt acttctgtgc aagtataaac     300
tggaactcct tctatggttt ggacgtctgg ggccaaggga ccacggtcac cgtctcctca     360

<210> SEQ ID NO 242
<211> LENGTH: 120
<212> TYPE: PRT
<213> ORGANISM: Artificial Sequence
<220> FEATURE:
<223> OTHER INFORMATION: synthetic

<400> SEQUENCE: 242

Glu Val Gln Leu Val Glu Ser Gly Gly Leu Val Gln Pro Gly Gly
1               5                   10                  15

Ser Leu Arg Leu Ser Cys Ala Ala Ser Gly Phe Thr Phe Ser Asn Tyr
            20                  25                  30

Glu Met Tyr Trp Val Arg Gln Ala Pro Gly Lys Gly Leu Glu Trp Val
        35                  40                  45

Ser Tyr Ile Ser Ser Ser Gly Thr Thr Ile Tyr Tyr Ala Asp Ser Val
    50                  55                  60

Lys Gly Arg Phe Ser Val Ser Arg Glu Asn Ala Arg Ser Ser Leu Tyr
65                  70                  75                  80

Leu Gln Met Asn Ser Leu Arg Val Glu Asp Ser Ala Val Tyr Phe Cys
                85                  90                  95

Ala Lys Tyr Asn Trp Asn Ser Phe Tyr Gly Leu Asp Val Trp Gly Gln
            100                 105                 110

Gly Thr Thr Val Thr Val Ser Ser
        115                 120

<210> SEQ ID NO 243
<211> LENGTH: 24
<212> TYPE: DNA
<213> ORGANISM: Artificial Sequence
<220> FEATURE:
<223> OTHER INFORMATION: synthetic

<400> SEQUENCE: 243
ggattcacct tcagtaatta tgaa                                          24

<210> SEQ ID NO 244
<211> LENGTH: 8
<212> TYPE: PRT
<213> ORGANISM: Artificial Sequence
<220> FEATURE:
<223> OTHER INFORMATION: synthetic

<400> SEQUENCE: 244

Gly Phe Thr Phe Ser Asn Tyr Glu
1               5

<210> SEQ ID NO 245
<211> LENGTH: 24
<212> TYPE: DNA
<213> ORGANISM: Artificial Sequence
<220> FEATURE:
<223> OTHER INFORMATION: synthetic

<400> SEQUENCE: 245
attagtagta gtggtactac cata                                          24

<210> SEQ ID NO 246
<211> LENGTH: 8
<212> TYPE: PRT
<213> ORGANISM: Artificial Sequence
<220> FEATURE:
<223> OTHER INFORMATION: synthetic

<400> SEQUENCE: 246

Ile Ser Ser Ser Gly Thr Thr Ile
1               5

<210> SEQ ID NO 247

```
<211> LENGTH: 39
<212> TYPE: DNA
<213> ORGANISM: Artificial Sequence
<220> FEATURE:
<223> OTHER INFORMATION: synthetic

<400> SEQUENCE: 247
gcgaagtata actggaactc cttctatggt ttggacgtc                    39

<210> SEQ ID NO 248
<211> LENGTH: 13
<212> TYPE: PRT
<213> ORGANISM: Artificial Sequence
<220> FEATURE:
<223> OTHER INFORMATION: synthetic

<400> SEQUENCE: 248

Ala Lys Tyr Asn Trp Asn Ser Phe Tyr Gly Leu Asp Val
1               5                   10

<210> SEQ ID NO 249
<211> LENGTH: 321
<212> TYPE: DNA
<213> ORGANISM: Artificial Sequence
<220> FEATURE:
<223> OTHER INFORMATION: synthetic

<400> SEQUENCE: 249
gccatccaga tgacccagtc tccatcctcc ctgtctgcat ctgtaggaga cagagtcacc    60
atcacttgcc gggcaagtca ggacattaga aatgatttag ctggtatca gcagaaacca   120 gggaaagccc ctaagctcct gatctctgct gcatccagtt tacagggtgg ggtcccatca   180
aggttcagcg gcagtggatc tggcacagat ttcactctca ccattagcag cctgcagcct   240
gcagattttg caacttatta ctgtctacaa gagtacaatt atgcactcac tttcggcgga   300
gggaccaagg tggagatcaa a                                            321

<210> SEQ ID NO 250
<211> LENGTH: 107
<212> TYPE: PRT
<213> ORGANISM: Artificial Sequence
<220> FEATURE:
<223> OTHER INFORMATION: synthetic

<400> SEQUENCE: 250

Ala Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Ile Arg Asn Asp
            20                  25                  30

Leu Gly Trp Tyr Gln Gln Lys Pro Gly Lys Ala Pro Lys Leu Leu Ile
        35                  40                  45

Ser Ala Ala Ser Ser Leu Gln Gly Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Ala Asp Phe Ala Thr Tyr Tyr Cys Leu Gln Glu Tyr Asn Tyr Ala Leu
                85                  90                  95

Thr Phe Gly Gly Gly Thr Lys Val Glu Ile Lys
            100                 105

<210> SEQ ID NO 251
<211> LENGTH: 18
```

```
<212> TYPE: DNA
<213> ORGANISM: Artificial Sequence
<220> FEATURE:
<223> OTHER INFORMATION: synthetic

<400> SEQUENCE: 251
caggacatta gaaatgat                                                   18

<210> SEQ ID NO 252
<211> LENGTH: 6
<212> TYPE: PRT
<213> ORGANISM: Artificial Sequence
<220> FEATURE:
<223> OTHER INFORMATION: synthetic

<400> SEQUENCE: 252

Gln Asp Ile Arg Asn Asp
1               5

<210> SEQ ID NO 253
<211> LENGTH: 9
<212> TYPE: DNA
<213> ORGANISM: Artificial Sequence
<220> FEATURE:
<223> OTHER INFORMATION: synthetic

<400> SEQUENCE: 253 gctgcatcc                                                              9

<210> SEQ ID NO 254
<211> LENGTH: 3
<212> TYPE: PRT
<213> ORGANISM: Artificial Sequence
<220> FEATURE:
<223> OTHER INFORMATION: synthetic

<400> SEQUENCE: 254

Ala Ala Ser
1

<210> SEQ ID NO 255
<211> LENGTH: 27
<212> TYPE: DNA
<213> ORGANISM: Artificial Sequence
<220> FEATURE:
<223> OTHER INFORMATION: synthetic

<400> SEQUENCE: 255
ctacaagagt acaattatgc actcact                                         27

<210> SEQ ID NO 256
<211> LENGTH: 9
<212> TYPE: PRT
<213> ORGANISM: Artificial Sequence
<220> FEATURE:
<223> OTHER INFORMATION: synthetic

<400> SEQUENCE: 256

Leu Gln Glu Tyr Asn Tyr Ala Leu Thr
1               5

<210> SEQ ID NO 257
<211> LENGTH: 369
<212> TYPE: DNA
<213> ORGANISM: Artificial Sequence
<220> FEATURE:
<223> OTHER INFORMATION: synthetic
```

<400> SEQUENCE: 257

```
gaggtgcagc tggtggagtc tgggggaggt tggtccagc ctggagggtc cctgagactc      60
tcctgtgcag cctctggatt caccttcagg gtttatgaaa tgaactgggt ccgccaggct    120
ccagggaagg ggctggagtg gatttcatac attggcagta gtggttttac catatactac    180
gcagactctg tgaagggccg attcaccatc tccagagaca acgccaagaa ctcactgttt    240
ctgcagctga acagcctgag agccgaggac acggctgttt attactgtgc gagagggtgg    300
aacgacggag ttcctaacta tttgggtatg gacgtctggg gccaaggcac cacggtcacc    360
gtctcctca                                                            369
```

<210> SEQ ID NO 258
<211> LENGTH: 123
<212> TYPE: PRT
<213> ORGANISM: Artificial Sequence
<220> FEATURE:
<223> OTHER INFORMATION: synthetic

<400> SEQUENCE: 258

```
Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Arg Val Tyr
            20                  25                  30

Glu Met Asn Trp Val Arg Gln Ala Pro Gly Lys Gly Leu Glu Trp Ile
        35                  40                  45

Ser Tyr Ile Gly Ser Ser Gly Phe Thr Ile Tyr Tyr Ala Asp Ser Val
    50                  55                  60

Lys Gly Arg Phe Thr Ile Ser Arg Asp Asn Ala Lys Asn Ser Leu Phe
65                  70                  75                  80

Leu Gln Leu Asn Ser Leu Arg Ala Glu Asp Thr Ala Val Tyr Tyr Cys
                85                  90                  95

Ala Arg Gly Trp Asn Asp Gly Val Pro Asn Tyr Leu Gly Met Asp Val
            100                 105                 110

Trp Gly Gln Gly Thr Thr Val Thr Val Ser Ser
        115                 120
```

<210> SEQ ID NO 259
<211> LENGTH: 24
<212> TYPE: DNA
<213> ORGANISM: Artificial Sequence
<220> FEATURE:
<223> OTHER INFORMATION: synthetic

<400> SEQUENCE: 259

```
ggattcacct tcagggttta tgaa                                            24
```

<210> SEQ ID NO 260
<211> LENGTH: 8
<212> TYPE: PRT
<213> ORGANISM: Artificial Sequence
<220> FEATURE:
<223> OTHER INFORMATION: synthetic

<400> SEQUENCE: 260

```
Gly Phe Thr Phe Arg Val Tyr Glu
1               5
```

<210> SEQ ID NO 261
<211> LENGTH: 24

```
<212> TYPE: DNA
<213> ORGANISM: Artificial Sequence
<220> FEATURE:
<223> OTHER INFORMATION: synthetic

<400> SEQUENCE: 261
attggcagta gtggttttac cata                                           24

<210> SEQ ID NO 262
<211> LENGTH: 8
<212> TYPE: PRT
<213> ORGANISM: Artificial Sequence
<220> FEATURE:
<223> OTHER INFORMATION: synthetic

<400> SEQUENCE: 262

Ile Gly Ser Ser Gly Phe Thr Ile
1               5

<210> SEQ ID NO 263
<211> LENGTH: 48
<212> TYPE: DNA
<213> ORGANISM: Artificial Sequence
<220> FEATURE:
<223> OTHER INFORMATION: synthetic

<400> SEQUENCE: 263
gcgagagggt ggaacgacgg agttcctaac tatttgggta tggacgtc                 48

<210> SEQ ID NO 264
<211> LENGTH: 16
<212> TYPE: PRT
<213> ORGANISM: Artificial Sequence
<220> FEATURE:
<223> OTHER INFORMATION: synthetic

<400> SEQUENCE: 264

Ala Arg Gly Trp Asn Asp Gly Val Pro Asn Tyr Leu Gly Met Asp Val
1               5                   10                  15

<210> SEQ ID NO 265
<211> LENGTH: 321
<212> TYPE: DNA
<213> ORGANISM: Artificial Sequence
<220> FEATURE:
<223> OTHER INFORMATION: synthetic

<400> SEQUENCE: 265
gacatccaga tgacccagtc tccatcctcc ctgtctgcat ctgtaggaga cagagtcacc    60
atcacttgcc aggcgagtca ggacattaac aaatatttaa attggtatca gcagaaacca   120
ggaaaagccc ctaaactcct gatctacgat gcatccaatt tggaaacagg ggtcccatca   180
aggttcagtg aagtggatc tgggacagat tttactttca ccatcagcag cctgcagcct   240
gaagatattg caagatatca ctgtcaacag tatgataaaa tcccgctcac tttcggcgga   300
gggaccaagg tggagatcaa a                                             321

<210> SEQ ID NO 266
<211> LENGTH: 107
<212> TYPE: PRT
<213> ORGANISM: Artificial Sequence
<220> FEATURE:
<223> OTHER INFORMATION: synthetic

<400> SEQUENCE: 266
```

-continued

```
Asp Ile Gln Met Thr Gln Ser Pro Ser Ser Leu Ser Ala Ser Val Gly
1               5                   10                  15

Asp Arg Val Thr Ile Thr Cys Gln Ala Ser Gln Asp Ile Asn Lys Tyr
            20                  25                  30

Leu Asn Trp Tyr Gln Gln Lys Pro Gly Lys Ala Pro Lys Leu Leu Ile
        35                  40                  45

Tyr Asp Ala Ser Asn Leu Glu Thr Gly Val Pro Ser Arg Phe Ser Gly
    50                  55                  60

Ser Gly Ser Gly Thr Asp Phe Thr Phe Thr Ile Ser Ser Leu Gln Pro
65                  70                  75                  80

Glu Asp Ile Ala Arg Tyr His Cys Gln Gln Tyr Asp Lys Ile Pro Leu
                85                  90                  95

Thr Phe Gly Gly Gly Thr Lys Val Glu Ile Lys
            100                 105
```

<210> SEQ ID NO 267
<211> LENGTH: 18
<212> TYPE: DNA
<213> ORGANISM: Artificial Sequence
<220> FEATURE:
<223> OTHER INFORMATION: synthetic

<400> SEQUENCE: 267
caggacatta acaaatat                                                    18

<210> SEQ ID NO 268
<211> LENGTH: 6
<212> TYPE: PRT
<213> ORGANISM: Artificial Sequence
<220> FEATURE:
<223> OTHER INFORMATION: synthetic

<400> SEQUENCE: 268

```
Gln Asp Ile Asn Lys Tyr
1               5
```

<210> SEQ ID NO 269
<211> LENGTH: 9
<212> TYPE: DNA
<213> ORGANISM: Artificial Sequence
<220> FEATURE:
<223> OTHER INFORMATION: synthetic

<400> SEQUENCE: 269 gatgcatcc                                                               9

<210> SEQ ID NO 270
<211> LENGTH: 3
<212> TYPE: PRT
<213> ORGANISM: Artificial Sequence
<220> FEATURE:
<223> OTHER INFORMATION: synthetic

<400> SEQUENCE: 270

```
Asp Ala Ser
1
```

<210> SEQ ID NO 271
<211> LENGTH: 27
<212> TYPE: DNA
<213> ORGANISM: Artificial Sequence
<220> FEATURE:
<223> OTHER INFORMATION: synthetic

```
<400> SEQUENCE: 271
caacagtatg ataaaatccc gctcact                                           27

<210> SEQ ID NO 272
<211> LENGTH: 9
<212> TYPE: PRT
<213> ORGANISM: Artificial Sequence
<220> FEATURE:
<223> OTHER INFORMATION: synthetic

<400> SEQUENCE: 272

Gln Gln Tyr Asp Lys Ile Pro Leu Thr
1               5

<210> SEQ ID NO 273
<211> LENGTH: 369
<212> TYPE: DNA
<213> ORGANISM: Artificial Sequence
<220> FEATURE:
<223> OTHER INFORMATION: synthetic

<400> SEQUENCE: 273
caggtgcagc tggtggagtc tgggggaggc gtggtccagc ctggggggtc cctgagactc        60
tcctgtgcag cgtctggatt caccttcagc agctatggca tgcactgggt ccgccaggct       120
ccaggcaagg ggctggagtg ggtggcagtt atctggtatg ttggaagtaa taaatactat       180
ggagagtccg tgaagggccg attcaccatc tccagagaca attccaagaa cacgctgtat       240
ttgcaaatga acagcctgag agacgaggac acggctatat attactgtgc gagagggggt       300
caactgggct ccttctacta ttacggtatg gacgtctggg gccaagggac cacggtcacc       360
gtctcctca                                                              369

<210> SEQ ID NO 274
<211> LENGTH: 123
<212> TYPE: PRT
<213> ORGANISM: Artificial Sequence
<220> FEATURE:
<223> OTHER INFORMATION: synthetic

<400> SEQUENCE: 274

Gln Val Gln Leu Val Glu Ser Gly Gly Gly Val Val Gln Pro Gly Arg
1               5                   10                  15

Ser Leu Arg Leu Ser Cys Ala Ala Ser Gly Phe Thr Phe Ser Ser Tyr
                20                  25                  30

Gly Met His Trp Val Arg Gln Ala Pro Gly Lys Gly Leu Glu Trp Val
            35                  40                  45

Ala Val Ile Trp Tyr Val Gly Ser Asn Lys Tyr Tyr Gly Glu Ser Val
        50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Asp Glu Asp Thr Ala Ile Tyr Tyr Cys
                85                  90                  95

Ala Arg Gly Gly Gln Leu Gly Ser Phe Tyr Tyr Tyr Gly Met Asp Val
            100                 105                 110

Trp Gly Gln Gly Thr Thr Val Thr Val Ser Ser
        115                 120

<210> SEQ ID NO 275
<211> LENGTH: 24
<212> TYPE: DNA
```

```
<213> ORGANISM: Artificial Sequence
<220> FEATURE:
<223> OTHER INFORMATION: synthetic

<400> SEQUENCE: 275
ggattcacct tcagcagcta tggc                                              24

<210> SEQ ID NO 276
<211> LENGTH: 8
<212> TYPE: PRT
<213> ORGANISM: Artificial Sequence
<220> FEATURE:
<223> OTHER INFORMATION: synthetic

<400> SEQUENCE: 276

Gly Phe Thr Phe Ser Ser Tyr Gly
1               5

<210> SEQ ID NO 277
<211> LENGTH: 24
<212> TYPE: DNA
<213> ORGANISM: Artificial Sequence
<220> FEATURE:
<223> OTHER INFORMATION: synthetic

<400> SEQUENCE: 277
atctggtatg ttggaagtaa taaa                                              24

<210> SEQ ID NO 278
<211> LENGTH: 8
<212> TYPE: PRT
<213> ORGANISM: Artificial Sequence
<220> FEATURE:
<223> OTHER INFORMATION: synthetic

<400> SEQUENCE: 278

Ile Trp Tyr Val Gly Ser Asn Lys
1               5

<210> SEQ ID NO 279
<211> LENGTH: 48
<212> TYPE: DNA
<213> ORGANISM: Artificial Sequence
<220> FEATURE:
<223> OTHER INFORMATION: synthetic

<400> SEQUENCE: 279
gcgagagggg gtcaactggg ctccttctac tattacggta tggacgtc                    48

<210> SEQ ID NO 280
<211> LENGTH: 16
<212> TYPE: PRT
<213> ORGANISM: Artificial Sequence
<220> FEATURE:
<223> OTHER INFORMATION: synthetic

<400> SEQUENCE: 280

Ala Arg Gly Gly Gln Leu Gly Ser Phe Tyr Tyr Tyr Gly Met Asp Val
1               5                   10                  15

<210> SEQ ID NO 281
<211> LENGTH: 321
<212> TYPE: DNA
<213> ORGANISM: Artificial Sequence
<220> FEATURE:
<223> OTHER INFORMATION: synthetic
```

```
<400> SEQUENCE: 281
gacatccaga tgacccagtc tccatcctcc ctgtctgcat ctgtaggaga cagagtcacc    60
atcacttgcc gggcaagtca gggcattaga aatgatttag gctggtatca gcagaaacca   120
gggaaagccc ctaagcgcct gatctatgat gtatccagtt tacaaagtgg ggtcccatca   180
aggttcagcg gcagtggatc tgggacagaa ttcactctca caatcagcag cctgcagcct   240
gaagatcttg caacttatta ctgtctacag cataatagtt acccgtggac gttcggccaa   300
gggaccaagg tggaaatcaa a                                              321

<210> SEQ ID NO 282
<211> LENGTH: 107
<212> TYPE: PRT
<213> ORGANISM: Artificial Sequence
<220> FEATURE:
<223> OTHER INFORMATION: synthetic

<400> SEQUENCE: 282

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Gly Ile Arg Asn Asp
            20                  25                  30

Leu Gly Trp Tyr Gln Gln Lys Pro Gly Lys Ala Pro Lys Arg Leu Ile
        35                  40                  45

Tyr Asp Val Ser Ser Leu Gln Ser Gly Val Pro Ser Arg Phe Ser Gly
    50                  55                  60

Ser Gly Ser Gly Thr Glu Phe Thr Leu Thr Ile Ser Ser Leu Gln Pro
65                  70                  75                  80

Glu Asp Leu Ala Thr Tyr Tyr Cys Leu Gln His Asn Ser Tyr Pro Trp
                85                  90                  95

Thr Phe Gly Gln Gly Thr Lys Val Glu Ile Lys
            100                 105

<210> SEQ ID NO 283
<211> LENGTH: 18
<212> TYPE: DNA
<213> ORGANISM: Artificial Sequence
<220> FEATURE:
<223> OTHER INFORMATION: synthetic

<400> SEQUENCE: 283
cagggcatta gaaatgat                                                   18

<210> SEQ ID NO 284
<211> LENGTH: 6
<212> TYPE: PRT
<213> ORGANISM: Artificial Sequence
<220> FEATURE:
<223> OTHER INFORMATION: synthetic

<400> SEQUENCE: 284

Gln Gly Ile Arg Asn Asp
1               5

<210> SEQ ID NO 285
<211> LENGTH: 9
<212> TYPE: DNA
<213> ORGANISM: Artificial Sequence
<220> FEATURE:
<223> OTHER INFORMATION: synthetic

<400> SEQUENCE: 285
``` gatgtatcc                                                                  9

<210> SEQ ID NO 286
<211> LENGTH: 3
<212> TYPE: PRT
<213> ORGANISM: Artificial Sequence
<220> FEATURE:
<223> OTHER INFORMATION: synthetic

<400> SEQUENCE: 286

Asp Val Ser
1

<210> SEQ ID NO 287
<211> LENGTH: 27
<212> TYPE: DNA
<213> ORGANISM: Artificial Sequence
<220> FEATURE:
<223> OTHER INFORMATION: synthetic

<400> SEQUENCE: 287
ctacagcata atagttaccc gtggacg                                             27

<210> SEQ ID NO 288
<211> LENGTH: 9
<212> TYPE: PRT
<213> ORGANISM: Artificial Sequence
<220> FEATURE:
<223> OTHER INFORMATION: synthetic

<400> SEQUENCE: 288

Leu Gln His Asn Ser Tyr Pro Trp Thr
1               5

<210> SEQ ID NO 289
<211> LENGTH: 360
<212> TYPE: DNA
<213> ORGANISM: Artificial Sequence
<220> FEATURE:
<223> OTHER INFORMATION: synthetic

<400> SEQUENCE: 289
caggtgcagc tggtggagtc tgggggaggc gtggtccagc ctgggaggtc cctgagaatt          60
tcctgtgcag cgtcaggatt caccttcaat aactatggct ccactgggt ccgccaggct          120 ccaggcaggg ggctggagtg ggtggcagtt atttggtatt ctggaagtaa taaatactat         180
ggagactccg tgaagggccg attcaccatc tccagagaca attccaaaaa tatattgtat         240
ctgcaaatga acagtctgag agccgaggac acggctatat attactgtgc gagatttccg         300
tttagcagca gttggctctt ggactactgg ggccagggaa ccctggtcac cgtctcctca         360

<210> SEQ ID NO 290
<211> LENGTH: 120
<212> TYPE: PRT
<213> ORGANISM: Artificial Sequence
<220> FEATURE:
<223> OTHER INFORMATION: synthetic

<400> SEQUENCE: 290

Gln Val Gln Leu Val Glu Ser Gly Gly Gly Val Val Gln Pro Gly Arg
1               5                   10                  15

Ser Leu Arg Ile Ser Cys Ala Ala Ser Gly Phe Thr Phe Asn Asn Tyr
            20                  25                  30

```
Gly Phe His Trp Val Arg Gln Ala Pro Gly Arg Gly Leu Glu Trp Val
             35                  40                  45

Ala Val Ile Trp Tyr Ser Gly Ser Asn Lys Tyr Tyr Gly Asp Ser Val
 50                  55                  60

Lys Gly Arg Phe Thr Ile Ser Arg Asp Asn Ser Lys Asn Ile Leu Tyr
 65                  70                  75                  80

Leu Gln Met Asn Ser Leu Arg Ala Glu Asp Thr Ala Ile Tyr Tyr Cys
                 85                  90                  95

Ala Arg Phe Pro Phe Ser Ser Ser Trp Leu Leu Asp Tyr Trp Gly Gln
                100                 105                 110

Gly Thr Leu Val Thr Val Ser Ser
        115                 120

<210> SEQ ID NO 291
<211> LENGTH: 24
<212> TYPE: DNA
<213> ORGANISM: Artificial Sequence
<220> FEATURE:
<223> OTHER INFORMATION: synthetic

<400> SEQUENCE: 291
ggattcacct tcaataacta tggc                                              24

<210> SEQ ID NO 292
<211> LENGTH: 8
<212> TYPE: PRT
<213> ORGANISM: Artificial Sequence
<220> FEATURE:
<223> OTHER INFORMATION: synthetic

<400> SEQUENCE: 292

Gly Phe Thr Phe Asn Asn Tyr Gly
 1               5

<210> SEQ ID NO 293
<211> LENGTH: 24
<212> TYPE: DNA
<213> ORGANISM: Artificial Sequence
<220> FEATURE:
<223> OTHER INFORMATION: synthetic

<400> SEQUENCE: 293
atttggtatt ctggaagtaa taaa                                              24

<210> SEQ ID NO 294
<211> LENGTH: 8
<212> TYPE: PRT
<213> ORGANISM: Artificial Sequence
<220> FEATURE:
<223> OTHER INFORMATION: synthetic

<400> SEQUENCE: 294

Ile Trp Tyr Ser Gly Ser Asn Lys
 1               5

<210> SEQ ID NO 295
<211> LENGTH: 39
<212> TYPE: DNA
<213> ORGANISM: Artificial Sequence
<220> FEATURE:
<223> OTHER INFORMATION: synthetic

<400> SEQUENCE: 295
gcgagatttc cgtttagcag cagttggctc ttggactac                              39
```

<210> SEQ ID NO 296
<211> LENGTH: 13
<212> TYPE: PRT
<213> ORGANISM: Artificial Sequence
<220> FEATURE:
<223> OTHER INFORMATION: synthetic

<400> SEQUENCE: 296

Ala Arg Phe Pro Phe Ser Ser Ser Trp Leu Leu Asp Tyr
1               5                   10

<210> SEQ ID NO 297
<211> LENGTH: 321
<212> TYPE: DNA
<213> ORGANISM: Artificial Sequence
<220> FEATURE:
<223> OTHER INFORMATION: synthetic

<400> SEQUENCE: 297
gacatccagt tgacccagtc tccatccttc ctgtctgcat ctgtaggaga cagagtcacc      60
ttcacttgct gggccagtca gggcattagt gattatttag cctggtatca acaaaaacca    120
gggaaagccc ctaaactcct gatctatgct gcatccgctt tgcaaagtgg ggtcccatca    180
aggttcagcg gcagtggatc tgggacagaa ttcactctca cagtcagcag cctacagcct    240
gaagattttg caacttatta ctgtcaacag cttaatagtt atccattcac tttcggccct    300
gggaccaaag tggatatcaa a                                               321

<210> SEQ ID NO 298
<211> LENGTH: 107
<212> TYPE: PRT
<213> ORGANISM: Artificial Sequence
<220> FEATURE:
<223> OTHER INFORMATION: synthetic

<400> SEQUENCE: 298

Asp Ile Gln Leu Thr Gln Ser Pro Ser Phe Leu Ser Ala Ser Val Gly
1               5                   10                  15

Asp Arg Val Thr Phe Thr Cys Trp Ala Ser Gln Gly Ile Ser Asp Tyr
            20                  25                  30

Leu Ala Trp Tyr Gln Gln Lys Pro Gly Lys Ala Pro Lys Leu Leu Ile
        35                  40                  45

Tyr Ala Ala Ser Ala Leu Gln Ser Gly Val Pro Ser Arg Phe Ser Gly
    50                  55                  60

Ser Gly Ser Gly Thr Glu Phe Thr Leu Thr Val Ser Ser Leu Gln Pro
65                  70                  75                  80

Glu Asp Phe Ala Thr Tyr Tyr Cys Gln Gln Leu Asn Ser Tyr Pro Phe
                85                  90                  95

Thr Phe Gly Pro Gly Thr Lys Val Asp Ile Lys
            100                 105

<210> SEQ ID NO 299
<211> LENGTH: 18
<212> TYPE: DNA
<213> ORGANISM: Artificial Sequence
<220> FEATURE:
<223> OTHER INFORMATION: synthetic

<400> SEQUENCE: 299
cagggcatta gtgattat                                                    18

<210> SEQ ID NO 300
<211> LENGTH: 6
<212> TYPE: PRT
<213> ORGANISM: Artificial Sequence
<220> FEATURE:
<223> OTHER INFORMATION: synthetic

<400> SEQUENCE: 300

Gln Gly Ile Ser Asp Tyr
1               5

<210> SEQ ID NO 301
<211> LENGTH: 9
<212> TYPE: DNA
<213> ORGANISM: Artificial Sequence
<220> FEATURE:
<223> OTHER INFORMATION: synthetic

<400> SEQUENCE: 301 gctgcatcc                                                                 9

<210> SEQ ID NO 302
<211> LENGTH: 3
<212> TYPE: PRT
<213> ORGANISM: Artificial Sequence
<220> FEATURE:
<223> OTHER INFORMATION: synthetic

<400> SEQUENCE: 302

Ala Ala Ser
1

<210> SEQ ID NO 303
<211> LENGTH: 27
<212> TYPE: DNA
<213> ORGANISM: Artificial Sequence
<220> FEATURE:
<223> OTHER INFORMATION: synthetic

<400> SEQUENCE: 303
caacagctta atagttatcc attcact                                            27

<210> SEQ ID NO 304
<211> LENGTH: 9
<212> TYPE: PRT
<213> ORGANISM: Artificial Sequence
<220> FEATURE:
<223> OTHER INFORMATION: synthetic

<400> SEQUENCE: 304

Gln Gln Leu Asn Ser Tyr Pro Phe Thr
1               5

<210> SEQ ID NO 305
<211> LENGTH: 357
<212> TYPE: DNA
<213> ORGANISM: Artificial Sequence
<220> FEATURE:
<223> OTHER INFORMATION: synthetic

<400> SEQUENCE: 305
cagctgcagc tgcaggagtc gggcccagga ctggtgaagc cttcggagac cctgtccctc        60
acctgcactg tctctggtgg ctccatcagc agtactaatc actactgggg ctggatccgc       120
cagcccccag ggaagggcct ggagtggatc ggtaatgtct attatattgg gaacgcctac       180

```
tacaacccgt ccctcaagac tggagtcacc ttttccgtag acacgtccaa gaaccagttc    240
tccctgaacc tgaggtctgt gaccgccgca gacacggcta tgtattactg tgcgagactt    300
tctaactgga atttcttgga cttgtggggc cagggaaccc tggtcaccgt ctcctca       357
```

<210> SEQ ID NO 306
<211> LENGTH: 119
<212> TYPE: PRT
<213> ORGANISM: Artificial Sequence
<220> FEATURE:
<223> OTHER INFORMATION: synthetic

<400> SEQUENCE: 306

```
Gln Leu Gln Leu Gln Glu Ser Gly Pro Gly Leu Val Lys Pro Ser Glu
1               5                   10                  15

Thr Leu Ser Leu Thr Cys Thr Val Ser Gly Gly Ser Ile Ser Ser Thr
            20                  25                  30

Asn His Tyr Trp Gly Trp Ile Arg Gln Pro Pro Gly Lys Gly Leu Glu
        35                  40                  45

Trp Ile Gly Asn Val Tyr Tyr Ile Gly Asn Ala Tyr Tyr Asn Pro Ser
    50                  55                  60

Leu Lys Thr Gly Val Thr Phe Ser Val Asp Thr Ser Lys Asn Gln Phe
65                  70                  75                  80

Ser Leu Asn Leu Arg Ser Val Thr Ala Ala Asp Thr Ala Met Tyr Tyr
                85                  90                  95

Cys Ala Arg Leu Ser Asn Trp Asn Phe Leu Asp Leu Trp Gly Gln Gly
            100                 105                 110

Thr Leu Val Thr Val Ser Ser
        115
```

<210> SEQ ID NO 307
<211> LENGTH: 30
<212> TYPE: DNA
<213> ORGANISM: Artificial Sequence
<220> FEATURE:
<223> OTHER INFORMATION: synthetic

<400> SEQUENCE: 307

```
ggtggctcca tcagcagtac taatcactac                                      30
```

<210> SEQ ID NO 308
<211> LENGTH: 10
<212> TYPE: PRT
<213> ORGANISM: Artificial Sequence
<220> FEATURE:
<223> OTHER INFORMATION: synthetic

<400> SEQUENCE: 308

```
Gly Gly Ser Ile Ser Ser Thr Asn His Tyr
1               5                   10
```

<210> SEQ ID NO 309
<211> LENGTH: 21
<212> TYPE: DNA
<213> ORGANISM: Artificial Sequence
<220> FEATURE:
<223> OTHER INFORMATION: synthetic

<400> SEQUENCE: 309

```
gtctattata ttgggaacgc c                                               21
```

<210> SEQ ID NO 310

<210> SEQ ID NO 310
<211> LENGTH: 7
<212> TYPE: PRT
<213> ORGANISM: Artificial Sequence
<220> FEATURE:
<223> OTHER INFORMATION: synthetic

<400> SEQUENCE: 310

Val Tyr Tyr Ile Gly Asn Ala
1               5

<210> SEQ ID NO 311
<211> LENGTH: 33
<212> TYPE: DNA
<213> ORGANISM: Artificial Sequence
<220> FEATURE:
<223> OTHER INFORMATION: synthetic

<400> SEQUENCE: 311
gcgagacttt ctaactggaa tttcttggac ttg    33

<210> SEQ ID NO 312
<211> LENGTH: 11
<212> TYPE: PRT
<213> ORGANISM: Artificial Sequence
<220> FEATURE:
<223> OTHER INFORMATION: synthetic

<400> SEQUENCE: 312

Ala Arg Leu Ser Asn Trp Asn Phe Leu Asp Leu
1               5                   10

<210> SEQ ID NO 313
<211> LENGTH: 318
<212> TYPE: DNA
<213> ORGANISM: Artificial Sequence
<220> FEATURE:
<223> OTHER INFORMATION: synthetic

<400> SEQUENCE: 313
gaaattgtga tgacgcagtc tccagccacc ctgtctgtgt ctccagggga aagagccacc    60
ctctcctgca gggccagtca gagtattagc agcaacttag cctggtacca gcagaaacct   120
ggccaggctc ccaggctcct catctatggt gcatccacca gggccactgg tatcccagcc   180
aggttcagtg gcagtgggtc tgggacagag ttcactctca ccatcagcag cctgcagtct   240
gaagattttg cagtttatta ctgtcagcaa tttaataact ggctctcttt cggcggaggg   300
accaaggtgg agatcaaa                                                  318

<210> SEQ ID NO 314
<211> LENGTH: 106
<212> TYPE: PRT
<213> ORGANISM: Artificial Sequence
<220> FEATURE:
<223> OTHER INFORMATION: synthetic

<400> SEQUENCE: 314

Glu Ile Val Met Thr Gln Ser Pro Ala Thr Leu Ser Val Ser Pro Gly
1               5                   10                  15

Glu Arg Ala Thr Leu Ser Cys Arg Ala Ser Gln Ser Ile Ser Ser Asn
            20                  25                  30

Leu Ala Trp Tyr Gln Gln Lys Pro Gly Gln Ala Pro Arg Leu Leu Ile
        35                  40                  45

Tyr Gly Ala Ser Thr Arg Ala Thr Gly Ile Pro Ala Arg Phe Ser Gly
    50                  55                  60

```
Ser Gly Ser Gly Thr Glu Phe Thr Leu Thr Ile Ser Ser Leu Gln Ser
65                  70                  75                  80

Glu Asp Phe Ala Val Tyr Tyr Cys Gln Gln Phe Asn Asn Trp Leu Ser
                85                  90                  95

Phe Gly Gly Gly Thr Lys Val Glu Ile Lys
            100                 105
```

```
<210> SEQ ID NO 315
<211> LENGTH: 18
<212> TYPE: DNA
<213> ORGANISM: Artificial Sequence
<220> FEATURE:
<223> OTHER INFORMATION: synthetic

<400> SEQUENCE: 315
cagagtatta gcagcaac                                                 18

<210> SEQ ID NO 316
<211> LENGTH: 6
<212> TYPE: PRT
<213> ORGANISM: Artificial Sequence
<220> FEATURE:
<223> OTHER INFORMATION: synthetic

<400> SEQUENCE: 316

Gln Ser Ile Ser Ser Asn
1               5

<210> SEQ ID NO 317
<211> LENGTH: 9
<212> TYPE: DNA
<213> ORGANISM: Artificial Sequence
<220> FEATURE:
<223> OTHER INFORMATION: synthetic

<400> SEQUENCE: 317 ggtgcatcc                                                            9

<210> SEQ ID NO 318
<211> LENGTH: 3
<212> TYPE: PRT
<213> ORGANISM: Artificial Sequence
<220> FEATURE:
<223> OTHER INFORMATION: synthetic

<400> SEQUENCE: 318

Gly Ala Ser
1

<210> SEQ ID NO 319
<211> LENGTH: 24
<212> TYPE: DNA
<213> ORGANISM: Artificial Sequence
<220> FEATURE:
<223> OTHER INFORMATION: synthetic

<400> SEQUENCE: 319
cagcaattta ataactggct ctct                                          24

<210> SEQ ID NO 320
<211> LENGTH: 8
<212> TYPE: PRT
<213> ORGANISM: Artificial Sequence
<220> FEATURE:
<223> OTHER INFORMATION: synthetic
```

<400> SEQUENCE: 320

Gln Gln Phe Asn Asn Trp Leu Ser
1               5

<210> SEQ ID NO 321
<211> LENGTH: 366
<212> TYPE: DNA
<213> ORGANISM: Artificial Sequence
<220> FEATURE:
<223> OTHER INFORMATION: synthetic

<400> SEQUENCE: 321

```
caggtgcagc tggtggagtc ggggggggc gtggtccagc ctgggaggtc cctgagactc      60
tcctgtgcag cgtctggatt caccttcagt acctatggca tgcactgggt ccgccaggct    120
ccaggcaagg ggctggagtg ggtggcagtt atatggtatg ttggaagtaa taaattctat    180
gcagactccg tgaagggccg attcaccatc tccagagaca attccaagaa cacgctgtat    240
ctgcaaatgg acagcctgag agccgaggac acggtgtgt atcactgtgc gagagacagt    300
atggttcggc cctattatta cggtatggac gtctggggcc aagggaccac ggtcaccgtc    360
tcctca                                                                366
```

<210> SEQ ID NO 322
<211> LENGTH: 122
<212> TYPE: PRT
<213> ORGANISM: Artificial Sequence
<220> FEATURE:
<223> OTHER INFORMATION: synthetic

<400> SEQUENCE: 322

Gln Val Gln Leu Val Glu Ser Gly Gly Val Val Gln Pro Gly Arg
1               5                   10                  15

Ser Leu Arg Leu Ser Cys Ala Ala Ser Gly Phe Thr Phe Ser Thr Tyr
            20                  25                  30

Gly Met His Trp Val Arg Gln Ala Pro Gly Lys Gly Leu Glu Trp Val
        35                  40                  45

Ala Val Ile Trp Tyr Val Gly Ser Asn Lys Phe Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asp Ser Leu Arg Ala Glu Asp Thr Gly Val Tyr His Cys
                85                  90                  95

Ala Arg Asp Ser Met Val Arg Pro Tyr Tyr Tyr Gly Met Asp Val Trp
            100                 105                 110

Gly Gln Gly Thr Thr Val Thr Val Ser Ser
        115                 120

<210> SEQ ID NO 323
<211> LENGTH: 24
<212> TYPE: DNA
<213> ORGANISM: Artificial Sequence
<220> FEATURE:
<223> OTHER INFORMATION: synthetic

<400> SEQUENCE: 323

```
ggattcacct tcagtaccta tggc                                            24
```

<210> SEQ ID NO 324
<211> LENGTH: 8

```
<212> TYPE: PRT
<213> ORGANISM: Artificial Sequence
<220> FEATURE:
<223> OTHER INFORMATION: synthetic

<400> SEQUENCE: 324

Gly Phe Thr Phe Ser Thr Tyr Gly
1               5

<210> SEQ ID NO 325
<211> LENGTH: 24
<212> TYPE: DNA
<213> ORGANISM: Artificial Sequence
<220> FEATURE:
<223> OTHER INFORMATION: synthetic

<400> SEQUENCE: 325
atatggtatg ttggaagtaa taaa                                          24

<210> SEQ ID NO 326
<211> LENGTH: 8
<212> TYPE: PRT
<213> ORGANISM: Artificial Sequence
<220> FEATURE:
<223> OTHER INFORMATION: synthetic

<400> SEQUENCE: 326

Ile Trp Tyr Val Gly Ser Asn Lys
1               5

<210> SEQ ID NO 327
<211> LENGTH: 45
<212> TYPE: DNA
<213> ORGANISM: Artificial Sequence
<220> FEATURE:
<223> OTHER INFORMATION: synthetic

<400> SEQUENCE: 327
gcgagagaca gtatggttcg gccctattat tacggtatgg acgtc                   45

<210> SEQ ID NO 328
<211> LENGTH: 15
<212> TYPE: PRT
<213> ORGANISM: Artificial Sequence
<220> FEATURE:
<223> OTHER INFORMATION: synthetic

<400> SEQUENCE: 328

Ala Arg Asp Ser Met Val Arg Pro Tyr Tyr Tyr Gly Met Asp Val
1               5                   10                  15

<210> SEQ ID NO 329
<211> LENGTH: 375
<212> TYPE: DNA
<213> ORGANISM: Artificial Sequence
<220> FEATURE:
<223> OTHER INFORMATION: synthetic

<400> SEQUENCE: 329
caggtgcagc tggtggagtc tgggggaggc gtggtccaac ctgggaggtc cctgagactc    60
tcctgttcag cgtctggatt caccctcagt aattttgtca tgcattgggt ccgccaggct   120
ccaggcaagg ggctggagtg gctggcagtc atattatatg atggaagtaa taaatattat   180
gcggactccg tgaagggccg attcaccatc tccagagaca attccaacaa caggctgtat   240
ctgcaaatga acagcctgag agccgaggac acggctcttt attactgtgc gagaggagag   300
```

```
tccttgggat cacctatcta ttattactac ggtttggacg tctggggcca agggaccacg    360
gtcaccgtct cctca                                                    375
```

<210> SEQ ID NO 330
<211> LENGTH: 125
<212> TYPE: PRT
<213> ORGANISM: Artificial Sequence
<220> FEATURE:
<223> OTHER INFORMATION: synthetic

<400> SEQUENCE: 330

```
Gln Val Gln Leu Val Glu Ser Gly Gly Val Val Gln Pro Gly Arg
1               5                   10                  15

Ser Leu Arg Leu Ser Cys Ser Ala Ser Gly Phe Thr Leu Ser Asn Phe
            20                  25                  30

Val Met His Trp Val Arg Gln Ala Pro Gly Lys Gly Leu Glu Trp Val
        35                  40                  45

Ala Val Ile Leu Tyr Asp Gly Ser Asn Lys Tyr Tyr Ala Asp Ser Val
    50                  55                  60

Lys Gly Arg Phe Thr Ile Ser Arg Asp Asn Ser Asn Asn Arg Leu Tyr
65                  70                  75                  80

Leu Gln Met Asn Ser Leu Arg Ala Glu Asp Thr Ala Leu Tyr Tyr Cys
                85                  90                  95

Ala Arg Gly Glu Ser Leu Gly Ser Pro Ile Tyr Tyr Tyr Gly Leu
            100                 105                 110

Asp Val Trp Gly Gln Gly Thr Thr Val Thr Val Ser Ser
        115                 120                 125
```

<210> SEQ ID NO 331
<211> LENGTH: 24
<212> TYPE: DNA
<213> ORGANISM: Artificial Sequence
<220> FEATURE:
<223> OTHER INFORMATION: synthetic

<400> SEQUENCE: 331

```
ggattcaccc tcagtaattt tgtc                                          24
```

<210> SEQ ID NO 332
<211> LENGTH: 8
<212> TYPE: PRT
<213> ORGANISM: Artificial Sequence
<220> FEATURE:
<223> OTHER INFORMATION: synthetic

<400> SEQUENCE: 332

```
Gly Phe Thr Leu Ser Asn Phe Val
1               5
```

<210> SEQ ID NO 333
<211> LENGTH: 24
<212> TYPE: DNA
<213> ORGANISM: Artificial Sequence
<220> FEATURE:
<223> OTHER INFORMATION: synthetic

<400> SEQUENCE: 333

```
atattatatg atggaagtaa taaa                                          24
```

<210> SEQ ID NO 334
<211> LENGTH: 8

<210> SEQ ID NO 334
<211> LENGTH: 7
<212> TYPE: PRT
<213> ORGANISM: Artificial Sequence
<220> FEATURE:
<223> OTHER INFORMATION: synthetic

<400> SEQUENCE: 334

Ile Leu Tyr Asp Gly Ser Asn Lys
1               5

<210> SEQ ID NO 335
<211> LENGTH: 54
<212> TYPE: DNA
<213> ORGANISM: Artificial Sequence
<220> FEATURE:
<223> OTHER INFORMATION: synthetic

<400> SEQUENCE: 335
gcgagaggag agtccttggg atcacctatc tattattact acggtttgga cgtc      54

<210> SEQ ID NO 336
<211> LENGTH: 18
<212> TYPE: PRT
<213> ORGANISM: Artificial Sequence
<220> FEATURE:
<223> OTHER INFORMATION: synthetic

<400> SEQUENCE: 336

Ala Arg Gly Glu Ser Leu Gly Ser Pro Ile Tyr Tyr Tyr Gly Leu
1               5                   10                  15

Asp Val

<210> SEQ ID NO 337
<211> LENGTH: 360
<212> TYPE: DNA
<213> ORGANISM: Artificial Sequence
<220> FEATURE:
<223> OTHER INFORMATION: synthetic

<400> SEQUENCE: 337
caggtgcagc tgcaggagtc gggcccagga ctggtgaagc cttcggagac cctgtccctc      60
acctgcattg tctctggtgg ctccatcagt ggttacttct ggaactggat ccggcagccc     120
ccagggaagg gacttgaatg gattggttat atctattaca gtgggaccac catctacaac     180
ccctccctca gagtcgatt caccatatca ctagacacgt ccaagaacca gttctcccta     240
aagctgacct ctgtgaccgc tgcggacacg gccgtatatt actgtgcgag agagtcgtat     300
aatccctcgc cgcgataaattt tgaccactgg ggccagggaa ccctggtcac cgtctcctca     360

<210> SEQ ID NO 338
<211> LENGTH: 120
<212> TYPE: PRT
<213> ORGANISM: Artificial Sequence
<220> FEATURE:
<223> OTHER INFORMATION: synthetic

<400> SEQUENCE: 338

Gln Val Gln Leu Gln Glu Ser Gly Pro Gly Leu Val Lys Pro Ser Glu
1               5                   10                  15

Thr Leu Ser Leu Thr Cys Ile Val Ser Gly Gly Ser Ile Ser Gly Tyr
                20                  25                  30

Phe Trp Asn Trp Ile Arg Gln Pro Pro Gly Lys Gly Leu Glu Trp Ile
            35                  40                  45

Gly Tyr Ile Tyr Tyr Ser Gly Thr Thr Ile Tyr Asn Pro Ser Leu Lys

```
                50                  55                  60
Ser Arg Phe Thr Ile Ser Leu Asp Thr Ser Lys Asn Gln Phe Ser Leu
 65                  70                  75                  80

Lys Leu Thr Ser Val Thr Ala Ala Asp Thr Ala Val Tyr Tyr Cys Ala
                 85                  90                  95

Arg Glu Ser Tyr Asn Pro Ser Pro Arg Tyr Phe Asp His Trp Gly Gln
            100                 105                 110

Gly Thr Leu Val Thr Val Ser Ser
        115                 120
```

<210> SEQ ID NO 339
<211> LENGTH: 24
<212> TYPE: DNA
<213> ORGANISM: Artificial Sequence
<220> FEATURE:
<223> OTHER INFORMATION: synthetic

<400> SEQUENCE: 339
ggtggctcca tcagtggtta cttc                                        24

<210> SEQ ID NO 340
<211> LENGTH: 8
<212> TYPE: PRT
<213> ORGANISM: Artificial Sequence
<220> FEATURE:
<223> OTHER INFORMATION: synthetic

<400> SEQUENCE: 340

```
Gly Gly Ser Ile Ser Gly Tyr Phe
 1               5
```

<210> SEQ ID NO 341
<211> LENGTH: 21
<212> TYPE: DNA
<213> ORGANISM: Artificial Sequence
<220> FEATURE:
<223> OTHER INFORMATION: synthetic

<400> SEQUENCE: 341
atctattaca gtgggaccac c                                           21

<210> SEQ ID NO 342
<211> LENGTH: 7
<212> TYPE: PRT
<213> ORGANISM: Artificial Sequence
<220> FEATURE:
<223> OTHER INFORMATION: synthetic

<400> SEQUENCE: 342

```
Ile Tyr Tyr Ser Gly Thr Thr
 1               5
```

<210> SEQ ID NO 343
<211> LENGTH: 42
<212> TYPE: DNA
<213> ORGANISM: Artificial Sequence
<220> FEATURE:
<223> OTHER INFORMATION: synthetic

<400> SEQUENCE: 343
gcgagagagt cgtataatcc ctcgccgcga tattttgacc ac                    42

<210> SEQ ID NO 344
<211> LENGTH: 14

```
<212> TYPE: PRT
<213> ORGANISM: Artificial Sequence
<220> FEATURE:
<223> OTHER INFORMATION: synthetic

<400> SEQUENCE: 344

Ala Arg Glu Ser Tyr Asn Pro Ser Pro Arg Tyr Phe Asp His
1               5                   10

<210> SEQ ID NO 345
<211> LENGTH: 375
<212> TYPE: DNA
<213> ORGANISM: Artificial Sequence
<220> FEATURE:
<223> OTHER INFORMATION: synthetic

<400> SEQUENCE: 345
caggtgcagc tggtggagtc tgggggaggc gtggtccagc ctggagggtc cctgagactc      60
tcctgtgcag cgtctggatt cagcttcagt agttatggca tgcactgggt ccgccaggct     120
ccaggcaagg ggctggagtg gatggcagtt atatggtatg ctggaagtaa taaattctat     180
gcagactccg tgaagggccg attcaccatc tccagagaca attccaagaa cacgctgtat     240
ctgcaaatga acagcctgac agccgaggac acggctgtat attactgtgc gagagggtcg     300
agtctagcag ctccagacct ctacaagtac ggaatggacg tctggggcca ggggaccacg     360
gtcaccgtct cctca                                                      375

<210> SEQ ID NO 346
<211> LENGTH: 125
<212> TYPE: PRT
<213> ORGANISM: Artificial Sequence
<220> FEATURE:
<223> OTHER INFORMATION: synthetic

<400> SEQUENCE: 346

Gln Val Gln Leu Val Glu Ser Gly Gly Gly Val Val Gln Pro Gly Arg
1               5                   10                  15

Ser Leu Arg Leu Ser Cys Ala Ala Ser Gly Phe Ser Phe Ser Ser Tyr
                20                  25                  30

Gly Met His Trp Val Arg Gln Ala Pro Gly Lys Gly Leu Glu Trp Met
            35                  40                  45

Ala Val Ile Trp Tyr Ala Gly Ser Asn Lys Phe Tyr Ala Asp Ser Val
        50                  55                  60

Lys Gly Arg Phe Thr Ile Ser Arg Asp Asn Ser Lys Asn Thr Leu Tyr
65                  70                  75                  80

Leu Gln Met Asn Ser Leu Thr Ala Glu Asp Thr Ala Val Tyr Tyr Cys
                85                  90                  95

Ala Arg Gly Ser Ser Leu Ala Ala Pro Asp Leu Tyr Lys Tyr Gly Met
            100                 105                 110

Asp Val Trp Gly Gln Gly Thr Thr Val Thr Val Ser Ser
        115                 120                 125

<210> SEQ ID NO 347
<211> LENGTH: 24
<212> TYPE: DNA
<213> ORGANISM: Artificial Sequence
<220> FEATURE:
<223> OTHER INFORMATION: synthetic

<400> SEQUENCE: 347
ggattcagct tcagtagtta tggc                                             24
```

<210> SEQ ID NO 348
<211> LENGTH: 8
<212> TYPE: PRT
<213> ORGANISM: Artificial Sequence
<220> FEATURE:
<223> OTHER INFORMATION: synthetic

<400> SEQUENCE: 348

Gly Phe Ser Phe Ser Ser Tyr Gly
1               5

<210> SEQ ID NO 349
<211> LENGTH: 24
<212> TYPE: DNA
<213> ORGANISM: Artificial Sequence
<220> FEATURE:
<223> OTHER INFORMATION: synthetic

<400> SEQUENCE: 349
atatggtatg ctggaagtaa taaa                                              24

<210> SEQ ID NO 350
<211> LENGTH: 8
<212> TYPE: PRT
<213> ORGANISM: Artificial Sequence
<220> FEATURE:
<223> OTHER INFORMATION: synthetic

<400> SEQUENCE: 350

Ile Trp Tyr Ala Gly Ser Asn Lys
1               5

<210> SEQ ID NO 351
<211> LENGTH: 54
<212> TYPE: DNA
<213> ORGANISM: Artificial Sequence
<220> FEATURE:
<223> OTHER INFORMATION: synthetic

<400> SEQUENCE: 351
gcgagagggt cgagtctagc agctccagac ctctacaagt acggaatgga cgtc             54

<210> SEQ ID NO 352
<211> LENGTH: 18
<212> TYPE: PRT
<213> ORGANISM: Artificial Sequence
<220> FEATURE:
<223> OTHER INFORMATION: synthetic

<400> SEQUENCE: 352

Ala Arg Gly Ser Ser Leu Ala Ala Pro Asp Leu Tyr Lys Tyr Gly Met
1               5                   10                  15

Asp Val

<210> SEQ ID NO 353
<211> LENGTH: 351
<212> TYPE: DNA
<213> ORGANISM: Artificial Sequence
<220> FEATURE:
<223> OTHER INFORMATION: synthetic

<400> SEQUENCE: 353
caggtgcagc tgcaggagtc gggcccagga ctggtgaagc cttcggagac cctgtccctc       60
acctgtacta tctctggtgg ctccatcagt aattccttct tgacctggat ccgacagccc      120

```
ccagggaagg gactggagtg gattggatat atctatcacc ggggaaacac tgattccaat    180
ccctccctca agagtcgagt caccatctca acagacccgt ccaagaatca gttctccctg    240
accctgcact ctgtgaccgc cgcagactcg gccatatatt actgtgcgcg gggacaattt    300
atggagtggt tgacttctg gggccaggga accctggtca ccgtctcctc a             351
```

<210> SEQ ID NO 354
<211> LENGTH: 117
<212> TYPE: PRT
<213> ORGANISM: Artificial Sequence
<220> FEATURE:
<223> OTHER INFORMATION: synthetic

<400> SEQUENCE: 354

```
Gln Val Gln Leu Gln Glu Ser Gly Pro Gly Leu Val Lys Pro Ser Glu
1               5                   10                  15

Thr Leu Ser Leu Thr Cys Thr Ile Ser Gly Gly Ser Ile Ser Asn Ser
            20                  25                  30

Phe Leu Thr Trp Ile Arg Gln Pro Pro Gly Lys Gly Leu Glu Trp Ile
        35                  40                  45

Gly Tyr Ile Tyr His Arg Gly Asn Thr Asp Ser Asn Pro Ser Leu Lys
    50                  55                  60

Ser Arg Val Thr Ile Ser Thr Asp Pro Ser Lys Asn Gln Phe Ser Leu
65                  70                  75                  80

Thr Leu His Ser Val Thr Ala Ala Asp Ser Ala Ile Tyr Tyr Cys Ala
                85                  90                  95

Arg Gly Gln Phe Met Glu Trp Phe Asp Phe Trp Gly Gln Gly Thr Leu
            100                 105                 110

Val Thr Val Ser Ser
        115
```

<210> SEQ ID NO 355
<211> LENGTH: 24
<212> TYPE: DNA
<213> ORGANISM: Artificial Sequence
<220> FEATURE:
<223> OTHER INFORMATION: synthetic

<400> SEQUENCE: 355

```
ggtggctcca tcagtaattc cttc                                           24
```

<210> SEQ ID NO 356
<211> LENGTH: 8
<212> TYPE: PRT
<213> ORGANISM: Artificial Sequence
<220> FEATURE:
<223> OTHER INFORMATION: synthetic

<400> SEQUENCE: 356

```
Gly Gly Ser Ile Ser Asn Ser Phe
1               5
```

<210> SEQ ID NO 357
<211> LENGTH: 21
<212> TYPE: DNA
<213> ORGANISM: Artificial Sequence
<220> FEATURE:
<223> OTHER INFORMATION: synthetic

<400> SEQUENCE: 357

```
atctatcacc ggggaaacac t                                              21
```

<210> SEQ ID NO 358
<211> LENGTH: 7
<212> TYPE: PRT
<213> ORGANISM: Artificial Sequence
<220> FEATURE:
<223> OTHER INFORMATION: synthetic

<400> SEQUENCE: 358

Ile Tyr His Arg Gly Asn Thr
1               5

<210> SEQ ID NO 359
<211> LENGTH: 33
<212> TYPE: DNA
<213> ORGANISM: Artificial Sequence
<220> FEATURE:
<223> OTHER INFORMATION: synthetic

<400> SEQUENCE: 359
gcgcggggac aatttatgga gtggtttgac ttc                                    33

<210> SEQ ID NO 360
<211> LENGTH: 11
<212> TYPE: PRT
<213> ORGANISM: Artificial Sequence
<220> FEATURE:
<223> OTHER INFORMATION: synthetic

<400> SEQUENCE: 360

Ala Arg Gly Gln Phe Met Glu Trp Phe Asp Phe
1               5                   10

<210> SEQ ID NO 361
<211> LENGTH: 375
<212> TYPE: DNA
<213> ORGANISM: Artificial Sequence
<220> FEATURE:
<223> OTHER INFORMATION: synthetic

<400> SEQUENCE: 361
caggtgcagc tggtggagtc tgggggaggc gtggtccagc ctggagggtc cctgagagtc       60
tcctgtgaag cgtctggatt caccctcagt agttatggca tgaactgggt ccgccaggct      120
ccaggcaagg ggctggagtg ggtggcagtt atatggtatg atggaagtaa taaatactat      180
tcagactccg tgaagggccg attcaccatc tccagagaca attccaagaa cacgctgtat      240
ctgcaaatga acggcctgag agacgatgac acggctgtgt attactgtgc gagagggag       300 cagctcggct ctcatgtcta ttattactat ggaatggacg tctggggcca agggaccacg      360
gtcaccgtct cctca                                                       375

<210> SEQ ID NO 362
<211> LENGTH: 125
<212> TYPE: PRT
<213> ORGANISM: Artificial Sequence
<220> FEATURE:
<223> OTHER INFORMATION: synthetic

<400> SEQUENCE: 362

Gln Val Gln Leu Val Glu Ser Gly Gly Gly Val Val Gln Pro Gly Arg
1               5                   10                  15

Ser Leu Arg Val Ser Cys Glu Ala Ser Gly Phe Thr Leu Ser Ser Tyr
            20                  25                  30

Gly Met Asn Trp Val Arg Gln Ala Pro Gly Lys Gly Leu Glu Trp Val
            35                  40                  45

Ala Val Ile Trp Tyr Asp Gly Ser Asn Lys Tyr Tyr Ser Asp Ser Val
 50                  55                  60

Lys Gly Arg Phe Thr Ile Ser Arg Asp Asn Ser Lys Asn Thr Leu Tyr
 65                  70                  75                  80

Leu Gln Met Asn Gly Leu Arg Asp Asp Thr Ala Val Tyr Tyr Cys
                 85                  90                  95

Ala Arg Gly Glu Gln Leu Gly Ser His Val Tyr Tyr Tyr Gly Met
             100                 105                 110

Asp Val Trp Gly Gln Gly Thr Thr Val Thr Val Ser Ser
         115                 120                 125

<210> SEQ ID NO 363
<211> LENGTH: 24
<212> TYPE: DNA
<213> ORGANISM: Artificial Sequence
<220> FEATURE:
<223> OTHER INFORMATION: synthetic

<400> SEQUENCE: 363
ggattcaccc tcagtagtta tggc                                   24

<210> SEQ ID NO 364
<211> LENGTH: 8
<212> TYPE: PRT
<213> ORGANISM: Artificial Sequence
<220> FEATURE:
<223> OTHER INFORMATION: synthetic

<400> SEQUENCE: 364

Gly Phe Thr Leu Ser Ser Tyr Gly
 1               5

<210> SEQ ID NO 365
<211> LENGTH: 24
<212> TYPE: DNA
<213> ORGANISM: Artificial Sequence
<220> FEATURE:
<223> OTHER INFORMATION: synthetic

<400> SEQUENCE: 365
atatggtatg atggaagtaa taaa                                   24

<210> SEQ ID NO 366
<211> LENGTH: 8
<212> TYPE: PRT
<213> ORGANISM: Artificial Sequence
<220> FEATURE:
<223> OTHER INFORMATION: synthetic

<400> SEQUENCE: 366

Ile Trp Tyr Asp Gly Ser Asn Lys
 1               5

<210> SEQ ID NO 367
<211> LENGTH: 54
<212> TYPE: DNA
<213> ORGANISM: Artificial Sequence
<220> FEATURE:
<223> OTHER INFORMATION: synthetic

<400> SEQUENCE: 367
gcgagagggg agcagctcgg ctctcatgtc tattattact atggaatgga cgtc    54

<210> SEQ ID NO 368
<211> LENGTH: 18
<212> TYPE: PRT
<213> ORGANISM: Artificial Sequence
<220> FEATURE:
<223> OTHER INFORMATION: synthetic

<400> SEQUENCE: 368

Ala Arg Gly Glu Gln Leu Gly Ser His Val Tyr Tyr Tyr Gly Met
1               5                   10                  15

Asp Val

<210> SEQ ID NO 369
<211> LENGTH: 375
<212> TYPE: DNA
<213> ORGANISM: Artificial Sequence
<220> FEATURE:
<223> OTHER INFORMATION: synthetic

<400> SEQUENCE: 369
caggtgcagc tggtggagtc tgggggaggc gtggtccagc ctgggaagtc cctgagactc      60
tcctgtgcag cgtctggatt caccttcagt aactatgtca tgcactgggt ccgccagact     120
ccaggcaagg ggctggagtg ggtggcgatt attttatttc ctggaagtaa taaatactat     180
gtagactccg tgcagggccg attcaccatc tccagagaca attccaagaa cacgctgtct     240
ctgcaaatga acagcctgag agccgaagac acggctgtat attactgtgc gaggggctcg     300
agtttgacag ctcttgacta ctactactac ggtctggacg tctggggcca agggaccacg     360
gtcaccgtct cctca                                                     375

<210> SEQ ID NO 370
<211> LENGTH: 125
<212> TYPE: PRT
<213> ORGANISM: Artificial Sequence
<220> FEATURE:
<223> OTHER INFORMATION: synthetic

<400> SEQUENCE: 370

Gln Val Gln Leu Val Glu Ser Gly Gly Gly Val Val Gln Pro Gly Lys
1               5                   10                  15

Ser Leu Arg Leu Ser Cys Ala Ala Ser Gly Phe Thr Phe Ser Asn Tyr
            20                  25                  30

Val Met His Trp Val Arg Gln Thr Pro Gly Lys Gly Leu Glu Trp Val
        35                  40                  45

Ala Ile Ile Leu Phe Pro Gly Ser Asn Lys Tyr Tyr Val Asp Ser Val
    50                  55                  60

Gln Gly Arg Phe Thr Ile Ser Arg Asp Asn Lys Asn Thr Leu Ser
65                  70                  75                  80

Leu Gln Met Asn Ser Leu Arg Ala Glu Asp Thr Ala Val Tyr Tyr Cys
                85                  90                  95

Ala Arg Gly Ser Ser Leu Thr Ala Leu Asp Tyr Tyr Tyr Gly Leu
            100                 105                 110

Asp Val Trp Gly Gln Gly Thr Thr Val Thr Val Ser Ser
        115                 120                 125

<210> SEQ ID NO 371
<211> LENGTH: 24
<212> TYPE: DNA
<213> ORGANISM: Artificial Sequence

```
<220> FEATURE:
<223> OTHER INFORMATION: synthetic

<400> SEQUENCE: 371
ggattcacct tcagtaacta tgtc                                              24

<210> SEQ ID NO 372
<211> LENGTH: 8
<212> TYPE: PRT
<213> ORGANISM: Artificial Sequence
<220> FEATURE:
<223> OTHER INFORMATION: synthetic

<400> SEQUENCE: 372

Gly Phe Thr Phe Ser Asn Tyr Val
1               5

<210> SEQ ID NO 373
<211> LENGTH: 24
<212> TYPE: DNA
<213> ORGANISM: Artificial Sequence
<220> FEATURE:
<223> OTHER INFORMATION: synthetic

<400> SEQUENCE: 373
attttatttc ctggaagtaa taaa                                              24

<210> SEQ ID NO 374
<211> LENGTH: 8
<212> TYPE: PRT
<213> ORGANISM: Artificial Sequence
<220> FEATURE:
<223> OTHER INFORMATION: synthetic

<400> SEQUENCE: 374

Ile Leu Phe Pro Gly Ser Asn Lys
1               5

<210> SEQ ID NO 375
<211> LENGTH: 54
<212> TYPE: DNA
<213> ORGANISM: Artificial Sequence
<220> FEATURE:
<223> OTHER INFORMATION: synthetic

<400> SEQUENCE: 375
gcgaggggct cgagtttgac agctcttgac tactactact acggtctgga cgtc             54

<210> SEQ ID NO 376
<211> LENGTH: 18
<212> TYPE: PRT
<213> ORGANISM: Artificial Sequence
<220> FEATURE:
<223> OTHER INFORMATION: synthetic

<400> SEQUENCE: 376

Ala Arg Gly Ser Ser Leu Thr Ala Leu Asp Tyr Tyr Tyr Tyr Gly Leu
1               5                   10                  15

Asp Val

<210> SEQ ID NO 377
<211> LENGTH: 375
<212> TYPE: DNA
<213> ORGANISM: Artificial Sequence
<220> FEATURE:
<223> OTHER INFORMATION: synthetic
```

<400> SEQUENCE: 377

```
caggtgcagc tggtggagtc tgggggaggc gtggtccagc ctggagagtc cctgagactc    60
tcctgtgcag cgtctggatt caccttcagt aactatgtca tgcactgggt ccgccaggct   120
ccaggcaagg gctggagtg gtggcaatt atatggtatg atggaactaa tgaagactat   180
gcagactccg tgaaggtccg attcaccatc tccagagaca tttccaagaa cacgctgtat   240
ctgcaaatga acagcctgag agccgaggac acggctgtat attactgtgc gagagattgg   300
tttgattgta gtagtaccag ctgctatagg tacttcgatc tctggggccg tggcaccctg   360
gtcactgtct cctca                                                    375
```

<210> SEQ ID NO 378
<211> LENGTH: 125
<212> TYPE: PRT
<213> ORGANISM: Artificial Sequence
<220> FEATURE:
<223> OTHER INFORMATION: synthetic

<400> SEQUENCE: 378

```
Gln Val Gln Leu Val Glu Ser Gly Gly Gly Val Val Gln Pro Gly Arg
1               5                   10                  15
Ser Leu Arg Leu Ser Cys Ala Ala Ser Gly Phe Thr Phe Ser Asn Tyr
            20                  25                  30
Val Met His Trp Val Arg Gln Ala Pro Gly Lys Gly Leu Glu Trp Val
        35                  40                  45
Ala Ile Ile Trp Tyr Asp Gly Thr Asn Glu Asp Tyr Ala Asp Ser Val
    50                  55                  60
Lys Val Arg Phe Thr Ile Ser Arg Asp Ile Ser Lys Asn Thr Leu Tyr
65                  70                  75                  80
Leu Gln Met Asn Ser Leu Arg Ala Glu Asp Thr Ala Val Tyr Tyr Cys
                85                  90                  95
Ala Arg Asp Trp Phe Asp Cys Ser Ser Thr Ser Cys Tyr Arg Tyr Phe
            100                 105                 110
Asp Leu Trp Gly Arg Gly Thr Leu Val Thr Val Ser Ser
        115                 120                 125
```

<210> SEQ ID NO 379
<211> LENGTH: 24
<212> TYPE: DNA
<213> ORGANISM: Artificial Sequence
<220> FEATURE:
<223> OTHER INFORMATION: synthetic

<400> SEQUENCE: 379

```
ggattcacct tcagtaacta tgtc                                           24
```

<210> SEQ ID NO 380
<211> LENGTH: 8
<212> TYPE: PRT
<213> ORGANISM: Artificial Sequence
<220> FEATURE:
<223> OTHER INFORMATION: synthetic

<400> SEQUENCE: 380

```
Gly Phe Thr Phe Ser Asn Tyr Val
1               5
```

<210> SEQ ID NO 381
<211> LENGTH: 24

<212> TYPE: DNA
<213> ORGANISM: Artificial Sequence
<220> FEATURE:
<223> OTHER INFORMATION: synthetic

<400> SEQUENCE: 381
atatggtatg atggaactaa tgaa    24

<210> SEQ ID NO 382
<211> LENGTH: 8
<212> TYPE: PRT
<213> ORGANISM: Artificial Sequence
<220> FEATURE:
<223> OTHER INFORMATION: synthetic

<400> SEQUENCE: 382

Ile Trp Tyr Asp Gly Thr Asn Glu
1               5

<210> SEQ ID NO 383
<211> LENGTH: 54
<212> TYPE: DNA
<213> ORGANISM: Artificial Sequence
<220> FEATURE:
<223> OTHER INFORMATION: synthetic

<400> SEQUENCE: 383
gcgagagatt ggtttgattg tagtagtacc agctgctata ggtacttcga tctc    54

<210> SEQ ID NO 384
<211> LENGTH: 18
<212> TYPE: PRT
<213> ORGANISM: Artificial Sequence
<220> FEATURE:
<223> OTHER INFORMATION: synthetic

<400> SEQUENCE: 384

Ala Arg Asp Trp Phe Asp Cys Ser Ser Thr Ser Cys Tyr Arg Tyr Phe
1               5                   10                  15

Asp Leu

<210> SEQ ID NO 385
<211> LENGTH: 375
<212> TYPE: DNA
<213> ORGANISM: Artificial Sequence
<220> FEATURE:
<223> OTHER INFORMATION: synthetic

<400> SEQUENCE: 385
caggtgcagc tggtggagtc tgggggaggc gtggtccagc ctgggaggtc cctgagactc    60
tcctgtgcag cgtctggatt caccttcagt aataataaca tgcactgggt ccgccaggct    120
ccaggcaagg ggctggagtg ggtggcagtt atatggtatg atggaagtaa taagattat    180 gtagactccg tgaagggccg attcaccatc tccagagaca attccaagaa cacgctgtat    240
ctgcaaatga acagtttgag agccgaggat acggctgtgt attattgtgc gagatttgta    300
gtagcgccag ctacgtactc ctactactac attatagacg tctggggcca agggaccacg    360
gtcaccgtct cctca    375

<210> SEQ ID NO 386
<211> LENGTH: 125
<212> TYPE: PRT
<213> ORGANISM: Artificial Sequence
<220> FEATURE:

<223> OTHER INFORMATION: synthetic

<400> SEQUENCE: 386

Gln Val Gln Leu Val Glu Ser Gly Gly Gly Val Val Gln Pro Gly Arg
1               5                   10                  15

Ser Leu Arg Leu Ser Cys Ala Ala Ser Gly Phe Thr Phe Ser Asn Asn
            20                  25                  30

Asn Met His Trp Val Arg Gln Ala Pro Gly Lys Gly Leu Glu Trp Val
        35                  40                  45

Ala Val Ile Trp Tyr Asp Gly Ser Asn Lys Asp Tyr Val Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Phe Val Val Ala Pro Ala Thr Tyr Ser Tyr Tyr Tyr Ile Ile
            100                 105                 110

Asp Val Trp Gly Gln Gly Thr Thr Val Thr Val Ser Ser
        115                 120                 125

<210> SEQ ID NO 387
<211> LENGTH: 24
<212> TYPE: DNA
<213> ORGANISM: Artificial Sequence
<220> FEATURE:
<223> OTHER INFORMATION: synthetic

<400> SEQUENCE: 387
ggattcacct tcagtaataa taac                                          24

<210> SEQ ID NO 388
<211> LENGTH: 8
<212> TYPE: PRT
<213> ORGANISM: Artificial Sequence
<220> FEATURE:
<223> OTHER INFORMATION: synthetic

<400> SEQUENCE: 388

Gly Phe Thr Phe Ser Asn Asn Asn
1               5

<210> SEQ ID NO 389
<211> LENGTH: 24
<212> TYPE: DNA
<213> ORGANISM: Artificial Sequence
<220> FEATURE:
<223> OTHER INFORMATION: synthetic

<400> SEQUENCE: 389
atatggtatg atggaagtaa taaa                                          24

<210> SEQ ID NO 390
<211> LENGTH: 8
<212> TYPE: PRT
<213> ORGANISM: Artificial Sequence
<220> FEATURE:
<223> OTHER INFORMATION: synthetic

<400> SEQUENCE: 390

Ile Trp Tyr Asp Gly Ser Asn Lys
1               5

<210> SEQ ID NO 391
<211> LENGTH: 54
<212> TYPE: DNA
<213> ORGANISM: Artificial Sequence
<220> FEATURE:
<223> OTHER INFORMATION: synthetic

<400> SEQUENCE: 391
gcgagatttg tagtagcgcc agctacgtac tcctactact acattataga cgtc        54

<210> SEQ ID NO 392
<211> LENGTH: 18
<212> TYPE: PRT
<213> ORGANISM: Artificial Sequence
<220> FEATURE:
<223> OTHER INFORMATION: synthetic

<400> SEQUENCE: 392

Ala Arg Phe Val Val Ala Pro Ala Thr Tyr Ser Tyr Tyr Tyr Ile Ile
1               5                   10                  15

Asp Val

<210> SEQ ID NO 393
<211> LENGTH: 378
<212> TYPE: DNA
<213> ORGANISM: Artificial Sequence
<220> FEATURE:
<223> OTHER INFORMATION: synthetic

<400> SEQUENCE: 393
caggtgcagc tggtggagtc tgggggaggc gtggtccagc ctggggaggtc cctgagactc    60 tcctgtgcag cctctggatt taccttcagt acctatggca tgcactgggt ccgccaggct   120
ccaggcaagg ggctggagtg ggtggcagtt atttcatatg atggaagaat taaatactat   180
gaagactccg tgaagggccg attcatcata tccagagaca actccaagaa cacactgtat   240
ctgcaagtga acaccctgag agctgaggac acggctgtgt attactgtgc gaaagagagg   300
agatattgta gtgatactaa tacctgctct gatgttttg atgtctgggg ccaggggaca   360
atggtcaccg tctcttca                                                378

<210> SEQ ID NO 394
<211> LENGTH: 126
<212> TYPE: PRT
<213> ORGANISM: Artificial Sequence
<220> FEATURE:
<223> OTHER INFORMATION: synthetic

<400> SEQUENCE: 394

Gln Val Gln Leu Val Glu Ser Gly Gly Gly Val Val Gln Pro Gly Arg
1               5                   10                  15

Ser Leu Arg Leu Ser Cys Ala Ala Ser Gly Phe Thr Phe Ser Thr Tyr
            20                  25                  30

Gly Met His Trp Val Arg Gln Ala Pro Gly Lys Gly Leu Glu Trp Val
        35                  40                  45

Ala Val Ile Ser Tyr Asp Gly Arg Ile Lys Tyr Tyr Glu Asp Ser Val
    50                  55                  60

Lys Gly Arg Phe Ile Ile Ser Arg Asp Asn Ser Lys Asn Thr Leu Tyr
65                  70                  75                  80

Leu Gln Val Asn Thr Leu Arg Ala Glu Asp Thr Ala Val Tyr Tyr Cys
                85                  90                  95

Ala Lys Glu Arg Arg Tyr Cys Ser Asp Thr Asn Thr Cys Ser Asp Val

```
               100                 105                 110
Phe Asp Val Trp Gly Gln Gly Thr Met Val Thr Val Ser Ser
        115                 120                 125

<210> SEQ ID NO 395
<211> LENGTH: 24
<212> TYPE: DNA
<213> ORGANISM: Artificial Sequence
<220> FEATURE:
<223> OTHER INFORMATION: synthetic

<400> SEQUENCE: 395
ggatttacct tcagtaccta tggc                                          24

<210> SEQ ID NO 396
<211> LENGTH: 8
<212> TYPE: PRT
<213> ORGANISM: Artificial Sequence
<220> FEATURE:
<223> OTHER INFORMATION: synthetic

<400> SEQUENCE: 396

Gly Phe Thr Phe Ser Thr Tyr Gly
1               5

<210> SEQ ID NO 397
<211> LENGTH: 24
<212> TYPE: DNA
<213> ORGANISM: Artificial Sequence
<220> FEATURE:
<223> OTHER INFORMATION: synthetic

<400> SEQUENCE: 397
atttcatatg atggaagaat taaa                                          24

<210> SEQ ID NO 398
<211> LENGTH: 8
<212> TYPE: PRT
<213> ORGANISM: Artificial Sequence
<220> FEATURE:
<223> OTHER INFORMATION: synthetic

<400> SEQUENCE: 398

Ile Ser Tyr Asp Gly Arg Ile Lys
1               5

<210> SEQ ID NO 399
<211> LENGTH: 57
<212> TYPE: DNA
<213> ORGANISM: Artificial Sequence
<220> FEATURE:
<223> OTHER INFORMATION: synthetic

<400> SEQUENCE: 399
gcgaaagaga ggagatattg tagtgatact aatacctgct ctgatgtttt tgatgtc      57

<210> SEQ ID NO 400
<211> LENGTH: 19
<212> TYPE: PRT
<213> ORGANISM: Artificial Sequence
<220> FEATURE:
<223> OTHER INFORMATION: synthetic

<400> SEQUENCE: 400

Ala Lys Glu Arg Arg Tyr Cys Ser Asp Thr Asn Thr Cys Ser Asp Val
1               5                   10                  15
```

<210> SEQ ID NO 401
<211> LENGTH: 324
<212> TYPE: DNA
<213> ORGANISM: Artificial Sequence
<220> FEATURE:
<223> OTHER INFORMATION: synthetic

<400> SEQUENCE: 401

```
gacatccaga tgacccagtc tccatcctcc ctgtctgcat ctgtaggaga cagagtcacc    60
atcacttgcc gggcaagtca gagcattagc agctatttaa attggtatca gcagaaacca   120
gggaaagccc ctaagctcct gatctatgct gcatccagtt tgcaaagtgg ggtcccgtca   180
aggttcagtg gcagtggatc tgggacagat ttcactctca ccatcagcag tctgcaacct   240
gaagattttg caacttacta ctgtcaacag agttacagta ccccctccga tcaccttcggc   300
caagggacac gactggagat taaa                                          324
```

<210> SEQ ID NO 402
<211> LENGTH: 108
<212> TYPE: PRT
<213> ORGANISM: Artificial Sequence
<220> FEATURE:
<223> OTHER INFORMATION: synthetic

<400> SEQUENCE: 402

Asp Ile Gln Met Thr Gln Ser Pro Ser Ser Leu Ser Ala Ser Val Gly
1               5                   10                  15
Asp Arg Val Thr Ile Thr Cys Arg Ala Ser Gln Ser Ile Ser Ser Tyr
            20                  25                  30
Leu Asn Trp Tyr Gln Gln Lys Pro Gly Lys Ala Pro Lys Leu Leu Ile
        35                  40                  45
Tyr Ala Ala Ser Ser Leu Gln Ser Gly Val Pro Ser Arg Phe Ser Gly
    50                  55                  60
Ser Gly Ser Gly Thr Asp Phe Thr Leu Thr Ile Ser Ser Leu Gln Pro
65                  70                  75                  80
Glu Asp Phe Ala Thr Tyr Tyr Cys Gln Gln Ser Tyr Ser Thr Pro Pro
                85                  90                  95
Ile Thr Phe Gly Gln Gly Thr Arg Leu Glu Ile Lys
            100                 105

<210> SEQ ID NO 403
<211> LENGTH: 18
<212> TYPE: DNA
<213> ORGANISM: Artificial Sequence
<220> FEATURE:
<223> OTHER INFORMATION: synthetic

<400> SEQUENCE: 403
cagagcatta gcagctat                                                  18

<210> SEQ ID NO 404
<211> LENGTH: 6
<212> TYPE: PRT
<213> ORGANISM: Artificial Sequence
<220> FEATURE:
<223> OTHER INFORMATION: synthetic

<400> SEQUENCE: 404

Gln Ser Ile Ser Ser Tyr

<210> SEQ ID NO 405
<211> LENGTH: 9
<212> TYPE: DNA
<213> ORGANISM: Artificial Sequence
<220> FEATURE:
<223> OTHER INFORMATION: synthetic

<400> SEQUENCE: 405 gctgcatcc                                                                  9

<210> SEQ ID NO 406
<211> LENGTH: 3
<212> TYPE: PRT
<213> ORGANISM: Artificial Sequence
<220> FEATURE:
<223> OTHER INFORMATION: synthetic

<400> SEQUENCE: 406

Ala Ala Ser
1

<210> SEQ ID NO 407
<211> LENGTH: 30
<212> TYPE: DNA
<213> ORGANISM: Artificial Sequence
<220> FEATURE:
<223> OTHER INFORMATION: synthetic

<400> SEQUENCE: 407
caacagagtt acagtacccc tccgatcacc                                          30

<210> SEQ ID NO 408
<211> LENGTH: 10
<212> TYPE: PRT
<213> ORGANISM: Artificial Sequence
<220> FEATURE:
<223> OTHER INFORMATION: synthetic

<400> SEQUENCE: 408

Gln Gln Ser Tyr Ser Thr Pro Pro Ile Thr
1               5                   10

<210> SEQ ID NO 409
<211> LENGTH: 194
<212> TYPE: PRT
<213> ORGANISM: Artificial Sequence
<220> FEATURE:
<223> OTHER INFORMATION: synthetic

<400> SEQUENCE: 409

Met His Arg Pro Arg Arg Arg Gly Thr Arg Pro Pro Leu Ala Leu
1               5                   10                  15

Leu Ala Ala Leu Leu Leu Ala Ala Arg Gly Ala Asp Ala Gln Arg Pro
                20                  25                  30

Thr Gly Gly Pro Gly Cys Gly Pro Gly Arg Leu Leu Leu Gly Thr Gly
                35                  40                  45

Thr Asp Ala Arg Cys Cys Arg Val His Thr Thr Arg Cys Cys Arg Asp
            50                  55                  60

Tyr Pro Gly Glu Glu Cys Cys Ser Glu Trp Asp Cys Met Cys Val Gln
65                  70                  75                  80

Pro Glu Phe His Cys Gly Asp Pro Cys Cys Thr Thr Cys Arg His His
                85                  90                  95

```
Pro Cys Pro Pro Gly Gln Gly Val Gln Ser Gln Gly Lys Phe Ser Phe
            100                 105                 110

Gly Phe Gln Cys Ile Asp Cys Ala Ser Gly Thr Phe Ser Gly Gly His
            115                 120                 125

Glu Gly His Cys Lys Pro Trp Thr Asp Cys Thr Gln Phe Gly Phe Leu
        130                 135                 140

Thr Val Phe Pro Gly Asn Lys Thr His Asn Ala Val Cys Val Pro Gly
145                 150                 155                 160

Ser Pro Pro Ala Glu Pro Gln Lys Leu Ile Ser Glu Glu Asp Leu
                165                 170                 175

Gly Gly Glu Gln Lys Leu Ile Ser Glu Glu Asp Leu His His His His
            180                 185                 190

His His
```

<210> SEQ ID NO 410
<211> LENGTH: 399
<212> TYPE: PRT
<213> ORGANISM: Artificial Sequence
<220> FEATURE:
<223> OTHER INFORMATION: synthetic

<400> SEQUENCE: 410

```
Met His Arg Pro Arg Arg Gly Thr Arg Pro Pro Leu Ala Leu
1               5                   10                  15

Leu Ala Ala Leu Leu Ala Ala Arg Gly Ala Asp Ala Gln Arg Pro
            20                  25                  30

Thr Gly Gly Pro Gly Cys Gly Pro Gly Arg Leu Leu Leu Gly Thr Gly
            35                  40                  45

Thr Asp Ala Arg Cys Cys Arg Val His Thr Thr Arg Cys Cys Arg Asp
50                  55                  60

Tyr Pro Gly Glu Glu Cys Cys Ser Glu Trp Asp Cys Met Cys Val Gln
65                  70                  75                  80

Pro Glu Phe His Cys Gly Asp Pro Cys Cys Thr Thr Cys Arg His His
            85                  90                  95

Pro Cys Pro Pro Gly Gln Gly Val Gln Ser Gln Gly Lys Phe Ser Phe
            100                 105                 110

Gly Phe Gln Cys Ile Asp Cys Ala Ser Gly Thr Phe Ser Gly Gly His
            115                 120                 125

Glu Gly His Cys Lys Pro Trp Thr Asp Cys Thr Gln Phe Gly Phe Leu
        130                 135                 140

Thr Val Phe Pro Gly Asn Lys Thr His Asn Ala Val Cys Val Pro Gly
145                 150                 155                 160

Ser Pro Pro Ala Glu Pro Glu Pro Arg Gly Pro Thr Ile Lys Pro Cys
                165                 170                 175

Pro Pro Cys Lys Cys Pro Ala Pro Asn Leu Leu Gly Gly Pro Ser Val
            180                 185                 190

Phe Ile Phe Pro Pro Lys Ile Lys Asp Val Leu Met Ile Ser Leu Ser
            195                 200                 205

Pro Ile Val Thr Cys Val Val Val Asp Val Ser Glu Asp Asp Pro Asp
            210                 215                 220

Val Gln Ile Ser Trp Phe Val Asn Asn Val Glu Val His Thr Ala Gln
225                 230                 235                 240

Thr Gln Thr His Arg Glu Asp Tyr Asn Ser Thr Leu Arg Val Val Ser
            245                 250                 255
```

```
Ala Leu Pro Ile Gln His Gln Asp Trp Met Ser Gly Lys Glu Phe Lys
                260                 265                 270

Cys Lys Val Asn Asn Lys Asp Leu Pro Ala Pro Ile Glu Arg Thr Ile
            275                 280                 285

Ser Lys Pro Lys Gly Ser Val Arg Ala Pro Gln Val Tyr Val Leu Pro
        290                 295                 300

Pro Pro Glu Glu Met Thr Lys Lys Gln Val Thr Leu Thr Cys Met
305                 310                 315                 320

Val Thr Asp Phe Met Pro Glu Asp Ile Tyr Val Glu Trp Thr Asn Asn
                325                 330                 335

Gly Lys Thr Glu Leu Asn Tyr Lys Asn Thr Glu Pro Val Leu Asp Ser
            340                 345                 350

Asp Gly Ser Tyr Phe Met Tyr Ser Lys Leu Arg Val Glu Lys Lys Asn
        355                 360                 365

Trp Val Glu Arg Asn Ser Tyr Ser Cys Ser Val Val His Glu Gly Leu
370                 375                 380

His Asn His His Thr Thr Lys Ser Phe Ser Arg Thr Pro Gly Lys
385                 390                 395

<210> SEQ ID NO 411
<211> LENGTH: 393
<212> TYPE: PRT
<213> ORGANISM: Artificial Sequence
<220> FEATURE:
<223> OTHER INFORMATION: synthetic

<400> SEQUENCE: 411

Met His Arg Pro Arg Arg Arg Gly Thr Arg Pro Pro Leu Ala Leu
1               5                   10                  15

Leu Ala Leu Leu Leu Ala Ala Arg Gly Ala Asp Ala Gln Arg Pro
                20                  25                  30

Thr Gly Gly Pro Gly Cys Gly Pro Gly Arg Leu Leu Leu Gly Thr Gly
            35                  40                  45

Thr Asp Ala Arg Cys Cys Arg Val His Thr Thr Arg Cys Cys Arg Asp
        50                  55                  60

Tyr Pro Gly Glu Glu Cys Cys Ser Glu Trp Asp Cys Met Cys Val Gln
65                  70                  75                  80

Pro Glu Phe His Cys Gly Asp Pro Cys Cys Thr Thr Cys Arg His His
                85                  90                  95

Pro Cys Pro Pro Gly Gln Gly Val Gln Ser Gln Gly Lys Phe Ser Phe
            100                 105                 110

Gly Phe Gln Cys Ile Asp Cys Ala Ser Gly Thr Phe Ser Gly Gly His
        115                 120                 125

Glu Gly His Cys Lys Pro Trp Thr Asp Cys Thr Gln Phe Gly Phe Leu
130                 135                 140

Thr Val Phe Pro Gly Asn Lys Thr His Asn Ala Val Cys Val Pro Gly
145                 150                 155                 160

Ser Pro Pro Ala Glu Pro Asp Lys Thr His Thr Cys Pro Pro Cys Pro
                165                 170                 175

Ala Pro Glu Leu Leu Gly Gly Pro Ser Val Phe Leu Phe Pro Pro Lys
            180                 185                 190

Pro Lys Asp Thr Leu Met Ile Ser Arg Thr Pro Glu Val Thr Cys Val
        195                 200                 205

Val Val Asp Val Ser His Glu Asp Pro Glu Val Lys Phe Asn Trp Tyr
210                 215                 220
```

Val Asp Gly Val Glu Val His Asn Ala Lys Thr Lys Pro Arg Glu Glu
225                 230                 235                 240

Gln Tyr Asn Ser Thr Tyr Arg Val Val Ser Val Leu Thr Val Leu His
            245                 250                 255

Gln Asp Trp Leu Asn Gly Lys Glu Tyr Lys Cys Lys Val Ser Asn Lys
            260                 265                 270

Ala Leu Pro Ala Pro Ile Glu Lys Thr Ile Ser Lys Ala Lys Gly Gln
            275                 280                 285

Pro Arg Glu Pro Gln Val Tyr Thr Leu Pro Pro Ser Arg Asp Glu Leu
            290                 295                 300

Thr Lys Asn Gln Val Ser Leu Thr Cys Leu Val Lys Gly Phe Tyr Pro
305                 310                 315                 320

Ser Asp Ile Ala Val Glu Trp Glu Ser Asn Gly Gln Pro Glu Asn Asn
            325                 330                 335

Tyr Lys Thr Thr Pro Pro Val Leu Asp Ser Asp Gly Ser Phe Phe Leu
            340                 345                 350

Tyr Ser Lys Leu Thr Val Asp Lys Ser Arg Trp Gln Gln Gly Asn Val
            355                 360                 365

Phe Ser Cys Ser Val Met His Glu Ala Leu His Asn His Tyr Thr Gln
370                 375                 380

Lys Ser Leu Ser Leu Ser Pro Gly Lys
385                 390

<210> SEQ ID NO 412
<211> LENGTH: 194
<212> TYPE: PRT
<213> ORGANISM: Artificial Sequence
<220> FEATURE:
<223> OTHER INFORMATION: synthetic

<400> SEQUENCE: 412

Met His Arg Pro Arg Arg Arg Gly Thr Arg Pro Pro Leu Ala Leu
1               5                   10                  15

Leu Ala Ala Leu Leu Leu Ala Ala Arg Gly Ala Asp Ala Gln Arg Pro
            20                  25                  30

Thr Gly Gly Pro Gly Cys Gly Pro Gly Arg Leu Leu Leu Gly Thr Gly
            35                  40                  45

Lys Asp Ala Arg Cys Cys Arg Val His Pro Thr Arg Cys Cys Arg Asp
    50                  55                  60

Tyr Gln Gly Glu Glu Cys Cys Ser Glu Trp Asp Cys Val Cys Val Gln
65                  70                  75                  80

Pro Glu Phe His Cys Gly Asn Pro Cys Cys Thr Thr Cys Gln His His
            85                  90                  95

Pro Cys Pro Ser Gly Gln Gly Val Gln Pro Gln Gly Lys Phe Ser Phe
            100                 105                 110

Gly Phe Arg Cys Val Asp Cys Ala Leu Gly Thr Phe Ser Arg Gly His
            115                 120                 125

Asp Gly His Cys Lys Pro Trp Thr Asp Cys Thr Gln Phe Gly Phe Leu
    130                 135                 140

Thr Val Phe Pro Gly Asn Lys Thr His Asn Ala Val Cys Val Pro Gly
145                 150                 155                 160

Ser Pro Pro Ala Glu Pro Glu Gln Lys Leu Ile Ser Glu Glu Asp Leu
            165                 170                 175

```
Gly Gly Glu Gln Lys Leu Ile Ser Glu Glu Asp Leu His His His
            180                 185                 190
His His

<210> SEQ ID NO 413
<211> LENGTH: 241
<212> TYPE: PRT
<213> ORGANISM: Artificial Sequence
<220> FEATURE:
<223> OTHER INFORMATION: synthetic

<400> SEQUENCE: 413

Met Ala Gln His Gly Ala Met Gly Ala Phe Arg Ala Leu Cys Gly Leu
1               5                   10                  15

Ala Leu Leu Cys Ala Leu Ser Leu Gly Gln Arg Pro Thr Gly Gly Pro
            20                  25                  30

Gly Cys Gly Pro Gly Arg Leu Leu Leu Gly Thr Gly Thr Asp Ala Arg
        35                  40                  45

Cys Cys Arg Val His Thr Thr Arg Cys Cys Arg Asp Tyr Pro Gly Glu
50                  55                  60

Glu Cys Cys Ser Glu Trp Asp Cys Met Cys Val Gln Pro Glu Phe His
65                  70                  75                  80

Cys Gly Asp Pro Cys Cys Thr Thr Cys Arg His His Pro Cys Pro Pro
                85                  90                  95

Gly Gln Gly Val Gln Ser Gln Gly Lys Phe Ser Phe Gly Phe Gln Cys
            100                 105                 110

Ile Asp Cys Ala Ser Gly Thr Phe Ser Gly Gly His Glu Gly His Cys
        115                 120                 125

Lys Pro Trp Thr Asp Cys Thr Gln Phe Gly Phe Leu Thr Val Phe Pro
    130                 135                 140

Gly Asn Lys Thr His Asn Ala Val Cys Val Pro Gly Ser Pro Pro Ala
145                 150                 155                 160

Glu Pro Leu Gly Trp Leu Thr Val Val Leu Leu Ala Val Ala Ala Cys
                165                 170                 175

Val Leu Leu Leu Thr Ser Ala Gln Leu Gly Leu His Ile Trp Gln Leu
            180                 185                 190

Arg Ser Gln Cys Met Trp Pro Arg Glu Thr Gln Leu Leu Leu Glu Val
        195                 200                 205

Pro Pro Ser Thr Glu Asp Ala Arg Ser Cys Gln Phe Pro Glu Glu Glu
    210                 215                 220

Arg Gly Glu Arg Ser Ala Glu Glu Lys Gly Arg Leu Gly Asp Leu Trp
225                 230                 235                 240

Val
```